(12) United States Patent
Pillutla et al.

(10) Patent No.: US 7,056,679 B2
(45) Date of Patent: Jun. 6, 2006

(54) TARGET SPECIFIC SCREENING AND ITS USE FOR IDENTIFYING TARGET BINDERS

(75) Inventors: Renuka Pillutla, Bridgewater, NJ (US); Renee Brissette, Clarksburg, NJ (US); Michael Spruyt, Mahwah, NJ (US); Olga Dedova, Highland Park, NJ (US); Arthur Blume, Annandale, NJ (US); John Prendergast, Lawrenceville, NJ (US); Neil Goldstein, Maplewood, NJ (US)

(73) Assignee: Antyra, Inc., Edison, NJ (US)

( * ) Notice: Subject to any disclaimer, the term of this patent is extended or adjusted under 35 U.S.C. 154(b) by 0 days.

(21) Appl. No.: 10/280,066

(22) Filed: Oct. 24, 2002

(65) Prior Publication Data

US 2003/0180718 A1 Sep. 25, 2003

Related U.S. Application Data

(60) Provisional application No. 60/345,471, filed on Oct. 24, 2001.

(51) Int. Cl.
*G01N 33/53* (2006.01)
(52) U.S. Cl. ............... 435/7.1; 435/6; 435/5; 435/4; 435/DIG. 17; 435/DIG. 15; 536/23.4; 536/23.1; 536/530; 536/300
(58) Field of Classification Search ............ 435/7.1, 435/6, 5, 4, DIG. 17, DIG. 15; 536/23.4, 536/23.1
See application file for complete search history.

(56) References Cited

U.S. PATENT DOCUMENTS

| 5,272,263 A | 12/1993 | Hession et al. ............ 536/23.5 |
| 5,969,108 A | 10/1999 | McCafferty et al. ..... 530/387.3 |
| 6,291,650 B1 | 9/2001 | Winter et al. ............ 530/387.3 |
| 6,395,511 B1 | 5/2002 | Brunkow et al. .......... 435/69.1 |
| 6,607,881 B1 * | 8/2003 | Borrebaeck et al. ........... 435/6 |

OTHER PUBLICATIONS

Hufton, S.E., "Phage display of cDNA repertoires: the pVI display system and its applications for the selection of immunogenic ligands," *Journal of Immunological Methods*, 1999, vol. 231, pp 39-51.
PCT International Search Report dated Jun. 4, 2004.

* cited by examiner

*Primary Examiner*—T. D. Wessendorf
(74) *Attorney, Agent, or Firm*—Morgan & Finnegan, LLP

(57) ABSTRACT

The invention relates to a modified phage display method for detecting and identifying target and target binders. The modified methods involve transforming host cells with two separate phages of a target or target library and a target-binder library, and selecting to eliminate the non-paired targets and binders. The invention also relates to antibodies that bind to complexes of target and target binders; nucleic acids encoding target and target binders peptides; and the use of sequence information inherent in the targets and target binders for target validation using in silico approaches. The invention further relates to diagnostics and therapeutics employing the disclosed target and target binder peptides or polynucletides and their use in small molecule drug discovery; diagnostic and therapeutic applications directed to cancers and similar disorders; and site directed assays for high throughput drug screening.

8 Claims, 34 Drawing Sheets

FIG. 1

| CLONE | SEQUENCE | BINDING RATIO OVER BACKGROUND | SEQ ID NO: |
|---|---|---|---|
| MOTIF 1: | ----------GCXXFXGFCV | | |
| DGI2-20R-4-H8₁₄ | ----------LVIGQRSFLSACSLFDGFCV | 9.5 | 505 |
| DGI2-20R-3-A1 | ----------EGNWFCAVFRGFCVGDRGPE | 7.1 | 506 |
| DGI2-20F-3-C1 | ----------GSVLERGCLEFSGFCFSLGH | 3.4 | 507 |
| DGI2-20R-3-C1 | ----------LFSATGCALMSGFCLGSDGS | 8.2 | 508 |
| DGI2-40F-4-E11₃₀ | V#CR##LCRLCRFSMRCGGLSLVLGSAAAFFCEVFVGFCV | 2.9 | 509 |
| DGI2-20R-4-H6₂₆ | ----------RRGVCEIFTGWCVGQTNERP | 9.6 | 510 |
|  |  |  | 511 |
| MOTIF 2: | ----------FRXWVEGφ | | |
| DGI2-20R-3-A2 | ----------QMSRVAFSPGESWRRWVEGV | 7.5 | 512 |
| DGI2-40F-3-D10₄₄ | DRVARLATPTAGTMAAGSLGYERTVGCDSQDWFRCVVEGL | 7.9 | 513 |
| DGI2-40F-3-A1 | ----------REFFNQASRGAWGYMFREWVEG | 4.5 | 514 |
| DGI2-20R-4-G4 | ----------VWAAWVEGSLLSPRQEPVRD | 10.2 | 515 |
|  |  |  | 516 |
| MOTIF 3: | ----------SXGWXFPGWR | | |
| DGI2-20R-3-C2 | ----------RDTTSQWSWISRGWEFPGWR | 6.2 | 517 |
| DGI2-20C-3-C10₃₉ | RPVVCLAGLTLAQFGWVFPGWRGWS | | 518 |
| DGI2-20R-3-C6 | ----------GIMQVAWGWREWRLMDLGMA | 6.0 | 519 |
| DGI2-40F-3-D11 | LHFGSVM-GWRPPGSLWSRPFGQVHPRSWSGS | 3.8 | 520 |
|  |  |  | 521 |
| MOTIF 4: | ----------φWR+WV+GSLXG | | |
| DGI2-20R-3-A5 | ----------VWRDWVNGEWGLRNREKPGV | 10.9 | 522 |
| DGI2-20R-4-G4 | ----------VWAAWVEGSLLSPRQEPVRD | 10.2 | 523 |
| DGI2-20R-3-A12₂ | ----------WWREWVDGSLRGGGGTVLKD | 9.6 | 524 |
| DGI2-20R-4-H1 | ----------GRWDGWEVCGEWGADDCASG | 9.3 | 525 |
| DGI2-20R-3-B5₂ | ----------EWRRWSEQLLGDGELRGDG | 8.7 | 526 |
| DGI2-20R-3-C6 | ----------GIMQVAWGWREWRLMDLGMA | 6.0 | 527 |
| DGI2-20R-PP-G5 | ----------GASRVDVGWRFWGKLWQRS | 2.4 | 528 |
| DGI2-20F-PP-H3 | DDIVCLFQFCIMFCWLDMGW | 2.3 | 529 |
| DGI2-20F-PP-E5₀₀f | --SIVSSRSGWQRGWIAWFAPV | 2.7 | 530 |
| DGI2-20F-PP-F8 | ----------LLLPVRWRBAQPRSLLMEWI | 2.0 | 531 |
|  |  |  | 532 |

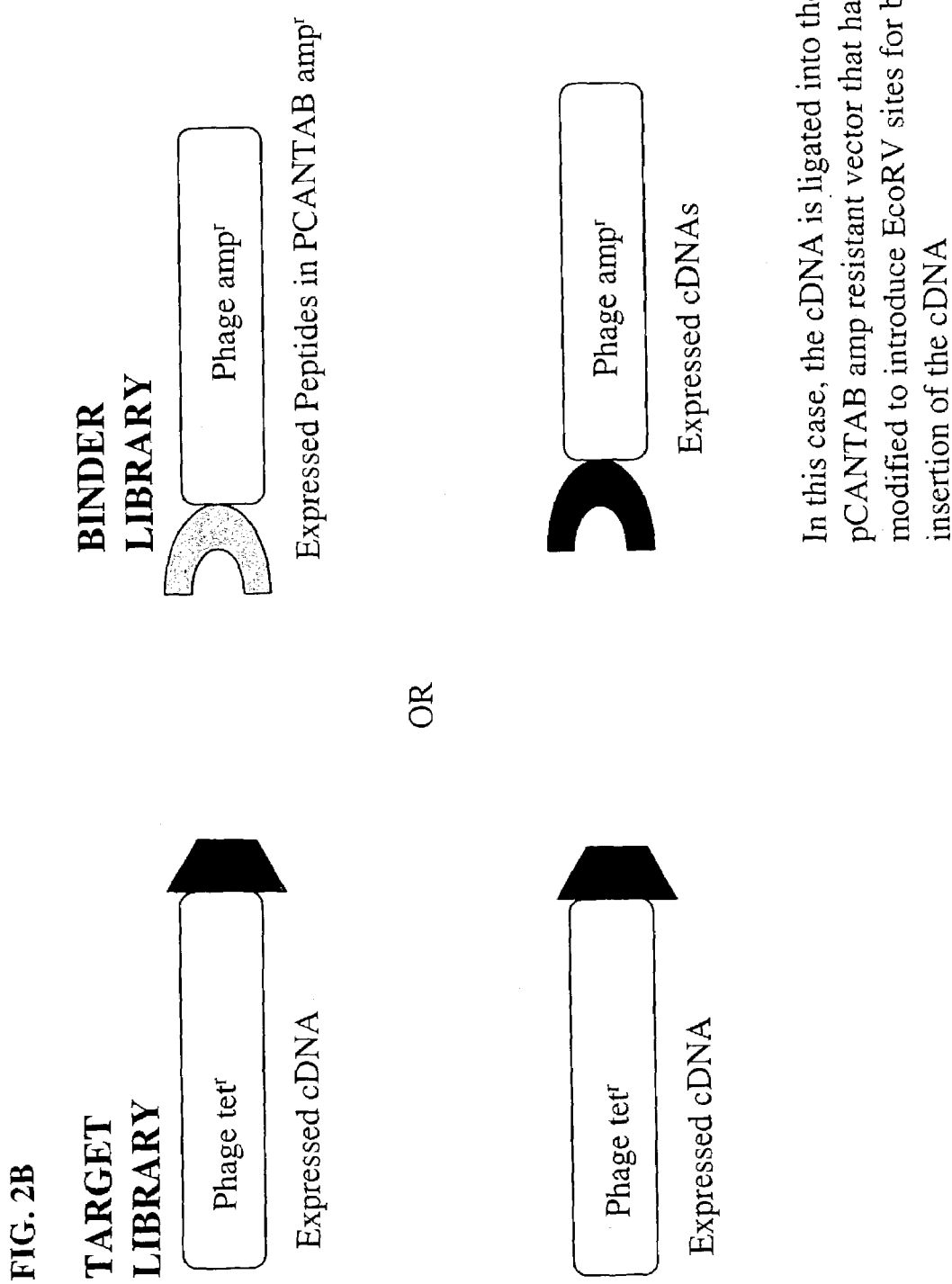

FIG. 3

CCGGCCATGGCGATGGTGCGGACTAAAGCAGACAGTGTTCCAGGCACTTA
CAGAAAAGTGGTGGCTGCTCGAGCCCCCAGAAAGGTGCTTGGTTCTTCCA
CCTCTGCCACTAATTCGACATCAGTTTCATCGAGGAAAGCTGAAAATAAA
TATGCAGGAGGGAACCCCGTTTGCGTGCGCCCAACTCCCAAGTGGCAAAA
AGGAATTGGAGAATTCTTTAGGTTGTCCCCTAAAGATTCTGAAAAGAGA
ATCAGATTCCTGAAGAGGCAGGAAGCAGTGGCTTAGGAAAAGCAAAGAG
AAAAGCATGTCCTTTGCAACCTGATCACACAAATGATGAAAAAGAAGCGG
CCGCAGGTGCGCCGGTGCCGTATCCGGATCCGCTGGAACCGCGTGCCGCA
TAG

FIG. 4

| Clone # | Sequence | E-Tag | DGI-2 | LDH | DGI2/LDH | SEQ ID NO: |
|---|---|---|---|---|---|---|
| 070902-DGI2-20M-PP-BC-H9 | LLRRVAMQHKSFLLVHGWVV | 7.0 | 6.6 | 1.2 | 5.5 | 227 |
| 070902-DGI2-20M-PP-BC-G8 | AIMRCGLVGVQRINFRLFGNPGRSD | 5.3 | 6.1 | 1.3 | 4.9 | 228 |
| 070902-DGI2-20M-PP-BC-E5 | GTKLSVSLQWPAWQARWFLV | 9.1 | 5.8 | 1.1 | 5.4 | 229 |
| 070902-DGI2-20M-PP-BC-C10 | GLILCPQRAFAALVLLRSCLRGGVP | 8.3 | 5.6 | 1.2 | 4.5 | 230 |
| 070902-DGI2-20M-PP-BC-B5 | QRSAPKGCGGSSRGVSGGCG | 8.6 | 4.3 | 1.2 | 3.6 | 231 |
| 070902-DGI2-20M-PP-BC-D8 | RSQRCRTLSVIMECCEMSAVARLWR | 6.5 | 4.1 | 1.1 | 3.6 | 232 |
| 070902-DGI2-20M-PP-BC-C5 | VARACYGLVAGFRLVRGAGDRGDCE | 9.0 | 3.9 | 1.3 | 3.1 | 233 |
| 070902-DGI2-20M-PP-BC-E8 | SEVSGVVLELQRDRMWRHGR | 7.9 | 3.9 | 1.3 | 3.1 | 234 |
| 070902-DGI2-20M-PP-BC-A8 | HSGSGRVAAGLDSQGRA | 9.5 | 3.6 | 1.2 | 3.0 | 235 |
| 070902-DGI2-20M-PP-BC-F10 | DRTTRVALPRGSAQSECMGF | 7.2 | 3.5 | 1.1 | 3.1 | 236 |
| 070902-DGI2-20M-PP-BC-F11 | SGALAGRRVVGFFQCAPESG | 8.3 | 3.4 | 1.4 | 2.5 | 237 |
| 070902-DGI2-20M-PP-BC-B6 | TITGWVQGIWGRDFARGIQS | 10.8 | 3.1 | 1.2 | 2.7 | 238 |
| 070902-DGI2-20M-PP-BC-E6 | ASAGDARQRGDGAPFSARVR | 5.5 | 3.0 | 1.0 | 3.0 | 239 |
| 070902-DGI2-20M-PP-BC-B9 | GGGGCGGVNELGLVVRLVGALSRVL | 1.2 | 2.6 | 1.1 | 2.3 | 240 |
| 070902-DGI2-20M-PP-BC-D6 | GIRHQRLRGWQVGRVGDGRE | 6.3 | 2.6 | 1.2 | 2.2 | 241 |
| 070902-DGI2-20M-PP-BC-B10 | RGGQRCQVMCRKGWVVARR | 1.2 | 2.0 | 1.1 | 1.8 | 242 |
| 070902-DGI2-20M-PP-BC-B12 | QVGENSDQLGCGAWHVLEQ | 3.4 | 1.7 | 0.9 | 1.8 | 243 |
| 070902-DGI2-20M-PP-BC-D11 | WARQRLNEPILGRGWNIEQW | 3.2 | 1.4 | 1.1 | 1.3 | 244 |

FIG. 5A

| Clone # | SEQUENCE | E-Tag | Hras | LDH | Sp/Irr | SEQ ID NO: |
|---|---|---|---|---|---|---|
| 0700902-Hras-20M-PP-BC-E5 | QWGQGPTVSIASWVLSLRRDRGG | 2.7 | 0.8 | 0.7 | 1.2 | 245 |
| 0700902-Hras-20M-PP-BC-C9 | ARGGGWARQDSLALCSRCR | 12.6 | 0.9 | 0.8 | 1.1 | 246 |
| 0700902-Hras-20M-PP-BC-B9 | DQSRSCPVAPCGGRWSVTVS | 12.5 | 0.8 | 0.8 | 1.0 | 247 |
| 0700902-Hras-20M-PP-BC-H11 | ALLGRRRNFLGPGGSNGPTWG | 3.3 | 0.6 | 0.5 | 1.1 | 248 |
| 0700902-Hras-20M-PP-BC-H10 | EVGWWADLLPRRLRRGR | 1.1 | 0.8 | 0.6 | 1.2 | 249 |
| 0700902-Hras-20M-PP-BC-G12 | GCRSHYESTGGYARARAIEQ | 7.6 | 0.7 | 0.5 | 1.4 | 250 |
| 0700902-Hras-20M-PP-BC-E8 | GFGVRVLLAHRQERGCSSI | 5.9 | 0.8 | 0.7 | 1.2 | 251 |
| 0700902-Hras-20M-PP-BC-B3 | GGGSEGDGGSPAGGGDVGTL | 7.8 | 0.8 | 0.8 | 1.0 | 252 |
| 0700902-Hras-20M-PP-BC-F12 | GGVLDARHGSQRRCLLWGIW | 4.4 | 0.7 | 0.5 | 1.3 | 253 |
| 0700902-Hras-20M-PP-BC-G11 | GR*QRFLCIA*FCAWESLAPDLPSTSSTAL | 1.4 | 0.8 | 0.7 | 1.1 | 254 |
| 0700902-Hras-20M-PP-BC-D9 | GRAICRRVGARCSQRSAIAVGGAWL | 5.0 | 0.7 | 0.7 | 1.0 | 255 |
| 0700902-Hras-20M-PP-BC-H8 | GRLRCLPHRGRGRRFRGRPCGGGSM | 3.8 | 0.6 | 0.5 | 1.2 | 256 |
| 0700902-Hras-20M-PP-BC-C2 | GRRGCWRVQPELAQVYGSG | 11.4 | 0.8 | 0.8 | 1.1 | 257 |
| 0700902-Hras-20M-PP-BC-G4 | GVGGKGRYQWGQRNGGGGFS | 1.5 | 0.7 | 0.7 | 1.0 | 258 |
| 0700902-Hras-20M-PP-BC-D8 | GVRRGGGVQRERELWVGLVT | 10.1 | 0.8 | 0.8 | 1.3 | 259 |
| 0700902-Hras-20M-PP-BC-D10 | HRPPCNQYVYLPQIIRTMTASGLGS | 9.5 | 1.1 | 1.2 | 1.1 | 260 |
| 0700902-Hras-20M-PP-BC-G8 | KGLFMTGLQSGCMRRVQGEQ | 2.1 | 1.3 | 0.8 | 0.9 | 261 |
| 0700902-Hras-20M-PP-BC-F10 | LLSLCRLTVSESWRELRVLGVGRGY | 6.1 | 0.7 | 0.7 | 1.1 | 262 |
| 0700902-Hras-20M-PP-BC-A7 | LRCLCPLGLEMPSWCGYDSQAFGYG | 10.9 | 1.0 | 0.8 | 1.3 | 263 |
| 0700902-Hras-20M-PP-BC-C10 | LVISLSGGVNSHFAVCVRFG | 2.9 | 0.8 | 0.8 | 1.0 | 264 |
| 0700902-Hras-20M-PP-BC-A2 | PAMGGLQRQVE#FAMCVVGGKGLVYV | 1.5 | 0.8 | 0.7 | 1.1 | 265 |
| 0700902-Hras-20M-PP-BC-C11 | RDWAVRVVGDVKRQQCATFG | 5.6 | 0.7 | 0.6 | 1.2 | 266 |
| 0700902-Hras-20M-PP-BC-C3 | REYNRPVLLRRGESGLSLLF | 9.5 | 0.7 | 0.7 | 1.1 | 267 |
| 0700902-Hras-20M-PP-BC-E3 | RFLASCRVLRRAHLGWRGSAQSAA | 6.2 | 0.7 | 0.7 | 1.1 | 268 |
| 0700902-Hras-20M-PP-BC-C7 | RRRAAYLSGMLAGTGAQNQR· | 2.5 | 0.8 | 0.9 | 1.0 | 269 |
| 0700902-Hras-20M-PP-BC-B10 | RTAVCHFTSGFSGWGYQWLVVVTWG | 4.1 | 0.7 | 0.7 | 1.1 | 270 |
| 0700902-Hras-20M-PP-BC-E9 | SQGARGPRGRGCGGRFNGQ | 1.1 | 0.7 | 0.7 | 1.0 | 271 |
| 0700902-Hras-20M-PP-BC-D12 | SRRGWICGTRQGACVWGSVH | 8.0 | 0.6 | 0.6 | 1.0 | 272 |

FIG. 5B

| Clone # | SEQUENCE | E-Tag | Hras | LDH | Sp/Irr | SEQ ID NO: |
|---|---|---|---|---|---|---|
| 0700902-Hras-20M-PP-BC-C4 | SRVRRWQQPHCGVSGGIMTM | 9.8 | 0.8 | 0.7 | 1.1 | 273 |
| 0700902-Hras-20M-PP-BC-G9 | SSKSCHSRPSVAIFQASQAACTWHL | 4.6 | 0.5 | 0.5 | 1.1 | 274 |
| 0700902-Hras-20M-PP-BC-B6 | SVARGDPWFSRGVGGGGIQP | 4.2 | 0.8 | 0.7 | 1.2 | 275 |
| 0700902-Hras-20M-PP-BC-B7 | SVARGDPWFSRGVGGGGIQP | 1.5 | 0.8 | 0.7 | 1.1 | 276 |
| 0700902-Hras-20M-PP-BC-B4 | SWAQCGFRARPGRVGGWVRPSIRLA | 2.3 | 0.8 | 0.7 | 1.1 | 277 |
| 0700902-Hras-20M-PP-BC-F5 | TVMDVRRRAYGGVRRMPVFR | 5.1 | 0.8 | 0.7 | 1.1 | 278 |
| 0700902-Hras-20M-PP-BC-C8 | VAWICLDANQGGDQFFTALMCPLYP | 3.6 | 0.8 | 0.8 | 1.0 | 279 |
| 0700902-Hras-20M-PP-BC-G1 | VNLRITVDVAKLVQDGTRW | 7.2 | 0.8 | 0.8 | 1.0 | 280 |
| 0700902-Hras-20M-PP-BC-B2 | VREHWMGRHRSTVGLGRNAR | 11.5 | 0.7 | 0.8 | 0.9 | 281 |
| 0700902-Hras-20M-PP-BC-D3 | WGSCKCRRPWVGAVQRGADF | 14.8 | 0.9 | 0.8 | 1.1 | 282 |
| 0700902-Hras-20M-PP-BC-H9 | YQQSCSRYRGMLPSRLIPDEPPTLA | 1.4 | 0.6 | 0.5 | 1.1 | 283 |

FIG. 6

| Clone # | Sequence | E-Tag | Leptin | LDH | Sp/Irr | SEQ ID NO: |
|---|---|---|---|---|---|---|
| 070902-Leptin-20M-PP-BC-B5 | YMRHCSGYVRTVRMSRTIRTGGRGG | 1.2 | 1.1 | 0.3 | 3.6 | 284 |

FIG. 7A

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A1R1_01.a b1.TXT | 623 | SP_HUM: Q14331 | 258 | 1.40E-02 | 0 | 0 | 147 | 269 | | 1 | 1 Q14331 homo sapiens (human). frg1. 6/2001 |
| A1R2_01.a b1.TXT | 708 | SP_HUM: Q14331 | 258 | 3.00E-60 | 0 | 0 | 106 | 483 | | -1 | 1 Q14331 homo sapiens (human). frg1. 6/2001 |
| A1R2_01.a b1.TXT | 708 | SP_HUM: Q14331 | 258 | 3.00E-60 | 1 | 0 | 483 | 569 | | -1 | 1 Q14331 homo sapiens (human). frg1. 6/2001 |
| A1R2_01.a b1.TXT | 708 | SP_HUM: Q9BZ01 | 182 | 9.00E-45 | 0 | 1 | 106 | 450 | | -1 | 1 Q9bz01 homo sapiens (human). ba348i14.2.1 (novel protein similar to fshd (fascioscapulohumeral muscular dystrophy) region gene 1 (frg1) |
| A1R2_01.a b1.TXT | 708 | SP_HUM: Q9BZ01 | 182 | 9.00E-45 | 0 | 0 | 476 | 520 | | -1 | 1 Q9bz01 homo sapiens (human). ba348i14.2.1 (novel protein similar to fshd (fascioscapulohumeral muscular dystrophy) region gene 1 (frg1) |
| A1R2_01.a b1.TXT | 708 | SP_HUM: Q9BZ01 | 182 | 9.00E-45 | 0 | 0 | 456 | 482 | | -1 | 1 Q9bz01 homo sapiens (human). ba348i14.2.1 (novel protein similar to fshd (fascioscapulohumeral muscular dystrophy) region gene 1 (frg1) |
| A1R2_01.a b1.TXT | 708 | SP_HUM: Q9BZ00 | 74 | 3.00E-28 | 0 | 1 | 178 | 396 | | -1 | 1 Q9bz00 homo sapiens (human). ba348i14.2.2 (novel protein similar to fshd (fascioscapulohumeral muscular dystrophy) region gene 1 (frg1) |

FIG. 7B

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A1R2_01.a b1.TXT | 708 | SP_HUM: Q9NQT6 | 498 | 7.30E+0 | 0 | 0 | 220 | 453 | | -1 | 1:Q9nqt6 homo sapiens (human). testis fascin. 10/2000 |
| A3R1_05.a b1.TXT | 682 | SP_HUM: Q14331 | 258 | 4.00E-27 | 1 | 0 | 8 | 406 | | 1 | 1:Q14331 homo sapiens (human). frg1. 6/2001 |
| A3R1_05.a b1.TXT | 682 | SP_HUM: Q9BZ01 | 182 | 3.00E-03 | 0 | 0 | 204 | 263 | | 1 | 1:Q9bz01 homo sapiens (human). ba348i14.2.1 (novel protein similar to fshd (fascioscapulohumeral muscular dystrophy) region gene 1 (frg1) |
| A3R1_05.a b1.TXT | 682 | SP_HUM: Q9BZ01 | 182 | 3.00E-03 | 0 | 0 | 275 | 325 | | 1 | 1:Q9bz01 homo sapiens (human). ba348i14.2.1 (novel protein similar to fshd (fascioscapulohumeral muscular dystrophy) region gene 1 (frg1) |
| A3R2_05.a b1.TXT | 693 | SP_HUM: Q14331 | 258 | 1.00E-85 | 0 | 0 | 13 | 471 | | -1 | 1:Q14331 homo sapiens (human). frg1. 6/2001 |
| A3R2_05.a b1.TXT | 693 | SP_HUM: Q14331 | 258 | 1.00E-85 | 0 | 0 | 471 | 503 | | -1 | 1:Q14331 homo sapiens (human). frg1. 6/2001 |
| A3R2_05.a b1.TXT | 693 | SP_HUM: Q9BZ01 | 182 | 1.00E-75 | 0 | 1 | 13 | 438 | | -1 | 1:Q9bz01 homo sapiens (human). ba348i14.2.1 (novel protein similar to fshd (fascioscapulohumeral muscular dystrophy) region gene 1 (frg1) |

FIG. 7C

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A3R2_05.a b1.TXT | 693 | SP_HUM: Q9BZ01 | 182 | 1.00E-75 | 0 | 0 | 464 | 505 | -1 | | 1 Q9bz01 homo sapiens (human). ba348i14.2.1 (novel protein similar to fshd (fascioscapulohumeral muscular dystrophy) region gene 1 (frg1) |
| A3R2_05.a b1.TXT | 693 | SP_HUM: Q9BZ01 | 182 | 1.00E-75 | 0 | 0 | 444 | 470 | -1 | | 1 Q9bz01 homo sapiens (human). ba348i14.2.1 (novel protein similar to fshd (fascioscapulohumeral muscular dystrophy) region gene 1 (frg1) |
| A3R2_05.a b1.TXT | 693 | SP_HUM: Q9BZ00 | 74 | 3.00E-32 | 0 | 1 | 163 | 384 | -1 | | 1 Q9bz00 homo sapiens (human). ba348i14.2.2 (novel protein similar to fshd (fascioscapulohumeral muscular dystrophy) region gene 1 (frg1) |
| A3R2_05.a b1.TXT | 693 | SP_HUM: Q9NQT6 | 498 | 7.10E+0 0 | 0 | 0 | 208 | 441 | -1 | | 1 Q9nqt6 homo sapiens (human). testis fascin. 10/2000 |
| A3R2_05.a b1.TXT | 693 | SW:FASC _HUMAN | 492 | 7.10E+0 0 | 0 | 0 | 160 | 387 | -1 | | 1 Q16658 homo sapiens (human). fascin (actin bundling protein) (singed-like protein). 8/2001 |
| A3R2_05.a b1.TXT | 693 | SP_HUM: Q9BRF1 | 493 | 7.10E+0 0 | 0 | 0 | 160 | 387 | -1 | | 1 Q9brf1 homo sapiens (human). singed (drosophila)-like (sea urchin fascin homolog like). 6/2001 |
| A5R1_09.a b1.TXT | 522 | SP_HUM: Q9H387 | 118 | 6.00E-08 | 0 | 0 | 8 | 94 | -1 | | 1 Q9h387 homo sapiens (human). pro2550. 3/2001 |

FIG. 7D

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A5R1_09.a b1.TXT | 522 | SP_HUM: Q9UI50 | 81 | 2.00E-06 | 0 | 0 | 12 | 98 | 1 | 1 | Q9ui50 homo sapiens (human). pro0657 (fragment). 5/2000 |
| A5R1_09.a b1.TXT | 522 | SP_HUM: Q9HA67 | 151 | 2.00E-06 | 0 | 0 | 2 | 97 | -1 | 1 | Q9ha67 homo sapiens (human). cdna flj12155 fis |
| A5R1_09.a b1.TXT | 522 | SP_HUM: Q9H5R3 | 232 | 4.00E-06 | 0 | 0 | 11 | 97 | -1 | 1 | Q9h5r3 homo sapiens (human). cdna: flj23147 fis |
| A5R1_09.a b1.TXT | 522 | SP_HUM: Q9H965 | 177 | 4.00E-06 | 0 | 0 | 11 | 88 | -1 | 1 | Q9h965 homo sapiens (human). cdna flj12983 fis |
| A5R1_09.a b1.TXT | 522 | SP_HUM: Q9H700 | 244 | 5.00E-05 | 0 | 0 | 11 | 94 | -1 | 1 | Q9h700 homo sapiens (human). cdna: flj21617 fis |
| A5R1_09.a b1.TXT | 522 | SP_HUM: Q9HCL6 | 1596 | 5.00E-05 | 0 | 0 | 3 | 98 | 1 | 1 | Q9hcl6 homo sapiens (human). kiaa1556 protein (fragment). 6/2001 |
| A5R1_09.a b1.TXT | 522 | SP_HUM: Q9NX85 | 152 | 4.00E-04 | 0 | 0 | 11 | 94 | -1 | 1 | Q9nx85 homo sapiens (human). cdna flj20378 fis |
| A5R1_09.a b1.TXT | 522 | SP_HUM: Q9HCN6 | 620 | 4.00E-04 | 0 | 0 | 9 | 98 | 1 | 1 | Q9hcn6 homo sapiens (human). platelet glycoprotein vi-3. 6/2001 |
| A5R1_09.a b1.TXT | 522 | SP_HUM: Q9NR08 | 231 | 6.00E-04 | 0 | 0 | 11 | 88 | -1 | 1 | Q9nr08 homo sapiens (human). ubiquitous tpr-motif protein y isoform (fragment). 10/2000 |
| A5R1_09.a b1.TXT | 522 | SP_HUM: Q9P147 | 102 | 6.00E-04 | 0 | 0 | 11 | 97 | -1 | 1 | Q9p147 homo sapiens (human). pro2822. 10/2000 |
| A5R1_09.a b1.TXT | 522 | SP_HUM: Q9H842 | 125 | 1.00E-03 | 0 | 0 | 11 | 97 | -1 | 1 | Q9h842 homo sapiens (human). cdna flj3954 fis |
| A5R1_09.a b1.TXT | 522 | SP_HUM: Q9P195 | 118 | 1.00E-03 | 0 | 0 | 11 | 97 | -1 | 1 | Q9p195 homo sapiens (human). pro1722. 10/2000 |

FIG. 7E

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A5R1_09.a b1.TXT | 522 | SP_HUM: Q16230 | 46 | 2.00E-03 | 0 | 0 | 11 | 97 | 1 | -1 | 1 Q16230 homo sapiens (human). neurofibromatosis 2 (nf2) (fragment). 11/1998 |
| A5R1_09.a b1.TXT | 522 | SP_HUM: Q9H6L7 | 506 | 2.00E-03 | 0 | 0 | 11 | 91 | 1 | -1 | 1 Q9h6l7 homo sapiens (human). cdna: flj22136 fis |
| A5R1_09.a b1.TXT | 522 | SP_HUM: Q9BYA5 | 162 | 2.00E-03 | 0 | 0 | 11 | 88 | 1 | -1 | 1 Q9bya5 homo sapiens (human). kiaa1655 protein (fragment). 6/2001 |
| A5R1_09.a b1.TXT | 522 | SP_HUM: Q9H5D5 | 162 | 2.00E-03 | 0 | 0 | 11 | 97 | 1 | -1 | 1 Q9h5d5 homo sapiens (human). cdna: flj23555 fis |
| A5R1_09.a b1.TXT | 522 | SP_HUM: Q9H5D5 | 162 | 2.00E-03 | 0 | 0 | 11 | 97 | 1 | -1 | 1 Q9h5d5 homo sapiens (human). cdna: flj23555 fis |
| A5R1_09.a b1.TXT | 522 | SP_HUM: Q9Y4Y2 | 134 | 3.00E-03 | 0 | 0 | 12 | 98 | 1 | 1 | 1 Q9y4y2 homo sapiens (human). e1 fusion protein. 6/2001 |
| A5R1_09.a b1.TXT | 522 | SP_HUM: O60448 | 375 | 3.00E-03 | 0 | 0 | 11 | 97 | 1 | -1 | 1 O60448 homo sapiens (human). neuronal thread protein ad7c-ntp. 8/1998 |
| A5R1_09.a b1.TXT | 522 | SP_HUM: O60448 | 375 | 3.00E-03 | 0 | 0 | 11 | 97 | 1 | -1 | 1 O60448 homo sapiens (human). neuronal thread protein ad7c-ntp. 8/1998 |
| A5R1_09.a b1.TXT | 522 | SP_HUM: Q9BXZ1 | 165 | 5.00E-03 | 0 | 0 | 11 | 94 | 1 | -1 | 1 Q9bxz1 homo sapiens (human). cyclophilin-like protein. 6/2001 |
| A5R1_09.a b1.TXT | 522 | SP_HUM: Q9UI48 | 61 | 8.00E-03 | 0 | 0 | 11 | 97 | 1 | -1 | 1 Q9ui48 homo sapiens (human). pro0663 (fragment). 5/2000 |
| A5R1_09.a b1.TXT | 522 | SW:TA2R _HUMAN | 369 | 1.10E-02 | 0 | 0 | 9 | 98 | 1 | -1 | 1 P21731 homo sapiens (human). thromboxane a2 receptor (txa2-r) (prostanoid tp receptor). 8/2001 |

FIG. 7F

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A5R1_09.a b1.TXT | 522 | SP_HUM:Q 9Y4Z8 | 34 | 1.10E-02 | 0 | 0 | 9 | 98 | | -1 | 1 Q9y4z8 homo sapiens (human). fanca protein (fragment). 11/1999 |
| A5R1_09.a b1.TXT | 522 | SP_HUM:Q 9HAD8 | 123 | 1.40E-02 | 0 | 0 | 18 | 98 | | -1 | 1 Q9had8 homo sapiens (human). cdna flj11786 fis |
| A5R1_09.a b1.TXT | 522 | SP_HUM:Q 9BR49 | 203 | 1.40E-02 | 0 | 0 | 9 | 89 | | -1 | 1 Q9br49 homo sapiens (human). dj1049g16.2.2 (continued from ba456n23.2 in em:al353777 and dj237j2.1 in em:al021394) (fragment). 6/2001 |
| A5R1_09.a b1.TXT | 522 | SP_HUM:Q 9C032 | 326 | 2.40E-02 | 0 | 0 | 9 | 86 | | -1 | 1 Q9c032 homo sapiens (human). tripartite motif protein trim5 isoform delta. 6/2001 |
| A5R1_09.a b1.TXT | 522 | SP_HUM:Q 9NUM9 | 275 | 4.00E-02 | 0 | 0 | 2 | 97 | | -1 | 1 Q9num9 homo sapiens (human). cdna flj11264 fis |
| A5R1_09.a b1.TXT | 522 | SP_HUM:Q 9UQD6 | 164 | 4.00E-02 | 0 | 0 | 11 | 94 | | -1 | 1 Q9uqd6 homo sapiens (human). bax epsilon. 6/2001 |
| A5R1_09.a b1.TXT | 522 | SP_HUM:Q 9BV35 | 482 | 4.00E-02 | 0 | 0 | 9 | 86 | | -1 | 1 Q9bv35 homo sapiens (human). unknown (protein for mgc:2615). 6/2001 |
| A5R1_09.a b1.TXT | 522 | SP_HUM:Q 9HBK0 | 163 | 5.30E-02 | 0 | 0 | 35 | 97 | | -1 | 1 Q9hbk0 homo sapiens (human). natural resistance-associated macrophage protein 1. 6/2001 |
| A5R1_09.a b1.TXT | 522 | SP_HUM:Q 14970 | 72 | 5.30E-02 | 0 | 0 | 35 | 97 | | -1 | 1 Q14970 homo sapiens (human). integral membrane protein (fragment). 6/2001 |
| A5R1_09.a b1.TXT | 522 | SP_HUM:Q 9HA45 | 121 | 5.30E-02 | 0 | 0 | 41 | 94 | | -1 | 1 Q9ha45 homo sapiens (human). cdna flj12267 fis |

FIG. 7G

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A5R1_09.a b1.TXT | 522 | SW:RMS1_HUMAN | 418 | 6.90E-02 | 0 | 0 | 0 | 39 | 95 | | 1 | 1;P49646 homo sapiens (human). very very hypothetical protein rmsa-1. 8/2001 |
| A5R1_09.a b1.TXT | 522 | SP_HUM:Q9UHT1 | 84 | 9.00E-02 | 0 | 0 | 11 | 97 | | -1 | 1;Q9uht1 homo sapiens (human). pro1902 protein. 3/2001 |
| A5R1_09.a b1.TXT | 522 | SP_HUM:Q9P1N7 | 123 | 1.20E-01 | 0 | 0 | 21 | 95 | | 1 | 1;Q9p1n7 homo sapiens (human). pro0974. 10/2000 |
| A5R1_09.a b1.TXT | 522 | SP_HUM:P78525 | 666 | 1.20E-01 | 0 | 0 | 11 | 100 | | -1 | 1;P78525 homo sapiens (human). myb proto-oncogene protein (c-myb). 6/2001 |
| A5R1_09.a b1.TXT | 522 | SP_HUM:O95074 | 40 | 1.20E-01 | 0 | 0 | 11 | 85 | | -1 | 1;O95074 homo sapiens (human). bax epsilon (fragment). 5/1999 |
| A5R1_09.a b1.TXT | 522 | SW:SGCE_HUMAN | 438 | 1.50E-01 | 0 | 0 | 35 | 94 | | -1 | 1;O43556 homo sapiens (human). epsilon-sarcoglycan precursor (epsilon-sg). 8/2001 |
| A5R1_09.a b1.TXT | 522 | SP_HUM:Q9HBC4 | 1150 | 2.00E-01 | 0 | 0 | 32 | 94 | | -1 | 1;Q9hbc4 homo sapiens (human). membrane-associated guanylate kinase magi3. 6/2001 |
| A5R1_09.a b1.TXT | 522 | SP_HUM:Q9BU27 | 70 | 2.00E-01 | 0 | 0 | 9 | 83 | | -1 | 1;Q9bu27 homo sapiens (human). similar to predicted osteoblast protein. 6/2001 |
| A5R1_09.a b1.TXT | 522 | SP_HUM:Q9NU66 | 141 | 4.50E-01 | 0 | 3 | 29 | 151 | | -1 | 1;Q9nu66 homo sapiens (human). ba145l22.1.8 (myelin/oligodendrocyte glycoprotein mog (isoform 8)) (fragment). 6/2001 |

FIG. 7H

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A5R1_09.a b1.TXT | 522 | SP_HUM:Q 07826 | 100 | 4.50E-01 | 0 | 0 | 0 | 38 | 97 | -1 | 1 Q07826 homo sapiens (human). x-linked retinopathy protein (fragment). 1/1999 |
| A5R1_09.a b1.TXT | 522 | SP_HUM:Q 9HBV5 | 110 | 5.80E-01 | 0 | 0 | 0 | 9 | 86 | | 1 Q9hbv5 homo sapiens (human). pp1200. 3/2001 |
| A5R1_09.a b1.TXT | 522 | SP_HUM:Q 9NRK0 | 113 | 7.60E-01 | 0 | 0 | 0 | 11 | 97 | -1 | 1 Q9nrk0 homo sapiens (human). truncated mevalonate kinase (fragment). 10/2000 |
| A5R1_09.a b1.TXT | 522 | SP_HUM:Q 9UHC9 | 1359 | 1.30E+0 0 | 0 | 3 | 0 | 40 | 138 | | 1 Q9uhc9 homo sapiens (human). niemann-pick c3 protein. 6/2001 |
| A5R1_09.a b1.TXT | 522 | SP_HUM:Q 9P0A7 | 171 | 1.70E+0 0 | 0 | 0 | 0 | 40 | 93 | -1 | 1 Q9p0a7 homo sapiens (human). hspc274. 10/2000 |
| A5R1_09.a b1.TXT | 522 | SP_HUM:Q 9H0A3 | 160 | 1.70E+0 0 | 0 | 0 | 0 | 11 | 88 | 1 | 1 Q9h0a3 homo sapiens (human). hypothetical 18.0 kda protein. 3/2001 |
| A5R1_09.a b1.TXT | 522 | SP_HUM:Q 9BYK6 | 96 | 1.70E+0 0 | 0 | 0 | 0 | 40 | 93 | -1 | 1 Q9byk6 homo sapiens (human). dj746j20.1.1 (hspc274 (isoform 1)) (fragment). 6/2001 |
| A5R1_09.a b1.TXT | 522 | SP_HUM:Q 9BWC6 | 502 | 2.20E+0 0 | 0 | 0 | 0 | 11 | 91 | 1 | 1 Q9bwc6 homo sapiens (human). similar to nuclear prelamin a recognition factor. 6/2001 |
| A5R1_09.a b1.TXT | 522 | SP_HUM:O 43263 | 699 | 2.20E+0 0 | 0 | 0 | 0 | 38 | 97 | -1 | 1 O43263 homo sapiens (human). rna editing deaminase 1. 6/2001 |
| A5R1_09.a b1.TXT | 522 | SP_HUM:Q 9H800 | 155 | 2.20E+0 0 | 0 | 0 | 0 | 11 | 97 | -1 | 1 Q9h800 homo sapiens (human). cdna flj14031 fis |
| A5R1_09.a b1.TXT | 522 | SP_HUM:Q 9H7F8 | 257 | 2.20E+0 0 | 0 | 0 | 0 | 29 | 97 | -1 | 1 Q9h7f8 homo sapiens (human). cdna: flj20958 fis |

FIG. 7I

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A5R1_09.a b1.TXT | 522 | SW:RED1_HUMAN | 741 | 2.20E+0 | 0 | 0 | 0 | 38 | 97 | | -1 | 1 P78563 homo sapiens (human). double-stranded rna-specific editase 1 (ec 3.5.-.-) (dsrna adenosine deaminase) (rna editing enzyme 1). 8/2001 |
| A5R1_09.a b1.TXT | 522 | SP_HUM:Q 9NWI4 | 208 | 2.90E+0 | 0 | 0 | 0 | 11 | 100 | | -1 | 1 Q9nwi4 homo sapiens (human). cdna flj20837 fis |
| A5R1_09.a b1.TXT | 522 | SP_HUM:Q 9NYI5 | 281 | 2.90E+0 | 0 | 0 | 0 | 9 | 65 | | -1 | 1 Q9nyi5 homo sapiens (human). mesenchymal stem cell protein dsc54. 10/2000 |
| A5R1_09.a b1.TXT | 522 | SP_HUM:Q 9P191 | 76 | 2.90E+0 | 0 | 0 | 0 | 11 | 58 | | -1 | 1 Q9p191 homo sapiens (human). pro1847. 10/2000 |
| A5R1_09.a b1.TXT | 522 | SP_HUM:Q 9ULL2 | 663 | 2.90E+0 | 0 | 0 | 0 | 9 | 89 | | -1 | 1 Q9ull2 homo sapiens (human). kiaa1208 protein (fragment). 6/2001 |
| A5R1_09.a b1.TXT | 522 | SP_HUM:Q 9H6G8 | 120 | 3.80E+0 | 0 | 0 | 0 | 40 | 93 | | -1 | 1 Q9h6g8 homo sapiens (human). cdna: flj22294 fis |
| A5R1_09.a b1.TXT | 522 | SP_HUM:Q 9Y3U4 | 522 | 3.80E+0 | 0 | 0 | 0 | 29 | 97 | | -1 | 1 Q9y3u4 homo sapiens (human). hypothetical 57.7 kda protein (fragment). 6/2001 |
| A5R1_09.a b1.TXT | 522 | SP_HUM:Q 9HBS7 | 130 | 8.40E+0 | 0 | 0 | 0 | 40 | 105 | | -1 | 1 Q9hbs7 homo sapiens (human). hypothetical 14.2 kda protein. 3/2001 |
| A5R2_09.a b1.TXT | 423 | SP_HUM:O 60448 | 375 | 1.60E+0 | 0 | 0 | 0 | 334 | 411 | | 1 | 1 O60448 homo sapiens (human). neuronal thread protein ad7c-ntp. 8/1998 |

FIG. 7J

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A5R2_09.a b1.TXT | 423 | SP_HUM:O 95566 | 312 | 8.00E+0 0 | 0 | 0 | 0 | 328 | 411 | 1 | 1:O95566 homo sapiens (human). hypothetical 35.3 kda protein. 10/2000 |
| A5R2_09.a b1.TXT | 423 | SP_HUM:O 95565 | 341 | 8.00E+0 0 | 0 | 0 | 0 | 328 | 411 | 1 | 1:O95565 homo sapiens (human). hypothetical 38.5 kda protein. 10/2000 |
| A6R2_11.a b1.TXT | 312 | SW:TNR2_ HUMAN | 461 | 1.00E-13 | 0 | 0 | 0 | 227 | 310 | -1 | 1:P20333 homo sapiens (human). tumor necrosis factor receptor 2 precursor (tumor necrosis factor binding protein 2) (tbpii) (p80) (tnf-r2) (p75) (cd120b) (etanercept). 8/2001 |
| A6R2_11.a b1.TXT | 312 | SW:TNR2_ HUMAN | 461 | 1.00E-13 | 0 | 0 | 0 | 58 | 219 | -1 | 1:P20333 homo sapiens (human). tumor necrosis factor receptor 2 precursor (tumor necrosis factor binding protein 2) (tbpii) (p80) (tnf-r2) (p75) (cd120b) (etanercept). 8/2001 |
| A6R2_11.a b1.TXT | 312 | SP_HUM:Q 16042 | 425 | 1.00E-13 | 0 | 0 | 0 | 227 | 310 | -1 | 1:Q16042 homo sapiens (human). tumor necrosis factor receptor (fragment). 6/2001 |
| A6R2_11.a b1.TXT | 312 | SP_HUM:Q 16042 | 425 | 1.00E-13 | 0 | 0 | 0 | 58 | 219 | -1 | 1:Q16042 homo sapiens (human). tumor necrosis factor receptor (fragment). 6/2001 |
| A6R2_11.a b1.TXT | 312 | SP_HUM:Q 9UIH1 | 30 | 1.00E-04 | 0 | 0 | 0 | 245 | 310 | -1 | 1:Q9uih1 homo sapiens (human). tumor necrosis factor receptor 2 (fragment). 5/2000 |

FIG. 7K

| QNAME | QLEN | S-NAME | S-LEN | EXP | Q-GAP | S-GAP | Q-START | Q-END | Q-STRAND | S-STRAND | DESCRIPTION |
|---|---|---|---|---|---|---|---|---|---|---|---|
| A6R2_11.a b1.TXT | 312 | SP_HUM:Q 9UIH0 | 78 | 6.90E-02 | 0 | 0 | 0 | 58 | 219 | -1 | 1 Q9uih0 homo sapiens (human). tumor necrosis factor receptor 2 (fragment). 5/2000 |
| A6R2_11.a b1.TXT | 312 | SP_HUM:O 95407 | 300 | 1.30E+0 | 0 | 0 | 0 | 230 | 310 | -1 | 1 O95407 homo sapiens (human). decoy receptor 3 (m68) (m68c) (m68e) (dj583p15.1.1). 6/2001 |

FIG. 8A

| DGI # | DGI Alias / Target ID | Clone Name | METHOD | Target DNA Acc. No. | Target Protein Acc. No. | Target Locus | HSPL Seq | Phenogenix Partner ID | Phenogenix Partner Protein Acc. No. |
|---|---|---|---|---|---|---|---|---|---|
| dgen-0101 | DGI-3 | dgen-0101-20M-3-AP-A158 | Biopanning | NM_021067 | NP_066545.1 | 9837 | TIRRWFCLAHWGT EGCLART (SEQ ID NO:538) | RAS-GAP2, Cytohesin 1,2,3,4 | Q15283, Q15438, Q99418, O43739, Q9UIA0 |
| dgen-0101 | DGI-3 | dgen-0101-20M-3-AP-C511 | Biopanning | NM_021067 | NP_066545.1 | 9837 | EWARCVVRWLVE GVVGQLGTVCGSS (SEQ ID NO:539) | TRIO (Triple functional domain protein) | O75962 |
| dgen-0101 | DGI-3 | dgen-0101-20M-3-AP-G32 | Biopanning | NM_021067 | NP_066545.1 | 9837 | GLGWRDPVCVPFR GMRLCLV (SEQ ID NO: 540) | GNRP (Guanine nucleotide releasing protein) | Q13972 |
| dgen-0102 | DGI-9 | No Entry | Biopanning | NM_006101 | NP_006092.1 | 10403 | | | |
| dgen-0103 | DGI-11 | | Biopanning | U03877 | AAA65590.1 | No Entry | | | |
| dgen-0104 | DGI-2 | dgen-0104-20M-3-KH-Motif1 | Biopanning | BC007101 | AAH07101.1 | 9768 | GCXXFXGFCV (SEQ ID NO:505) | | |
| dgen-0104 | DGI-2 | dgen-0104-20M-3-KH-Motif2 | Biopanning | BC007101 | AAH07101.1 | 9768 | FRXWVEGφ (SEQ ID NO:512) | | |

FIG. 8B

| DGI # | DGI Alias / Target ID | Clone Name | METHOD | Target DNA Acc. No. | Target Protein Acc. No. | Target Locus | HSPL Seq | Phenogenix Partner ID | Phenogenix Partner Protein Acc. No. |
|---|---|---|---|---|---|---|---|---|---|
| dgen-0104 | DGI-2 | dgen-0104-20M-3-KH-Motif3 | Biopanning | BC007101 | AAH07101.1 | 9768 | SXGWXFPGWR (SEQ ID NO:517) | | |
| dgen-0105 | NUDT5 (nudix hydrolase) | 073002-cDNATet-20F20C40R-PP-DC-B11 | Proteome Panning | AF218818 | AAF25479.1 | 11164 | IGRQLGGGVAMDCDVAVGER (SEQ ID NO:541) | No significant hits | |
| dgen-0106 | TNFR2 | 073002-cDNATet-20F20C40R-PP-DC-G11 | Proteome Panning | AB030951 | BAA89054.1 | No Entry | | | |
| dgen-0107 | thymosin beta-10 | 073002-cDNATet-20F20C40R-PP-DC-G5 | Proteome Panning | S54005 | AAB25225.1 | 9168 | | | |
| dgen-0108 | Solute carrier family 25 (mitochondrial adenine nucleotide translocator) | 072402-cDNATet-20M-PP-DC-F3 | Proteome Panning | BC008737 | AAH08737.1 | 292 | | | |

FIG. 8C

| DGI # | DGI Alias / Target ID | Clone Name | METHOD | Target DNA Acc. No. | Target Protein Acc. No. | Target Locus | HSPL Seq | Phenogenix Partner ID | Phenogenix Partner Protein Acc. No. |
|---|---|---|---|---|---|---|---|---|---|
| dgen-0109 | FRG1 | 072402-cDNATet-20M-PP-DC-clone 25 | Proteome Panning | L76159 | Q14331 | 2483 | SKRLCAAGYQD LNVQRWRALRL GPMA (SEQ ID NO:542) | PKD1 (Polycystin precursor) | P98161 |
| dgen-0110 | Ribosomal Protein S20 | 073002-cDNATet-20F20C40R-PP-DC-B10 | Proteome Panning | BC007507 | AAH07507.1 | 6224 | QNWWTHRWVG DIVLRFGTTR (SEQ ID NO:543) | 28S ribosomal protein S17 | Q9Y2R5 |
| dgen-0110 | Ribosomal Protein S20 | 073002-cDNATet-20F20C40R-PP-DC-E11 | Proteome Panning | BC007507 | AAH07507.1 | 6224 | QRTGRLCNRGT ARFASSVGL (SEQ ID NO:544) | 60S ribosomal protein L8 | P25120 |
| dgen-0110 | Ribosomal Protein S20 | 073002-cDNATet-20F20C40R-PP-DC-F2 | Proteome Panning | BC007507 | AAH07507.1 | 6224 | PACRRFSRRLAP SRDRGSGP (SEQ ID NO:545) | | |
| dgen-0111 | SAC3 (Sac domain containing inositol phosphatase 3) | 073002-cDNATet-20F20C40R-PP-DC-C12 | Proteome Panning | D87464 | Q92562 | 9896 | QRVSCSPLEHTY GGLYGDMGAS WRG (SEQ ID NO:546) | No significant hits | |

FIG. 8D

| DGI # | DGI Alias / Target ID | Clone Name | METHOD | Target DNA Acc. No. | Target Protein Acc. No. | Target Locus | HSPL Seq | Phenogenix Partner ID | Phenogenix Partner Protein Acc. No. |
|---|---|---|---|---|---|---|---|---|---|
| dgen-0111 | SAC3 (Sac domain containing inositol phosphatase 3) | 073002-cDNATet-20F20C40R-PP-DC-D10 | Proteome Panning | D87464 | Q92562 | 9896 | TLNSCLSGVIAC #CRLSGITIH (SEQ ID NO:547) | No significant hits | |
| dgen-0111 | SAC3 (Sac domain containing inositol phosphatase 3) | 073002-cDNATet-20F20C40R-PP-DC-D2 | Proteome Panning | D87464 | Q92562 | 9896 | LTGQCNWARDP CVVGVTMVVRR ASG (SEQ ID NO:548) | No significant hits | |
| dgen-0111 | SAC3 (Sac domain containing inositol phosphatase 3) | 073002-cDNATet-20F20C40R-PP-DC-F9 | Proteome Panning | D87464 | Q92562 | 9896 | QVILCCVPGLGL VFMRDALGVRA GH (SEQ ID NO:549) | PROML1 (Prominin-like protein) | O43490 |

FIG. 8E

| DGI # | DGI Alias / Target ID | Clone Name | METHOD | Target DNA Acc. No. | Target Protein Acc. No. | Target Locus | HSPL Seq | Phenogenix Partner ID | Phenogenix Partner Protein Acc. No. |
|---|---|---|---|---|---|---|---|---|---|
| dgen-0111 | SAC3 (Sac domain containing inositol phosphatase 3) | 073002-cDNATet-20F20C40R-PP-DC-G9 | Proteome Panning | D87464 | Q92562 | 9896 | WI#AELFGYAGL DMLHVMSGFSE VACLLTVPNQS (SEQ ID NO:550) | No significant hits | |
| dgen-0111 | SAC3 (Sac domain containing inositol phosphatase 3) | No Entry | Proteome Panning | D87464 | Q92562 | 9896 | SFLRASSVSLRSS LVTLPRVSGVL (SEQ ID NO:551) | Phakinin | Q13515 |
| dgen-0112 | Cytochrome c oxidase subunit VIB | 073002-cDNATet-20F20C40R-PP-DC-C2 | Proteome Panning | BC002478 | AAH02478.1 | 1340 | SGWPVGGGPVC IALRLAGRR (SEQ ID NO:552) | | |
| dgen-0113 | Similar to CGI-16 (unknown function) | 072402-cDNATet-20M-PP-DC-D12 | Proteome Panning | AK024337 | No Entry | No Entry | | | |

FIG. 8F

| DGI # | DGI Alias / Target ID | Clone Name | METHOD | Target DNA Acc. No. | Target Protein Acc. No. | Target Locus | HSPL Seq | Phenogenix Partner ID | Phenogenix Partner Protein Acc. No. |
|---|---|---|---|---|---|---|---|---|---|
| dgen-0114 | cDNA FLJ20541 (unknown function) | 072402-cDNATet-20M-PP-DC-H2 | Proteome Panning | AK000548 | No Entry | No Entry | | | |
| dgen-0115 | Human homolog of yeast ribosomal protein S28 | 073002-cDNATet-20F20C40R-PP-DC-C7 | Proteome Panning | D14530 | BAA03400.1 | No Entry | RTGFCCSAGCQVRVLT RPEGTIGMV (SEQ ID NO:553) | | |
| dgen-0116 | RCC1 | 011002-OVcDNATet-20F-PP-DC-D1 | Proteome Panning | D00591 | BAA00469.1 | No Entry | YAVGVQPAIRVGVNL DVHMS (SEQ ID NO:554) | No significant hits | |
| dgen-0117 | DGI-5 | DGI5-20M-4-D2 | Biopanning | NM_024320.1 | NP_077296.1 | 79170 | MTVHRLIFTGDKGRA YYSVP (SEQ ID NO:288) | | |
| dgen-0118 | DGI-7 | DGI7-20M-4-G2₂ | Biopanning | X76717 | CAA54136.1 | 4500 | GWRLFLTGVLGGSKN GHASL (SEQ ID NO:327) | | |
| dgen-0119 | VEGF | VEGF-20F-4-F8₄₂ | Biopanning | NM_003376 | NP_003367.2 | 7422 | WGKTAGECGTLLWQ MGRAWF (SEQ ID NO:347) | | |
| dgen-0120 | VEGF-R1/FLT1 | VEGFR1-20F-4-E12₄₆ | Biopanning | NM_002019 | NP_002010 | 2321 | LGFGSGAHPTTREDWI ELFR (SEQ ID NO:372) | | |

FIG. 8G

| DGI # | DGI Alias / Target ID | Clone Name | METHOD | Target DNA Acc. No. | Target Protein Acc. No. | Target Locus | HSPL Seq | Phenogenix Partner ID | Phenogenix Partner Protein Acc. No. |
|---|---|---|---|---|---|---|---|---|---|
| dgen-0121 | VEGF-R2 / FLK1 / KDR | VEGFR2-20F-3-B1 | Biopanning | AF035121 | AAB88005.1 | 3791 | FLFPLHFLSPWSVGT SHSRI (SEQ ID NO:407) | | |
| dgen-0122 | VEGF-R3 | VEGFR3-20F-3-G1$_{12}$ | Biopanning | NM_002020 | NP_002011 | 2324 | FMSPYSLMLRHGL MGERQRG (SEQ ID NO:427) | | |
| dgen-0123 | EGFR | EGFR-20M-4-E12$_6$ | Biopanning | NM_005228 | NP_005219 | 1956 | AVSRLLGDTQRLIG YLQEPL (SEQ ID NO:435) | | |
| dgen-0124 | FGFR1-alpha | | | | | | | | |
| dgen-0125 | FGFR1-beta | | | | | | | | |
| dgen-0126 | Tie-1 | Tie1BP2-20F-C11$_6$ | Biopanning | NM_005424 | NP_005415.1 | 7075 | RRVDAGGAVVYLD RWGNVSV (SEQ ID NO:473) | | |
| dgen-0127 | Caspase-3 | Caspase3-20C-3-A3$_4$ | Biopanning | NM_004346 | NP_004337 | 836 | LRQWCRWVMGASR RMPFICAGWDGP (SEQ ID NO:555) | | |
| dgen-0128 | PARP | PARP-20F-4-G11$_2$ | Biopanning | NM_001618 | NP_001609 | 142 | LSRPVIPWTSGEIGR ATRQD (SEQ ID NO:556) | | |

FIG. 9A

| Clone # | Sequence | Etag | DGI5 | IGFR | DGI5/IGFR | SEQ ID NO: |
|---|---|---|---|---|---|---|
| DGI5-20M-4-E1 | MGHMPYRIMRDGSFDVRHEG | 20.8 | 4.4 | 1.1 | 3.9 | 285 |
| DGI5-20M-4-A5 | HTGRLFNSFFGWPSFFRSWE | 14.0 | 3.9 | 1.5 | 2.7 | 286 |
| DGI5-20M-4-H3₁₁ | MTPMGGWRDPRLGSPVSHVG | 22.4 | 3.6 | 1.3 | 2.7 | 287 |
| DGI5-20M-4-D2 | MTVHRLIFTGDKGRAYYSVP | 25.9 | 3.2 | 0.9 | 3.5 | 288 |
| DGI5-20M-4-C6 | LTVPGIFQHRQAAFLRGSSG | 19.0 | 3.1 | 1.2 | 2.6 | 289 |
| DGI5-20M-4-A7 | MTWRGLPASQFRLDGRPAFV | 27.4 | 2.8 | 1.0 | 2.8 | 290 |
| DGI5-20M-4-H1 | GHFSRPPVLGSRDGGWVRAM | 26.1 | 2.8 | 1.2 | 2.4 | 291 |
| DGI5-20M-4-B12 | GRICSSWFAPIGCAFDVRGR | 33.4 | 2.7 | 0.8 | 3.3 | 292 |
| DGI5-20M-4-C7 | MTLHSPYFARVNPNGSSVSV | 26.0 | 2.7 | 1.0 | 2.6 | 293 |
| DGI5-20M-4-G2 | MTMTPQALFRPAWERGSYMG | 27.7 | 2.6 | 1.0 | 2.7 | 294 |
| DGI5-20M-4-F2 | LTRLPPDRHYSFGERSRVPT | 27.6 | 2.6 | 1.1 | 2.4 | 295 |
| DGI5-20M-4-A8 | MATVNGHYPAPLIRRAPSTT | 22.7 | 2.5 | 0.9 | 2.9 | 296 |
| DGI5-20M-4-C4 | LSRYPVLSTSHLPRNRDIPG | 31.6 | 2.5 | 1.0 | 2.5 | 297 |
| DGI5-20M-4-D1 | LTHRAVLEYPGISSGGAFHQ | 16.5 | 2.5 | 1.0 | 2.5 | 298 |
| DGI5-20M-4-E3 | MTRYGGPFSGVFPLTPRGTG | 23.6 | 2.4 | 0.9 | 2.7 | 299 |
| DGI5-20M-4-G3 | MILGPRGMVTHSQHERGSNH | 26.7 | 2.3 | 0.9 | 2.6 | 300 |
| DGI5-20M-4-G4₃ | MTALNYRGGSWGLNGGQGRL | 17.5 | 2.3 | 1.1 | 2.1 | 301 |
| DGI5-20M-4-E4 | MGRLPPMGLVGERGGLRPFI | 25.1 | 2.2 | 0.9 | 2.5 | 302 |
| DGI5-20M-4-D6 | FVRVPLLHVEGRGGPLRHID | 30.2 | 2.2 | 0.9 | 2.4 | 303 |
| DGI5-20M-4-C2 | MTVGPWRDRVASSAPDGLWF | 27.4 | 2.1 | 0.9 | 2.4 | 304 |
| DGI5-20M-4-G6 | LSRMPDRKVVDPRSYRLGWT | 27.8 | 2.1 | 1.1 | 1.9 | 305 |
| DGI5-20M-4-A2 | MTPQFLIPSPSHSARVGTRG | 19.2 | 2.0 | 0.9 | 2.2 | 306 |
| DGI5-20M-4-F12 | MFDIFSWMHPWSLWPGSASG | 10.3 | 1.9 | 0.7 | 2.7 | 307 |
| DGI5-20M-4-C11₂ | FSSRMALPLTSYRSLPSAGG | 29.6 | 1.9 | 1.0 | 2.0 | 308 |
| DGI5-20M-4-B2 | MAPRLPDTHVHRTGGRSAMT | 32.3 | 1.9 | 0.9 | 2.0 | 309 |
| DGI5-20M-4-B1 | MSSFVGNMSPPWTQIREGSS | 14.5 | 1.9 | 0.9 | 2.0 | 310 |
| DGI5-20M-4-D4 | MTGFIRNDGTMARGVPNGRI | 31.3 | 1.9 | 0.9 | 2.0 | 311 |
| DGI5-20M-4-G1 | MQVGRWGTDRHVENGRMDGF | 1.8 | 1.8 | 1.1 | 1.9 | 312 |
| DGI5-20M-4-A3 | FTTSRLGPQCVARIVLSLLAM | 32.3 | 1.8 | 0.8 | 2.2 | 313 |
| DGI5-20M-4-F3 | MALIPRAYQPDGVGGVDSYD | 21.8 | 1.8 | 0.8 | 2.2 | 314 |
| DGI5-20M-4-A9 | MGGRWWHAADGDVMGVPKGV | 22.6 | 1.8 | 0.8 | 2.2 | 315 |
| DGI5-20M-4-E6 | FPFRSMWQHFWGPAGVPYIE | 21.1 | 1.8 | 1.0 | 1.9 | 316 |
| DGI5-20M-4-B9 | VTPFPRIASGSWPGVVRDWD | 36.8 | 1.8 | 1.0 | 1.8 | 317 |

FIG. 9B

| | | | | | |
|---|---|---|---|---|---|
| DGI5-20M-4-F5 | FSRVPSPFHCIGQACTPSRV | 17.0 | 1.8 | 1.2 | 1.5 |
| DGI5-20M-4-E7 | MGPRMVGEDFNTDRGRFRYP | 22.8 | 1.7 | 0.8 | 2.1 |
| DGI5-20M-4-E8 | HGLEAIAMTRVPWEMGYPDS | 32.1 | 1.7 | 0.9 | 1.9 |
| DGI5-20M-4-G10 | MGVHRGLIPRLD.RSWEEQI | 18.0 | 1.7 | 1.1 | 1.6 |
| DGI5-20M-4-E12 | LSIPGLMVDRWLSGPASDRR | 17.8 | 1.6 | 0.8 | 1.9 |
| DGI5-20M-4-A6 | MSMFQQRGYWSNQEGRWSGS | 11.8 | 1.6 | 0.9 | 1.8 |
| DGI5-20M-4-F6 | LTTWLPTWYVRGSAATQGEF | 22.9 | 1.6 | 0.9 | 1.7 |
| DGI5-20M-4-H7 | PTARNLADPRMPAWGSRVTV | 4.0 | 1.5 | 0.7 | 2.1 |
| DGI5-20M-4-D12 | MGRAPHWSDPVPGLWLSPGE | 17.4 | 1.5 | 0.9 | 1.6 |

FIG. 10

| Clone # | Sequence | E-Tag | DGI7 | LDH | DGI7/LDH | SEQ ID NO: |
|---|---|---|---|---|---|---|
| DGI7-20M-4-G2$_2$ | GWRLFLTGVLGGSKNGHASL | 32.4 | 8.2 | 1.1 | 7.8 | 327 |
| DGI7-20M-4-G11$_8$ | LRPVCLQEQRVSFFGDWVRVALFSA | 17.1 | 7.9 | 1.0 | 7.7 | 328 |
| DGI7-20M-4-B4$_2$ | LWRGMAEWVVRRPIGASSTG | 30.4 | 6.7 | 1.4 | 5.0 | 329 |
| DGI7-20M-4-F6 | RGAGLMQWFGWYGTRFGGSR | 19.9 | 5.4 | 1.8 | 3.1 | 330 |
| DGI7-20M-4-F11 | TLMRWGLLGRGALSVWGDGD | 39.7 | 5.0 | 2.3 | 2.2 | 331 |
| DGI7-20M-4-G9 | SLLLWALQLRGMAGALTSGS | 28.5 | 4.8 | 0.9 | 5.2 | 332 |
| DGI7-20M-4-D3$_2$ | AVRSWRLFLAGALGSRGGLG | 26.5 | 4.4 | 1.0 | 4.5 | 333 |
| DGI7-20M-4-E2 | GTMTSTLVSETSFFGRSRTMWQLIVRGVQ | 26.3 | 4.4 | 1.1 | 4.1 | 334 |
| DGI7-20M-4-G6 | LLRYGWERWVVARQGQVGNGAP | 23.9 | 3.7 | 0.7 | 5.2 | 335 |
| DGI7-20M-4-G10 | RQGVEMLARWLFPWYRSSPE | 29.2 | 3.5 | 0.9 | 3.8 | 336 |
| DGI7-20M-4-H9 | DLPGWGGLFRTWATLRNGGS | 35.8 | 3.5 | 1.0 | 3.4 | 337 |
| DGI7-20M-4-D1$_2$ | AVLGWGWSWDQWVSGDLQAS | 39.6 | 3.2 | 1.3 | 2.5 | 338 |
| DGI7-20M-4-B3 | WLRVLAERRWGGSGSQGGPG | 25.6 | 2.9 | 1.1 | 2.7 | 339 |
| DGI7-20M-4-E3 | FIRGWWSFPLTGRAVPEFD | 31.6 | 2.8 | 0.9 | 3.2 | 340 |
| DGI7-20M-4-H2 | LGTDWHILGSSIWRLIRGTD | 23.5 | 2.5 | 1.0 | 2.5 | 341 |
| DGI7-20M-4-H5 | RRCLGSWLVGLGAIGCGDKG | 25.5 | 2.3 | 1.1 | 2.1 | 342 |
| DGI7-20M-4-G1$_2$ | IRTAEVRPEMISWRQFPSLW | 14.5 | 2.3 | 1.3 | 1.7 | 343 |
| DGI7-20M-4-B12 | LYRSWAQALIERAWGVASS | 22.6 | 2.2 | 1.1 | 2.0 | 344 |
| DGI7-20M-4-C5 | REWAAGWASFLGRL | 26.5 | 2.1 | 0.9 | 2.4 | 345 |
| DGI7-20M-4-A2 | VFRGATTWGRAWNSVLGRGQ | 36.2 | 1.9 | 1.2 | 1.6 | 346 |

FIG. 11

| Clone | Sequence | Etag | VEGF | BSA | VEGF/BSA | SEQ ID NO: |
|---|---|---|---|---|---|---|
| VEGF-20F-4-F8$_{42}$ | WGKTAGECGTLLWQMGRAWF | 31.4 | 9.8 | 1.1 | 9.1 | 347 |
| VEGF-20F-4-E11$_5$ | SDFGDGGMSLLWRLARLWGN | 34.5 | 4.8 | 1.0 | 4.7 | 348 |
| VEGF-20F-4-F2$_2$ | LSPWRMVWPAERR | 36.6 | 4.0 | 1.2 | 3.2 | 349 |
| VEGF-20F-3-C7 | GVFSHQARALVGGNTTPNSR | 26.9 | 3.6 | 1.5 | 2.5 | 350 |
| VEGF-20F-3-C5 | FFPMLSVAFPGRVHYAASSVS | 17.1 | 3.4 | 1.2 | 2.8 | 351 |
| VEGF-20F-4-F6 | WGKTDGECGTLLWQMGRAWF | 20.5 | 3.3 | 1.0 | 3.2 | 352 |
| VEGF-20F-3-D1 | MAMMNFHGGDRATTMVRGLS | 27.0 | 3.0 | 1.1 | 2.7 | 353 |
| VEGF-20F-4-H2 | MSMLLPGHNPPYAAAHLRHV | 38.8 | 2.8 | 1.2 | 2.3 | 354 |
| VEGF-20F-3-B11$_2$ | LQIPSRFISRYTAGGNSTSS | 34.2 | 2.6 | 1.3 | 2.0 | 355 |
| VEGF-20F-4-G4 | MTFMGSRWVSGGNPHWRNIR | 33.4 | 2.5 | 1.1 | 2.3 | 356 |
| VEGF-20F-3-D3$_2$ | MSSHFYRSPGIGMYSGARVS | 32.4 | 2.4 | 1.3 | 1.9 | 357 |
| VEGF-20F-3-A2$_5$ | MTMHAPGLFRAPQPGAGGNR | 15.5 | 2.4 | 1.3 | 1.8 | 358 |
| VEGF-20F-3-D9$_3$ | MSRHPRGWEVLDGVPSGNSR | 32.6 | 2.3 | 1.1 | 2.0 | 359 |
| VEGF-20F-3-B7 | LMVPGVLRHIPRQGPFIAPL | 27.2 | 2.1 | 1.1 | 1.8 | 360 |
| VEGF-20F-3-D6 | MSPFVKLGRNVPTGERAVGK | 20.2 | 1.7 | 1.0 | 1.7 | 361 |
| VEGF-20F-3-B9 | MTSRLNLGRHASDGVQAGVP | 22.0 | 1.7 | 1.0 | 1.7 | 362 |
| VEGF-20F-3-D7 | LSSRLGLLHAWGIGAPLRPR | 27.4 | 1.6 | 1.1 | 1.5 | 363 |
| VEGF-20F-4-E3 | LTLFSSHRAAVGPPSGTRGL | 8.5 | 1.6 | 1.1 | 1.4 | 364 |
| VEGF-20F-3-B3 | LARPFVCGPYLFGRWGKCPV | 11.9 | 1.6 | 1.2 | 1.3 | 365 |
| VEGF-20F-3-C1 | LSVVPRSELVGSRGSSSAPT | 22.1 | 1.6 | 1.2 | 1.3 | 366 |
| VEGF-20F-3-A5$_3$ | MGNRGVMSSFHSSMQEGGGH | 22.6 | 1.5 | 1.0 | 1.5 | 367 |
| VEGF-20F-3-D10 | MITAGPRRHISNLVHSAGWD | 23.1 | 1.5 | 1.0 | 1.5 | 368 |
| VEGF-20F-3-A1 | GVFSHQARALLGGNTTPNSR | 31.0 | 1.5 | 1.1 | 1.4 | 369 |
| VEGF-20F-3-B4 | GTFAWPFTVSSRRSSVTGDA | 10.3 | 1.5 | 1.2 | 1.3 | 370 |
| VEGF-20F-3-B12 | GASRLLGPASRDTGGVVGG | 35.2 | 1.5 | 1.2 | 1.2 | 371 |

FIG. 12A

| Clone | SEQUENCE | ETAG | VEGFR1 | BSA | R1/BSA | SEQ ID NO: |
|---|---|---|---|---|---|---|
| VEGFR1-20F-4-E12₄₆ | LGFGSGAHPTREDWIELFR | 62.9 | 53.3 | 1.5 | 34.5 | 372 |
| VEGFR1-20F-3-B1 | LTSRIHVDPRVRWHLAREGS | 60.7 | 51.7 | 1.2 | 42.1 | 373 |
| VEGFR1-20F-3-C1 | LTPSYLLSWRVGGHRHVDEH | 53.3 | 48.3 | 1.2 | 41.6 | 374 |
| VEGFR1-20F-4-E1₂ | FLFPLHFLSPWSVGTSHSRI | 51.0 | 47.5 | 1.2 | 40.1 | 375 |
| VEGFR1-20F-4-G1₂ | MFLPGLLPWRARPVSHGYGY | 56.9 | 46.5 | 1.3 | 35.9 | 376 |
| VEGFR1-20F-3-A5₂ | GARFPLSLARPAPDPNVAPL | 52.2 | 45.9 | 1.8 | 25.5 | 377 |
| VEGFR1-20F-3-C3₃ | MTLPSSVLRPVRGPALSTSG | 55.6 | 45.8 | 1.3 | 35.3 | 378 |
| VEGFR1-20F-3-D7 | MTGNLPERRAAQLQHAHREV | 54.7 | 45.8 | 1.2 | 37.2 | 379 |
| VEGFR1-20F-4-E2₂ | FWRPSFMHGFMHGHFPAVTGS | 54.2 | 45.0 | 1.2 | 36.2 | 380 |
| VEGFR1-20F-3-A2 | MFPLYHLVKRSRTRDGAVLG | 49.1 | 44.8 | 1.3 | 35.1 | 381 |
| VEGFR1-20F-3-D2 | LARPLAMVGFVRDAWLGRGS | 50.8 | 43.3 | 1.1 | 37.7 | 382 |
| VEGFR1-20F-4-H2 | FYPFLWSRQFQGTMAHRGMG | 51.2 | 40.8 | 0.9 | 43.2 | 383 |
| VEGFR1-20F-4-H3 | MGRRPWIPYQVRLDMGSQRH | 51.0 | 40.4 | 1.0 | 39.6 | 384 |
| VEGFR1-20F-3-D5₂ | FEVLSADARGVLGWMLMLRG | 51.3 | 40.2 | 1.2 | 33.7 | 385 |
| VEGFR1-20F-4-F1 | WGGGWMDWFFWGRTTGRLRP | 47.9 | 39.5 | 1.2 | 34.1 | 386 |
| VEGFR1-20F-3-A4₃ | FASPAMYMGRTSPWGRAYDG | 52.0 | 39.4 | 1.6 | 24.3 | 387 |
| VEGFR1-20F-4-G3₂ | MGRHPGLSRVGDGARMEPST | 46.8 | 38.9 | 1.1 | 35.7 | 388 |
| VEGFR1-20F-4-H4 | MSPLGLVASHPRIYLPRISK | 53.3 | 37.9 | 1.3 | 29.8 | 389 |
| VEGFR1-20F-4-G4 | FMSPYSLMLRHGLMGERQRG | 49.6 | 37.5 | 1.2 | 30.3 | 390 |
| VEGFR1-20F-3-A7 | LTRVPGFPAPYSGISRSQLS | 43.8 | 36.9 | 1.4 | 25.6 | 391 |
| VEGFR1-20F-3-D4 | LTPRFVVDSNRGPLARSSGE | 47.7 | 36.9 | 1.1 | 33.9 | 392 |
| VEGFR1-20F-4-H1 | MTRVLPGRGNLYPMQTVGKI | 45.7 | 35.0 | 1.0 | 35.0 | 393 |
| VEGFR1-20F-4-F3 | MVRNGGVTRLLQGHAQRNPV | 41.6 | 19.4 | 1.2 | 16.5 | 394 |
| VEGFR1-20F-3-C4 | MGPMLGSVVRPGQSRDGGSW | 41.7 | 16.7 | 1.2 | 13.6 | 395 |
| VEGFR1-20F-4-H10 | EGIGWEAVLGRVARFCNQDG | 39.4 | 14.3 | 1.0 | 14.1 | 396 |
| VEGFR1-20F-3-B7 | MMLMRGRDGAQMGWPSTRLR | 20.1 | 4.4 | 1.0 | 4.4 | 397 |
| VEGFR1-20F-3-D9 | LSMHPAYRLYPDAGRPGRSD | 41.3 | 2.7 | 1.2 | 2.2 | 398 |
| VEGFR1-20F-3-C5₂ | FNFPGLWASWDLKRPRVRLN | 15.5 | 2.7 | 1.3 | 2.0 | 399 |
| VEGFR1-20F-3-D11 | GLWRSQVFNTSWGARSGHGM | 30.0 | 2.0 | 1.1 | 1.8 | 400 |
| VEGFR1-20F-3-B6 | YPSGGAQGVWNWLWRMMTWG | 42.5 | 1.9 | 1.2 | 1.6 | 401 |
| VEGFR1-20F-3-B9 | MGHVIVRPQNSRALGPGGWH | 16.6 | 1.9 | 1.1 | 1.7 | 402 |
| VEGFR1-20F-3-C9 | LGRMPYPGGLSNHVERVSRG | 45.5 | 1.9 | 1.1 | 1.7 | 403 |

FIG. 12B

| Clone | SEQUENCE | ETAG | VEGFR1 | BSA | R1/BSA | SEQ ID NO: |
|---|---|---|---|---|---|---|
| VEGFR1-20F-3-B8₂ | MTGWQRFDANRPVGRSQGEK | 44.0 | 1.8 | 1.2 | 1.5 | 404 |
| VEGFR1-20F-3-D3 | MGAVPSRMRMLMQPTLVPRG | 27.3 | 1.6 | 0.8 | 2.0 | 405 |
| VEGFR1-20F-3-A1 | LTPRLGLSPWPGVTGRTRPV | 41.8 | 1.5 | 1.0 | 1.5 | 406 |

FIG. 13

| CLONE# | Sequence | Etag | VEGFR2 | BSA | R2/BSA | SEQ ID NO: |
|---|---|---|---|---|---|---|
| VEGFR2-20F-B1 | FLFPLHFLSPWSVGTSHSRI | 38.7 | 3.0 | 1.2 | 2.5 | 407 |
| VEGFR2-20F-G2 | MVRNGGVTRLLQGHAQRNPV | 33.7 | 3.3 | 1.4 | 2.4 | 408 |
| VEGFR2-20F-D3₂ | MFLPGLLPWRARPVSHGYGY | 16.4 | 2.8 | 1.2 | 2.3 | 409 |
| VEGFR2-20F-E1 | FYPFLWSRQFQGTMAHRGMG | 22.9 | 2.5 | 1.1 | 2.3 | 410 |
| VEGFR2-20F-H1 | MGPMLGSVVRPGQSRDGGSW | 34.1 | 2.4 | 1.0 | 2.3 | 411 |
| VEGFR2-20F-B7 | WGGGWMDWFFWGRTTGRLRP | 21.3 | 2.3 | 1.0 | 2.3 | 412 |
| VEGFR2-20F-F9 | MGAVPSRMRMLMQPTLVPRG | 29.4 | 3.1 | 1.5 | 2.1 | 413 |
| VEGFR2-20F-D2₂ | FWRPSFMHGFMGHFPAVTGS | 35.6 | 3.0 | 1.4 | 2.1 | 414 |
| VEGFR2-20F-A7 | LTPRLGLSPWPGVTGRTRPV | 35.8 | 2.5 | 1.2 | 2.1 | 415 |
| VEGFR2-20F-H12₃ | MTLPSSVLRPVRGPALSTSG | 29.3 | 2.7 | 1.3 | 2.0 | 416 |
| VEGFR2-20F-H4₂ | MFPLYHLVKRSRTRDGAVLG | 11.5 | 2.4 | 1.2 | 2.0 | 417 |
| VEGFR2-20F-C2 | LTPRFVVDSNRGPLARSSGE | 35.6 | 2.3 | 1.1 | 2.0 | 418 |
| VEGFR2-20F-H2 | LARPLAMVGFVRDAWLGRGS | 37.0 | 2.2 | 1.1 | 2.0 | 419 |
| VEGFR2-20F-C6 | FASPAMYMGRTSPWGRAYDG | 38.6 | 2.5 | 1.3 | 1.9 | 420 |
| VEGFR2-20F-E12₃ | MGRHPGLSRVGDGARMEPST | 31.7 | 2.3 | 1.2 | 1.9 | 421 |
| VEGFR2-20F-H4₂ | LTSRIHVDPRVRWHLAREGS | 26.5 | 4.3 | 2.3 | 1.8 | 422 |
| VEGFR2-20F-A11₂ | MTRYPSGLYQRHPAGRGQLE | 28.1 | 2.4 | 1.4 | 1.7 | 423 |
| VEGFR2-20F-C3 | MTRVLPGRGNLYPMQTVGKI | 27.3 | 2.3 | 1.3 | 1.7 | 424 |
| VEGFR2-20F-B12 | LTPSYLLSWRVGGHRHVDEH | 16.8 | 2.1 | 1.3 | 1.7 | 425 |
| VEGFR2-20F-A12 | MGRRPWIPYQVRLDMGSQRH | 14.5 | 2.1 | 1.3 | 1.6 | 426 |
| VEGFR2-20F-G6 | | | | | | |

FIG. 14

| CLONE# | Sequence | Etag | VEGFR3 | BSA | R3/BSA | SEQ ID NO: |
|---|---|---|---|---|---|---|
| VEGFR3-20F-G1$_{12}$ | FMSPYSLMLRHGLMGERQRG | 23.3 | 2.9 | 1.3 | 2.3 | 427 |
| VEGFR3-20F-E8 | MTVWRWGSRPWGISGGFPSL | 14.6 | 2.4 | 1.1 | 2.3 | 428 |
| VEGFR3-20F-D4 | MSPLGLVASHPRIYLPRISK | 25.7 | 2.2 | 1.1 | 2.1 | 429 |
| VEGFR3-20F-F5 | LTSVASSLIRWPRPPVLEGI | 26.8 | 2.1 | 1.0 | 2.0 | 430 |
| VEGFR3-20F-E10 | MSGLRWRDVWAERLGMGFH | 27.7 | 2.1 | 1.1 | 2.0 | 431 |
| VEGFR3-20F-H11 | MAPRLVARFDSKAALSNTAG | 30.9 | 2.1 | 1.3 | 1.7 | 432 |
| VEGFR3-20F-H7 | MMPLGFAHRIGRSAGVGSSP | 22.3 | 2.1 | 1.2 | 1.7 | 433 |

FIG. 15

| Clone # | Lib | Sequence | E-Tag | EGFR | LDH | EGFR/LDH | SEQ ID NO: |
|---|---|---|---|---|---|---|---|
| EGFR-20Mα-4-G10$_7$ | 20R | RWWVGRRCPSGLCNVGFSGG | 24.3 | 16.4 | 1.1 | 14.6 | 434 |
| EGFR-20Mβ-4-E12$_6$ | 20R | AVSRLLGDTQRLIGYLQEPL | 11.9 | 14.9 | 1.2 | 12.3 | 435 |
| EGFR-20Mβ-4-C8$_{83}$ | 20R | GYPVCSLSGGRVECRQARGG | 15.8 | 13.6 | 1.3 | 10.5 | 436 |
| EGFR-20Mβ-4-F4 | 20R | GSFRSLGFGDEFFQRYGVGG | 12.0 | 10.8 | 1.2 | 9.0 | 437 |
| EGFR-20Mα-4-F7$_{24}$ | 20C | LRRICQALLPTLAGKAWCDAWGRGT | 24.0 | 4.7 | 1.1 | 4.3 | 438 |
| EGFR-40Mα-4-C1$_{2-fs}$ | 40R | SSASAAGERWGYPGSCSDGG | 1.1 | 1.5 | 1.0 | 1.6 | 439 |

FIG. 16A

| Clone # | Sequence | E-Tag | FGFR1 | BSA | FGFR1/BSA | SEQ ID NO: |
|---|---|---|---|---|---|---|
| FGFR1α-20R-A11₂ | QVCVRGELFGGPAPFWYCAG | 12.6 | 15.0 | 1.2 | 12.3 | 440 |
| FGFR1α-20F-C4₂ | HISGTVCRFDPGLPGGLIGC | 1.5 | 15.3 | 1.6 | 9.9 | 441 |
| FGFR1β-20F-B11₂ | GSEYVCRGS-SWGDFGAWVC | 21.8 | 12.7 | 1.4 | 9.2 | 442 |
| FGFR1β-20C-D10 | YPPMCLDPMYGVVFCGPGEGLGNHA | 20.5 | 11.4 | 1.3 | 9.1 | 443 |
| FGFR1α-20C-E2 | YYRLCFHGGMWKPYEPGHQGWCARV | 11.8 | 13.0 | 1.5 | 8.9 | 444 |
| FGFR1β-20C-D9 | GTRACWRVWDSDRMSSVVRCGVSVF | 17.3 | 11.4 | 1.3 | 8.9 | 445 |
| FGFR1β-20F-C4 | CQVLLSFGVADGVWLFDKEC | 16.9 | 10.8 | 1.3 | 8.2 | 446 |
| FGFR1β-20C-A10 | RSSYCFWAVIRGGGWGRQCFGVDS | 17.6 | 14.8 | 1.8 | 8.0 | 447 |
| FGFR1α-20C-B2 | DKRDCLERVGGIAWVRTECQGGWR | 15.5 | 13.3 | 1.7 | 8.0 | 448 |
| FGFR1β-20C-H8₂ | GGHPCRVPFHFVGNRPSWLVGSCAT | 9.4 | 11.1 | 1.4 | 7.8 | 449 |
| FGFR1β-20C-B7 | RRMTRFAPNCADLLLPGAPFTLMPSPGCVG | 27.9 | 10.7 | 1.4 | 7.6 | 450 |
| FGFR1β-20R-B7 | WLQLCSLYGLFPFCDRPLGQGQVAG | 17.2 | 10.3 | 1.4 | 7.6 | 451 |
| FGFR1β-20C-F8₃ | RPTLCAPFVDSVGTRLCFDRWGDLG | 16.6 | 11.9 | 1.6 | 7.2 | 452 |
| FGFR1β-20C-D2 | WLRWCATRWLRGEGDGCGFLEPRAG | 17.3 | 12.2 | 1.7 | 7.1 | 453 |
| FGFR1β-20C-C10 | GRLRCRAGFWAVMGLGRVERIGGTC | 19.8 | 11.8 | 1.7 | 7.0 | 454 |
| FGFR1β-20C-D8₂ | QVWLCDGVMGGCVRKDLRSLLYFPR | 18.1 | 14.7 | 2.1 | 6.9 | 455 |
| FGFR1β-20C-F2 | RSYRCNRLTVYGWKAPFCVSGSGSL | 20.6 | 12.8 | 2.3 | 5.6 | 456 |
| FGFR1β-20C-F3₃ | SARSCIHGATVARWQTMFGAIIHGC | 23.6 | 11.7 | 2.1 | 5.6 | 457 |
| FGFR1β-20C-B4₂ | LYRACNSRFPSSIAYCSLFGYRSSK | 14.0 | 9.2 | 1.6 | 5.6 | 458 |
| FGFR1β-20C-B6 | STFRTCRTVSRITSGEHAAPFVACTQ | 18.3 | 10.9 | 2.0 | 5.5 | 459 |
| FGFR1β-20C-E8 | RAWICGLGVFDAHTGSSGFIPCSRGG | 16.8 | 22.5 | 4.4 | 5.1 | 460 |
| FGFR1β-20C-F1 | GVWFCAPLLVNGSRTGFASCDRGGR | 15.8 | 11.9 | 2.6 | 4.5 | 461 |
| FGFR1β-20C-C7 | SSRVCGMISHEGDLAMGQLYNRRPV | 20.8 | 14.2 | 3.2 | 4.4 | 462 |
| FGFR1β-20C-G6 | YLCARGERFWGASRFCYWSG | 16.5 | 14.6 | 3.6 | 4.0 | 463 |
| FGFR1α-20R-A10 | GLIDCLYQGVYYWCVTGAGIFPSRD | 14.7 | 11.8 | 3.2 | 3.7 | 464 |
| FGFR1β-20C-G7 | FVAAVACFKLHPTWGVVSCD | 13.7 | 16.1 | 4.4 | 3.6 | 465 |
| FGFR1β-20F-B9 | IWLFCAHCPTALISVPSAFGSLDLG | 19.2 | 9.5 | 2.7 | 3.5 | 466 |
| FGFR1β-20C-E11 | RGCVLEALSGGACLFDYWSG | 17.9 | 12.1 | 3.5 | 3.4 | 467 |
| FGFR1β-20R-B1 | IWFEPGMICRFSRGEGLQSC | 16.5 | 13.5 | 4.1 | 3.3 | 468 |

FIG. 16B

| Clone # | Sequence | E-Tag | FGFR1 | BSA | FGFR1/BSA | SEQ ID NO: |
|---|---|---|---|---|---|---|
| FGFR1β-20F-A1 | VRRGDVCEYNGNLFWAAECN | 19.6 | 7.0 | 2.7 | 2.6 | 469 |
| FGFR1β-20C-C1 | RQGFCANILHPTMGNRVACNVQDWF | 17.6 | 8.0 | 3.5 | 2.3 | 470 |
| FGFR1α-20C-A2 | FIHRCCMGVFTCINGGVADIGFSVS | 16.5 | 4.6 | 2.0 | 2.3 | 471 |
| FGFR1β-20R-G9 | TTMTRAPLFAVEESDAVPRVRGGPRRREA | 17.0 | 2.5 | 1.3 | 2.0 | 472 |

FIG. 17A

| Clone | Sequence | E-Tag | Tie-1 | BSA | Tie/BSA | SEQ ID NO: |
|---|---|---|---|---|---|---|
| Tie1-20F-3-H7$_{19}$ | RRVDAGGAVVYLDRWGNVSV | 25.3 | 32.4 | 1.2 | 26.2 | 473 |
| Tie1-20C-3-B12$_{44}$ | RIDRCVLLDRWGNTVGRRCQKTRA | 28.7 | 25.4 | 1.0 | 24.5 | 474 |
| Tie1-20F-3-H11$_{36}$ | DDPRCWLQGGYYICRAPDRA | 13.7 | 24.1 | 1.2 | 20.0 | 475 |
| Tie1-20C-3-D11$_6$ | DELACGYWGELWGLCSYGRSIPANK | 29.1 | 23.8 | 1.1 | 22.0 | 476 |
| Tie1-20F-3-B12$_2$ | RVLSRECFMIFESIGRTVVC | 12.1 | 22.6 | 0.8 | 26.9 | 477 |
| Tie1-20F-3-A4 | VVFLDRWGNPQYLGVKASGG | 14.5 | 13.6 | 0.9 | 15.0 | 478 |
| Tie1-20C-3-A2$_3$ | GVFWCEPVRGRSWWGRNGCFTQEPG | 24.6 | 10.1 | 1.0 | 10.1 | 479 |
| Tie1-20F-4-H5$_6$ | GALRWCTFQEGFGVGRLGVC | 14.0 | 9.8 | 0.9 | 10.4 | 480 |
| Tie1-20C-4-E1$_2$ | SLWGCSGRAVLFLDSVGNPTGTVRC | 15.4 | 7.5 | 1.1 | 6.7 | 481 |
| Tie1-20C-4-E7 | RSSGCWLRQLVGYDEGRAWVWSCL | 18.9 | 7.4 | 1.1 | 7.0 | 482 |
| Tie1-20C-3-D3$_2$ | VQRLCVRGGLWSVCRGSISAESAAV | 23.5 | 7.2 | 1.1 | 6.3 | 483 |
| Tie1-20C-3-D12 | RTAPCSGLPWLLLHGQLRCARLVQE | 26.4 | 6.8 | 1.1 | 6.4 | 484 |
| Tie1-20C-3-D8$_4$ | VGRCWARVGRVWTWYGMSYPLCRQ | 19.8 | 5.7 | 1.1 | 5.0 | 485 |
| Tie1-20C-4-F1$_2$ | VRRWCDTQWLIPDMCRHVWNSWGGRM | 23.6 | 4.1 | 1.1 | 3.8 | 486 |
| Tie1-20C-3-A9 | GPIQCLVWSQSAPGVWGVGSGIGCV | 24.6 | 3.7 | 1.1 | 3.4 | 487 |
| Tie1-20F-3-D11 | LSRVPLLTRMQPDVVRAGDG | 16.5 | 3.0 | 1.4 | 2.1 | 488 |
| Tie1-20C-3-A6 | GREVCMARLNGFQPWGVSTRGARSQ | 17.2 | 3.0 | 1.8 | 1.7 | 489 |
| Tie1-20C-3-B5 | RGHWCTIGGSNNYSGRFWFTRWFCD | 22.3 | 2.7 | 1.0 | 2.7 | 490 |
| Tie1-20F-3-C12 | FSRSPPATSRVGAVLEG | 15.0 | 2.2 | 1.1 | 2.0 | 491 |
| Tie1-20F-3-A3 | GVFNLRPVFGSRYLQPQTSA | 11.1 | 2.2 | 1.3 | 1.7 | 492 |
| Tie1-20C-3-A7 | ARRWCDESEMGLRQLVLASPRALRG | 21.3 | 1.9 | 1.0 | 1.8 | 493 |
| Tie1-20F-3-D10 | MGSLGWVEAPSGVFPGDGGQ | 22.4 | 1.8 | 1.2 | 1.5 | 494 |

FIG. 17B

| Clone | Sequence | E-Tag | Tie-1 | BSA | Tie/BSA | SEQ ID NO: |
|---|---|---|---|---|---|---|
| Tie1-20F-3-D1 | FTRPYNGERGSVVLSAADQT | 23.0 | 1.8 | 1.1 | 1.5 | 495 |
| Tie1-20C-3-D10 | WTLLCSSTITTLPAQMLSMSAPPPR | 25.4 | 1.7 | 1.2 | 1.5 | 496 |
| Tie1-20F-3-D3 | FARWEPNFWQPTEAPSARGV | 22.9 | 1.6 | 1.1 | 1.5 | 497 |
| Tie1-20C-3-A4 | ARVACWSDRVPGQHRARRVWILGTQ | 33.3 | 1.6 | 1.5 | 1.1 | 498 |
| Tie1-20F-3-F7 | MTMNSVYQFHSADDKAIAPR | 20.0 | 1.5 | 1.1 | 1.4 | 499 |
| Tie1-20F-3-C4 | MGWATWEHGNVQGRGGLEHI | 25.1 | 1.5 | 1.1 | 1.4 | 500 |
| Tie1-20F-3-C6 | GMFGVYRTLERGALTGPGSS | 24.0 | 1.5 | 1.1 | 1.3 | 501 |
| Tie1-20F-3-C2 | FTRATSLPIGNVSGNPGRLS | 21.1 | 1.5 | 1.1 | 1.3 | 502 |
| Tie1-20C-3-B2 | RGARCTLALAHWSGGNQRIGDRLGG | 21.9 | 1.5 | 1.1 | 1.3 | 503 |
| Tie1-20C-3-D2 | AYLSCEYTAMFLGPVRRQEISQSRA | 23.1 | 1.5 | 1.2 | 1.3 | 504 |

SEQUENCE LISTING

<160> NUMBER OF SEQ ID NOS: 556

<210> SEQ ID NO 1
<211> LENGTH: 20
<212> TYPE: PRT
<213> ORGANISM: Escherichia coli

```
<220> FEATURE:
<221> NAME/KEY: MISC_FEATURE
<223> OTHER INFORMATION: DGI-2-20F-PP-C3

<400> SEQUENCE: 1

Leu Gly Arg Thr Phe Val Trp Gly Thr Cys Leu His Leu Ser Val Ser
1               5                   10                  15

Arg Phe Gly His
            20

<210> SEQ ID NO 2
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-C9

<400> SEQUENCE: 2

Tyr Ala Met Ser Ser Arg Glu Cys Gly Ile Arg Asn Ser Gly Leu Ile
1               5                   10                  15

Leu Ser Met Trp
            20

<210> SEQ ID NO 3
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-F10

<400> SEQUENCE: 3

Val Val His Thr Arg Ala Trp Gly Ser Trp Ala Tyr Gly Phe Val Leu
1               5                   10                  15

Arg Asn Arg Gly
            20

<210> SEQ ID NO 4
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-B3

<400> SEQUENCE: 4

Arg Gly Ser Leu Leu Leu Thr Leu Pro Arg Leu Ser Gly Ala Val Gly
1               5                   10                  15

Thr Ala Tyr Gly
            20

<210> SEQ ID NO 5
<211> LENGTH: 16
<212> TYPE: PRT
<213> ORGANISM: Escherichia coli
<220> FEATURE:
<221> NAME/KEY: MISC_FEATURE
<223> OTHER INFORMATION: DGI-2-20F-PP-D6

<400> SEQUENCE: 5

Gly Ile Thr Gly Leu Phe Cys Leu Cys Leu Arg Ser Ser Gln Ser Ile
1               5                   10                  15
```

```
<210> SEQ ID NO 6
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-A22

<400> SEQUENCE: 6

Val Cys Ser Gly Gly Lys Gly Thr Trp Leu Glu Ile Pro Asp Arg Val
 1               5                  10                  15

Arg Ser Ser Thr
            20

<210> SEQ ID NO 7
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-B2

<400> SEQUENCE: 7

Arg Ser Tyr Pro Arg Leu Cys Lys Gln Lys Gly Gly Val Ile Gly Arg
 1               5                  10                  15

Met Leu Pro Gly
            20

<210> SEQ ID NO 8
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-A6

<400> SEQUENCE: 8

Val Cys Gly Gln Arg Val Ala Arg Met Gln Leu Asn Lys Thr Ile Arg
 1               5                  10                  15

Lys Leu Asp Ser
            20

<210> SEQ ID NO 9
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-F1

<400> SEQUENCE: 9

Glu Arg Val Ser Lys Cys Val Gly Arg Gly Ser Gly Arg Ser Val Gly
 1               5                  10                  15

Gln Phe Gly Gly
            20

<210> SEQ ID NO 10
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-C4
```

-continued

```
<400> SEQUENCE: 10

Ser Ile Ile Leu Ala Gly Cys Val Trp Val Met Pro Cys Gly Gln Asn
1               5                   10                  15

Leu Gly Gly Val
            20

<210> SEQ ID NO 11
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-C7

<400> SEQUENCE: 11

Ser Ser Val Trp Ala Thr Trp Gly Ser Asp Leu Arg Thr Phe Gly Ser
1               5                   10                  15

Val Gly Phe Leu
            20

<210> SEQ ID NO 12
<211> LENGTH: 21
<212> TYPE: PRT
<213> ORGANISM: Escherichia coli
<220> FEATURE:
<221> NAME/KEY: MISC_FEATURE
<223> OTHER INFORMATION: DGI-2-20F-PP-E6

<400> SEQUENCE: 12

Glu Val Phe Val Ser Val Trp Val Phe Arg Phe Arg Val Met Pro Val
1               5                   10                  15

Thr Pro Gly Gly Thr
            20

<210> SEQ ID NO 13
<211> LENGTH: 21
<212> TYPE: PRT
<213> ORGANISM: Escherichia coli
<220> FEATURE:
<221> NAME/KEY: MISC_FEATURE
<223> OTHER INFORMATION: DGI-2-20F-PP-D9

<400> SEQUENCE: 13

Val Arg Ala Val Tyr Ser Arg Asp Ala Tyr Asn Glu Val Gly Arg Trp
1               5                   10                  15

Met Arg Val Gly Ile
            20

<210> SEQ ID NO 14
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-A3

<400> SEQUENCE: 14

Ser Leu Phe Glu Arg Ser Ala Arg Ser Arg Tyr His Gly Ser Pro Asp
1               5                   10                  15

Cys Asn Gly Ser
            20
```

```
<210> SEQ ID NO 15
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-C10

<400> SEQUENCE: 15

Asp Arg Ser Arg Ala Pro Leu Cys Ala Asp Lys Ser Gly Arg Trp Gln
1               5                   10                  15

Arg Tyr Arg Arg
            20

<210> SEQ ID NO 16
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-E5

<400> SEQUENCE: 16

Ser Ile Val Ser Ser Arg Ser Gly Trp Gln Arg Gly Trp Ile Ala Trp
1               5                   10                  15

Phe Ala Pro Val
            20

<210> SEQ ID NO 17
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-A4

<400> SEQUENCE: 17

Arg Val Ser Tyr Glu Met Leu Gly Arg Arg Arg Ser Met His Gly
1               5                   10                  15

Ser Ser Met Arg
            20

<210> SEQ ID NO 18
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-G6

<400> SEQUENCE: 18

Gly Ser Thr Arg Leu Arg Val Thr Val Arg Phe Cys Ser Glu Thr Gly
1               5                   10                  15

Thr Pro Gly Cys
            20

<210> SEQ ID NO 19
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-C2
```

```
<400> SEQUENCE: 19

Gly Leu Tyr Gln Arg Gly Leu Ala Pro Arg Cys Arg Gly Glu Arg Phe
1               5                   10                  15

Gly Val Arg Asn
            20

<210> SEQ ID NO 20
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-D5

<400> SEQUENCE: 20

Trp Val Val Ala Leu Arg Arg Ile Arg Leu Gly Leu Arg Arg Gly Val
1               5                   10                  15

Glu Cys Leu Leu
            20

<210> SEQ ID NO 21
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-A9

<400> SEQUENCE: 21

Thr Phe Thr Arg Asp Val Ala Gly Pro Ala Val Ser Phe Val Arg Leu
1               5                   10                  15

His Ser Trp Asn
            20

<210> SEQ ID NO 22
<211> LENGTH: 21
<212> TYPE: PRT
<213> ORGANISM: Escherichia coli
<220> FEATURE:
<221> NAME/KEY: MISC_FEATURE
<223> OTHER INFORMATION: DGI-2-20F-PP-A7

<400> SEQUENCE: 22

Gly Gly Asp Leu Gly Glu Gln Gly Val Gln Leu Cys Pro Asp Val Val
1               5                   10                  15

Arg Gly Gly Ser Leu
            20

<210> SEQ ID NO 23
<211> LENGTH: 21
<212> TYPE: PRT
<213> ORGANISM: Escherichia coli
<220> FEATURE:
<221> NAME/KEY: MISC_FEATURE
<223> OTHER INFORMATION: DGI-2-20F-PP-B11

<400> SEQUENCE: 23

Val Gly His Leu Leu Ser Arg Cys Ala His His Ser Pro Gly Met Gly
1               5                   10                  15

Ala Ser Pro Tyr Gly
            20
```

```
<210> SEQ ID NO 24
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-D4

<400> SEQUENCE: 24

Asp Arg His Arg Ala Phe Val Ala Glu Gly Leu Asp Gly Phe Arg His
1               5                   10                  15

Ser Thr Gly Val
            20

<210> SEQ ID NO 25
<211> LENGTH: 21
<212> TYPE: PRT
<213> ORGANISM: Escherichia coli
<220> FEATURE:
<221> NAME/KEY: MISC_FEATURE
<223> OTHER INFORMATION: DGI-2-20F-PP-F3

<400> SEQUENCE: 25

Glu Gly Gln Arg Val Val Phe Leu Phe Gly Ala Leu Val Ala Gly Leu
1               5                   10                  15

Cys Trp Arg Asp Arg
            20

<210> SEQ ID NO 26
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-C12

<400> SEQUENCE: 26

Pro Val Tyr Arg Val Ala Met Cys Arg Ile Ser Val Gly Cys Ser Ala
1               5                   10                  15

Gly Ala Trp Phe
            20

<210> SEQ ID NO 27
<211> LENGTH: 19
<212> TYPE: PRT
<213> ORGANISM: Escherichia coli
<220> FEATURE:
<221> NAME/KEY: MISC_FEATURE
<223> OTHER INFORMATION: DGI-2-20F-PP-E8
<220> FEATURE:
<221> NAME/KEY: MISC_FEATURE
<223> OTHER INFORMATION: Stop codon: TAA after residue 1

<400> SEQUENCE: 27

Ser Ala Arg Ser Leu Met Thr Gly Val Val Ala Val Cys Ile Val Trp
1               5                   10                  15

Arg Gly Pro

<210> SEQ ID NO 28
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-B6
```

```
<400> SEQUENCE: 28

Leu Phe Arg Phe Ser Gly Thr Gly Met Ala Ser Leu Pro Cys Val Gly
1               5                   10                  15

Trp His Leu Val
            20

<210> SEQ ID NO 29
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-A82

<400> SEQUENCE: 29

Cys Tyr Leu Ser Arg Leu Phe Arg Ser Gly Gln Gly Ile Gly Gln Phe
1               5                   10                  15

Gly His Val Glu
            20

<210> SEQ ID NO 30
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-G4
<220> FEATURE:
<221> NAME/KEY: MISC_FEATURE
<223> OTHER INFORMATION: Stop codon: TAA after residue 5

<400> SEQUENCE: 30

Val Leu Cys Leu Glu Ala Leu Gly Leu Ser Gly Leu Gly Trp Arg Val
1               5                   10                  15

Val Val Gly Pro
            20

<210> SEQ ID NO 31
<211> LENGTH: 18
<212> TYPE: PRT
<213> ORGANISM: Escherichia coli
<220> FEATURE:
<221> NAME/KEY: MISC_FEATURE
<223> OTHER INFORMATION: DGI-2-20F-PP-G10
<220> FEATURE:
<221> NAME/KEY: MISC_FEATURE
<223> OTHER INFORMATION: 2 Stop codons: 2 TAA after residue 16

<400> SEQUENCE: 31

Leu Gly Arg Ile Val Arg Pro Cys Val Val Arg Leu Cys Gly Gly Val
1               5                   10                  15

Gly Val

<210> SEQ ID NO 32
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-C11
```

```
<400> SEQUENCE: 32

Thr Pro Val Ala Ile Ser Ile Pro Ala Gly Val Cys Ser Thr Ser Val
1               5                   10                  15

Cys Gly Arg Asp
            20

<210> SEQ ID NO 33
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-F2

<400> SEQUENCE: 33

Val Thr Gly Thr Arg Phe Arg Gly Phe Ala Val Ala Cys Val Arg Met
1               5                   10                  15

Gly Thr Trp His
            20

<210> SEQ ID NO 34
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-B42

<400> SEQUENCE: 34

Ser Leu Leu Cys Val Val Cys Arg Pro Val Ser Gly Gly Arg Ala Leu
1               5                   10                  15

Gly Gly Val Pro
            20

<210> SEQ ID NO 35
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-A10

<400> SEQUENCE: 35

Arg Arg Phe Val Arg Cys Ser Val Pro Val Ala Leu Arg Ser Ala Val
1               5                   10                  15

Pro Val Ser Val
            20

<210> SEQ ID NO 36
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-G2

<400> SEQUENCE: 36

Val Ser Gly Val Pro Asp Gly Ser Met Arg Ala Ala Gln Leu Ala Ser
1               5                   10                  15

Gly Tyr Trp Cys
            20
```

```
<210> SEQ ID NO 37
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-G5

<400> SEQUENCE: 37

Gly Ala Ser Arg Val Val Asp Val Gly Trp Arg Phe Trp Gly Lys Leu
1               5                   10                  15

Trp Gln Arg Ser
            20

<210> SEQ ID NO 38
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-F5

<400> SEQUENCE: 38

Gly Gly Ser Leu Pro Val Lys Ser Gly Gln Leu Val Thr Cys Cys Thr
1               5                   10                  15

Ser Lys Gly Gly
            20

<210> SEQ ID NO 39
<211> LENGTH: 21
<212> TYPE: PRT
<213> ORGANISM: Escherichia coli
<220> FEATURE:
<221> NAME/KEY: MISC_FEATURE
<223> OTHER INFORMATION: DGI-2-20F-PP-D8

<400> SEQUENCE: 39

Val Val Gly Tyr Ala Gln Gly Asp Gly Leu Glu Gly Gly Leu Gly Ser
1               5                   10                  15

Ser Arg Asp Gly Ser
            20

<210> SEQ ID NO 40
<211> LENGTH: 21
<212> TYPE: PRT
<213> ORGANISM: Escherichia coli
<220> FEATURE:
<221> NAME/KEY: MISC_FEATURE
<223> OTHER INFORMATION: DGI-2-20F-PP-B12

<400> SEQUENCE: 40

Arg Gln Arg Ser Gly Gly Arg Trp Val Val Asp Arg Val Thr Arg Val
1               5                   10                  15

Ala Ser Thr Ser Pro
            20

<210> SEQ ID NO 41
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-H3
```

```
<400> SEQUENCE: 41

Asp Asp Ile Val Cys Leu Phe Gln Phe Cys Ile Met Phe Cys Trp Leu
1               5                   10                  15

Asp Met Gly Trp
            20

<210> SEQ ID NO 42
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-D2

<400> SEQUENCE: 42

Ser Val Thr Ile Ser Thr Ser Cys Arg Thr Gly Cys Pro Ala Gly Tyr
1               5                   10                  15

Leu Arg Arg Asp
            20

<210> SEQ ID NO 43
<211> LENGTH: 21
<212> TYPE: PRT
<213> ORGANISM: Escherichia coli
<220> FEATURE:
<221> NAME/KEY: MISC_FEATURE
<223> OTHER INFORMATION: DGI-2-20F-PP-D3

<400> SEQUENCE: 43

Val Gln Ser Gly Arg Asp Leu Gly Gly Leu Leu Arg Gly Gly Thr Gly
1               5                   10                  15

Thr Glu Ala Ser Pro
            20

<210> SEQ ID NO 44
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-C5

<400> SEQUENCE: 44

Ser Val Ser Gly Gly Gly Val Phe Gly Thr Gly Gly Arg Val Arg His
1               5                   10                  15

Gln Val Ser Gly
            20

<210> SEQ ID NO 45
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-F12

<400> SEQUENCE: 45

Val Gly Gln Ser Ser Gly Asp Ala Arg Pro Leu Ala Asn Leu Phe Val
1               5                   10                  15

Phe Pro Phe Val
            20
```

```
<210> SEQ ID NO 46
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-H4

<400> SEQUENCE: 46

Cys Cys Ala Trp Asn Gly Val Gly Val Gly Gly Leu Gly Trp Arg Val
1               5                   10                  15

Val Val Gly Pro
            20

<210> SEQ ID NO 47
<211> LENGTH: 19
<212> TYPE: PRT
<213> ORGANISM: Escherichia coli
<220> FEATURE:
<221> NAME/KEY: MISC_FEATURE
<223> OTHER INFORMATION: DGI-2-20F-PP-F7
<220> FEATURE:
<221> NAME/KEY: MISC_FEATURE
<223> OTHER INFORMATION: Stop codon: TGA after residue 4

<400> SEQUENCE: 47

Asp Ser Glu Ala Arg Val Trp Tyr Ser Gly Phe Leu Arg Arg Leu Gly
1               5                   10                  15

His Met Cys

<210> SEQ ID NO 48
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-E11

<400> SEQUENCE: 48

Ser Ala Phe Gly Cys Pro Leu Pro Arg Ala Leu Gly Gly Gly Gly Ala
1               5                   10                  15

Arg Phe Tyr Ala
            20

<210> SEQ ID NO 49
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-D1

<400> SEQUENCE: 49

Arg Ile Ser Val Gly Gln Cys Gly Thr Ser Arg Cys Gly Gly Gly Arg
1               5                   10                  15

Arg Gly Gly Gly
            20

<210> SEQ ID NO 50
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-F8
```

```
<400> SEQUENCE: 50

Leu Leu Leu Pro Val Arg Trp Arg Asp Ala Gln Pro Arg Ser Leu Leu
1               5                   10                  15
Met Glu Trp Ile
            20

<210> SEQ ID NO 51
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-E10

<400> SEQUENCE: 51

Met Gly Ala Asp Thr Cys Met Gly Gly Lys Met Pro Phe Asp Gln Met
1               5                   10                  15
Phe Gly Ala Val
            20

<210> SEQ ID NO 52
<211> LENGTH: 17
<212> TYPE: PRT
<213> ORGANISM: Escherichia coli
<220> FEATURE:
<221> NAME/KEY: MISC_FEATURE
<223> OTHER INFORMATION: DGI-2-20F-PP-B9
<220> FEATURE:
<221> NAME/KEY: MISC_FEATURE
<223> OTHER INFORMATION: Stop codon: TAA after residue 16

<400> SEQUENCE: 52

Leu Gly Pro Ala His Pro His Gly Arg Val Cys Arg Val Ser Ser Ser
1               5                   10                  15
Ser

<210> SEQ ID NO 53
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-B10

<400> SEQUENCE: 53

Lys Val Trp Gly Cys Gly Ala Arg Arg Gly Trp Glu Arg Leu Gly His
1               5                   10                  15
Leu Asn Gln Val
            20

<210> SEQ ID NO 54
<211> LENGTH: 19
<212> TYPE: PRT
<213> ORGANISM: Escherichia coli
<220> FEATURE:
<221> NAME/KEY: MISC_FEATURE
<223> OTHER INFORMATION: DGI-2-20F-PP-H7

<400> SEQUENCE: 54

Phe Arg Val Ala Leu Leu Ser Val Ser Ala Gly Pro Cys Glu Gly Ser
1               5                   10                  15
Gly Asn Thr
```

```
<210> SEQ ID NO 55
<211> LENGTH: 21
<212> TYPE: PRT
<213> ORGANISM: Escherichia coli
<220> FEATURE:
<221> NAME/KEY: MISC_FEATURE
<223> OTHER INFORMATION: DGI-2-20F-PP-E1

<400> SEQUENCE: 55

Phe Gly Ser Thr Ala Tyr Ala Asp Met Leu Ser Gln Phe Arg Lys Phe
1               5                   10                  15

Ala Met Asn Ile Ser
            20

<210> SEQ ID NO 56
<211> LENGTH: 21
<212> TYPE: PRT
<213> ORGANISM: Escherichia coli
<220> FEATURE:
<221> NAME/KEY: MISC_FEATURE
<223> OTHER INFORMATION: DGI-2-20F-PP-E2

<400> SEQUENCE: 56

Phe Gly Arg Asp Gly Asp Gly Ile Gln Arg Arg Gln Gly Gly Phe Ser
1               5                   10                  15

Trp Val Gly Asp Arg
            20

<210> SEQ ID NO 57
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-H1

<400> SEQUENCE: 57

Arg Asp His Arg Tyr Val Gly Trp Gly Arg Ala Thr Phe Arg His Asp
1               5                   10                  15

Gln Ser Val Trp
            20

<210> SEQ ID NO 58
<211> LENGTH: 19
<212> TYPE: PRT
<213> ORGANISM: Escherichia coli
<220> FEATURE:
<221> NAME/KEY: MISC_FEATURE
<223> OTHER INFORMATION: DGI-2-20F-PP-H11
<220> FEATURE:
<221> NAME/KEY: MISC_FEATURE
<223> OTHER INFORMATION: Stop codon: TAA after residue 4

<400> SEQUENCE: 58

Val Ser Gly Tyr Ser Leu Trp Trp Cys Gly Pro Gly Trp Gly Pro Arg
1               5                   10                  15

Ser Gly Arg

<210> SEQ ID NO 59
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-H8
```

-continued

```
<400> SEQUENCE: 59

Ser Arg Gly Met Ala Glu Ala Gln Phe Ser Ala Trp Pro Val Leu Ala
1               5                   10                  15

Val Phe Pro Leu
            20

<210> SEQ ID NO 60
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-H6

<400> SEQUENCE: 60

Arg Gly Val Asn Ser Asp Met Pro Arg Leu Tyr Ile Cys Arg Ala Asp
1               5                   10                  15

Gly Gln Gly Gln
            20

<210> SEQ ID NO 61
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-E7

<400> SEQUENCE: 61

Gly Ala Ile Arg Leu Ser Gly Ala Ala Trp Thr Ala Ser Arg Thr Gly
1               5                   10                  15

Gly Arg Ala Ser
            20

<210> SEQ ID NO 62
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-H9
<220> FEATURE:
<221> NAME/KEY: MISC_FEATURE
<223> OTHER INFORMATION: Stop codon: TGA after residue 17

<400> SEQUENCE: 62

Asp Val Gly Ala Val Val Arg Ser Gly His Cys Ala Ser Arg Pro Gly
1               5                   10                  15

Glu Gln Val Arg
            20

<210> SEQ ID NO 63
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-H10

<400> SEQUENCE: 63

Gly Arg Ala Gly Thr Ser Met Thr Glu Leu Val Ala Trp Gly Phe Val
1               5                   10                  15

Gln Arg Val Gly
            20
```

-continued

```
<210> SEQ ID NO 64
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-PP-G1

<400> SEQUENCE: 64

Arg Thr Leu Phe Ile Asn Gly Gly Cys Cys Gly Lys Gly Ser Gly Gly
1               5                   10                  15

Gly Arg Pro Leu
            20

<210> SEQ ID NO 65
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-F120

<400> SEQUENCE: 65

Gly Trp Ser Asp Phe Val Ala Thr Gly Ser Trp Ser Gly Gln Val Ser
1               5                   10                  15

Ala Ala Leu Asn
            20

<210> SEQ ID NO 66
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-G114

<400> SEQUENCE: 66

Asp Gly Arg Gly Trp Gly Ala Met Trp Met Arg Trp Ala Glu Gly Leu
1               5                   10                  15

Gly Ala Asp Ile
            20

<210> SEQ ID NO 67
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-3-A5

<400> SEQUENCE: 67

Val Trp Arg Asp Trp Val Asn Gly Thr Val Gly Leu Arg Asn Arg Glu
1               5                   10                  15

Lys Pro Gly Val
            20

<210> SEQ ID NO 68
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-G4
```

```
<400> SEQUENCE: 68

Val Trp Ala Ala Trp Val Glu Gly Ser Leu Leu Ser Pro Arg Gln Glu
1               5                   10                  15

Pro Val Arg Asp
            20

<210> SEQ ID NO 69
<211> LENGTH: 25
<212> TYPE: PRT
<213> ORGANISM: Escherichia coli
<220> FEATURE:
<221> NAME/KEY: MISC_FEATURE
<223> OTHER INFORMATION: DGI-2-20R-4-H2

<400> SEQUENCE: 69

Gly His Gly Ala Gly Asp Trp Ala Ala Glu Leu Phe Val Cys Pro Val
1               5                   10                  15

Ala Phe Leu Thr Gly Phe Ala Trp Arg
            20                  25

<210> SEQ ID NO 70
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-A122

<400> SEQUENCE: 70

Trp Trp Arg Glu Trp Val Asp Gly Ser Leu Arg Gly Gly Gly Gly Thr
1               5                   10                  15

Val Leu Lys Asp
            20

<210> SEQ ID NO 71
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-H626

<400> SEQUENCE: 71

Arg Arg Gly Val Cys Glu Ile Phe Thr Gly Trp Cys Val Gly Gln Thr
1               5                   10                  15

Asn Glu Arg Pro
            20

<210> SEQ ID NO 72
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-H814

<400> SEQUENCE: 72

Leu Val Ile Gly Gln Arg Ser Phe Leu Ser Ala Cys Ser Leu Phe Asp
1               5                   10                  15

Gly Phe Cys Val
            20
```

<210> SEQ ID NO 73
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-H1

<400> SEQUENCE: 73

Gly Arg Trp Asp Gly Trp Glu Val Cys Gly Ile Trp Gly Ala Asp Asp
1               5                   10                  15

Cys Ala Ser Gly
            20

<210> SEQ ID NO 74
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-F93

<400> SEQUENCE: 74

Leu Ser Leu Glu Gly Gly Trp Met Trp Asp Thr Lys Gly Gly Asp Gly
1               5                   10                  15

Gly Ser Ala Gln
            20

<210> SEQ ID NO 75
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-B52

<400> SEQUENCE: 75

Leu Trp Arg Arg Trp Ser Glu Gly Gln Leu Leu Gly Asp Gly Glu Leu
1               5                   10                  15

Arg Gly Asp Gly
            20

<210> SEQ ID NO 76
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-D4

<400> SEQUENCE: 76

Cys Gly Gly Trp Gly Ala Met Trp Glu Ala Trp Val Gln Gly Leu Asn
1               5                   10                  15

Gly Ala Gly Cys
            20

<210> SEQ ID NO 77
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-C11

```
<400> SEQUENCE: 77

Ser Arg Glu Leu Gly Lys Trp Gly Arg Leu Trp Gln Asp Trp Ser Ser
1               5                   10                  15

Gly Asn Phe Ser
            20

<210> SEQ ID NO 78
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-B4

<400> SEQUENCE: 78

Arg Lys Gly Trp Gly Val Phe Cys Ile Pro Gly Leu Arg Phe Cys Asp
1               5                   10                  15

Trp Ser Asp Pro
            20

<210> SEQ ID NO 79
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-D3

<400> SEQUENCE: 79

Trp Phe Val Gly Gln Val Glu Lys Phe Ser Arg Gly Val Gly Gly Trp
1               5                   10                  15

Trp Pro Thr Gly
            20

<210> SEQ ID NO 80
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-C1

<400> SEQUENCE: 80

Leu Phe Ser Ala Thr Gly Cys Ala Leu Met Ser Gly Phe Cys Leu Gly
1               5                   10                  15

Ser Asp Gly Ser
            20

<210> SEQ ID NO 81
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-D2

<400> SEQUENCE: 81

Phe Arg Met Trp Val Gln Ser Cys Phe Trp Gly Gln Pro Gly Thr Gly
1               5                   10                  15

Cys Gly Glu Gly
            20
```

<210> SEQ ID NO 82
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-C3

<400> SEQUENCE: 82

Thr Ile Asp Val Ala Arg Arg Phe Gly Tyr Gly Trp Trp Asp Leu Trp
1               5                   10                  15

Leu Asp Gly Asp
            20

<210> SEQ ID NO 83
<211> LENGTH: 17
<212> TYPE: PRT
<213> ORGANISM: Escherichia coli
<220> FEATURE:
<221> NAME/KEY: MISC_FEATURE
<223> OTHER INFORMATION: DGI-2-20R-4-G22

<400> SEQUENCE: 83

Val Ser Phe Ala His Asp Trp Gly Arg Trp Trp Tyr Gln Trp Glu Val
1               5                   10                  15

Gly

<210> SEQ ID NO 84
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-D1044

<400> SEQUENCE: 84

Asp Arg Val Ala Arg Leu Ala Thr Pro Thr Ala Gly Thr Met Ala Ala
1               5                   10                  15

Gly Ser Leu Gly Tyr Glu Arg Thr Val Gly Cys Asp Ser Gln Asp Trp
            20                  25                  30

Phe Arg Cys Val Val Glu Gly Leu
        35                  40

<210> SEQ ID NO 85
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-B10

<400> SEQUENCE: 85

Gln Leu Asp Cys Leu Val Trp Gly Leu Pro Gly Leu Arg Cys Asp Arg
1               5                   10                  15

Pro Leu Glu Gln
            20

<210> SEQ ID NO 86
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-G122

-continued

```
<400> SEQUENCE: 86

Arg Asp Thr Met Cys Gly Ser Val Ser Trp Gly Ile Pro Gly Cys Glu
1               5                   10                  15

Tyr Ser Gly Met
            20

<210> SEQ ID NO 87
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-A2

<400> SEQUENCE: 87

Gln Met Ser Arg Val Ala Phe Ser Pro Gly Glu Ser Trp Arg Arg Trp
1               5                   10                  15

Val Glu Gly Val
            20

<210> SEQ ID NO 88
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-G99

<400> SEQUENCE: 88

Asp Gln Arg Val Val Gly Ser Gly Trp Phe Glu Arg Leu Arg Asn Trp
1               5                   10                  15

Tyr Asp Arg Ala
            20

<210> SEQ ID NO 89
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-A1

<400> SEQUENCE: 89

Glu Gly Asn Trp Phe Cys Ala Val Phe Arg Gly Phe Cys Val Gly Asp
1               5                   10                  15

Arg Gly Pro Glu
            20

<210> SEQ ID NO 90
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-E6

<400> SEQUENCE: 90

Val Leu Gly Ala Asp Ala Gly Met Ile Trp Phe Met Asp Gly Cys Gly
1               5                   10                  15

Ile Arg Cys Arg
            20
```

```
<210> SEQ ID NO 91
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-A8

<400> SEQUENCE: 91

Arg Ser Ile Arg Leu Gln Leu Ile Asp Glu Ala Cys Gln Phe Phe Asp
 1               5                  10                  15

Gly Leu Cys Thr
            20

<210> SEQ ID NO 92
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-4-F97

<400> SEQUENCE: 92

Gln Val Gly Gly Met Thr Gln Val Gly Ala Thr Val Leu Ser Val Val
 1               5                  10                  15

Thr Gly Arg Gly Ser Cys Asp Gly Glu Asp Ala Trp Tyr Pro Pro Gly
            20                  25                  30

Val Thr Val Gly Leu Gly Leu Cys
        35                  40

<210> SEQ ID NO 93
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-D127

<400> SEQUENCE: 93

Ser Trp Ala Cys Gly Leu Leu Trp Pro Gly Glu Cys Gly Ser Gln Val
 1               5                  10                  15

Ala Arg Arg Gly
            20

<210> SEQ ID NO 94
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-D9

<400> SEQUENCE: 94

Trp Gly Cys Val Phe Arg Gln Trp Ala Ser Gly Ser Gly Ala Gly Cys
 1               5                  10                  15

Ala Arg Arg His
            20

<210> SEQ ID NO 95
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-H112
```

```
<400> SEQUENCE: 95

Ser Leu Glu Cys Trp Ala Met Pro Gly Met Val Val Arg Leu Val Gly
1               5                  10                  15

Cys Asp Gly Pro
            20

<210> SEQ ID NO 96
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-B1

<400> SEQUENCE: 96

Trp Trp Glu Arg Phe Val Trp Gly Arg Pro Val Asp Asp Gly Val Val
1               5                  10                  15

Val Met Ala Thr
            20

<210> SEQ ID NO 97
<211> LENGTH: 15
<212> TYPE: PRT
<213> ORGANISM: Escherichia coli
<220> FEATURE:
<221> NAME/KEY: MISC_FEATURE
<223> OTHER INFORMATION: DGI-2-20R-3-A10

<400> SEQUENCE: 97

Arg Arg Ile Leu Pro Trp Ser Phe Pro Gly Cys Gly Arg Met Cys
1               5                  10                  15

<210> SEQ ID NO 98
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-C2

<400> SEQUENCE: 98

Arg Asp Thr Thr Ser Gln Trp Ser Trp Ile Ser Arg Gly Trp Glu Phe
1               5                  10                  15

Pro Gly Trp Arg
            20

<210> SEQ ID NO 99
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-A11

<400> SEQUENCE: 99

Trp Ala Ala Ser Cys Phe Trp Gly His Val Ala Leu Gly Cys Gly Arg
1               5                  10                  15

Asn Gly Gln Gly
            20

<210> SEQ ID NO 100
<211> LENGTH: 20
<212> TYPE: PRT
<213> ORGANISM: Escherichia coli
```

```
<220> FEATURE:
<221> NAME/KEY: MISC_FEATURE
<223> OTHER INFORMATION: DGI-2-20F-3-B5

<400> SEQUENCE: 100

Arg Glu Arg Trp Gly Thr Ala Trp Asn Leu Trp Thr Glu Gly Val Val
1               5                   10                  15

Asp Val Arg Pro
            20

<210> SEQ ID NO 101
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-C6

<400> SEQUENCE: 101

Gly Ile Met Gln Val Ala Trp Gly Trp Arg Glu Trp Arg Leu Trp Asp
1               5                   10                  15

Leu Gly Met Ala
            20

<210> SEQ ID NO 102
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-B11

<400> SEQUENCE: 102

Gly Trp Gly Cys Ser Val Pro Gly Ile Leu Cys Val Gly Gly His Arg
1               5                   10                  15

Gln Gly Gly Gly
            20

<210> SEQ ID NO 103
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-A6

<400> SEQUENCE: 103

Gly Gly Gly Arg Glu Ser Trp Gly Gly Trp Phe Met Gly Trp Gly
1               5                   10                  15

Ser Gly Ala Gly
            20

<210> SEQ ID NO 104
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-C8
```

```
<400> SEQUENCE: 104

Tyr Gly Thr Ala Gly Leu Phe Leu Arg Arg Ala Cys Thr Met Ser Asp
1               5                   10                  15

Pro Gly Asp Pro Leu Gly Arg Arg Gly Tyr Thr Gly Trp Gly Val Leu
            20                  25                  30

Trp Asp Glu Trp Val Thr Gly Ser
        35                  40

<210> SEQ ID NO 105
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-B12

<400> SEQUENCE: 105

Asp Gly Lys His Leu Thr Lys Trp Ser Gly Arg Gly Trp Trp Ser Ala
1               5                   10                  15

Trp Val Gly Gly
            20

<210> SEQ ID NO 106
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-4-F9

<400> SEQUENCE: 106

Leu Pro Gln Ser Arg Trp Leu Ser Glu Ala Trp Ala Ser Trp Val Asp
1               5                   10                  15

Gly Val Val Asp
            20

<210> SEQ ID NO 107
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-C8

<400> SEQUENCE: 107

Val Val Arg Gln Gly Cys Met Ala Phe Ser Gly Leu Cys Ser Gly Val
1               5                   10                  15

Thr Glu Ser Glu
            20

<210> SEQ ID NO 108
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-C424
```

```
-continued

<400> SEQUENCE: 108

Thr Val Lys Phe Gln Gly Val Val Gln Glu Arg Ser Arg Ile Ala Gly
1               5                   10                  15

Phe Arg Tyr Cys Gly Asp His Ala Val Ser Trp Gly Leu Ala Gly Cys
            20                  25                  30

Pro Ala Leu Arg Asp Lys Leu Gln
        35                  40

<210> SEQ ID NO 109
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-D7

<400> SEQUENCE: 109

Val His Ser Gln Gly Arg Met Trp Ala Ile Pro Gly Leu Arg Gly Gly
1               5                   10                  15

Thr Gly Ala Ser
            20

<210> SEQ ID NO 110
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-C7

<400> SEQUENCE: 110

Met Gly Val Val Leu Glu Cys Glu Gly Gly Trp Ser Ile Pro Gly Gln
1               5                   10                  15

Thr Cys Tyr Phe
            20

<210> SEQ ID NO 111
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-B3

<400> SEQUENCE: 111

Met Phe Gln Asp Val Ala Cys Asp Leu Trp His Ser Val Arg Cys Leu
1               5                   10                  15

Arg Arg Asp Val
            20

<210> SEQ ID NO 112
<211> LENGTH: 23
<212> TYPE: PRT
<213> ORGANISM: Escherichia coli
<220> FEATURE:
<221> NAME/KEY: MISC_FEATURE
<223> OTHER INFORMATION: DGI-2-20R-3-A7

<400> SEQUENCE: 112

Val Leu Gln Arg Ser Leu Trp Lys Asp Trp Val Asp Gly Val Met His
1               5                   10                  15

Gly Gly Gly Ser Arg Gly Val
            20
```

-continued

```
<210> SEQ ID NO 113
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-4-F122

<400> SEQUENCE: 113

Arg Ser Gln Val Arg Val Val Ser Arg Glu Arg Ser Thr Pro Val Leu
1               5                   10                  15

His Arg Ile Glu Cys Leu Leu Phe Ser Gly Trp Cys Val Thr Ser Gly
            20                  25                  30

Ser Asp Glu Gly Val Val Trp Gly
        35                  40

<210> SEQ ID NO 114
<211> LENGTH: 25
<212> TYPE: PRT
<213> ORGANISM: Escherichia coli
<220> FEATURE:
<221> NAME/KEY: MISC_FEATURE
<223> OTHER INFORMATION: DGI-2-20C-3-C1039

<400> SEQUENCE: 114

Arg Pro Val Val Cys Leu Ala Gly Leu Thr Leu Ala Gln Phe Gly Trp
1               5                   10                  15

Val Phe Pro Gly Trp Arg Gly Trp Ser
            20                  25

<210> SEQ ID NO 115
<211> LENGTH: 18
<212> TYPE: PRT
<213> ORGANISM: Escherichia coli
<220> FEATURE:
<221> NAME/KEY: MISC_FEATURE
<223> OTHER INFORMATION: DGI-2-20R-3-D10

<400> SEQUENCE: 115

Ile Ser Gly Gln Val Trp Ser Ser Trp Arg Phe Pro Gly Trp Gly Gly
1               5                   10                  15

Lys Phe

<210> SEQ ID NO 116
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-G7

<400> SEQUENCE: 116

Tyr Thr Pro Ala Ser Ile Leu Thr Gly Phe Gln Arg Gly Tyr Glu Gly
1               5                   10                  15

Ala Gly Asn Gly
            20

<210> SEQ ID NO 117
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-4-E62
```

-continued

```
<400> SEQUENCE: 117

Thr Cys Trp His Arg Gly Leu Asn Val Val Arg Tyr Ser Val Asn Phe
1               5                   10                  15

Gly Val Arg Asp Ala Arg Leu Thr Thr Gln Gly Met Ala Trp Phe Pro
            20                  25                  30

Pro Gly Cys Gly Gln Gly Cys Val
        35                  40

<210> SEQ ID NO 118
<211> LENGTH: 22
<212> TYPE: PRT
<213> ORGANISM: Escherichia coli
<220> FEATURE:
<221> NAME/KEY: MISC_FEATURE
<223> OTHER INFORMATION: DGI-2-40F-3-A1

<400> SEQUENCE: 118

Arg Glu Phe Phe Asn Gln Ala Ser Arg Gly Ala Trp Gly Tyr Met Phe
1               5                   10                  15

Arg Glu Trp Val Glu Gly
            20

<210> SEQ ID NO 119
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-C4

<400> SEQUENCE: 119

Ser Arg Pro Gly Trp Cys Ser Arg Gly Thr Ala Trp Gly Phe Pro Gly
1               5                   10                  15

Cys Ser Ser Ser
            20

<210> SEQ ID NO 120
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-F1212

<400> SEQUENCE: 120

Met Ser Ser Thr Ala Trp Thr Asp Arg Ile Leu Gln Arg Gly Ile Gly
1               5                   10                  15

Leu Gly Pro Val
            20

<210> SEQ ID NO 121
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-E82

<400> SEQUENCE: 121

Asp Ala Gly Ile Gly Trp Val Gly Ser Met Trp Phe Pro Pro Gly Cys
1               5                   10                  15

Ile Gly Ala Cys
            20
```

```
<210> SEQ ID NO 122
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-4-E3

<400> SEQUENCE: 122

Arg Asn Trp Leu Asp Lys Asp Cys Val Trp Met Gly Asp Cys Gly Ala
1               5                   10                  15

Arg Ala Gly Glu
            20

<210> SEQ ID NO 123
<211> LENGTH: 25
<212> TYPE: PRT
<213> ORGANISM: Escherichia coli
<220> FEATURE:
<221> NAME/KEY: MISC_FEATURE
<223> OTHER INFORMATION: DGI-2-20C-4-H316

<400> SEQUENCE: 123

Arg Trp Ser Ile Cys Arg Gly Leu Gln Tyr Ser Ile Pro Gly Cys Ala
1               5                   10                  15

Val Glu Asp Leu Ser Asp Val Met Ala
            20                  25

<210> SEQ ID NO 124
<211> LENGTH: 31
<212> TYPE: PRT
<213> ORGANISM: Escherichia coli
<220> FEATURE:
<221> NAME/KEY: MISC_FEATURE
<223> OTHER INFORMATION: DGI-2-40F-3-D11

<400> SEQUENCE: 124

Leu His Phe Gly Ser Val Met Gly Trp Arg Pro Pro Gly Ser Leu Trp
1               5                   10                  15

Ser Arg Pro Phe Gly Gln Val His Pro Arg Ser Trp Ser Gly Ser
            20                  25                  30

<210> SEQ ID NO 125
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-H12

<400> SEQUENCE: 125

Met Ser Thr Leu Gln Gly Pro Gly His Leu Phe Gln Met Leu Arg Arg
1               5                   10                  15

Ala Ser Leu Gly
            20

<210> SEQ ID NO 126
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-C1
```

```
<400> SEQUENCE: 126

Gly Ser Val Leu Glu Arg Gly Cys Leu Glu Phe Ser Gly Phe Cys Phe
1               5                   10                  15

Ser Leu Gly His
            20

<210> SEQ ID NO 127
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-A9

<400> SEQUENCE: 127

Leu Gln Ile Val Arg Pro Ala Gly Trp Lys Met Pro Gly Gln Val Gly
1               5                   10                  15

Tyr Tyr Ile Gly
            20

<210> SEQ ID NO 128
<211> LENGTH: 34
<212> TYPE: PRT
<213> ORGANISM: Escherichia coli
<220> FEATURE:
<221> NAME/KEY: MISC_FEATURE
<223> OTHER INFORMATION: DGI-2-40F-4-F6

<400> SEQUENCE: 128

Ser Tyr Arg Asn Phe Ala Met Gln Ser Ser Leu Gln Val Arg Arg Gly
1               5                   10                  15

Ser Val Val Glu Asp Gly Thr Cys Trp Trp Glu Gly Val Arg Cys Tyr
            20                  25                  30

Ser Gly

<210> SEQ ID NO 129
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-C12

<400> SEQUENCE: 129

Leu Thr Pro Tyr Ser Leu Ala Arg Ser Trp Leu Ser Gly Arg Pro Ser
1               5                   10                  15

Thr Gly Ala Thr
            20

<210> SEQ ID NO 130
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-B7

<400> SEQUENCE: 130

Ser Trp Arg Leu Trp Val Ser Gly Glu Leu Gln Gly Asp Arg Arg Lys
1               5                   10                  15

Gly Leu Arg Gly
            20
```

<210> SEQ ID NO 131
<211> LENGTH: 32
<212> TYPE: PRT
<213> ORGANISM: Escherichia coli
<220> FEATURE:
<221> NAME/KEY: MISC_FEATURE
<223> OTHER INFORMATION: DGI-2-40F-3-D72

<400> SEQUENCE: 131

Met Gly Ser Leu Gly Pro Phe Gly Asn Ile Asn Ser Leu Ala Ser Gly
1               5                   10                  15

Ile Gly Ser Val Arg Asn Arg Pro Leu Leu Pro Leu His Gly Ser Pro
            20                  25                  30

<210> SEQ ID NO 132
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-H7

<400> SEQUENCE: 132

Leu Ser His Pro Met Ser Pro Leu Arg Ala Ala Ser Gln Met Ala Leu
1               5                   10                  15

Thr Gln Gly Val
            20

<210> SEQ ID NO 133
<211> LENGTH: 37
<212> TYPE: PRT
<213> ORGANISM: Escherichia coli
<220> FEATURE:
<221> NAME/KEY: MISC_FEATURE
<223> OTHER INFORMATION: DGI-2-40F-4-E1130
<220> FEATURE:
<221> NAME/KEY: MISC_FEATURE
<223> OTHER INFORMATION: Stop codon: TAA after residues 1 and 3

<400> SEQUENCE: 133

Val Cys Arg Leu Cys Arg Leu Cys Arg Phe Ser Met Arg Cys Gly Gly
1               5                   10                  15

Leu Ser Leu Val Leu Gly Ser Ala Ala Ala Phe Phe Cys Glu Val Phe
            20                  25                  30

Val Gly Phe Cys Val
            35

<210> SEQ ID NO 134
<211> LENGTH: 25
<212> TYPE: PRT
<213> ORGANISM: Escherichia coli
<220> FEATURE:
<221> NAME/KEY: MISC_FEATURE
<223> OTHER INFORMATION: DGI-2-20C-4-E926

<400> SEQUENCE: 134

Arg Met Tyr Asn Cys His Tyr Ile Glu Arg Leu Tyr Asp Trp His Ala
1               5                   10                  15

Gly Arg Ile Leu Leu Gln Asp Pro Ala
            20                  25

<210> SEQ ID NO 135
<211> LENGTH: 20
<212> TYPE: PRT
<213> ORGANISM: Escherichia coli

```
<220> FEATURE:
<221> NAME/KEY: MISC_FEATURE
<223> OTHER INFORMATION: DGI-2-20F-3-A1

<400> SEQUENCE: 135

Cys Arg Asn Phe Gly Val Ile Trp Gly Ala Gly Trp Val Ser Pro Gly
1               5                   10                  15

Cys Glu Asp Ile
            20

<210> SEQ ID NO 136
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-B6

<400> SEQUENCE: 136

Thr Ser Cys Gln Val Met Phe Leu Ala Gly Gln His Leu Leu Ser Arg
1               5                   10                  15

Val Pro Arg Leu
            20

<210> SEQ ID NO 137
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-E2

<400> SEQUENCE: 137

Thr Ala Asn Gly His Arg Tyr Gly Gly Cys Gly Leu Trp Cys Lys Trp
1               5                   10                  15

Met Ser Gly Met
            20

<210> SEQ ID NO 138
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-D7

<400> SEQUENCE: 138

Ala Leu Arg Ser Leu Gly Ser Gly Gly Phe Gly Trp Gln Ala Gly Arg
1               5                   10                  15

Ala Ser Pro Gln Gly Met Thr His Phe Pro Tyr Phe Gly Trp Ser Gly
            20                  25                  30

Met Pro Thr Ala Arg Val Arg Pro
        35                  40

<210> SEQ ID NO 139
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-D6
```

-continued

<400> SEQUENCE: 139

Gly Leu Glu Pro Val Pro Phe Gln Thr Asp Lys Arg Ile Ala Met Gly
1               5                   10                  15

Trp Thr Arg Glu Trp Leu Val Asn Gly Tyr Gly Ala Ala His Arg Arg
            20                  25                  30

Asp Ala Arg Met Gln Ser Gly His
        35                  40

<210> SEQ ID NO 140
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-B102

<400> SEQUENCE: 140

Gly Leu Arg Ala Cys Asp Thr Tyr Leu Gly Phe Cys Val Gly Ala Arg
1               5                   10                  15

Arg Ile Asp Asp
            20

<210> SEQ ID NO 141
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-C6

<400> SEQUENCE: 141

Gln Met Phe Ser Lys Gly Asn Trp Leu Ala His Pro Glu Gly Gly Val
1               5                   10                  15

Ala Leu Gly Leu Ser Arg Glu Ser Gln Leu Phe Arg Ser Cys Arg Glu
            20                  25                  30

Phe Gly Tyr Cys Met Gly Pro Met
        35                  40

<210> SEQ ID NO 142
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-D12

<400> SEQUENCE: 142

Gln Gly Ser Ala His Val Val Arg Pro Pro Gly Val Tyr Asp Val Pro
1               5                   10                  15

Trp Lys Val Gly Met Phe Phe His Pro Gln Asn Trp Pro Asn Ser Trp
            20                  25                  30

Gly Arg Ala Tyr Phe Arg Ser Gly
        35                  40

<210> SEQ ID NO 143
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-F6

```
<400> SEQUENCE: 143

Gly Asn Lys Cys Phe Pro Pro His Asp Leu Phe Trp Asp Pro Cys Asp
1               5                  10                  15

Gln Leu Gln Ser
            20

<210> SEQ ID NO 144
<211> LENGTH: 39
<212> TYPE: PRT
<213> ORGANISM: Escherichia coli
<220> FEATURE:
<221> NAME/KEY: MISC_FEATURE
<223> OTHER INFORMATION: DGI-2-40F-4-F12

<400> SEQUENCE: 144

Gly Leu Tyr Arg Arg Ala Gly Asp Ala Ser Val Gly Phe Ser Arg Trp
1               5                  10                  15

Gly Arg Phe Asp Cys Gln Val Tyr Phe Ser Val Glu Cys Leu Leu Gly
            20                  25                  30

Ser Ser Trp Gly Gly Tyr Ser
        35

<210> SEQ ID NO 145
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-D6

<400> SEQUENCE: 145

Ala Cys Ser Val Gly Thr Ala Leu Val Phe Pro Gln Arg Trp Trp Tyr
1               5                  10                  15

Leu Gly Arg Ser
            20

<210> SEQ ID NO 146
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-C10

<400> SEQUENCE: 146

Ser Leu Ser Leu Tyr Trp Asp Ala Gln Val Gly Cys Glu Val Phe Trp
1               5                  10                  15

Gly Tyr Cys Val
            20

<210> SEQ ID NO 147
<211> LENGTH: 23
<212> TYPE: PRT
<213> ORGANISM: Escherichia coli
<220> FEATURE:
<221> NAME/KEY: MISC_FEATURE
<223> OTHER INFORMATION: DGI-2-40F-3-C92

<400> SEQUENCE: 147

Arg Phe Trp Ser Val Ser Tyr Gln Gly Gly Arg Val Met Cys Arg Glu
1               5                  10                  15

Trp Gly Tyr Cys Leu Pro Ile
            20
```

```
<210> SEQ ID NO 148
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-A7

<400> SEQUENCE: 148

Leu Ser Leu Ser Val Val Arg Ser Met Gly Ala Ser Ala Pro
1               5                   10                  15

Gln Arg Gln Val
            20

<210> SEQ ID NO 149
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-B11

<400> SEQUENCE: 149

Leu Ala Pro Met Phe Leu Gln Asn Gln Val Arg Thr Trp Ala Ala Ser
1               5                   10                  15

Arg Arg Pro Leu Pro Ala Gly Pro Ser Asn Ala Arg Cys Glu Thr Gly
            20                  25                  30

Ser Leu Ser Pro Trp Val Pro Cys
        35                  40

<210> SEQ ID NO 150
<211> LENGTH: 25
<212> TYPE: PRT
<213> ORGANISM: Escherichia coli
<220> FEATURE:
<221> NAME/KEY: MISC_FEATURE
<223> OTHER INFORMATION: DGI-2-20C-3-C65

<400> SEQUENCE: 150

Thr Pro Asp Arg Cys Leu Ile Tyr Ser Ser Ile Gln Cys Leu Leu Glu
1               5                   10                  15

Tyr Ser Ala Arg Arg Gly Ser Ala Asp
            20                  25

<210> SEQ ID NO 151
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-B122

<400> SEQUENCE: 151

His Ser Gly Asn Arg Gln Ser Gly Ser Arg Arg Thr His Leu Leu Asn
1               5                   10                  15

Ile Phe Cys Ser Ser Asp Thr Phe Val Phe Pro Gly Trp Ser Ala Tyr
            20                  25                  30

Leu Ser Arg Val Cys Pro Gly Asp
        35                  40

<210> SEQ ID NO 152
<211> LENGTH: 40
<212> TYPE: PRT
<213> ORGANISM: Escherichia coli
```

```
<220> FEATURE:
<221> NAME/KEY: MISC_FEATURE
<223> OTHER INFORMATION: DGI-2-40F-3-B116

<400> SEQUENCE: 152

Gly Val Val Arg Ala Gln Gln Gly Leu Arg Tyr Glu Leu Gln Gly Asp
1               5                   10                  15

Arg Tyr Arg Leu Arg Arg Thr Gln Trp Leu Thr Val Thr Tyr Cys Ser
            20                  25                  30

Pro Ser Trp Ala Phe Ala Gly Cys
        35                  40

<210> SEQ ID NO 153
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-C12

<400> SEQUENCE: 153

Arg Trp Ser Leu Pro Ala Tyr Leu Cys Arg Phe Val Ser Gln Ala Ser
1               5                   10                  15

Cys Asn Ser Arg
            20

<210> SEQ ID NO 154
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-B7

<400> SEQUENCE: 154

Trp Ala Gly Ser Thr Asp Leu Trp Gln Leu Trp Ser Leu Trp Val Lys
1               5                   10                  15

Pro Glu Leu Arg
            20

<210> SEQ ID NO 155
<211> LENGTH: 24
<212> TYPE: PRT
<213> ORGANISM: Escherichia coli
<220> FEATURE:
<221> NAME/KEY: MISC_FEATURE
<223> OTHER INFORMATION: DGI-2-20R-4-G6

<400> SEQUENCE: 155

Pro Ala Met Gly His Cys Met Gln Val Leu Gly Pro Val Leu Glu Gly
1               5                   10                  15

Arg Ser Arg Asp Gln Val Gly Arg
            20

<210> SEQ ID NO 156
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-E4
```

```
<400> SEQUENCE: 156

Leu Thr Trp Gly Pro Gln Phe Gly Ser Leu Gln Val Tyr Ser Arg His
1               5                   10                  15

Arg Gly Leu Pro
            20

<210> SEQ ID NO 157
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-D10

<400> SEQUENCE: 157

Thr Leu Val Thr Glu Gly Asn Lys Gly Ser Val Lys Ala His Lys Asp
1               5                   10                  15

Ile Gly Val Trp Gln Leu Trp Trp Asp Trp Leu Ser Val Thr Asp Ser
            20                  25                  30

Glu Thr Val Gly Arg Val Ser His
        35                  40

<210> SEQ ID NO 158
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-A6

<400> SEQUENCE: 158

Phe Ser Ser Thr Gly Ile Leu Leu Arg Ser Gly Arg Ala Thr Ala Val
1               5                   10                  15

Gly His Val Thr
            20

<210> SEQ ID NO 159
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-G8

<400> SEQUENCE: 159

Gly Met Trp Ile Arg Pro Asn Gly His Met Phe Leu Gln Gly Gly Tyr
1               5                   10                  15

Thr Ala Arg Ser
            20

<210> SEQ ID NO 160
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-3-D5

<400> SEQUENCE: 160

Val Ala Phe Gly Glu Gln Ile Arg Val Ala Met Ala Gly Thr Leu Trp
1               5                   10                  15

Gln Arg Trp Arg
            20
```

-continued

```
<210> SEQ ID NO 161
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-D112

<400> SEQUENCE: 161

Tyr Asp Gln Val Trp Asn Ser Leu Leu Ala Ala Val Leu Gly Gly Gln
1               5                   10                  15

Glu Leu Val Asn
            20

<210> SEQ ID NO 162
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-G32

<400> SEQUENCE: 162

Leu Ser Val Phe Arg Pro Gly Gln Phe Pro His Val Gly Ala Arg Gly
1               5                   10                  15

Val Ser Arg Thr
            20

<210> SEQ ID NO 163
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-B10

<400> SEQUENCE: 163

Met Gln Ala Ala Ser Thr Leu Ser Thr Tyr Met Gly Ala Ile Arg Met
1               5                   10                  15

Gly Tyr Pro Ile Leu His Trp Asp Arg Gly Gly Val Gln Arg Val Asp
            20                  25                  30

Pro Gly Leu Tyr Arg Gly Arg Val
        35                  40

<210> SEQ ID NO 164
<211> LENGTH: 32
<212> TYPE: PRT
<213> ORGANISM: Escherichia coli
<220> FEATURE:
<221> NAME/KEY: MISC_FEATURE
<223> OTHER INFORMATION: DGI-2-40F-3-A24

<400> SEQUENCE: 164

Arg Cys Phe Gln Asp Gly Arg Met Leu Ala Leu Ser Pro Thr Tyr Leu
1               5                   10                  15

Ile Arg Arg Ser Val Ser Pro Leu Val Val Gly Pro Leu Pro Thr Pro
            20                  25                  30

<210> SEQ ID NO 165
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-C2
```

<400> SEQUENCE: 165

Met Ala Val Leu Pro Ala Ala Arg Asp Phe Gly Gly Val Val Gln Gly
1               5                   10                  15

Gly Val Ser Gly
            20

<210> SEQ ID NO 166
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-C7

<400> SEQUENCE: 166

His Pro Trp Val Thr Asn Met Leu Val Phe Gln Arg Pro Pro Pro Pro
1               5                   10                  15

Gly Phe Trp Leu Ser Asp Thr Thr Pro Arg Gln Arg Asn Gly Leu Gly
            20                  25                  30

Gln Val Glu Arg Pro Ser Val Asp
        35                  40

<210> SEQ ID NO 167
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-B1

<400> SEQUENCE: 167

Leu Ser Arg Ile Trp Arg Gly Val Ile Glu Ser Ala Arg Glu Val Glu
1               5                   10                  15

Ser Arg Gly Ile
            20

<210> SEQ ID NO 168
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20R-4-E5

<400> SEQUENCE: 168

Leu His Arg Leu Gly Gln Ser Met Gly Gly Thr Leu Asp His Leu Gln
1               5                   10                  15

Gly Trp Gly Val
            20

<210> SEQ ID NO 169
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-D9

-continued

<400> SEQUENCE: 169

Arg Arg Thr Ser Ala Asp Thr Asp Gln Leu Ser Arg Trp Glu Gly Ala
1               5                   10                  15

Gln Ala Phe Ser Ser Leu Arg Ser Ala Leu Ser Glu Arg Leu Asp Ser
            20                  25                  30

Leu Arg Pro Gly Leu Pro Pro Ser
        35                  40

<210> SEQ ID NO 170
<211> LENGTH: 9
<212> TYPE: PRT
<213> ORGANISM: Escherichia coli
<220> FEATURE:
<221> NAME/KEY: MISC_FEATURE
<223> OTHER INFORMATION: DGI-2-40F-3-A4

<400> SEQUENCE: 170

Trp Phe Thr His Val Val Glu Lys Phe
1               5

<210> SEQ ID NO 171
<211> LENGTH: 39
<212> TYPE: PRT
<213> ORGANISM: Escherichia coli
<220> FEATURE:
<221> NAME/KEY: MISC_FEATURE
<223> OTHER INFORMATION: DGI-2-40F-3-C10

<400> SEQUENCE: 171

Trp Arg Ala Arg Ser Ser Gly Tyr Leu Phe Ala Leu Thr Pro Asn Phe
1               5                   10                  15

Gly Val Pro His Pro Ser Ser Ala Leu Arg Arg Met His Gly Leu Met
            20                  25                  30

Ala Arg Asp Leu Arg Pro Val
        35

<210> SEQ ID NO 172
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-C3

<400> SEQUENCE: 172

Phe Ser Ser Val Leu Gly Leu Leu Asp Arg Arg Gly Val Pro Val Val
1               5                   10                  15

Val Gly Glu Asp
            20

<210> SEQ ID NO 173
<211> LENGTH: 25
<212> TYPE: PRT
<213> ORGANISM: Escherichia coli
<220> FEATURE:
<221> NAME/KEY: MISC_FEATURE
<223> OTHER INFORMATION: DGI-2-20C-3-D12

<400> SEQUENCE: 173

Leu Val Ile Gln Cys Ser Ala Ser Val Val Ala Cys Asp Leu Tyr Trp
1               5                   10                  15

Asn Tyr Val Gly Cys Leu Ala Ala Gly
            20                  25

```
<210> SEQ ID NO 174
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-C52

<400> SEQUENCE: 174

Gly Leu Leu Phe Thr Ser Ser Pro Tyr Gln Cys Phe Trp Val His Cys
1               5                   10                  15

Thr Leu Thr Met Ser Pro Leu Ser Val Leu Gly Asp Leu Ser Ser Thr
            20                  25                  30

Ile Gly Arg Met Arg Ala Ser Arg
        35                  40

<210> SEQ ID NO 175
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-B72

<400> SEQUENCE: 175

Pro Lys Asp Gly Ala Ala Phe Lys Gly Ser Asp Phe Ile Gln Gly Gly
1               5                   10                  15

Gln Thr Val Met Glu Arg Ala Pro Ala Leu Trp Trp Arg Asp Gly Gly
            20                  25                  30

Gly Gln Trp Glu Ala Pro Ser Thr
        35                  40

<210> SEQ ID NO 176
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-B95

<400> SEQUENCE: 176

Asp Tyr Lys Thr Cys Val Ser Gln His Val His Pro Leu Phe Gly Glu
1               5                   10                  15

Tyr Phe Tyr His Lys Val Thr His Met Ser Ile Leu Ser Pro Thr Phe
            20                  25                  30

Arg Val Thr Ser Leu Tyr Gly Lys
        35                  40

<210> SEQ ID NO 177
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-B5

<400> SEQUENCE: 177

Arg Ser Arg Ser Ser Gly Ala Ser Gly Ser Met Leu Arg Val Gln
1               5                   10                  15

Asn His Met Val Leu Gly Ser Trp Met Val Arg Gln Pro Met Gly Ser
            20                  25                  30

Met Thr Pro Phe His Gly His Gly
        35                  40
```

<210> SEQ ID NO 178
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-B4

<400> SEQUENCE: 178

Leu Trp Leu Pro Cys Gly Leu Leu Val Arg Pro Ala Gln Phe Tyr Phe
1               5                   10                  15

Tyr Phe Ser Pro Leu Arg His Phe Leu Ser Ser Val Gly Ser Leu
            20                  25                  30

Ser Phe Pro Leu Ser Leu Leu Val
        35                  40

<210> SEQ ID NO 179
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI-2-20F-3-C5

<400> SEQUENCE: 179

Leu Gly Asn Ala Ser Ser Leu Ile Pro Phe Leu Arg Ser Val Gln Glu
1               5                   10                  15

Ser Gly Val Arg
            20

<210> SEQ ID NO 180
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-B6

<400> SEQUENCE: 180

Gln Ser Asn Val Trp Val Leu Val Gly Val Ile Met Gln Gly Val Trp
1               5                   10                  15

Tyr Gln Arg Gln His Tyr Cys Val Tyr Val Met Leu Leu Ser Asp Gln
            20                  25                  30

Val Ser Val Leu Leu Ala Val Ala
        35                  40

<210> SEQ ID NO 181
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-A7

<400> SEQUENCE: 181

Cys Ala Tyr Arg Trp Gly Leu Phe Arg Gly Pro Gly Arg Val Asp Tyr
1               5                   10                  15

Asp Leu Gln Val Val Gly Ile Met Met Trp Pro Gly Pro Ile Pro Asp
            20                  25                  30

Arg Ser Ser Arg Gly Ser Val Ala
        35                  40

```
<210> SEQ ID NO 182
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-A12

<400> SEQUENCE: 182

Arg Arg Thr Gln Pro Ala Tyr Arg Ser Gly Ala Asp Asp Arg Thr Ser
1               5                   10                  15

Gly Phe Tyr Cys Tyr Val Thr Ser Ala Leu Ser Ala Gly Ala Trp Met
            20                  25                  30

Pro Phe Leu Pro Arg Arg Leu Ala
        35                  40

<210> SEQ ID NO 183
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-D3

<400> SEQUENCE: 183

Val Gln Phe Ala Met Thr Leu Ser Ser Arg Leu Trp Gln His Ala Arg
1               5                   10                  15

His Pro Leu Thr Asp Asp Ala Pro Pro Thr Val Ser Phe Gly Thr Arg
            20                  25                  30

Arg Glu Thr Leu Ala Gly Lys Ala
        35                  40

<210> SEQ ID NO 184
<211> LENGTH: 25
<212> TYPE: PRT
<213> ORGANISM: Escherichia coli
<220> FEATURE:
<221> NAME/KEY: MISC_FEATURE
<223> OTHER INFORMATION: DGI-2-20C-3-A12

<400> SEQUENCE: 184

Gly Glu Val Asp Cys Val Tyr Ala Leu Thr His Arg Phe Leu Ser Pro
1               5                   10                  15

Gln Val Gln Tyr His His Arg Pro Val
            20                  25

<210> SEQ ID NO 185
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-B1

<400> SEQUENCE: 185

His Gly Thr Arg Leu Arg Gly Val Asp Tyr Val Met Thr Trp Ala Gly
1               5                   10                  15

Trp Gln Gly Tyr Ser Ser Arg Lys His Val Gln Gln Ala Val Ala Gly
            20                  25                  30

Ser Ser Pro Gly Ser Asp Glu Leu
        35                  40
```

```
<210> SEQ ID NO 186
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-A8

<400> SEQUENCE: 186

Gly Gln Ile Ser Leu Ala Gly Val Ala Val Cys Ser Ser Glu Arg Met
1               5                   10                  15

Leu Leu Ala Phe Ser Ser Arg Val Phe Leu Pro Gly Leu Lys Val Pro
            20                  25                  30

Val Thr Thr Ser Gln Arg Gly Ser
        35                  40

<210> SEQ ID NO 187
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-A1

<400> SEQUENCE: 187

Gln Tyr Phe Ala Arg Gly Ser Phe Gln Phe Gly Leu Ser His Val Leu
1               5                   10                  15

Ser Ala Ala Ala Ala Phe His Leu Tyr Val Phe Cys Lys Arg Leu Ser
            20                  25                  30

Arg Gly Phe Gly Ile Lys Asp Asp
        35                  40

<210> SEQ ID NO 188
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI-2-40F-3-D1

<400> SEQUENCE: 188

Met Gly Gln Gly Phe His Tyr Asn Arg Gln Pro Tyr Met Ser His Gln
1               5                   10                  15

Cys Tyr Ala Phe Thr Phe Ser Thr Pro Phe Leu Asp Gly Asp Arg Ile
            20                  25                  30

Pro His Gly Val Ser Arg Gly Leu
        35                  40

<210> SEQ ID NO 189
<211> LENGTH: 33
<212> TYPE: PRT
<213> ORGANISM: Escherichia coli
<220> FEATURE:
<221> NAME/KEY: MISC_FEATURE
<223> OTHER INFORMATION: DGI-2-20C-3-B3

<400> SEQUENCE: 189

Asp Tyr Lys Gly Arg Thr Met Thr Ser Pro Ile Met Ser Ala Leu Pro
1               5                   10                  15

Val Tyr Asp Arg Leu His Gly Ala Ile Gly Ser Arg Gly Gln Asn Met
            20                  25                  30

Asp
```

-continued

```
<210> SEQ ID NO 190
<211> LENGTH: 17
<212> TYPE: PRT
<213> ORGANISM: Escherichia coli
<220> FEATURE:
<221> NAME/KEY: MISC_FEATURE
<223> OTHER INFORMATION: E-tag

<400> SEQUENCE: 190

Ala Ala Ala Gly Ala Pro Val Pro Tyr Pro Asp Pro Leu Glu Pro Arg
1               5                   10                  15

Pro

<210> SEQ ID NO 191
<211> LENGTH: 25
<212> TYPE: DNA
<213> ORGANISM: Artificial
<220> FEATURE:
<223> OTHER INFORMATION: Synthetic random primer
<220> FEATURE:
<221> NAME/KEY: random primer
<222> LOCATION: (1)..(25)
<220> FEATURE:
<221> NAME/KEY: misc_feature
<222> LOCATION: (20)..(24)
<223> OTHER INFORMATION: n= a,g,t, or c

<400> SEQUENCE: 191
gctcgccctc ggcggccgcn nnnnt                                          25

<210> SEQ ID NO 192
<211> LENGTH: 19
<212> TYPE: PRT
<213> ORGANISM: Escherichia coli
<220> FEATURE:
<221> NAME/KEY: MISC_FEATURE
<223> OTHER INFORMATION: lac Z promoter

<400> SEQUENCE: 192

Met Ala Pro Asp Ala Val Phe Ser Pro Tyr Ala Ser Val Arg Tyr Phe
1               5                   10                  15

Thr Pro His

<210> SEQ ID NO 193
<211> LENGTH: 48
<212> TYPE: DNA
<213> ORGANISM: Artificial
<220> FEATURE:
<223> OTHER INFORMATION: Synthetic GFP forward cloning primer
<220> FEATURE:
<221> NAME/KEY: misc_feature
<223> OTHER INFORMATION: GFP forward cloning primer

<400> SEQUENCE: 193
gccattcttg gtaccgcggc cgccccggtc gccaccatgg tgagcaag                 48

<210> SEQ ID NO 194
<211> LENGTH: 44
<212> TYPE: DNA
<213> ORGANISM: Artificial
<220> FEATURE:
<223> OTHER INFORMATION: Synthetic GFP reverse cloning primer
<220> FEATURE:
<221> NAME/KEY: misc_feature
<223> OTHER INFORMATION: GFP reverse cloning primer
```

-continued

```
<400> SEQUENCE: 194
ggaattcctg catatgctac tatcgagatc tgagtccgga cttg         44

<210> SEQ ID NO 195
<211> LENGTH: 65
<212> TYPE: DNA
<213> ORGANISM: Artificial
<220> FEATURE:
<223> OTHER INFORMATION: Synthetic TNFR2 forward primer
<220> FEATURE:
<221> NAME/KEY: misc_feature
<223> OTHER INFORMATION: TNFR2 forward primer

<400> SEQUENCE: 195
gatttccttg cggtaccggc ccagccggcc atggcccccg ggatggcgtt gcccgcccag   60
gtggc                                                              65

<210> SEQ ID NO 196
<211> LENGTH: 36
<212> TYPE: DNA
<213> ORGANISM: Artificial
<220> FEATURE:
<223> OTHER INFORMATION: Synthetic TNFR2 reverse primer
<220> FEATURE:
<221> NAME/KEY: misc_feature
<223> OTHER INFORMATION: TNFR2 reverse primer

<400> SEQUENCE: 196
gattttcgcg gccgcgtcgc cagtgctccc ttcagc                  36

<210> SEQ ID NO 197
<211> LENGTH: 250
<212> TYPE: PRT
<213> ORGANISM: Escherichia coli
<220> FEATURE:
<221> NAME/KEY: MISC_FEATURE
<223> OTHER INFORMATION: GFP protein

<400> SEQUENCE: 197
```

Gly Arg His His Gly Glu Gln Gly Arg Gly Ala Val His Arg Gly Gly
1               5                   10                  15

Ala His Pro Gly Arg Ala Gly Arg Arg Lys Arg Pro Gln Val Gln
            20                  25                  30

Arg Val Arg Arg Gly Arg Gly Arg Cys His Leu Arg Gln Ala Asp Pro
        35                  40                  45

Glu Val His Leu His His Arg Gln Ala Ala Arg Ala Leu Ala His Pro
    50                  55                  60

Arg Asp His Pro Asp Leu Arg Arg Ala Val Leu Gln Pro Leu Pro Arg
65                  70                  75                  80

Pro His Glu Ala Ala Arg Leu Leu Gln Val Arg His Ala Arg Arg Leu
                85                  90                  95

Arg Pro Gly Ala His His Leu Leu Gln Gly Arg Arg Gln Leu Gln Asp
            100                 105                 110

Pro Arg Arg Gly Glu Val Arg Gly Arg His Pro Gly Glu Pro His Arg
        115                 120                 125

Ala Glu Gly His Arg Leu Gln Gly Gly Arg Gln His Pro Gly Ala Gln
    130                 135                 140

Ala Gly Val Gln Leu Gln Gln Pro Gln Arg Leu Tyr His Gly Arg Gln
145                 150                 155                 160

Ala Glu Glu Arg His Gln Gly Glu Leu Gln Asp Pro Pro Gln His Arg
                165                 170                 175

-continued

```
Gly Arg Gln Arg Ala Ala Arg Pro Leu Pro Ala Glu His Pro His
            180                 185                 190

Arg Arg Arg Pro Arg Ala Ala Ala Arg Gln Pro Leu Pro Glu His Pro
        195                 200                 205

Val Arg Pro Glu Gln Arg Pro Gln Arg Glu Ala Arg Ser His Gly Pro
    210                 215                 220

Ala Gly Val Arg Asp Arg Arg Asp His Ser Arg His Gly Arg Ala
225                 230                 235                 240

Val Gln Val Arg Thr Gln Ile Ser Ile Val
                245                 250
```

<210> SEQ ID NO 198
<211> LENGTH: 48
<212> TYPE: DNA
<213> ORGANISM: Artificial
<220> FEATURE:
<223> OTHER INFORMATION: Synthetic Kan Forward primer
<220> FEATURE:
<221> NAME/KEY: misc_feature
<223> OTHER INFORMATION: Kan Forward primer

<400> SEQUENCE: 198
gcattaatct atagcggccg ccattgaaca agatggattg cacgcagg                48

<210> SEQ ID NO 199
<211> LENGTH: 45
<212> TYPE: DNA
<213> ORGANISM: Artificial
<220> FEATURE:
<223> OTHER INFORMATION: Synthetic Kan reverse primer
<220> FEATURE:
<221> NAME/KEY: misc_feature
<223> OTHER INFORMATION: Kan Reverse primer

<400> SEQUENCE: 199
gcattactat cccatatgtc atcagaagaa ctcgtcaaga aggcg                   45

<210> SEQ ID NO 200
<211> LENGTH: 263
<212> TYPE: PRT
<213> ORGANISM: Escherichia coli
<220> FEATURE:
<221> NAME/KEY: MISC_FEATURE
<223> OTHER INFORMATION: Kan ORF

<400> SEQUENCE: 200

```
Ile Glu Gln Asp Gly Leu His Ala Gly Ser Pro Ala Ala Trp Val Glu
1               5                   10                  15

Arg Leu Phe Gly Tyr Asp Trp Ala Gln Gln Thr Ile Gly Cys Ser Asp
            20                  25                  30

Ala Ala Val Phe Arg Leu Ser Ala Gln Gly Arg Pro Val Leu Phe Val
        35                  40                  45

Lys Thr Asp Leu Ser Gly Ala Leu Asn Glu Leu Gln Asp Glu Ala Ala
    50                  55                  60

Arg Leu Ser Trp Leu Ala Thr Thr Gly Val Pro Cys Ala Ala Val Leu
65                  70                  75                  80

Asp Val Val Thr Glu Ala Gly Arg Asp Trp Leu Leu Leu Gly Glu Val
                85                  90                  95

Pro Gly Gln Asp Leu Leu Ser Ser His Leu Ala Pro Ala Glu Lys Val
            100                 105                 110

Ser Ile Met Ala Asp Ala Met Arg Arg Leu His Thr Leu Asp Pro Ala
        115                 120                 125
```

```
Thr Cys Pro Phe Asp His Gln Ala Lys His Arg Ile Glu Arg Ala Arg
        130                 135                 140

Thr Arg Met Glu Ala Gly Leu Val Asp Gln Asp Asp Leu Asp Glu Glu
145                 150                 155                 160

His Gln Gly Leu Ala Pro Ala Glu Leu Phe Ala Arg Leu Lys Ala Ser
                165                 170                 175

Met Pro Asp Gly Glu Asp Leu Val Val Thr His Gly Asp Ala Cys Leu
            180                 185                 190

Pro Asn Ile Met Val Glu Asn Gly Arg Phe Ser Gly Phe Ile Asp Cys
        195                 200                 205

Gly Arg Leu Gly Val Ala Asp Arg Tyr Gln Asp Ile Ala Leu Ala Thr
    210                 215                 220

Arg Asp Ile Ala Glu Glu Leu Gly Gly Glu Trp Ala Asp Arg Phe Leu
225                 230                 235                 240

Val Leu Tyr Gly Ile Ala Ala Pro Asp Ser Gln Arg Ile Ala Phe Tyr
                245                 250                 255

Arg Leu Leu Asp Glu Phe Phe
            260
```

<210> SEQ ID NO 201
<211> LENGTH: 29
<212> TYPE: DNA
<213> ORGANISM: Artificial
<220> FEATURE:
<223> OTHER INFORMATION: Synthetic Puc 19 reverse primer
<220> FEATURE:
<221> NAME/KEY: misc_feature
<223> OTHER INFORMATION: Puc 19 reverse primer

<400> SEQUENCE: 201
gcttccggct cgtatgttgt gtggaattg                              29

<210> SEQ ID NO 202
<211> LENGTH: 27
<212> TYPE: DNA
<213> ORGANISM: Artificial
<220> FEATURE:
<223> OTHER INFORMATION: Synthetic Kan reverse primer
<220> FEATURE:
<221> NAME/KEY: misc_feature
<223> OTHER INFORMATION: Kan reverse primer

<400> SEQUENCE: 202
cagtcatagc cgaatagcct ctccacc                                27

<210> SEQ ID NO 203
<211> LENGTH: 10
<212> TYPE: PRT
<213> ORGANISM: Escherichia coli
<220> FEATURE:
<221> NAME/KEY: MISC_FEATURE
<223> OTHER INFORMATION: Myc tag

<400> SEQUENCE: 203

```
Glu Gln Lys Leu Ile Ser Glu Glu Asp Leu
1               5                   10
```

<210> SEQ ID NO 204
<211> LENGTH: 8
<212> TYPE: PRT
<213> ORGANISM: Escherichia coli
<220> FEATURE:
<221> NAME/KEY: MISC_FEATURE
<223> OTHER INFORMATION: linker sequence

```
<400> SEQUENCE: 204

Pro Ala Gly Gly Ala Met Ala Ala
1               5

<210> SEQ ID NO 205
<211> LENGTH: 18
<212> TYPE: DNA
<213> ORGANISM: Artificial
<220> FEATURE:
<223> OTHER INFORMATION: PAMA forward "peptide" sequence forward primer
<220> FEATURE:
<221> NAME/KEY: misc_feature
<223> OTHER INFORMATION: PAMA forward "peptide" sequence forward primer

<400> SEQUENCE: 205
gcccagccgg ccatggcc                                                    18

<210> SEQ ID NO 206
<211> LENGTH: 25
<212> TYPE: DNA
<213> ORGANISM: Artificial
<220> FEATURE:
<223> OTHER INFORMATION: Synthetic Myc forward 1 primer (Version A for
      Frame 2 and 3)
<220> FEATURE:
<221> NAME/KEY: misc_feature
<223> OTHER INFORMATION: Myc forward 1 primer (Version A for Frame 2 and
      3)

<400> SEQUENCE: 206
ggccgccgaa cagaaactga ttagc                                            25

<210> SEQ ID NO 207
<211> LENGTH: 22
<212> TYPE: DNA
<213> ORGANISM: Artificial
<220> FEATURE:
<223> OTHER INFORMATION: Synthetic Myc forward 2 primer (Version A for
      Frame 2 and 3)
<220> FEATURE:
<221> NAME/KEY: misc_feature
<223> OTHER INFORMATION: Myc forward 2 primer (Version B for Frame 2 and
      3)

<400> SEQUENCE: 207
gatggccgcc gaacagaaac tg                                               22

<210> SEQ ID NO 208
<211> LENGTH: 55
<212> TYPE: DNA
<213> ORGANISM: Artificial
<220> FEATURE:
<223> OTHER INFORMATION: Synthetic Myc Frame 2 forward primer
<220> FEATURE:
<221> NAME/KEY: misc_feature
<223> OTHER INFORMATION: Myc Frame 2 forward primer

<400> SEQUENCE: 208
ccgaacagaa actgattagc gaagaagatc tgcccgggtt gcccgcccag gtggc           55

<210> SEQ ID NO 209
<211> LENGTH: 53
<212> TYPE: DNA
<213> ORGANISM: Artificial
<220> FEATURE:
<223> OTHER INFORMATION: Synthetic Myc Frame 3 forward primer
<220> FEATURE:
<221> NAME/KEY: misc_feature
<223> OTHER INFORMATION: Myc Frame 3 forward primer
```

-continued

```
<400> SEQUENCE: 209
ccgaacagaa actgattagc gaagaagatc tgcccgggtt tgcccgccca ggt        53

<210> SEQ ID NO 210
<211> LENGTH: 36
<212> TYPE: DNA
<213> ORGANISM: Artificial
<220> FEATURE:
<223> OTHER INFORMATION: TNFR2 reverse primer
<220> FEATURE:
<221> NAME/KEY: misc_feature
<223> OTHER INFORMATION: TNFR2 reverse primer

<400> SEQUENCE: 210
gattttcgcg gccgcgtcgc cagtgctccc ttcagc                           36

<210> SEQ ID NO 211
<211> LENGTH: 54
<212> TYPE: DNA
<213> ORGANISM: Artificial
<220> FEATURE:
<223> OTHER INFORMATION: Synthetic forward ligation primer
<220> FEATURE:
<221> NAME/KEY: misc_feature
<223> OTHER INFORMATION: Forward ligation primer

<400> SEQUENCE: 211
tgttcctttc tatgcggccc agccggccat ggcgatggtg cggactaaag caga        54

<210> SEQ ID NO 212
<211> LENGTH: 54
<212> TYPE: DNA
<213> ORGANISM: Artificial
<220> FEATURE:
<223> OTHER INFORMATION: Synthetic reverse ligation primer
<220> FEATURE:
<221> NAME/KEY: misc_feature
<223> OTHER INFORMATION: Reverse ligation primer

<400> SEQUENCE: 212
cgaaatcttt tggactcaca ctgcggccgc ttcttttcca tcatttgtgt gatc        54

<210> SEQ ID NO 213
<211> LENGTH: 30
<212> TYPE: DNA
<213> ORGANISM: Artificial
<220> FEATURE:
<223> OTHER INFORMATION: Synthetic forward cloning primer
<220> FEATURE:
<221> NAME/KEY: misc_feature
<223> OTHER INFORMATION: Forward cloning primer

<400> SEQUENCE: 213
ccctgaggag cgatgacgga atataagctg                                  30

<210> SEQ ID NO 214
<211> LENGTH: 30
<212> TYPE: DNA
<213> ORGANISM: Artificial
<220> FEATURE:
<223> OTHER INFORMATION: Synthetic reverse cloning primer
<220> FEATURE:
<221> NAME/KEY: misc_feature
<223> OTHER INFORMATION: Reverse cloning primer

<400> SEQUENCE: 214
gtccccctca cctgcgtcag gagagcacac                                  30
```

```
<210> SEQ ID NO 215
<211> LENGTH: 34
<212> TYPE: DNA
<213> ORGANISM: Artificial
<220> FEATURE:
<223> OTHER INFORMATION: Synthetic activation forward primer
<220> FEATURE:
<221> NAME/KEY: misc_feature
<223> OTHER INFORMATION: Activation forward primer

<400> SEQUENCE: 215
atgacggaat ataagctggt ggtggtggtc gccg                              34

<210> SEQ ID NO 216
<211> LENGTH: 25
<212> TYPE: DNA
<213> ORGANISM: Artificial
<220> FEATURE:
<223> OTHER INFORMATION: Synthetic forward cloning oligo
<220> FEATURE:
<221> NAME/KEY: misc_feature
<223> OTHER INFORMATION: Forward cloning oligo

<400> SEQUENCE: 216
ccatcctggg aaggaaaatg cattg                                        25

<210> SEQ ID NO 217
<211> LENGTH: 30
<212> TYPE: DNA
<213> ORGANISM: Artificial
<220> FEATURE:
<223> OTHER INFORMATION: Synthetic reverse cloning oligo
<220> FEATURE:
<221> NAME/KEY: misc_feature
<223> OTHER INFORMATION: Reverse cloning oligo

<400> SEQUENCE: 217
agggaaattg acagagtcct ggataagggg                                   30

<210> SEQ ID NO 218
<211> LENGTH: 48
<212> TYPE: DNA
<213> ORGANISM: Artificial
<220> FEATURE:
<223> OTHER INFORMATION: Synthetic Hras forward primer
<220> FEATURE:
<221> NAME/KEY: misc_feature
<223> OTHER INFORMATION: Hras forward primer

<400> SEQUENCE: 218
cttaaagctt ggcccagccg gccatggcgg aatataagct ggtggtgg               48

<210> SEQ ID NO 219
<211> LENGTH: 45
<212> TYPE: DNA
<213> ORGANISM: Artificial
<220> FEATURE:
<223> OTHER INFORMATION: Synthetic Leptin ligand forward primer
<220> FEATURE:
<221> NAME/KEY: misc_feature
<223> OTHER INFORMATION: Leptin ligand forward primer

<400> SEQUENCE: 219
gcggcccagc cggccatggc gcattgggga accctgtgcg gattc                  45

<210> SEQ ID NO 220
<211> LENGTH: 49
<212> TYPE: DNA
<213> ORGANISM: Artificial
```

<220> FEATURE:
<223> OTHER INFORMATION: Synthetic Hras reverse primer
<220> FEATURE:
<221> NAME/KEY: misc_feature
<223> OTHER INFORMATION: Hras reverse primer

<400> SEQUENCE: 220
gcaattctct gagctcgcgg ccgcggagag cacacacttg cagctcatg          49

<210> SEQ ID NO 221
<211> LENGTH: 41
<212> TYPE: DNA
<213> ORGANISM: Artificial
<220> FEATURE:
<223> OTHER INFORMATION: Synthetic Leptin ligand reverse primer
<220> FEATURE:
<221> NAME/KEY: misc_feature
<223> OTHER INFORMATION: Leptin ligand reverse primer

<400> SEQUENCE: 221
gattccttgc ggccgcgcac ccagggctga ggtccagctg c                  41

<210> SEQ ID NO 222
<211> LENGTH: 13
<212> TYPE: PRT
<213> ORGANISM: Escherichia coli
<220> FEATURE:
<221> NAME/KEY: MISC_FEATURE
<223> OTHER INFORMATION: E-tag epitope

<400> SEQUENCE: 222

Gly Ala Pro Val Pro Tyr Pro Asp Pro Leu Glu Pro Arg
1               5                   10

<210> SEQ ID NO 223
<211> LENGTH: 36
<212> TYPE: DNA
<213> ORGANISM: Artificial
<220> FEATURE:
<223> OTHER INFORMATION: Synthetic DGI-2 KpnI forward primer
<220> FEATURE:
<221> NAME/KEY: misc_feature
<223> OTHER INFORMATION: DGI-2 Kpn I forward primer

<400> SEQUENCE: 223
ggatccgggt accatggtgc ggactaaagc agacag                        36

<210> SEQ ID NO 224
<211> LENGTH: 39
<212> TYPE: DNA
<213> ORGANISM: Artificial
<220> FEATURE:
<223> OTHER INFORMATION: Synthetic DGI-2 Hind III reverse primer
<220> FEATURE:
<221> NAME/KEY: misc_feature
<223> OTHER INFORMATION: DGI-2 Hind III reverse primer

<400> SEQUENCE: 224
ggccagaagc ttttcttttt catcatttgt gtgatcagg                     39

<210> SEQ ID NO 225
<211> LENGTH: 32
<212> TYPE: DNA
<213> ORGANISM: Artificial
<220> FEATURE:
<223> OTHER INFORMATION: Synthetic DGI-2 Nde I forward primer
<220> FEATURE:
<221> NAME/KEY: misc_feature
<223> OTHER INFORMATION: DGI 2 Nde I forward primer

```
<400> SEQUENCE: 225
gatctacata tggtgcggac taaagcagac ag                                    32

<210> SEQ ID NO 226
<211> LENGTH: 42
<212> TYPE: DNA
<213> ORGANISM: Artificial
<220> FEATURE:
<223> OTHER INFORMATION: Synthetic DGI-2 Hind III reverse primer
<220> FEATURE:
<221> NAME/KEY: misc_feature
<223> OTHER INFORMATION: DGI 2 Hind III reverse primer

<400> SEQUENCE: 226
gatggccagg tcgacttctt tttcatcatt tgtgtgatca gg                         42

<210> SEQ ID NO 227
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-H9

<400> SEQUENCE: 227

Leu Leu Arg Arg Val Ala Met Gln His Lys Ser Phe Leu Leu Val His
 1               5                  10                  15

Gly Trp Val Val
            20

<210> SEQ ID NO 228
<211> LENGTH: 25
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-G8

<400> SEQUENCE: 228

Ala Ile Met Arg Cys Gly Leu Val Gly Val Gln Arg Ile Trp Phe Arg
 1               5                  10                  15

Leu Phe Gly Asn Pro Gly Arg Ser Asp
            20                  25

<210> SEQ ID NO 229
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-E5

<400> SEQUENCE: 229

Gly Thr Lys Leu Ser Val Ser Leu Gln Trp Pro Ala Trp Gln Ala Arg
 1               5                  10                  15

Trp Phe Leu Val
            20

<210> SEQ ID NO 230
<211> LENGTH: 25
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-C10
```

-continued

```
<400> SEQUENCE: 230

Gly Leu Ile Leu Cys Pro Gln Arg Ala Phe Ala Ala Leu Val Leu Leu
1               5                   10                  15
Arg Ser Cys Leu Arg Gly Gly Val Pro
            20                  25

<210> SEQ ID NO 231
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-B5

<400> SEQUENCE: 231

Gln Arg Ser Ala Pro Lys Gly Cys Gly Gly Ser Ser Arg Gly Val Ser
1               5                   10                  15
Gly Gly Cys Gly
            20

<210> SEQ ID NO 232
<211> LENGTH: 25
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-D8

<400> SEQUENCE: 232

Arg Ser Gln Arg Cys Arg Thr Leu Ser Val Ile Met Glu Cys Cys Glu
1               5                   10                  15
Met Ser Ala Val Ala Arg Leu Trp Arg
            20                  25

<210> SEQ ID NO 233
<211> LENGTH: 25
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-C5

<400> SEQUENCE: 233

Val Ala Arg Ala Cys Tyr Gly Leu Val Ala Gly Phe Arg Leu Val Arg
1               5                   10                  15
Gly Ala Gly Asp Arg Gly Asp Cys Glu
            20                  25

<210> SEQ ID NO 234
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-E8

<400> SEQUENCE: 234

Ser Glu Val Ser Gly Val Val Leu Glu Leu Gln Arg Asp Arg Met Trp
1               5                   10                  15
Arg His Gly Arg
            20
```

```
<210> SEQ ID NO 235
<211> LENGTH: 17
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-A8

<400> SEQUENCE: 235

His Ser Gly Ser Gly Arg Val Ala Ala Gly Leu Asp Ser Gln Gly Arg
1               5                   10                  15

Ala

<210> SEQ ID NO 236
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-F10

<400> SEQUENCE: 236

Asp Arg Thr Thr Arg Val Ala Leu Pro Arg Gly Ser Ala Gln Ser Glu
1               5                   10                  15

Cys Met Gly Phe
            20

<210> SEQ ID NO 237
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-F11

<400> SEQUENCE: 237

Ser Gly Ala Leu Ala Gly Arg Arg Val Val Gly Phe Phe Gln Cys Ala
1               5                   10                  15

Pro Glu Ser Gly
            20

<210> SEQ ID NO 238
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-B6

<400> SEQUENCE: 238

Thr Ile Thr Gly Trp Val Gln Gly Ile Trp Gly Arg Asp Phe Ala Arg
1               5                   10                  15

Gly Ile Gln Ser
            20

<210> SEQ ID NO 239
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-E6
```

-continued

```
<400> SEQUENCE: 239

Ala Ser Ala Gly Asp Ala Arg Gln Arg Gly Asp Gly Ala Pro Phe Ser
1               5                   10                  15

Ala Arg Val Arg
            20

<210> SEQ ID NO 240
<211> LENGTH: 25
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-B9

<400> SEQUENCE: 240

Gly Gly Gly Gly Cys Gly Gly Val Asn Glu Leu Gly Leu Val Val Arg
1               5                   10                  15

Leu Val Gly Ala Leu Ser Arg Val Leu
            20                  25

<210> SEQ ID NO 241
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-D6

<400> SEQUENCE: 241

Gly Ile Arg His Gln Arg Leu Arg Gly Trp Gln Val Gly Arg Val Gly
1               5                   10                  15

Asp Gly Arg Glu
            20

<210> SEQ ID NO 242
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-B10

<400> SEQUENCE: 242

Arg Gly Gly Gln Arg Cys Gln Val Met Met Cys Arg Lys Gly Trp Val
1               5                   10                  15

Val Ala Arg Arg
            20

<210> SEQ ID NO 243
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-B12

<400> SEQUENCE: 243

Gln Val Gly Glu Asn Ser Asp Gln Leu Gly Cys Gly Gly Ala Trp His
1               5                   10                  15

Val Leu Glu Gln
            20
```

<210> SEQ ID NO 244
<211> LENGTH: 20
<212> TYPE: PRT
<213> ORGANISM: Eschericia coli
<220> FEATURE:
<221> NAME/KEY: MISC_FEATURE
<223> OTHER INFORMATION: 07902-DGI2-20M-PP-BC-D11

<400> SEQUENCE: 244

Trp Ala Arg Gln Arg Leu Asn Glu Pro Ile Leu Gly Arg Gly Trp Asn
1               5                   10                  15

Ile Glu Gln Trp
            20

<210> SEQ ID NO 245
<211> LENGTH: 23
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-E5

<400> SEQUENCE: 245

Gln Trp Gly Gln Gly Pro Thr Val Ser Ile Ala Ser Trp Val Leu Ser
1               5                   10                  15

Leu Arg Arg Asp Arg Gly Gly
            20

<210> SEQ ID NO 246
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-C9

<400> SEQUENCE: 246

Ala Arg Gly Gly Gly Gly Trp Ala Arg Gln Asp Ser Leu Ala Leu Cys
1               5                   10                  15

Ser Arg Cys Arg
            20

<210> SEQ ID NO 247
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-B9

<400> SEQUENCE: 247

Asp Gln Ser Arg Ser Cys Pro Val Ala Pro Cys Gly Gly Arg Trp Ser
1               5                   10                  15

Val Thr Val Ser
            20

<210> SEQ ID NO 248
<211> LENGTH: 21
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-H11

-continued

```
<400> SEQUENCE: 248

Ala Leu Leu Gly Arg Arg Arg Asn Phe Leu Gly Pro Gly Gly Ser Asn
1               5                   10                  15

Gly Pro Thr Trp Gly
            20

<210> SEQ ID NO 249
<211> LENGTH: 17
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-H10

<400> SEQUENCE: 249

Glu Val Gly Trp Trp Ala Asp Leu Leu Pro Arg Arg Leu Arg Arg Gly
1               5                   10                  15

Arg

<210> SEQ ID NO 250
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-G12

<400> SEQUENCE: 250

Gly Cys Arg Ser His Tyr Glu Ser Thr Gly Gly Tyr Ala Arg Ala Arg
1               5                   10                  15

Ala Ile Glu Gln
            20

<210> SEQ ID NO 251
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-E8

<400> SEQUENCE: 251

Gly Phe Gly Val Arg Val Arg Leu Leu Ala His Arg Gln Glu Arg Gly
1               5                   10                  15

Cys Ser Ser Ile
            20

<210> SEQ ID NO 252
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-B3

<400> SEQUENCE: 252

Gly Gly Gly Ser Glu Gly Asp Gly Gly Ser Pro Ala Gly Gly Gly Asp
1               5                   10                  15

Val Gly Thr Leu
            20
```

```
<210> SEQ ID NO 253
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-F12

<400> SEQUENCE: 253

Gly Gly Val Leu Asp Ala Arg His Gly Ser Gln Arg Arg Cys Leu Leu
1               5                   10                  15

Trp Gly Ile Trp
            20

<210> SEQ ID NO 254
<211> LENGTH: 28
<212> TYPE: PRT
<213> ORGANISM: Escherichia coli
<220> FEATURE:
<221> NAME/KEY: MISC_FEATURE
<223> OTHER INFORMATION: 0700902-Hras-20M-PP-BC-G11

<400> SEQUENCE: 254

Gly Arg Gln Arg Phe Leu Cys Ile Ala Phe Cys Ala Trp Glu Ser Leu
1               5                   10                  15

Ala Pro Asp Leu Pro Ser Thr Ser Ser Thr Ala Leu
            20                  25

<210> SEQ ID NO 255
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-D9

<400> SEQUENCE: 255

Gly Arg Ala Ile Cys Arg Arg Val Gly Ala Arg Cys Ser Gln Arg Ser
1               5                   10                  15

Ala Ile Ala Val Gly Gly Ala Trp Leu
            20                  25

<210> SEQ ID NO 256
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-H8

<400> SEQUENCE: 256

Gly Arg Leu Arg Cys Leu Pro His Arg Gly Arg Gly Arg Arg Phe Arg
1               5                   10                  15

Gly Arg Pro Cys Gly Gly Gly Ser Met
            20                  25

<210> SEQ ID NO 257
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-C2
```

```
<400> SEQUENCE: 257

Gly Arg Arg Gly Cys Gly Trp Arg Val Gln Pro Glu Leu Ala Gln Val
1               5                   10                  15

Tyr Gly Ser Gly
            20

<210> SEQ ID NO 258
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-G4

<400> SEQUENCE: 258

Gly Val Gly Gly Lys Gly Arg Tyr Gln Trp Gly Gln Arg Asn Gly Gly
1               5                   10                  15

Gly Gly Phe Ser
            20

<210> SEQ ID NO 259
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-D8

<400> SEQUENCE: 259

Gly Val Arg Arg Gly Gly Gly Val Gln Arg Glu Arg Glu Leu Trp Val
1               5                   10                  15

Gly Leu Val Thr
            20

<210> SEQ ID NO 260
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-D10

<400> SEQUENCE: 260

His Arg Pro Pro Cys Asn Gln Tyr Val Tyr Leu Pro Gln Ile Ile Arg
1               5                   10                  15

Thr Met Thr Ala Ser Gly Leu Gly Ser
            20                  25

<210> SEQ ID NO 261
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-G8

<400> SEQUENCE: 261

Lys Gly Leu Phe Met Thr Gly Leu Gln Ser Gly Cys Met Arg Arg Val
1               5                   10                  15

Gln Gly Glu Gln
            20
```

```
<210> SEQ ID NO 262
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-F10

<400> SEQUENCE: 262

Leu Leu Ser Leu Cys Arg Leu Thr Val Ser Glu Ser Trp Arg Glu Leu
 1               5                  10                  15

Arg Val Leu Gly Val Gly Arg Gly Tyr
            20                  25

<210> SEQ ID NO 263
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-A7

<400> SEQUENCE: 263

Leu Arg Cys Leu Cys Pro Leu Gly Leu Glu Met Pro Ser Trp Cys Gly
 1               5                  10                  15

Tyr Asp Ser Gln Ala Phe Gly Tyr Gly
            20                  25

<210> SEQ ID NO 264
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-C10

<400> SEQUENCE: 264

Leu Val Ile Ser Leu Ser Gly Gly Val Asn Ser His Phe Ala Val Cys
 1               5                  10                  15

Val Arg Phe Gly
            20

<210> SEQ ID NO 265
<211> LENGTH: 25
<212> TYPE: PRT
<213> ORGANISM: Escherichia coli
<220> FEATURE:
<221> NAME/KEY: MISC_FEATURE
<223> OTHER INFORMATION: 0700902-Hras-20M-PP-BC-A2

<400> SEQUENCE: 265

Pro Ala Met Gly Gly Leu Gln Arg Gln Val Glu Phe Ala Trp Cys Val
 1               5                  10                  15

Val Gly Gly Lys Gly Leu Val Tyr Val
            20                  25

<210> SEQ ID NO 266
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-C11
```

-continued

```
<400> SEQUENCE: 266

Arg Asp Trp Ala Val Arg Val Val Gly Asp Val Lys Arg Gln Gln Cys
1               5                   10                  15

Ala Thr Phe Gly
            20

<210> SEQ ID NO 267
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-C3

<400> SEQUENCE: 267

Arg Glu Tyr Asn Arg Pro Val Leu Leu Arg Arg Gly Glu Ser Gly Leu
1               5                   10                  15

Ser Leu Leu Phe
            20

<210> SEQ ID NO 268
<211> LENGTH: 24
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-E3

<400> SEQUENCE: 268

Arg Phe Leu Ala Ser Cys Arg Val Leu Arg Arg Ala His Leu Gly Trp
1               5                   10                  15

Arg Gly Ser Ala Gln Ser Ala Ala
            20

<210> SEQ ID NO 269
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-C7

<400> SEQUENCE: 269

Arg Arg Arg Ala Ala Tyr Leu Ser Gly Met Leu Ala Gly Thr Gly Ala
1               5                   10                  15

Gln Asn Gln Arg
            20

<210> SEQ ID NO 270
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-B10

<400> SEQUENCE: 270

Arg Thr Ala Val Cys His Phe Thr Ser Gly Phe Ser Gly Trp Gly Tyr
1               5                   10                  15

Gln Trp Leu Val Val Val Thr Trp Gly
            20                  25
```

<210> SEQ ID NO 271
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-E9

<400> SEQUENCE: 271

Ser Gln Gly Ala Arg Gly Gly Pro Arg Gly Arg Gly Cys Gly Gly Arg
1               5                   10                  15

Phe Asn Gly Gln
            20

<210> SEQ ID NO 272
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-D12

<400> SEQUENCE: 272

Ser Arg Arg Gly Trp Ile Cys Gly Thr Arg Gln Gly Ala Cys Val Trp
1               5                   10                  15

Gly Ser Val His
            20

<210> SEQ ID NO 273
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-C4

<400> SEQUENCE: 273

Ser Arg Val Arg Arg Trp Gln Gln Pro His Cys Gly Val Ser Gly Gly
1               5                   10                  15

Ile Met Thr Met
            20

<210> SEQ ID NO 274
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-G9

<400> SEQUENCE: 274

Ser Ser Lys Ser Cys His Ser Arg Pro Ser Val Ala Ile Phe Gln Ala
1               5                   10                  15

Ser Gln Ala Ala Cys Thr Trp His Leu
            20                  25

<210> SEQ ID NO 275
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-B6

-continued

```
<400> SEQUENCE: 275

Ser Val Ala Arg Gly Asp Pro Trp Phe Ser Arg Gly Val Gly Gly
1               5                   10                  15

Gly Ile Gln Pro
            20

<210> SEQ ID NO 276
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-B7

<400> SEQUENCE: 276

Ser Val Ala Arg Gly Asp Pro Trp Phe Ser Arg Gly Val Gly Gly
1               5                   10                  15

Gly Ile Gln Pro
            20

<210> SEQ ID NO 277
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-B4

<400> SEQUENCE: 277

Ser Trp Ala Gln Cys Gly Phe Arg Ala Arg Pro Gly Arg Val Gly Gly
1               5                   10                  15

Trp Val Arg Pro Ser Ile Arg Leu Ala
            20                  25

<210> SEQ ID NO 278
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-F5

<400> SEQUENCE: 278

Thr Val Met Asp Val Arg Arg Arg Ala Tyr Gly Gly Val Arg Arg Met
1               5                   10                  15

Pro Val Phe Arg
            20

<210> SEQ ID NO 279
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-C8

<400> SEQUENCE: 279

Val Ala Trp Ile Cys Leu Asp Ala Asn Gln Gly Gly Asp Gln Phe Phe
1               5                   10                  15

Thr Ala Leu Met Cys Pro Leu Tyr Pro
            20                  25
```

<210> SEQ ID NO 280
<211> LENGTH: 19
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-G1

<400> SEQUENCE: 280

Val Asn Leu Arg Ile Thr Val Asp Val Ala Lys Leu Val Gln Asp Gly
1               5                   10                  15

Thr Arg Trp

<210> SEQ ID NO 281
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-B2

<400> SEQUENCE: 281

Val Arg Glu His Trp Met Gly Arg His Arg Ser Thr Val Gly Leu Gly
1               5                   10                  15

Arg Asn Ala Arg
            20

<210> SEQ ID NO 282
<211> LENGTH: 20
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-D3

<400> SEQUENCE: 282

Trp Gly Ser Cys Lys Cys Arg Arg Pro Trp Val Gly Ala Val Gln Arg
1               5                   10                  15

Gly Ala Asp Phe
            20

<210> SEQ ID NO 283
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-H9

<400> SEQUENCE: 283

Tyr Gln Gln Ser Cys Ser Arg Tyr Arg Gly Trp Leu Pro Ser Arg Leu
1               5                   10                  15

Ile Pro Asp Glu Pro Pro Thr Leu Ala
            20                  25

<210> SEQ ID NO 284
<211> LENGTH: 25
<212> TYPE: PRT
<213> ORGANISM: Eschericia coli
<220> FEATURE:
<221> NAME/KEY: MISC_FEATURE
<223> OTHER INFORMATION: 0700902-Hras-20M-PP-BC-B5

```
<400> SEQUENCE: 284

Tyr Met Arg His Cys Ser Gly Tyr Val Arg Thr Val Arg Met Ser Arg
1               5                   10                  15

Thr Ile Arg Thr Gly Gly Arg Gly Gly
            20                  25

<210> SEQ ID NO 285
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-E1

<400> SEQUENCE: 285

Met Gly His Met Pro Tyr Arg Ile Met Arg Asp Gly Ser Phe Asp Val
1               5                   10                  15

Arg His Glu Gly
            20

<210> SEQ ID NO 286
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-A5

<400> SEQUENCE: 286

His Thr Gly Arg Leu Phe Asn Ser Phe Phe Gly Trp Pro Ser Phe Phe
1               5                   10                  15

Arg Ser Trp Glu
            20

<210> SEQ ID NO 287
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-H311

<400> SEQUENCE: 287

Met Thr Pro Met Gly Gly Trp Arg Asp Pro Arg Leu Gly Ser Pro Val
1               5                   10                  15

Ser His Val Gly
            20

<210> SEQ ID NO 288
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-D2

<400> SEQUENCE: 288

Met Thr Val His Arg Leu Ile Phe Thr Gly Asp Lys Gly Arg Ala Tyr
1               5                   10                  15

Tyr Ser Val Pro
            20
```

```
<210> SEQ ID NO 289
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-C6

<400> SEQUENCE: 289

Leu Thr Val Pro Gly Ile Phe Gln His Arg Gln Ala Ala Phe Leu Arg
 1               5                  10                  15

Gly Ser Ser Gly
            20

<210> SEQ ID NO 290
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-A7

<400> SEQUENCE: 290

Met Thr Trp Arg Gly His Pro Ala Ser Gln Phe Arg Leu Asp Gly Arg
 1               5                  10                  15

Pro Ala Phe Val
            20

<210> SEQ ID NO 291
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-H1

<400> SEQUENCE: 291

Gly His Phe Ser Arg Pro Pro Val Leu Gly Ser Arg Asp Gly Gly Trp
 1               5                  10                  15

Val Arg Ala Met
            20

<210> SEQ ID NO 292
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-B12

<400> SEQUENCE: 292

Gly Arg Thr Cys Ser Ser Trp Phe Ala Pro Ile Gly Cys Ala Phe Asp
 1               5                  10                  15

Val Arg Gly Arg
            20

<210> SEQ ID NO 293
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-C7
```

```
<400> SEQUENCE: 293

Met Thr Leu His Ser Pro Tyr Phe Ala Arg Val Asn Pro Asn Gly Ser
1               5                   10                  15

Ser Val Ser Val
            20

<210> SEQ ID NO 294
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-G2

<400> SEQUENCE: 294

Met Thr Met Thr Pro Gln Ala Leu Phe Arg Pro Ala Trp Glu Arg Gly
1               5                   10                  15

Ser Tyr Met Gly
            20

<210> SEQ ID NO 295
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-F2

<400> SEQUENCE: 295

Leu Thr Arg Leu Pro Pro Asp Arg His Tyr Ser Phe Gly Glu Arg Ser
1               5                   10                  15

Arg Val Pro Thr
            20

<210> SEQ ID NO 296
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-A8

<400> SEQUENCE: 296

Met Ala Thr Val Asn Gly His Tyr Pro Ala Pro Leu Ile Arg Arg Ala
1               5                   10                  15

Pro Ser Thr Thr
            20

<210> SEQ ID NO 297
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-C4

<400> SEQUENCE: 297

Leu Ser Arg Tyr Pro Val Leu Ser Thr Ser His Leu Pro Arg Asn Arg
1               5                   10                  15

Asp Ile Pro Gly
            20
```

-continued

```
<210> SEQ ID NO 298
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-D1

<400> SEQUENCE: 298

Leu Thr His Arg Ala Val Leu Glu Tyr Pro Gly Ile Ser Ser Gly Gly
1               5                   10                  15

Ala Phe His Gln
            20

<210> SEQ ID NO 299
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-E3

<400> SEQUENCE: 299

Met Thr Arg Tyr Gly Gly Pro Phe Ser Gly Val Phe Pro Leu Thr Pro
1               5                   10                  15

Arg Gly Thr Gly
            20

<210> SEQ ID NO 300
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-G3

<400> SEQUENCE: 300

Met Ile Leu Gly Pro Arg Gly Met Val Thr His Ser Gln His Glu Arg
1               5                   10                  15

Gly Ser Asn His
            20

<210> SEQ ID NO 301
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-G43

<400> SEQUENCE: 301

Met Thr Ala Leu Asn Tyr Arg Gly Gly Ser Trp Gly Leu Asn Gly Gly
1               5                   10                  15

Gln Gly Arg Leu
            20

<210> SEQ ID NO 302
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-E4
```

-continued

```
<400> SEQUENCE: 302

Met Gly Arg Leu Pro Pro Met Gly Leu Val Gly Glu Arg Gly Gly Leu
1               5                   10                  15

Arg Pro Phe Ile
            20

<210> SEQ ID NO 303
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-D6

<400> SEQUENCE: 303

Phe Val Arg Val Pro Leu Leu His Val Glu Gly Arg Gly Gly Pro Leu
1               5                   10                  15

Arg His Ile Asp
            20

<210> SEQ ID NO 304
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-C2

<400> SEQUENCE: 304

Met Thr Val Gly Pro Trp Arg Asp Arg Val Ala Ser Ser Ala Pro Asp
1               5                   10                  15

Gly Leu Trp Phe
            20

<210> SEQ ID NO 305
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-G6

<400> SEQUENCE: 305

Leu Ser Arg Met Pro Asp Arg Lys Val Val Asp Pro Arg Ser Tyr Arg
1               5                   10                  15

Leu Gly Trp Thr
            20

<210> SEQ ID NO 306
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-A2

<400> SEQUENCE: 306

Met Thr Pro Gln Phe Leu Ile Pro Ser Pro Ser His Ser Ala Arg Val
1               5                   10                  15

Gly Thr Arg Gly
            20
```

```
<210> SEQ ID NO 307
<211> LENGTH: 21
<212> TYPE: PRT
<213> ORGANISM: Eschericia coli
<220> FEATURE:
<221> NAME/KEY: MISC_FEATURE
<223> OTHER INFORMATION: DGI5-20M-4-F12

<400> SEQUENCE: 307

Ala Met Phe Asp Ile Phe Ser Trp Met His Pro Trp Ser Leu Trp Pro
1               5                   10                  15

Gly Ser Ala Ser Gly
            20

<210> SEQ ID NO 308
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-C112

<400> SEQUENCE: 308

Phe Ser Ser Arg Met Ala Leu Pro Leu Thr Ser Tyr Arg Ser Leu Pro
1               5                   10                  15

Ser Ala Gly Gly
            20

<210> SEQ ID NO 309
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-B2

<400> SEQUENCE: 309

Met Ala Pro Arg Leu Pro Asp Thr His Val His Arg Thr Gly Gly Arg
1               5                   10                  15

Ser Ala Met Thr
            20

<210> SEQ ID NO 310
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-B1

<400> SEQUENCE: 310

Met Ser Ser Phe Val Gly Asn Met Ser Pro Pro Trp Thr Gln Ile Arg
1               5                   10                  15

Glu Gly Ser Ser
            20

<210> SEQ ID NO 311
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-D4
```

-continued

```
<400> SEQUENCE: 311

Met Thr Gly Phe Ile Arg Asn Asp Gly Thr Met Ala Arg Gly Val Pro
1               5                   10                  15

Asn Gly Arg Ile
            20

<210> SEQ ID NO 312
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-G1

<400> SEQUENCE: 312

Met Gln Val Gly Arg Trp Gly Thr Asp Arg His Val Glu Asn Gly Arg
1               5                   10                  15

Met Asp Gly Phe
            20

<210> SEQ ID NO 313
<211> LENGTH: 21
<212> TYPE: PRT
<213> ORGANISM: Eschericia coli
<220> FEATURE:
<221> NAME/KEY: MISC_FEATURE
<223> OTHER INFORMATION: DGI5-20M-4-A3

<400> SEQUENCE: 313

Phe Thr Thr Ser Arg Leu Gly Pro Gln Cys Val Ala Arg Ile Val Leu
1               5                   10                  15

Ser Leu Leu Ala Met
            20

<210> SEQ ID NO 314
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-F3

<400> SEQUENCE: 314

Met Ala Leu Ile Pro Arg Ala Tyr Gln Pro Asp Gly Val Gly Gly Val
1               5                   10                  15

Asp Ser Tyr Asp
            20

<210> SEQ ID NO 315
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-A9

<400> SEQUENCE: 315

Met Gly Gly Arg Trp Trp His Ala Ala Asp Gly Asp Val Met Gly Val
1               5                   10                  15

Pro Lys Gly Val
            20
```

```
<210> SEQ ID NO 316
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-E6

<400> SEQUENCE: 316

Phe Pro Phe Arg Ser Met Trp Gln His Phe Trp Gly Pro Ala Gly Val
1               5                   10                  15

Pro Tyr Ile Glu
            20

<210> SEQ ID NO 317
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-B9

<400> SEQUENCE: 317

Val Thr Pro Phe Pro Arg Ile Ala Ser Gly Ser Trp Pro Gly Val Val
1               5                   10                  15

Arg Asp Trp Asp
            20

<210> SEQ ID NO 318
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-F5

<400> SEQUENCE: 318

Phe Ser Arg Val Pro Ser Pro Phe His Cys Ile Gly Gln Ala Cys Thr
1               5                   10                  15

Pro Ser Arg Val
            20

<210> SEQ ID NO 319
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-E7

<400> SEQUENCE: 319

Met Gly Pro Arg Trp Val Gly Glu Asp Phe Asn Thr Asp Arg Gly Arg
1               5                   10                  15

Phe Arg Tyr Pro
            20

<210> SEQ ID NO 320
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-E8
```

-continued

<400> SEQUENCE: 320

His Gly Leu Glu Ala Ile Ala Met Thr Arg Val Pro Trp Glu Met Gly
1               5                   10                  15

Tyr Pro Asp Ser
            20

<210> SEQ ID NO 321
<211> LENGTH: 19
<212> TYPE: PRT
<213> ORGANISM: Eschericia coli
<220> FEATURE:
<221> NAME/KEY: MISC_FEATURE
<223> OTHER INFORMATION: DGI5-20M-4-G10

<400> SEQUENCE: 321

Met Gly Val His Arg Gly Leu Ile Pro Arg Leu Asp Arg Ser Trp Glu
1               5                   10                  15

Glu Gln Thr

<210> SEQ ID NO 322
<211> LENGTH: 21
<212> TYPE: PRT
<213> ORGANISM: Eschericia coli
<220> FEATURE:
<221> NAME/KEY: MISC_FEATURE
<223> OTHER INFORMATION: DGI5-20M-4-E12

<400> SEQUENCE: 322

Ala Leu Ser Ile Pro Gly Leu Met Val Asp Arg Trp Leu Ser Gly Pro
1               5                   10                  15

Ala Ser Asp Arg Arg
            20

<210> SEQ ID NO 323
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-A6

<400> SEQUENCE: 323

Met Ser Met Phe Gln Gln Arg Gly Tyr Trp Ser Asn Gln Glu Gly Arg
1               5                   10                  15

Trp Ser Gly Ser
            20

<210> SEQ ID NO 324
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-F6

<400> SEQUENCE: 324

Leu Thr Thr Trp Leu Pro Thr Trp Tyr Val Arg Gly Ser Ala Ala Thr
1               5                   10                  15

Gln Gly Glu Phe
            20

<210> SEQ ID NO 325
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-H7

<400> SEQUENCE: 325

Phe Thr Ala Arg Asn Leu Ala Asp Pro Arg Met Pro Ala Trp Gly Ser
1               5                   10                  15

Arg Val Thr Val
            20

<210> SEQ ID NO 326
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI5-20M-4-D12

<400> SEQUENCE: 326

Met Gly Arg Ala Pro His Trp Ser Asp Pro Val Pro Gly Leu Trp Leu
1               5                   10                  15

Ser Pro Gly Glu
            20

<210> SEQ ID NO 327
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-G22

<400> SEQUENCE: 327

Gly Trp Arg Leu Phe Leu Thr Gly Val Leu Gly Gly Ser Lys Asn Gly
1               5                   10                  15

His Ala Ser Leu
            20

<210> SEQ ID NO 328
<211> LENGTH: 25
<212> TYPE: PRT
<213> ORGANISM: Eschericia coli
<220> FEATURE:
<221> NAME/KEY: MISC_FEATURE
<223> OTHER INFORMATION: DGI7-20M-4-G118

<400> SEQUENCE: 328

Leu Arg Pro Val Cys Leu Gln Glu Gln Arg Val Ser Phe Phe Gly Asp
1               5                   10                  15

Trp Val Arg Val Ala Leu Phe Ser Ala
            20                  25

<210> SEQ ID NO 329
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-B42

```
<400> SEQUENCE: 329

Leu Trp Arg Gly Trp Ala Glu Trp Val Val Arg Arg Pro Ile Gly Ala
1               5                   10                  15

Ser Ser Thr Gly
            20

<210> SEQ ID NO 330
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-F6

<400> SEQUENCE: 330

Arg Gly Ala Gly Leu Met Gln Trp Phe Gly Trp Tyr Gly Thr Arg Phe
1               5                   10                  15

Gly Gly Ser Arg
            20

<210> SEQ ID NO 331
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-F11

<400> SEQUENCE: 331

Thr Leu Met Arg Trp Gly Leu Leu Gly Arg Gly Ala Leu Ser Val Trp
1               5                   10                  15

Gly Asp Gly Asp
            20

<210> SEQ ID NO 332
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-G9

<400> SEQUENCE: 332

Ser Leu Leu Leu Trp Ala Leu Gln Leu Arg Gly Met Ala Gly Ala Leu
1               5                   10                  15

Thr Ser Gly Ser
            20

<210> SEQ ID NO 333
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-D32

<400> SEQUENCE: 333

Ala Val Arg Ser Trp Arg Leu Phe Leu Ala Gly Ala Leu Gly Ser Arg
1               5                   10                  15

Gly Gly Leu Gly
            20
```

```
<210> SEQ ID NO 334
<211> LENGTH: 29
<212> TYPE: PRT
<213> ORGANISM: Eschericia coli
<220> FEATURE:
<221> NAME/KEY: MISC_FEATURE
<223> OTHER INFORMATION: DGI7-20M-4-E2

<400> SEQUENCE: 334

Gly Thr Met Thr Ser Thr Leu Val Ser Glu Thr Ser Phe Phe Gly Arg
1               5                   10                  15

Ser Arg Thr Met Trp Gln Leu Ile Val Arg Gly Val Gln
            20                  25

<210> SEQ ID NO 335
<211> LENGTH: 23
<212> TYPE: PRT
<213> ORGANISM: Eschericia coli
<220> FEATURE:
<221> NAME/KEY: MISC_FEATURE
<223> OTHER INFORMATION: DGI7-20M-4-G6

<400> SEQUENCE: 335

Leu Leu Arg Tyr Gly Trp Glu Arg Trp Val Val Ala Arg Gln Gly Gln
1               5                   10                  15

Gly Val Gly Asn Gly Ala Pro
            20

<210> SEQ ID NO 336
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-G10

<400> SEQUENCE: 336

Arg Gln Gly Val Glu Met Leu Ala Arg Trp Leu Phe Pro Trp Tyr Arg
1               5                   10                  15

Ser Ser Pro Glu
            20

<210> SEQ ID NO 337
<211> LENGTH: 21
<212> TYPE: PRT
<213> ORGANISM: Eschericia coli
<220> FEATURE:
<221> NAME/KEY: MISC_FEATURE
<223> OTHER INFORMATION: DGI7-20M-4-H9

<400> SEQUENCE: 337

Ala Asp Leu Pro Gly Trp Gly Gly Leu Phe Arg Thr Trp Ala Thr Leu
1               5                   10                  15

Arg Asn Gly Gly Ser
            20

<210> SEQ ID NO 338
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-D12
```

-continued

```
<400> SEQUENCE: 338

Ala Val Leu Gly Trp Gly Trp Ser Trp Asp Gln Trp Val Ser Gly Asp
1               5                   10                  15

Leu Gln Ala Ser
            20

<210> SEQ ID NO 339
<211> LENGTH: 21
<212> TYPE: PRT
<213> ORGANISM: Eschericia coli
<220> FEATURE:
<221> NAME/KEY: MISC_FEATURE
<223> OTHER INFORMATION: DGI7-20M-4-B3

<400> SEQUENCE: 339

Ala Trp Leu Arg Val Leu Ala Glu Arg Arg Trp Gly Gly Ser Gly Ser
1               5                   10                  15

Gln Gly Gly Pro Gly
            20

<210> SEQ ID NO 340
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-E3

<400> SEQUENCE: 340

Phe Ile Arg Gly Trp Val Trp Ser Phe Pro Leu Thr Gly Arg Ala Val
1               5                   10                  15

Pro Glu Phe Asp
            20

<210> SEQ ID NO 341
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-H2

<400> SEQUENCE: 341

Leu Gly Thr Asp Trp His Ile Leu Gly Ser Ser Ile Trp Arg Leu Ile
1               5                   10                  15

Arg Gly Thr Asp
            20

<210> SEQ ID NO 342
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-H5

<400> SEQUENCE: 342

Arg Arg Cys Leu Gly Ser Trp Leu Val Gly Leu Gly Ala Ile Gly Cys
1               5                   10                  15

Gly Asp Lys Gly
            20
```

```
<210> SEQ ID NO 343
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-G12

<400> SEQUENCE: 343

Ile Arg Thr Ala Glu Val Arg Pro Glu Met Ile Ser Trp Arg Gln Phe
1               5                   10                  15

Phe Ser Leu Trp
            20

<210> SEQ ID NO 344
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-B12

<400> SEQUENCE: 344

Leu Tyr Arg Ser Trp Ala Gln Ala Leu Ile Glu Arg Ala Trp Gly Gly
1               5                   10                  15

Val Ala Ser Ser
            20

<210> SEQ ID NO 345
<211> LENGTH: 14
<212> TYPE: PRT
<213> ORGANISM: Eschericia coli
<220> FEATURE:
<221> NAME/KEY: MISC_FEATURE
<223> OTHER INFORMATION: DGI7-20M-4-C5

<400> SEQUENCE: 345

Arg Glu Trp Ala Ala Gly Trp Ala Ser Phe Leu Gly Arg Leu
1               5                   10

<210> SEQ ID NO 346
<211> LENGTH: 20
<212> TYPE: PRT
<213> ORGANISM: Eschericia coli
<220> FEATURE:
<221> NAME/KEY: MISC_FEATURE
<223> OTHER INFORMATION: DGI7-20M-4-A2

<400> SEQUENCE: 346

Val Phe Arg Gly Ala Thr Thr Trp Gly Arg Ala Trp Asn Ser Val Leu
1               5                   10                  15

Gly Arg Gly Gln
            20

<210> SEQ ID NO 347
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-4-F842
<220> FEATURE:
<221> NAME/KEY: MISC_FEATURE
<222> LOCATION: (14)..(14)
<223> OTHER INFORMATION: X or Q represents a CAG stop
```

```
<400> SEQUENCE: 347

Trp Gly Lys Thr Ala Gly Glu Cys Gly Thr Leu Leu Trp Xaa Met Gly
1               5                   10                  15

Arg Ala Trp Phe
            20

<210> SEQ ID NO 348
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-4-E115

<400> SEQUENCE: 348

Ser Asp Phe Gly Asp Gly Gly Met Ser Leu Leu Trp Arg Leu Ala Arg
1               5                   10                  15

Leu Trp Gly Asn
            20

<210> SEQ ID NO 349
<211> LENGTH: 14
<212> TYPE: PRT
<213> ORGANISM: Eschericia coli
<220> FEATURE:
<221> NAME/KEY: MISC_FEATURE
<223> OTHER INFORMATION: VEGF-20F-4-F22

<400> SEQUENCE: 349

Leu Ser Pro Trp Arg Trp Met Val Trp Pro Ala Glu Arg Arg
1               5                   10

<210> SEQ ID NO 350
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-C7

<400> SEQUENCE: 350

Gly Val Phe Ser His Gln Ala Arg Ala Leu Val Gly Gly Asn Thr Thr
1               5                   10                  15

Pro Asn Ser Arg
            20

<210> SEQ ID NO 351
<211> LENGTH: 21
<212> TYPE: PRT
<213> ORGANISM: Eschericia coli
<220> FEATURE:
<221> NAME/KEY: MISC_FEATURE
<223> OTHER INFORMATION: VEGF-20F-3-C5

<400> SEQUENCE: 351

Phe Phe Pro Met Leu Ser Val Ala Phe Pro Gly Arg Val His Tyr Ala
1               5                   10                  15

Ala Ser Ser Val Ser
            20

<210> SEQ ID NO 352
<211> LENGTH: 20
<212> TYPE: PRT
<213> ORGANISM: Eschericia coli
```

```
<220> FEATURE:
<221> NAME/KEY: MISC_FEATURE
<223> OTHER INFORMATION: VEGF-20F-4-F6

<400> SEQUENCE: 352

Trp Gly Lys Thr Asp Gly Glu Cys Gly Thr Leu Leu Trp Gln Met Gly
1               5                   10                  15

Arg Ala Trp Phe
            20

<210> SEQ ID NO 353
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-D1

<400> SEQUENCE: 353

Met Ala Met Met Asn Phe His Gly Gly Asp Arg Ala Thr Thr Met Val
1               5                   10                  15

Arg Gly Leu Ser
            20

<210> SEQ ID NO 354
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-4-H2

<400> SEQUENCE: 354

Met Ser Met Leu Leu Pro Gly His Asn Pro Pro Tyr Ala Ala Ala His
1               5                   10                  15

Leu Arg His Val
            20

<210> SEQ ID NO 355
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-B112

<400> SEQUENCE: 355

Leu Gln Ile Pro Ser Arg Phe Ile Ser Arg Tyr Thr Ala Gly Gly Asn
1               5                   10                  15

Ser Thr Ser Ser
            20

<210> SEQ ID NO 356
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-4-G4

<400> SEQUENCE: 356

Met Thr Phe Met Gly Ser Arg Trp Val Ser Gly Gly Asn Pro His Trp
1               5                   10                  15

Arg Asn Ile Arg
            20
```

<210> SEQ ID NO 357
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-D32

<400> SEQUENCE: 357

Met Ser Ser His Phe Tyr Arg Ser Pro Gly Ile Gly Met Tyr Ser Gly
1               5                   10                  15

Ala Arg Val Ser
            20

<210> SEQ ID NO 358
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-A25

<400> SEQUENCE: 358

Met Thr Met His Ala Pro Gly Leu Phe Arg Ala Pro Gln Pro Gly Ala
1               5                   10                  15

Gly Gly Asn Arg
            20

<210> SEQ ID NO 359
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-D93

<400> SEQUENCE: 359

Met Ser Arg His Pro Arg Gly Trp Glu Val Leu Asp Gly Val Pro Ser
1               5                   10                  15

Gly Asn Ser Arg
            20

<210> SEQ ID NO 360
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-B7

<400> SEQUENCE: 360

Leu Met Val Pro Gly Val Leu Arg His Ile Pro Arg Gln Gly Pro Phe
1               5                   10                  15

Ile Ala Pro Leu
            20

<210> SEQ ID NO 361
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-D6

-continued

```
<400> SEQUENCE: 361

Met Ser Pro Phe Val Lys Leu Gly Arg Asn Val Pro Thr Gly Glu Arg
1               5                   10                  15

Ala Val Gly Lys
            20

<210> SEQ ID NO 362
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-B9

<400> SEQUENCE: 362

Met Thr Ser Arg Leu Asn Leu Gly Arg His Ala Ser Asp Gly Val Gln
1               5                   10                  15

Ala Gly Val Pro
            20

<210> SEQ ID NO 363
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-D7

<400> SEQUENCE: 363

Leu Ser Ser Arg Leu Gly Leu Leu His Ala Trp Gly Ile Gly Ala Pro
1               5                   10                  15

Leu Arg Pro Arg
            20

<210> SEQ ID NO 364
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-4-E3

<400> SEQUENCE: 364

Leu Thr Leu Phe Ser Ser His Arg Ala Ala Val Gly Pro Pro Ser Gly
1               5                   10                  15

Thr Arg Gly Leu
            20

<210> SEQ ID NO 365
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-B3

<400> SEQUENCE: 365

Leu Ala Arg Pro Phe Val Cys Gly Pro Tyr Leu Phe Gly Arg Trp Gly
1               5                   10                  15

Lys Cys Pro Val
            20
```

<210> SEQ ID NO 366
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-C1

<400> SEQUENCE: 366

Leu Ser Val Val Pro Arg Ser Glu Leu Val Gly Ser Arg Gly Ser Ser
1               5                   10                  15

Ser Ala Pro Thr
            20

<210> SEQ ID NO 367
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-A53

<400> SEQUENCE: 367

Met Gly Asn Arg Gly Val Met Ser Ser Phe His Ser Ser Met Gln Glu
1               5                   10                  15

Gly Gly Gly His
            20

<210> SEQ ID NO 368
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-D10

<400> SEQUENCE: 368

Met Ile Thr Ala Gly Pro Arg Arg His Ile Ser Asn Leu Val His Ser
1               5                   10                  15

Ala Gly Trp Asp
            20

<210> SEQ ID NO 369
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-A1

<400> SEQUENCE: 369

Gly Val Phe Ser His Gln Ala Arg Ala Leu Leu Gly Gly Asn Thr Thr
1               5                   10                  15

Pro Asn Ser Arg
            20

<210> SEQ ID NO 370
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-B4

-continued

```
<400> SEQUENCE: 370

Gly Thr Phe Ala Trp Pro Phe Thr Val Ser Ser Arg Arg Ser Ser Val
1               5                   10                  15

Thr Gly Asp Ala
            20

<210> SEQ ID NO 371
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGF-20F-3-B12

<400> SEQUENCE: 371

Gly Ala Ser Arg Leu Leu Gly Pro Ala Ser Arg Asp Thr Gly Gly
1               5                   10                  15

Val Val Gly Gly
            20

<210> SEQ ID NO 372
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-E1246

<400> SEQUENCE: 372

Leu Gly Phe Gly Ser Gly Ala His Pro Thr Thr Arg Glu Asp Trp Ile
1               5                   10                  15

Glu Leu Phe Arg
            20

<210> SEQ ID NO 373
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-B1

<400> SEQUENCE: 373

Leu Thr Ser Arg Ile His Val Asp Pro Arg Val Arg Trp His Leu Ala
1               5                   10                  15

Arg Glu Gly Ser
            20

<210> SEQ ID NO 374
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-C1

<400> SEQUENCE: 374

Leu Thr Pro Ser Tyr Leu Leu Ser Trp Arg Val Gly Gly His Arg His
1               5                   10                  15

Val Asp Glu His
            20
```

<210> SEQ ID NO 375
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-E12

<400> SEQUENCE: 375

Phe Leu Phe Pro Leu His Phe Leu Ser Pro Trp Ser Val Gly Thr Ser
1               5                   10                  15

His Ser Arg Ile
            20

<210> SEQ ID NO 376
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-G12

<400> SEQUENCE: 376

Met Phe Leu Pro Gly Leu Leu Pro Trp Arg Ala Arg Pro Val Ser His
1               5                   10                  15

Gly Tyr Gly Tyr
            20

<210> SEQ ID NO 377
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-A52

<400> SEQUENCE: 377

Gly Ala Arg Phe Pro Leu Ser Leu Ala Arg Pro Ala Pro Asp Pro Asn
1               5                   10                  15

Val Ala Pro Leu
            20

<210> SEQ ID NO 378
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-C33

<400> SEQUENCE: 378

Met Thr Leu Pro Ser Ser Val Leu Arg Pro Val Arg Gly Pro Ala Leu
1               5                   10                  15

Ser Thr Ser Gly
            20

<210> SEQ ID NO 379
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-D7

```
<400> SEQUENCE: 379

Met Thr Gly Asn Leu Pro Glu Arg Arg Ala Ala Gln Leu Gln His Ala
1               5                   10                  15

His Arg Glu Val
            20

<210> SEQ ID NO 380
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-E22

<400> SEQUENCE: 380

Phe Trp Arg Pro Ser Phe Met His Gly Phe Met Gly His Phe Pro Ala
1               5                   10                  15

Val Thr Gly Ser
            20

<210> SEQ ID NO 381
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-A2

<400> SEQUENCE: 381

Met Phe Pro Leu Tyr His Leu Val Lys Arg Ser Arg Thr Arg Asp Gly
1               5                   10                  15

Ala Val Leu Gly
            20

<210> SEQ ID NO 382
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-D2

<400> SEQUENCE: 382

Leu Ala Arg Pro Leu Ala Met Val Gly Phe Val Arg Asp Ala Trp Leu
1               5                   10                  15

Gly Arg Gly Ser
            20

<210> SEQ ID NO 383
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-H2

<400> SEQUENCE: 383

Phe Tyr Pro Phe Leu Trp Ser Arg Gln Phe Gln Gly Thr Met Ala His
1               5                   10                  15

Arg Gly Met Gly
            20
```

-continued

```
<210> SEQ ID NO 384
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-H3

<400> SEQUENCE: 384

Met Gly Arg Arg Pro Trp Ile Pro Tyr Gln Val Arg Leu Asp Met Gly
1               5                   10                  15

Ser Gln Arg His
            20

<210> SEQ ID NO 385
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-D52

<400> SEQUENCE: 385

Phe Glu Val Leu Ser Ala Asp Ala Arg Gly Val Leu Gly Trp Met Leu
1               5                   10                  15

Met Leu Arg Gly
            20

<210> SEQ ID NO 386
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-F1

<400> SEQUENCE: 386

Trp Gly Gly Gly Trp Met Asp Trp Phe Phe Trp Gly Arg Thr Thr Gly
1               5                   10                  15

Arg Leu Arg Pro
            20

<210> SEQ ID NO 387
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-A43

<400> SEQUENCE: 387

Phe Ala Ser Pro Ala Met Tyr Met Gly Arg Thr Ser Pro Trp Gly Arg
1               5                   10                  15

Ala Tyr Asp Gly
            20

<210> SEQ ID NO 388
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-G32
```

```
<400> SEQUENCE: 388

Met Gly Arg His Pro Gly Leu Ser Arg Val Gly Asp Gly Ala Arg Met
1               5                   10                  15

Glu Pro Ser Thr
            20

<210> SEQ ID NO 389
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-H4

<400> SEQUENCE: 389

Met Ser Pro Leu Gly Leu Val Ala Ser His Pro Arg Ile Tyr Leu Pro
1               5                   10                  15

Arg Ile Ser Lys
            20

<210> SEQ ID NO 390
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-G4

<400> SEQUENCE: 390

Phe Met Ser Pro Tyr Ser Leu Met Leu Arg His Gly Leu Met Gly Glu
1               5                   10                  15

Arg Gln Arg Gly
            20

<210> SEQ ID NO 391
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-A7

<400> SEQUENCE: 391

Leu Thr Arg Val Pro Gly Phe Pro Ala Pro Tyr Ser Gly Ile Ser Arg
1               5                   10                  15

Ser Gln Leu Ser
            20

<210> SEQ ID NO 392
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-D4

<400> SEQUENCE: 392

Leu Thr Pro Arg Phe Val Val Asp Ser Asn Arg Gly Pro Leu Ala Arg
1               5                   10                  15

Ser Ser Gly Glu
            20
```

```
<210> SEQ ID NO 393
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-H1

<400> SEQUENCE: 393

Met Thr Arg Val Leu Pro Gly Arg Gly Asn Leu Tyr Pro Met Gln Thr
1               5                   10                  15

Val Gly Lys Ile
            20

<210> SEQ ID NO 394
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-F3

<400> SEQUENCE: 394

Met Val Arg Asn Gly Gly Val Thr Arg Leu Leu Gln Gly His Ala Gln
1               5                   10                  15

Arg Asn Pro Val
            20

<210> SEQ ID NO 395
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-C4

<400> SEQUENCE: 395

Met Gly Pro Met Leu Gly Ser Val Val Arg Pro Gly Gln Ser Arg Asp
1               5                   10                  15

Gly Gly Ser Trp
            20

<210> SEQ ID NO 396
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-4-H10

<400> SEQUENCE: 396

Glu Gly Ile Gly Trp Glu Ala Val Leu Gly Arg Val Ala Arg Phe Cys
1               5                   10                  15

Asn Gln Asp Gly
            20

<210> SEQ ID NO 397
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-B7
```

-continued

```
<400> SEQUENCE: 397

Met Met Leu Met Arg Gly Arg Asp Gly Ala Gln Met Gly Trp Pro Ser
1               5                   10                  15

Thr Arg Leu Arg
            20

<210> SEQ ID NO 398
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-D9

<400> SEQUENCE: 398

Leu Ser Met His Pro Ala Tyr Arg Leu Tyr Pro Asp Ala Gly Arg Pro
1               5                   10                  15

Gly Arg Ser Asp
            20

<210> SEQ ID NO 399
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-C52

<400> SEQUENCE: 399

Phe Asn Phe Pro Gly Leu Trp Ala Ser Trp Asp Leu Lys Arg Pro Arg
1               5                   10                  15

Val Arg Leu Asn
            20

<210> SEQ ID NO 400
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-D11

<400> SEQUENCE: 400

Gly Leu Trp Arg Ser Gln Val Phe Asn Thr Ser Trp Gly Ala Arg Ser
1               5                   10                  15

Gly His Gly Met
            20

<210> SEQ ID NO 401
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-B6

<400> SEQUENCE: 401

Tyr Pro Ser Gly Gly Ala Gln Gly Val Trp Asn Trp Leu Trp Arg Met
1               5                   10                  15

Met Thr Trp Gly
            20
```

-continued

<210> SEQ ID NO 402
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-B9

<400> SEQUENCE: 402

Met Gly His Val Ile Val Arg Pro Gln Asn Ser Arg Ala Leu Gly Pro
1               5                   10                  15

Gly Gly Trp His
            20

<210> SEQ ID NO 403
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-C9

<400> SEQUENCE: 403

Leu Gly Arg Met Pro Tyr Pro Gly Gly Leu Ser Asn His Val Glu Arg
1               5                   10                  15

Val Ser Arg Gly
            20

<210> SEQ ID NO 404
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-B82

<400> SEQUENCE: 404

Met Thr Gly Trp Gln Arg Phe Asp Ala Asn Arg Pro Val Gly Arg Ser
1               5                   10                  15

Gln Gly Glu Lys
            20

<210> SEQ ID NO 405
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-D3

<400> SEQUENCE: 405

Met Gly Ala Val Pro Ser Arg Met Arg Met Leu Met Gln Pro Thr Leu
1               5                   10                  15

Val Pro Arg Gly
            20

<210> SEQ ID NO 406
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR1-20F-3-A1

-continued

```
<400> SEQUENCE: 406

Leu Thr Pro Arg Leu Gly Leu Ser Pro Trp Pro Gly Val Thr Gly Arg
1               5                   10                  15

Thr Arg Pro Val
            20

<210> SEQ ID NO 407
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-B1

<400> SEQUENCE: 407

Phe Leu Phe Pro Leu His Phe Leu Ser Pro Trp Ser Val Gly Thr Ser
1               5                   10                  15

His Ser Arg Ile
            20

<210> SEQ ID NO 408
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-G2

<400> SEQUENCE: 408

Met Val Arg Asn Gly Gly Val Thr Arg Leu Leu Gln Gly His Ala Gln
1               5                   10                  15

Arg Asn Pro Val
            20

<210> SEQ ID NO 409
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-D32

<400> SEQUENCE: 409

Met Phe Leu Pro Gly Leu Leu Pro Trp Arg Ala Arg Pro Val Ser His
1               5                   10                  15

Gly Tyr Gly Tyr
            20

<210> SEQ ID NO 410
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-E1

<400> SEQUENCE: 410

Phe Tyr Pro Phe Leu Trp Ser Arg Gln Phe Gln Gly Thr Met Ala His
1               5                   10                  15

Arg Gly Met Gly
            20
```

```
<210> SEQ ID NO 411
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-H1

<400> SEQUENCE: 411

Met Gly Pro Met Leu Gly Ser Val Val Arg Pro Gly Gln Ser Arg Asp
1               5                   10                  15

Gly Gly Ser Trp
            20

<210> SEQ ID NO 412
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-B7

<400> SEQUENCE: 412

Trp Gly Gly Gly Trp Met Asp Trp Phe Phe Trp Gly Arg Thr Thr Gly
1               5                   10                  15

Arg Leu Arg Pro
            20

<210> SEQ ID NO 413
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-F9

<400> SEQUENCE: 413

Met Gly Ala Val Pro Ser Arg Met Arg Met Leu Met Gln Pro Thr Leu
1               5                   10                  15

Val Pro Arg Gly
            20

<210> SEQ ID NO 414
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-D22

<400> SEQUENCE: 414

Phe Trp Arg Pro Ser Phe Met His Gly Phe Met Gly His Phe Pro Ala
1               5                   10                  15

Val Thr Gly Ser
            20

<210> SEQ ID NO 415
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-A7
```

```
<400> SEQUENCE: 415

Leu Thr Pro Arg Leu Gly Leu Ser Pro Trp Pro Gly Val Thr Gly Arg
1               5                   10                  15

Thr Arg Pro Val
            20

<210> SEQ ID NO 416
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-H123

<400> SEQUENCE: 416

Met Thr Leu Pro Ser Ser Val Leu Arg Pro Val Arg Gly Pro Ala Leu
1               5                   10                  15

Ser Thr Ser Gly
            20

<210> SEQ ID NO 417
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-C2

<400> SEQUENCE: 417

Met Phe Pro Leu Tyr His Leu Val Lys Arg Ser Arg Thr Arg Asp Gly
1               5                   10                  15

Ala Val Leu Gly
            20

<210> SEQ ID NO 418
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-H2

<400> SEQUENCE: 418

Leu Thr Pro Arg Phe Val Val Asp Ser Asn Arg Gly Pro Leu Ala Arg
1               5                   10                  15

Ser Ser Gly Glu
            20

<210> SEQ ID NO 419
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-C6

<400> SEQUENCE: 419

Leu Ala Arg Pro Leu Ala Met Val Gly Phe Val Arg Asp Ala Trp Leu
1               5                   10                  15

Gly Arg Gly Ser
            20
```

```
<210> SEQ ID NO 420
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-E123

<400> SEQUENCE: 420

Phe Ala Ser Pro Ala Met Tyr Met Gly Arg Thr Ser Pro Trp Gly Arg
1               5                   10                  15

Ala Tyr Asp Gly
            20

<210> SEQ ID NO 421
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-H42

<400> SEQUENCE: 421

Met Gly Arg His Pro Gly Leu Ser Arg Val Gly Asp Gly Ala Arg Met
1               5                   10                  15

Glu Pro Ser Thr
            20

<210> SEQ ID NO 422
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-A112

<400> SEQUENCE: 422

Leu Thr Ser Arg Ile His Val Asp Pro Arg Val Arg Trp His Leu Ala
1               5                   10                  15

Arg Glu Gly Ser
            20

<210> SEQ ID NO 423
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-C3

<400> SEQUENCE: 423

Met Thr Arg Tyr Pro Ser Gly Leu Tyr Gln Arg His Pro Ala Gly Arg
1               5                   10                  15

Gly Gln Leu Glu
            20

<210> SEQ ID NO 424
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-B12
```

-continued

```
<400> SEQUENCE: 424

Met Thr Arg Val Leu Pro Gly Arg Gly Asn Leu Tyr Pro Met Gln Thr
1               5                   10                  15

Val Gly Lys Ile
            20

<210> SEQ ID NO 425
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-A12

<400> SEQUENCE: 425

Leu Thr Pro Ser Tyr Leu Leu Ser Trp Arg Val Gly Gly His Arg His
1               5                   10                  15

Val Asp Glu His
            20

<210> SEQ ID NO 426
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR2-20F-G6

<400> SEQUENCE: 426

Met Gly Arg Arg Pro Trp Ile Pro Tyr Gln Val Arg Leu Asp Met Gly
1               5                   10                  15

Ser Gln Arg His
            20

<210> SEQ ID NO 427
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR3-20F-G112

<400> SEQUENCE: 427

Phe Met Ser Pro Tyr Ser Leu Met Leu Arg His Gly Leu Met Gly Glu
1               5                   10                  15

Arg Gln Arg Gly
            20

<210> SEQ ID NO 428
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR3-20F-E8

<400> SEQUENCE: 428

Met Thr Val Trp Arg Trp Gly Ser Arg Pro Trp Gly Ile Ser Gly Gly
1               5                   10                  15

Phe Pro Ser Leu
            20
```

<210> SEQ ID NO 429
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR3-20F-D4

<400> SEQUENCE: 429

Met Ser Pro Leu Gly Leu Val Ala Ser His Pro Arg Ile Tyr Leu Pro
1               5                   10                  15

Arg Ile Ser Lys
            20

<210> SEQ ID NO 430
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR3-20F-F-5

<400> SEQUENCE: 430

Leu Thr Ser Val Ala Ser Ser Leu Ile Arg Trp Pro Arg Pro Pro Val
1               5                   10                  15

Leu Glu Gly Ile
            20

<210> SEQ ID NO 431
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR3-20F-E10

<400> SEQUENCE: 431

Met Ser Gly Leu Arg Trp Arg Asp Val Trp Ala Glu Arg Leu Gly Met
1               5                   10                  15

Gly Gly Phe His
            20

<210> SEQ ID NO 432
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR3-20F-H11

<400> SEQUENCE: 432

Met Ala Pro Arg Leu Val Ala Arg Phe Asp Ser Lys Ala Ala Leu Ser
1               5                   10                  15

Asn Thr Ala Gly
            20

<210> SEQ ID NO 433
<211> LENGTH: 20
<212> TYPE: PRT
<213> ORGANISM: Eschericia coli
<220> FEATURE:
<221> NAME/KEY: MISC_FEATURE
<223> OTHER INFORMATION: VEGFR3-20F-H7

-continued

```
<400> SEQUENCE: 433

Met Met Pro Leu Gly Phe Ala His Arg Ile Gly Arg Ser Ala Gly Val
1               5                   10                  15

Gly Ser Ser Pro
            20

<210> SEQ ID NO 434
<211> LENGTH: 20
<212> TYPE: PRT
<213> ORGANISM: Eschericia coli
<220> FEATURE:
<221> NAME/KEY: MISC_FEATURE
<223> OTHER INFORMATION: EGFR-20Ma-4-G107

<400> SEQUENCE: 434

Arg Trp Trp Val Gly Arg Arg Cys Pro Ser Gly Leu Cys Asn Val Gly
1               5                   10                  15

Phe Ser Gly Gly
            20

<210> SEQ ID NO 435
<211> LENGTH: 20
<212> TYPE: PRT
<213> ORGANISM: Eschericia coli
<220> FEATURE:
<221> NAME/KEY: MISC_FEATURE
<223> OTHER INFORMATION: EGFR-20Mb-4-E126
<220> FEATURE:
<221> NAME/KEY: MISC_FEATURE
<222> LOCATION: (17)..(17)
<223> OTHER INFORMATION: X or Q represents a CAG stop

<400> SEQUENCE: 435

Ala Val Ser Arg Leu Leu Gly Asp Thr Gln Arg Leu Ile Gly Tyr Leu
1               5                   10                  15

Xaa Glu Pro Leu
            20

<210> SEQ ID NO 436
<211> LENGTH: 20
<212> TYPE: PRT
<213> ORGANISM: Eschericia coli
<220> FEATURE:
<221> NAME/KEY: MISC_FEATURE
<223> OTHER INFORMATION: EGFR-20Mb-4-C883

<400> SEQUENCE: 436

Gly Tyr Pro Val Cys Ser Leu Ser Gly Gly Arg Val Glu Cys Arg Gln
1               5                   10                  15

Ala Arg Gly Gly
            20

<210> SEQ ID NO 437
<211> LENGTH: 20
<212> TYPE: PRT
<213> ORGANISM: Eschericia coli
<220> FEATURE:
<221> NAME/KEY: MISC_FEATURE
<223> OTHER INFORMATION: EGFR-20Mb-4-F4

<400> SEQUENCE: 437

Gly Ser Phe Arg Ser Leu Gly Phe Gly Asp Glu Phe Phe Gln Arg Tyr
1               5                   10                  15

Gly Val Gly Gly
            20
```

-continued

<210> SEQ ID NO 438
<211> LENGTH: 25
<212> TYPE: PRT
<213> ORGANISM: Eschericia coli
<220> FEATURE:
<221> NAME/KEY: MISC_FEATURE
<223> OTHER INFORMATION: EGFR-20Ma-4-F724

<400> SEQUENCE: 438

Leu Arg Arg Ile Cys Gln Ala Leu Leu Pro Thr Leu Ala Gly Lys Ala
1               5                   10                  15

Trp Cys Asp Ala Trp Gly Arg Gly Thr
            20                  25

<210> SEQ ID NO 439
<211> LENGTH: 20
<212> TYPE: PRT
<213> ORGANISM: Eschericia coli
<220> FEATURE:
<221> NAME/KEY: MISC_FEATURE
<223> OTHER INFORMATION: EGFR-40Ma-4-C12-fs

<400> SEQUENCE: 439

Ser Ser Ala Ser Ala Ala Gly Glu Arg Trp Gly Tyr Pro Gly Ser Cys
1               5                   10                  15

Ser Asp Gly Gly
            20

<210> SEQ ID NO 440
<211> LENGTH: 20
<212> TYPE: PRT
<213> ORGANISM: Eschericia coli
<220> FEATURE:
<221> NAME/KEY: MISC_FEATURE
<223> OTHER INFORMATION: FGFR1a-20R-A112

<400> SEQUENCE: 440

Gln Val Cys Val Arg Gly Glu Leu Phe Gly Gly Pro Ala Pro Phe Trp
1               5                   10                  15

Tyr Cys Ala Gly
            20

<210> SEQ ID NO 441
<211> LENGTH: 20
<212> TYPE: PRT
<213> ORGANISM: Eschericia coli
<220> FEATURE:
<221> NAME/KEY: MISC_FEATURE
<223> OTHER INFORMATION: FGFR1a-20F-C42

<400> SEQUENCE: 441

His Ile Ser Gly Thr Val Cys Arg Phe Asp Pro Gly Leu Pro Gly Gly
1               5                   10                  15

Leu Ile Gly Cys
            20

<210> SEQ ID NO 442
<211> LENGTH: 20
<212> TYPE: PRT
<213> ORGANISM: Eschericia coli
<220> FEATURE:
<221> NAME/KEY: MISC_FEATURE
<223> OTHER INFORMATION: FGFR1b-20F-B112

-continued

```
<400> SEQUENCE: 442

Gly Ser Glu Tyr Val Cys Arg Gly Ser Ile Ser Trp Gly Asp Phe Gly
1               5                   10                  15

Ala Trp Val Cys
            20

<210> SEQ ID NO 443
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-D10

<400> SEQUENCE: 443

Tyr Pro Pro Met Cys Leu Asp Pro Met Tyr Gly Val Val Phe Cys Gly
1               5                   10                  15

Pro Gly Glu Gly Leu Gly Asn His Ala
            20                  25

<210> SEQ ID NO 444
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1a-20C-E2

<400> SEQUENCE: 444

Tyr Tyr Arg Leu Cys Phe His Gly Gly Met Trp Lys Pro Tyr Glu Pro
1               5                   10                  15

Gly His Gln Gly Trp Cys Ala Arg Val
            20                  25

<210> SEQ ID NO 445
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-D9

<400> SEQUENCE: 445

Gly Thr Arg Ala Cys Trp Arg Val Trp Asp Ser Asp Arg Met Ser Ser
1               5                   10                  15

Val Val Arg Cys Gly Val Ser Val Phe
            20                  25

<210> SEQ ID NO 446
<211> LENGTH: 20
<212> TYPE: PRT
<213> ORGANISM: Eschericia coli
<220> FEATURE:
<221> NAME/KEY: MISC_FEATURE
<223> OTHER INFORMATION: FGFR1b-20F-C4

<400> SEQUENCE: 446

Cys Gln Val Leu Leu Ser Phe Gly Val Ala Asp Gly Val Trp Leu Phe
1               5                   10                  15

Asp Lys Glu Cys
            20
```

<210> SEQ ID NO 447
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-A10

<400> SEQUENCE: 447

Arg Ser Ser Tyr Cys Phe Trp Ala Val Ile Arg Gly Gly Gly Trp
1               5                   10                  15

Gly Arg Gln Cys Phe Gly Val Asp Ser
            20                  25

<210> SEQ ID NO 448
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1a-20C-B2

<400> SEQUENCE: 448

Asp Lys Arg Asp Cys Leu Glu Arg Val Gly Gly Ile Ala Trp Val Val
1               5                   10                  15

Arg Thr Glu Cys Gln Gly Gly Trp Arg
            20                  25

<210> SEQ ID NO 449
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-H82

<400> SEQUENCE: 449

Gly Gly His Pro Cys Arg Val Pro Phe His Phe Val Gly Asn Arg Pro
1               5                   10                  15

Ser Trp Leu Val Gly Ser Cys Ala Thr
            20                  25

<210> SEQ ID NO 450
<211> LENGTH: 30
<212> TYPE: PRT
<213> ORGANISM: Eschericia coli
<220> FEATURE:
<221> NAME/KEY: MISC_FEATURE
<223> OTHER INFORMATION: FGFR1b-20R-B7

<400> SEQUENCE: 450

Arg Arg Met Thr Arg Phe Ala Pro Asn Cys Ala Asp Leu Leu Pro
1               5                   10                  15

Gly Ala Pro Phe Thr Leu Met Pro Ser Pro Gly Cys Val Gly
            20                  25                  30

<210> SEQ ID NO 451
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-F83

```
<400> SEQUENCE: 451

Trp Leu Gln Leu Cys Ser Leu Tyr Gly Leu Phe Pro Phe Cys Asp Arg
1               5                   10                  15

Pro Leu Gly Gln Gly Gln Val Ala Gly
            20                  25

<210> SEQ ID NO 452
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-D2

<400> SEQUENCE: 452

Arg Pro Thr Leu Cys Ala Pro Phe Val Asp Ser Val Gly Thr Arg Leu
1               5                   10                  15

Cys Phe Asp Arg Trp Gly Asp Leu Gly
            20                  25

<210> SEQ ID NO 453
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-C10

<400> SEQUENCE: 453

Trp Leu Arg Trp Cys Ala Thr Arg Trp Leu Arg Gly Glu Gly Asp Gly
1               5                   10                  15

Cys Gly Phe Leu Glu Pro Arg Ala Gly
            20                  25

<210> SEQ ID NO 454
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-D82

<400> SEQUENCE: 454

Gly Arg Leu Arg Cys Arg Ala Gly Phe Trp Ala Val Met Gly Leu Gly
1               5                   10                  15

Arg Val Glu Arg Ile Gly Gly Thr Cys
            20                  25

<210> SEQ ID NO 455
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-F2

<400> SEQUENCE: 455

Gln Val Trp Leu Cys Asp Gly Val Met Gly Gly Cys Val Arg Lys Asp
1               5                   10                  15

Leu Arg Ser Leu Leu Tyr Phe Pro Arg
            20                  25
```

<210> SEQ ID NO 456
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-F33

<400> SEQUENCE: 456

Arg Ser Tyr Arg Cys Asn Arg Leu Thr Val Tyr Gly Trp Lys Ala Pro
1               5                   10                  15

Phe Cys Val Ser Gly Ser Gly Ser Leu
            20                  25

<210> SEQ ID NO 457
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-B42

<400> SEQUENCE: 457

Ser Ala Arg Ser Cys Ile His Gly Ala Thr Val Ala Arg Trp Gln Thr
1               5                   10                  15

Met Phe Gly Ala Ile Ile His Gly Cys
            20                  25

<210> SEQ ID NO 458
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-B6

<400> SEQUENCE: 458

Leu Tyr Arg Ala Cys Asn Ser Arg Phe Pro Ser Ser Ile Ala Tyr Cys
1               5                   10                  15

Ser Leu Phe Gly Tyr Arg Ser Ser Lys
            20                  25

<210> SEQ ID NO 459
<211> LENGTH: 26
<212> TYPE: PRT
<213> ORGANISM: Eschericia coli
<220> FEATURE:
<221> NAME/KEY: MISC_FEATURE
<223> OTHER INFORMATION: FGFR1b-20C-E8

<400> SEQUENCE: 459

Ser Thr Phe Arg Thr Cys Arg Thr Val Ser Arg Ile Thr Ser Gly Glu
1               5                   10                  15

His Ala Ala Pro Phe Val Ala Cys Thr Gln
            20                  25

<210> SEQ ID NO 460
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-F1

-continued

```
<400> SEQUENCE: 460

Arg Ala Trp Ile Cys Gly Leu Gly Val Phe Asp Ala His Thr Gly Ser
1               5                   10                  15

Gly Phe Ile Pro Cys Ser Arg Gly Gly
            20                  25

<210> SEQ ID NO 461
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-C7

<400> SEQUENCE: 461

Gly Val Trp Phe Cys Ala Pro Leu Leu Val Asn Gly Ser Arg Thr Gly
1               5                   10                  15

Phe Ala Ser Cys Asp Arg Gly Gly Arg
            20                  25

<210> SEQ ID NO 462
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-G6

<400> SEQUENCE: 462

Ser Ser Arg Val Cys Gly Met Ile Ser His Glu Gly Asp Leu Ala Met
1               5                   10                  15

Gly Gln Leu Tyr Asn Arg Arg Pro Val
            20                  25

<210> SEQ ID NO 463
<211> LENGTH: 20
<212> TYPE: PRT
<213> ORGANISM: Eschericia coli
<220> FEATURE:
<221> NAME/KEY: MISC_FEATURE
<223> OTHER INFORMATION: FGFR1a-20R-A10

<400> SEQUENCE: 463

Tyr Leu Cys Ala Arg Gly Glu Arg Phe Trp Gly Ala Ser Arg Phe Cys
1               5                   10                  15

Tyr Trp Ser Gly
            20

<210> SEQ ID NO 464
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1a-20C-G7

<400> SEQUENCE: 464

Gly Leu Ile Asp Cys Leu Tyr Gln Gly Val Tyr Tyr Trp Cys Val Thr
1               5                   10                  15

Gly Ala Gly Ile Phe Pro Ser Arg Asp
            20                  25
```

<210> SEQ ID NO 465
<211> LENGTH: 20
<212> TYPE: PRT
<213> ORGANISM: Eschericia coli
<220> FEATURE:
<221> NAME/KEY: MISC_FEATURE
<223> OTHER INFORMATION: FGFR1a-20F-B9

<400> SEQUENCE: 465

Phe Val Ala Ala Val Ala Cys Phe Lys Leu His Pro Thr Trp Gly Val
1               5                   10                  15

Val Ser Cys Asp
            20

<210> SEQ ID NO 466
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-E11

<400> SEQUENCE: 466

Ile Trp Leu Phe Cys Ala His Cys Pro Thr Ala Leu Ile Ser Val Pro
1               5                   10                  15

Ser Ala Phe Gly Ser Leu Asp Leu Gly
            20                  25

<210> SEQ ID NO 467
<211> LENGTH: 20
<212> TYPE: PRT
<213> ORGANISM: Eschericia coli
<220> FEATURE:
<221> NAME/KEY: MISC_FEATURE
<223> OTHER INFORMATION: FGFR1b-20R-B1

<400> SEQUENCE: 467

Arg Gly Cys Val Leu Glu Ala Leu Ser Gly Gly Ala Cys Leu Phe Asp
1               5                   10                  15

Tyr Trp Ser Gly
            20

<210> SEQ ID NO 468
<211> LENGTH: 20
<212> TYPE: PRT
<213> ORGANISM: Eschericia coli
<220> FEATURE:
<221> NAME/KEY: MISC_FEATURE
<223> OTHER INFORMATION: FGFR1b-20F-G8

<400> SEQUENCE: 468

Ile Trp Phe Glu Pro Gly Met Ile Cys Arg Phe Ser Arg Gly Glu Gly
1               5                   10                  15

Leu Gln Ser Cys
            20

<210> SEQ ID NO 469
<211> LENGTH: 20
<212> TYPE: PRT
<213> ORGANISM: Eschericia coli
<220> FEATURE:
<221> NAME/KEY: MISC_FEATURE
<223> OTHER INFORMATION: FGFR1b-20F-A1

-continued

```
<400> SEQUENCE: 469

Val Arg Arg Gly Asp Val Cys Glu Tyr Asn Gly Asn Leu Phe Trp Ala
1               5                   10                  15

Ala Glu Cys Asn
            20

<210> SEQ ID NO 470
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1b-20C-C1

<400> SEQUENCE: 470

Arg Gln Gly Phe Cys Ala Asn Ile Leu His Pro Thr Met Gly Asn Arg
1               5                   10                  15

Val Ala Cys Asn Val Gln Asp Trp Phe
            20                  25

<210> SEQ ID NO 471
<211> LENGTH: 25
<212> TYPE: PRT
<213> ORGANISM: Eschericia coli
<220> FEATURE:
<221> NAME/KEY: MISC_FEATURE
<223> OTHER INFORMATION: FGFR1a-20C-A2

<400> SEQUENCE: 471

Phe Ile His Arg Cys Gly Met Gly Val Phe Thr Cys Ile Asn Gly Gly
1               5                   10                  15

Val Ala Asp Ile Gly Phe Ser Val Ser
            20                  25

<210> SEQ ID NO 472
<211> LENGTH: 29
<212> TYPE: PRT
<213> ORGANISM: Eschericia coli
<220> FEATURE:
<221> NAME/KEY: MISC_FEATURE
<223> OTHER INFORMATION: FGFR1b-20R-G9

<400> SEQUENCE: 472

Thr Thr Met Thr Arg Ala Pro Leu Phe Ala Val Glu Glu Ser Asp Ala
1               5                   10                  15

Val Pro Arg Val Arg Gly Gly Pro Arg Arg Arg Glu Ala
            20                  25

<210> SEQ ID NO 473
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-H719

<400> SEQUENCE: 473

Arg Arg Val Asp Ala Gly Gly Ala Val Val Tyr Leu Asp Arg Trp Gly
1               5                   10                  15

Asn Val Ser Val
            20
```

```
<210> SEQ ID NO 474
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-B1244

<400> SEQUENCE: 474

Arg Ile Asp Arg Cys Tyr Val Leu Leu Asp Arg Trp Gly Asn Thr Val
1               5                   10                  15

Gly Arg Arg Cys Gln Lys Thr Arg Ala
            20                  25

<210> SEQ ID NO 475
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-H1136

<400> SEQUENCE: 475

Asp Asp Pro Arg Cys Trp Leu Gln Gly Gly Tyr Tyr Ile Cys Arg Ala
1               5                   10                  15

Pro Asp Arg Ala
            20

<210> SEQ ID NO 476
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-D116

<400> SEQUENCE: 476

Asp Glu Leu Ala Cys Gly Tyr Trp Gly Glu Leu Trp Gly Leu Cys Ser
1               5                   10                  15

Tyr Gly Arg Ser Ile Pro Ala Asn Lys
            20                  25

<210> SEQ ID NO 477
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-B122

<400> SEQUENCE: 477

Arg Val Leu Ser Arg Glu Cys Phe Met Ile Phe Glu Ser Ile Gly Arg
1               5                   10                  15

Thr Val Val Cys
            20

<210> SEQ ID NO 478
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-A4
```

```
<400> SEQUENCE: 478

Val Val Phe Leu Asp Arg Trp Gly Asn Pro Gln Tyr Leu Gly Val Lys
1               5                   10                  15

Ala Ser Gly Gly
            20

<210> SEQ ID NO 479
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-A23

<400> SEQUENCE: 479

Gly Val Phe Trp Cys Glu Pro Val Arg Gly Arg Ser Trp Trp Gly Arg
1               5                   10                  15

Asn Gly Cys Phe Thr Gln Glu Pro Gly
            20                  25

<210> SEQ ID NO 480
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-4-H56

<400> SEQUENCE: 480

Gly Ala Leu Arg Trp Cys Thr Phe Gln Glu Gly Pro Gly Val Gly Arg
1               5                   10                  15

Leu Gly Val Cys
            20

<210> SEQ ID NO 481
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-4-E12

<400> SEQUENCE: 481

Ser Leu Trp Gly Cys Ser Gly Arg Ala Val Leu Phe Leu Asp Ser Val
1               5                   10                  15

Gly Asn Pro Thr Gly Thr Val Arg Cys
            20                  25

<210> SEQ ID NO 482
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-4-E7

<400> SEQUENCE: 482

Arg Ser Ser Gly Cys Trp Leu Arg Gln Leu Val Gly Val Tyr Asp Glu
1               5                   10                  15

Gly Arg Ala Trp Val Trp Ser Cys Leu
            20                  25
```

-continued

```
<210> SEQ ID NO 483
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-D32

<400> SEQUENCE: 483

Val Gln Arg Leu Cys Val Arg Gly Gly Leu Trp Ser Val Cys Arg Gly
1               5                   10                  15

Ser Ile Ser Ala Glu Ser Ala Ala Val
            20                  25

<210> SEQ ID NO 484
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-D12

<400> SEQUENCE: 484

Arg Thr Ala Pro Cys Ser Gly Leu Pro Trp Leu Leu Leu His Gly Gln
1               5                   10                  15

Leu Arg Cys Ala Arg Leu Val Gln Glu
            20                  25

<210> SEQ ID NO 485
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-D84

<400> SEQUENCE: 485

Val Gly Arg Gly Cys Trp Ala Arg Val Gly Arg Val Trp Thr Trp Tyr
1               5                   10                  15

Gly Met Ser Tyr Pro Leu Cys Arg Gln
            20                  25

<210> SEQ ID NO 486
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-4-F12

<400> SEQUENCE: 486

Val Arg Arg Trp Cys Asp Thr Gln Trp Leu Ile Pro Asp Met Cys Arg
1               5                   10                  15

His Val Trp Ser Trp Gly Gly Arg Met
            20                  25

<210> SEQ ID NO 487
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-A9
```

```
<400> SEQUENCE: 487

Gly Pro Ile Gln Cys Leu Val Trp Ser Gln Ser Ala Pro Gly Val Trp
1               5                   10                  15

Gly Val Gly Ser Gly Ile Gly Cys Val
            20                  25

<210> SEQ ID NO 488
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-D11

<400> SEQUENCE: 488

Leu Ser Arg Val Pro Leu Leu Thr Arg Met Gln Pro Asp Val Val Arg
1               5                   10                  15

Ala Gly Asp Gly
            20

<210> SEQ ID NO 489
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-A6

<400> SEQUENCE: 489

Gly Arg Glu Val Cys Met Ala Arg Leu Asn Gly Phe Gln Pro Trp Gly
1               5                   10                  15

Val Ser Thr Arg Gly Ala Arg Ser Gln
            20                  25

<210> SEQ ID NO 490
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-B5

<400> SEQUENCE: 490

Arg Gly His Trp Cys Thr Ile Gly Gly Ser Asn Asn Tyr Ser Gly Arg
1               5                   10                  15

Phe Trp Phe Thr Arg Trp Phe Cys Asp
            20                  25

<210> SEQ ID NO 491
<211> LENGTH: 17
<212> TYPE: PRT
<213> ORGANISM: Eschericia coli
<220> FEATURE:
<221> NAME/KEY: MISC_FEATURE
<223> OTHER INFORMATION: Tie1-20F-3-C12

<400> SEQUENCE: 491

Phe Ser Arg Ser Pro Pro Ala Thr Ser Arg Val Gly Ala Val Leu Glu
1               5                   10                  15

Gly
```

<210> SEQ ID NO 492
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-A3

<400> SEQUENCE: 492

Gly Val Phe Asn Leu Arg Pro Val Phe Gly Ser Arg Tyr Leu Gln Pro
1               5                   10                  15

Gln Thr Ser Ala
            20

<210> SEQ ID NO 493
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-A7

<400> SEQUENCE: 493

Ala Arg Arg Trp Cys Asp Glu Ser Glu Met Gly Leu Arg Gln Leu Val
1               5                   10                  15

Leu Ala Ser Pro Arg Ala Leu Arg Gly
            20                  25

<210> SEQ ID NO 494
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-D10

<400> SEQUENCE: 494

Met Gly Ser Leu Gly Trp Val Glu Ala Pro Ser Gly Val Phe Pro Gly
1               5                   10                  15

Asp Gly Gly Gln
            20

<210> SEQ ID NO 495
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-D1

<400> SEQUENCE: 495

Phe Thr Arg Pro Tyr Asn Gly Glu Arg Gly Ser Val Val Leu Ser Ala
1               5                   10                  15

Ala Asp Gln Thr
            20

<210> SEQ ID NO 496
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-D10

-continued

```
<400> SEQUENCE: 496

Trp Thr Leu Leu Cys Ser Ser Thr Ile Thr Thr Leu Pro Ala Gln Met
1               5                   10                  15

Leu Ser Met Ser Ala Pro Pro Arg
            20              25

<210> SEQ ID NO 497
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-D3

<400> SEQUENCE: 497

Phe Ala Arg Trp Glu Pro Asn Phe Trp Gln Pro Thr Glu Ala Pro Ser
1               5                   10                  15

Ala Arg Gly Val
            20

<210> SEQ ID NO 498
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-A4

<400> SEQUENCE: 498

Ala Arg Val Ala Cys Trp Ser Asp Arg Val Pro Gly Gln His Arg Ala
1               5                   10                  15

Arg Arg Val Trp Ile Leu Gly Thr Gln
            20                  25

<210> SEQ ID NO 499
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-F7

<400> SEQUENCE: 499

Met Thr Met Asn Ser Val Tyr Gln Phe His Ser Ala Asp Asp Lys Ala
1               5                   10                  15

Ile Ala Pro Arg
            20

<210> SEQ ID NO 500
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-C4

<400> SEQUENCE: 500

Met Gly Trp Ala Thr Trp Glu His Gly Asn Val Gln Gly Arg Gly Gly
1               5                   10                  15

Leu Glu His Ile
            20
```

```
<210> SEQ ID NO 501
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-C6

<400> SEQUENCE: 501

Gly Met Phe Gly Val Tyr Arg Thr Leu Glu Arg Gly Ala Leu Thr Gly
1               5                   10                  15

Pro Gly Ser Ser
            20

<210> SEQ ID NO 502
<211> LENGTH: 20
<212> TYPE: PRT
<213> ORGANISM: Eschericia coli
<220> FEATURE:
<221> NAME/KEY: MISC_FEATURE
<223> OTHER INFORMATION: Tie1-20F-3-C2

<400> SEQUENCE: 502

Phe Thr Arg Ala Thr Ser Leu Pro Ile Gly Asn Val Ser Gly Asn Pro
1               5                   10                  15

Gly Arg Leu Ser
            20

<210> SEQ ID NO 503
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-B2

<400> SEQUENCE: 503

Arg Gly Ala Arg Cys Thr Leu Ala Leu Ala His Trp Ser Gly Gly Asn
1               5                   10                  15

Gln Arg Ile Gly Asp Arg Leu Gly Gly
            20                  25

<210> SEQ ID NO 504
<211> LENGTH: 25
<212> TYPE: PRT
<213> ORGANISM: Eschericia coli
<220> FEATURE:
<221> NAME/KEY: MISC_FEATURE
<223> OTHER INFORMATION: Tie1-20C-3-D2

<400> SEQUENCE: 504

Ala Tyr Leu Ser Cys Glu Tyr Thr Ala Met Phe Leu Gly Pro Val Arg
1               5                   10                  15

Arg Gln Glu Ile Ser Gln Ser Arg Ala
            20                  25

<210> SEQ ID NO 505
<211> LENGTH: 10
<212> TYPE: PRT
<213> ORGANISM: Escherichia coli
<220> FEATURE:
<221> NAME/KEY: MISC_FEATURE
<223> OTHER INFORMATION: Motif 1
<220> FEATURE:
<221> NAME/KEY: MISC_FEATURE
<222> LOCATION: (3)..(4)
<223> OTHER INFORMATION: X=unknown or other
```

```
<220> FEATURE:
<221> NAME/KEY: MISC_FEATURE
<222> LOCATION: (6)..(6)
<223> OTHER INFORMATION: X=unknown or other

<400> SEQUENCE: 505

Gly Cys Xaa Xaa Phe Xaa Gly Phe Cys Val
1               5                   10

<210> SEQ ID NO 506
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-4-H814

<400> SEQUENCE: 506

Leu Val Ile Gly Gln Arg Ser Phe Leu Ser Ala Cys Ser Leu Phe Asp
1               5                   10                  15

Gly Phe Cys Val
            20

<210> SEQ ID NO 507
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-3-A1

<400> SEQUENCE: 507

Glu Gly Asn Trp Phe Cys Ala Val Phe Arg Gly Phe Cys Val Gly Asp
1               5                   10                  15

Arg Gly Pro Glu
            20

<210> SEQ ID NO 508
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20F-3-C1

<400> SEQUENCE: 508

Gly Ser Val Leu Glu Arg Gly Cys Leu Glu Phe Ser Gly Phe Cys Phe
1               5                   10                  15

Ser Leu Gly His
            20

<210> SEQ ID NO 509
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-3-C1

<400> SEQUENCE: 509

Leu Phe Ser Ala Thr Gly Cys Ala Leu Met Ser Gly Phe Cys Leu Gly
1               5                   10                  15

Ser Asp Gly Ser
            20
```

```
<210> SEQ ID NO 510
<211> LENGTH: 37
<212> TYPE: PRT
<213> ORGANISM: Escherichia coli
<220> FEATURE:
<221> NAME/KEY: MISC_FEATURE
<223> OTHER INFORMATION: DGI2-40F-4-E1130; # = TAA stop (after residue
      1; 2#s after residue 3)

<400> SEQUENCE: 510

Val Cys Arg Leu Cys Arg Leu Cys Arg Phe Ser Met Arg Cys Gly Gly
1               5                   10                  15

Leu Ser Leu Val Leu Gly Ser Ala Ala Ala Phe Phe Cys Glu Val Phe
            20                  25                  30

Val Gly Phe Cys Val
        35

<210> SEQ ID NO 511
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-4-H626

<400> SEQUENCE: 511

Arg Arg Gly Val Cys Glu Ile Phe Thr Gly Trp Cys Val Gly Gln Thr
1               5                   10                  15

Asn Glu Arg Pro
            20

<210> SEQ ID NO 512
<211> LENGTH: 8
<212> TYPE: PRT
<213> ORGANISM: Escherichia coli
<220> FEATURE:
<221> NAME/KEY: MISC_FEATURE
<223> OTHER INFORMATION: Motif 2
<220> FEATURE:
<221> NAME/KEY: MISC_FEATURE
<222> LOCATION: (3)..(3)
<223> OTHER INFORMATION: X=unknown or other
<220> FEATURE:
<221> NAME/KEY: MISC_FEATURE
<222> LOCATION: (8)..(8)
<223> OTHER INFORMATION: X=A, F, G, I, L, M, T, V, and W

<400> SEQUENCE: 512

Phe Arg Xaa Trp Val Glu Gly Xaa
1               5

<210> SEQ ID NO 513
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-3-A2

<400> SEQUENCE: 513

Gln Met Ser Arg Val Ala Phe Ser Pro Gly Glu Ser Trp Arg Trp
1               5                   10                  15

Val Glu Gly Val
            20
```

```
<210> SEQ ID NO 514
<211> LENGTH: 40
<212> TYPE: PRT
<213> ORGANISM: Escherichia coli
<220> FEATURE:
<221> NAME/KEY: MISC_FEATURE
<223> OTHER INFORMATION: DGI2-40F-3-D1044

<400> SEQUENCE: 514

Asp Arg Val Ala Arg Leu Ala Thr Pro Thr Ala Gly Thr Met Ala Ala
1               5                   10                  15

Gly Ser Leu Gly Tyr Glu Arg Thr Val Gly Cys Asp Ser Gln Asp Trp
            20                  25                  30

Phe Arg Cys Val Val Glu Gly Leu
        35                  40

<210> SEQ ID NO 515
<211> LENGTH: 22
<212> TYPE: PRT
<213> ORGANISM: Escherichia coli
<220> FEATURE:
<221> NAME/KEY: MISC_FEATURE
<223> OTHER INFORMATION: DGI2-40F-3-A1

<400> SEQUENCE: 515

Arg Glu Phe Phe Asn Gln Ala Ser Arg Gly Ala Trp Gly Tyr Met Phe
1               5                   10                  15

Arg Glu Trp Val Glu Gly
            20

<210> SEQ ID NO 516
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-4-G4; Q=CAG stop (residue 15)

<400> SEQUENCE: 516

Val Trp Ala Ala Trp Val Glu Gly Ser Leu Leu Ser Pro Arg Gln Glu
1               5                   10                  15

Pro Val Arg Asp
            20

<210> SEQ ID NO 517
<211> LENGTH: 10
<212> TYPE: PRT
<213> ORGANISM: Escherichia coli
<220> FEATURE:
<221> NAME/KEY: MISC_FEATURE
<223> OTHER INFORMATION: Motif 3
<220> FEATURE:
<221> NAME/KEY: MISC_FEATURE
<222> LOCATION: (2)..(2)
<223> OTHER INFORMATION: X=unknown or other
<220> FEATURE:
<221> NAME/KEY: MISC_FEATURE
<222> LOCATION: (5)..(5)
<223> OTHER INFORMATION: X=unknown or other

<400> SEQUENCE: 517

Ser Xaa Gly Trp Xaa Phe Pro Gly Trp Arg
1               5                   10
```

```
<210> SEQ ID NO 518
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-3-C2

<400> SEQUENCE: 518

Arg Asp Thr Thr Ser Gln Trp Ser Trp Ile Ser Arg Gly Trp Glu Phe
1               5                   10                  15

Pro Gly Trp Arg
            20

<210> SEQ ID NO 519
<211> LENGTH: 25
<212> TYPE: PRT
<213> ORGANISM: Escherichia coli
<220> FEATURE:
<221> NAME/KEY: MISC_FEATURE
<223> OTHER INFORMATION: DGI2-20C-3-C1039

<400> SEQUENCE: 519

Arg Pro Val Val Cys Leu Ala Gly Leu Thr Leu Ala Gln Phe Gly Trp
1               5                   10                  15

Val Phe Pro Gly Trp Arg Gly Trp Ser
            20                  25

<210> SEQ ID NO 520
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-3-C6

<400> SEQUENCE: 520

Gly Ile Met Gln Val Ala Trp Gly Trp Arg Glu Trp Arg Leu Trp Asp
1               5                   10                  15

Leu Gly Met Ala
            20

<210> SEQ ID NO 521
<211> LENGTH: 31
<212> TYPE: PRT
<213> ORGANISM: Escherichia coli
<220> FEATURE:
<221> NAME/KEY: MISC_FEATURE
<223> OTHER INFORMATION: DGI2-40F-3-D11
<220> FEATURE:
<221> NAME/KEY: MISC_FEATURE
<222> LOCATION: (22)..(22)
<223> OTHER INFORMATION: X or Q represents a CAG stop

<400> SEQUENCE: 521

Leu His Phe Gly Ser Val Met Gly Trp Arg Pro Pro Gly Ser Leu Trp
1               5                   10                  15

Ser Arg Pro Phe Gly Xaa Val His Pro Arg Ser Trp Ser Gly Ser
            20                  25                  30

<210> SEQ ID NO 522
<211> LENGTH: 12
<212> TYPE: PRT
<213> ORGANISM: Escherichia coli
<220> FEATURE:
<221> NAME/KEY: MISC_FEATURE
<223> OTHER INFORMATION: Motif 4
```

```
<220> FEATURE:
<221> NAME/KEY: MISC_FEATURE
<222> LOCATION: (1)..(1)
<223> OTHER INFORMATION: X=A, F, G, I, L, M, T, V, and W
<220> FEATURE:
<221> NAME/KEY: MISC_FEATURE
<222> LOCATION: (4)..(4)
<223> OTHER INFORMATION: X=D, E, K, R, H, N, and Q
<220> FEATURE:
<221> NAME/KEY: MISC_FEATURE
<222> LOCATION: (7)..(7)
<223> OTHER INFORMATION: X=D, E, K, R, H, N, and Q
<220> FEATURE:
<221> NAME/KEY: MISC_FEATURE
<222> LOCATION: (11)..(11)
<223> OTHER INFORMATION: X=unknown or other amino acid

<400> SEQUENCE: 522

Xaa Trp Arg Xaa Trp Val Xaa Gly Ser Leu Xaa Gly
1               5                   10

<210> SEQ ID NO 523
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-3-A5

<400> SEQUENCE: 523

Val Trp Arg Asp Trp Val Asn Gly Thr Val Gly Leu Arg Asn Arg Glu
1               5                   10                  15

Lys Pro Gly Val
            20

<210> SEQ ID NO 524
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-4-G4
<220> FEATURE:
<221> NAME/KEY: MISC_FEATURE
<222> LOCATION: (15)..(15)
<223> OTHER INFORMATION: X or Q represents a CAG stop

<400> SEQUENCE: 524

Val Trp Ala Ala Trp Val Glu Gly Ser Leu Leu Ser Pro Arg Xaa Glu
1               5                   10                  15

Pro Val Arg Asp
            20

<210> SEQ ID NO 525
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-3-A122

<400> SEQUENCE: 525

Trp Trp Arg Glu Trp Val Asp Gly Ser Leu Arg Gly Gly Gly Gly Thr
1               5                   10                  15

Val Leu Lys Asp
            20
```

-continued

```
<210> SEQ ID NO 526
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-4-H1

<400> SEQUENCE: 526

Gly Arg Trp Asp Gly Trp Glu Val Cys Gly Ile Trp Gly Ala Asp Asp
1               5                   10                  15

Cys Ala Ser Gly
            20

<210> SEQ ID NO 527
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-3-B52

<400> SEQUENCE: 527

Leu Trp Arg Arg Trp Ser Glu Gly Gln Leu Leu Gly Asp Gly Glu Leu
1               5                   10                  15

Arg Gly Asp Gly
            20

<210> SEQ ID NO 528
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20R-3-C6

<400> SEQUENCE: 528

Gly Ile Met Gln Val Ala Trp Gly Trp Arg Glu Trp Arg Leu Trp Asp
1               5                   10                  15

Leu Gly Met Ala
            20

<210> SEQ ID NO 529
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20F-PP-G5
<220> FEATURE:
<221> NAME/KEY: MISC_FEATURE
<222> LOCATION: (18)..(18)
<223> OTHER INFORMATION: X or Q represents a CAG stop

<400> SEQUENCE: 529

Gly Ala Ser Arg Val Val Asp Val Gly Trp Arg Phe Trp Gly Lys Leu
1               5                   10                  15

Trp Xaa Arg Ser
            20

<210> SEQ ID NO 530
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20F-PP-H3
```

```
<220> FEATURE:
<221> NAME/KEY: MISC_FEATURE
<222> LOCATION: (8)..(8)
<223> OTHER INFORMATION: X or Q represents a CAG stop.

<400> SEQUENCE: 530

Asp Asp Ile Val Cys Leu Phe Xaa Phe Cys Ile Met Phe Cys Trp Leu
1               5                   10                  15

Asp Met Gly Trp
            20

<210> SEQ ID NO 531
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20F-PP-E5oof

<400> SEQUENCE: 531

Ser Ile Val Ser Ser Arg Ser Gly Trp Gln Arg Gly Trp Ile Ala Trp
1               5                   10                  15

Phe Ala Pro Val
            20

<210> SEQ ID NO 532
<211> LENGTH: 20
<212> TYPE: PRT
<213> ORGANISM: Escherichia coli
<220> FEATURE:
<221> NAME/KEY: MISC_FEATURE
<223> OTHER INFORMATION: DGI2-20F-PP-F8
<220> FEATURE:
<221> NAME/KEY: MISC_FEATURE
<222> LOCATION: (11)..(11)
<223> OTHER INFORMATION: X or Q represents a CAG stop

<400> SEQUENCE: 532

Leu Leu Leu Pro Val Arg Trp Arg Asp Ala Xaa Pro Arg Ser Leu Leu
1               5                   10                  15

Met Glu Trp Ile
            20

<210> SEQ ID NO 533
<211> LENGTH: 402
<212> TYPE: DNA
<213> ORGANISM: Homo sapiens
<220> FEATURE:
<221> NAME/KEY: misc_feature
<223> OTHER INFORMATION: DGI-2

<400> SEQUENCE: 533
ccggccatgg cgatggtgcg gactaaagca gacagtgttc caggcactta cagaaaagtg      60
gtggctgctc gagccccag aaaggtgctt ggttcttcca cctctgccac taattcgaca     120
tcagtttcat cgaggaaagc tgaaaataaa tatgcaggag ggaacccgt ttgcgtgcgc     180 ccaactccca agtggcaaaa aggaattgga gaattcttta ggttgtcccc taaagattct    240
gaaaaagaga atcagattcc tgaagaggca ggaagcagtg gcttaggaaa agcaaagaga    300
aaagcatgtc ctttgcaacc tgatcacaca aatgatgaaa agaagcggc cgcaggtgcg     360 ccggtgccgt atccggatcc gctggaaccg cgtgccgcat ag                       402
```

```
<210> SEQ ID NO 534
<211> LENGTH: 20
<212> TYPE: PRT
<213> ORGANISM: Artificial
<220> FEATURE:
<223> OTHER INFORMATION: Synthetic target binder sequence.
      DGI9-20M-4-A4(14); 20F

<400> SEQUENCE: 534

Phe Leu Leu Gln Asp Phe Ile Met Asp Ala Gly Ser Phe Val Lys Pro
1               5                   10                  15

Ile Gly Val Gly
            20

<210> SEQ ID NO 535
<211> LENGTH: 20
<212> TYPE: PRT
<213> ORGANISM: artificial
<220> FEATURE:
<223> OTHER INFORMATION: Synthetic target binder sequence.
      DGI9-20M-4-E3; 20F

<400> SEQUENCE: 535

Met Ala Gly Phe Arg Gly Ser Gly Leu Ser Gly Tyr Ser Glu Ala Arg
1               5                   10                  15

Leu Pro Arg Val
            20

<210> SEQ ID NO 536
<211> LENGTH: 20
<212> TYPE: PRT
<213> ORGANISM: artificial
<220> FEATURE:
<223> OTHER INFORMATION: Synthetic target binder sequence.
      DGI9-20M-4-A6(27); 20R

<400> SEQUENCE: 536

Trp Asp Trp Ser Arg Phe Gly Ala Gln Leu Arg Gly Ala Ile Leu Gly
1               5                   10                  15

Arg Ala Thr Gly
            20

<210> SEQ ID NO 537
<211> LENGTH: 20
<212> TYPE: PRT
<213> ORGANISM: artificial
<220> FEATURE:
<223> OTHER INFORMATION: Synthetic target binder sequence.
      DGI9-20M-4-A12; 20R

<400> SEQUENCE: 537

Ser Arg Leu Ala Leu Ser Ser Gln His Gly Leu Ser Leu Val Ala Gly
1               5                   10                  15

Arg Arg Arg Gly
            20

<210> SEQ ID NO 538
<211> LENGTH: 20
<212> TYPE: PRT
<213> ORGANISM: Artificial
<220> FEATURE:
<223> OTHER INFORMATION: DGI-3; dgen-0101-20M-3-AP-A158
```

-continued

```
<400> SEQUENCE: 538

Thr Ile Arg Arg Trp Phe Cys Leu Ala His Trp Gly Thr Glu Gly Cys
1               5                   10                  15

Leu Ala Arg Thr
            20

<210> SEQ ID NO 539
<211> LENGTH: 25
<212> TYPE: PRT
<213> ORGANISM: Artificial
<220> FEATURE:
<223> OTHER INFORMATION: DGI-3; dgen-0101-20M-3-AP-C511

<400> SEQUENCE: 539

Glu Trp Ala Arg Cys Val Val Arg Trp Leu Val Glu Gly Val Val Gly
1               5                   10                  15

Gln Leu Gly Thr Val Cys Gly Ser Ser
            20                  25

<210> SEQ ID NO 540
<211> LENGTH: 20
<212> TYPE: PRT
<213> ORGANISM: Artificial
<220> FEATURE:
<223> OTHER INFORMATION: DGI-3; dgen-0101-20M-3-AP-G32

<400> SEQUENCE: 540

Gly Leu Gly Trp Arg Asp Pro Val Cys Val Pro Phe Arg Gly Met Arg
1               5                   10                  15

Leu Cys Leu Val
            20

<210> SEQ ID NO 541
<211> LENGTH: 20
<212> TYPE: PRT
<213> ORGANISM: Artificial
<220> FEATURE:
<223> OTHER INFORMATION: NUDT5 (nudix hydrolase);
      073002-cDNATet-20F20C40R-PP-DC-B11
<220> FEATURE:
<221> NAME/KEY: MISC_FEATURE
<222> LOCATION: (4)..(4)
<223> OTHER INFORMATION: X or Q represents a CAG stop

<400> SEQUENCE: 541

Ile Gly Arg Xaa Leu Gly Gly Gly Val Ala Met Asp Cys Asp Val Ala
1               5                   10                  15

Val Gly Glu Arg
            20

<210> SEQ ID NO 542
<211> LENGTH: 26
<212> TYPE: PRT
<213> ORGANISM: Artificial
<220> FEATURE:
<223> OTHER INFORMATION: FRG1; 072402-CDNATET-20M-PP-DC-CLONE 25
<220> FEATURE:
<221> NAME/KEY: MISC_FEATURE
<222> LOCATION: (10)..(10)
<223> OTHER INFORMATION: X or Q represents a CAG stop
<220> FEATURE:
<221> NAME/KEY: MISC_FEATURE
<222> LOCATION: (15)..(15)
<223> OTHER INFORMATION: X or Q represents a CAG stop
```

```
-continued

<400> SEQUENCE: 542

Ser Lys Arg Leu Cys Ala Ala Gly Tyr Xaa Asp Leu Asn Val Xaa Arg
1               5                   10                  15

Trp Arg Ala Leu Arg Leu Gly Pro Met Ala
            20                  25

<210> SEQ ID NO 543
<211> LENGTH: 20
<212> TYPE: PRT
<213> ORGANISM: Artificial
<220> FEATURE:
<223> OTHER INFORMATION: Ribosomal Protein S20;
      073002-cDNATet-20F20C40R-PP-DC-B10

<400> SEQUENCE: 543

Gln Asn Trp Trp Thr His Arg Trp Val Gly Asp Ile Val Leu Arg Phe
1               5                   10                  15

Gly Thr Thr Arg
            20

<210> SEQ ID NO 544
<211> LENGTH: 20
<212> TYPE: PRT
<213> ORGANISM: Artificial
<220> FEATURE:
<223> OTHER INFORMATION: Ribosomal Protein S20;
      073002-cDNATet-20F20C40R-PP-DC-E11
<220> FEATURE:
<221> NAME/KEY: MISC_FEATURE
<222> LOCATION: (1)..(1)
<223> OTHER INFORMATION: X or Q represents a CAG stop

<400> SEQUENCE: 544

Xaa Arg Thr Gly Arg Leu Cys Asn Arg Gly Thr Ala Arg Phe Ala Ser
1               5                   10                  15

Ser Val Gly Leu
            20

<210> SEQ ID NO 545
<211> LENGTH: 20
<212> TYPE: PRT
<213> ORGANISM: Artificial
<220> FEATURE:
<223> OTHER INFORMATION: Ribosomal Protein S20;
      073002-cDNATet-20F20C40R-PP-DC-F2

<400> SEQUENCE: 545

Pro Ala Cys Arg Arg Phe Ser Arg Arg Leu Ala Pro Ser Arg Asp Arg
1               5                   10                  15

Gly Ser Gly Pro
            20

<210> SEQ ID NO 546
<211> LENGTH: 25
<212> TYPE: PRT
<213> ORGANISM: Artificial
<220> FEATURE:
<223> OTHER INFORMATION: SAC3 (Sac domain containing inositol
      phosphatase 3); 073002-cDNATet-20F20C40R-PP-DC-C12
<220> FEATURE:
<221> NAME/KEY: MISC_FEATURE
<222> LOCATION: (1)..(1)
<223> OTHER INFORMATION: X or Q represents a CAG stop
```

```
<400> SEQUENCE: 546

Xaa Arg Val Ser Cys Ser Pro Leu Glu His Thr Tyr Gly Gly Leu Tyr
1               5                   10                  15

Gly Asp Met Gly Ala Ser Trp Arg Gly
            20                  25

<210> SEQ ID NO 547
<211> LENGTH: 21
<212> TYPE: PRT
<213> ORGANISM: Artificial
<220> FEATURE:
<223> OTHER INFORMATION: SAC3 (Sac domain containing inositol
      phosphatase 3); 073002-cDNATet-20F20C40R-PP-DC-D10
<220> FEATURE:
<221> NAME/KEY: MISC_FEATURE
<222> LOCATION: (12)..(13)
<223> OTHER INFORMATION: # Stop codon: TAA after residue 12 and before
      residue 13

<400> SEQUENCE: 547

Thr Leu Asn Ser Cys Leu Ser Gly Val Ile Ala Cys Cys Arg Leu Ser
1               5                   10                  15

Gly Ile Thr Ile His
            20

<210> SEQ ID NO 548
<211> LENGTH: 25
<212> TYPE: PRT
<213> ORGANISM: Artificial
<220> FEATURE:
<223> OTHER INFORMATION: SAC3 (Sac domain containing inositol
      phosphatase 3); 073002-cDNATet-20F20C40R-PP-DC-D2
<220> FEATURE:
<221> NAME/KEY: MISC_FEATURE
<222> LOCATION: (4)..(4)
<223> OTHER INFORMATION: X or Q represents a CAG stop

<400> SEQUENCE: 548

Leu Thr Gly Xaa Cys Asn Trp Ala Arg Asp Pro Cys Val Val Gly Val
1               5                   10                  15

Thr Met Val Val Arg Arg Ala Ser Gly
            20                  25

<210> SEQ ID NO 549
<211> LENGTH: 25
<212> TYPE: PRT
<213> ORGANISM: Artificial
<220> FEATURE:
<223> OTHER INFORMATION: SAC3 (Sac domain containing inositol
      phosphatase 3); 073002-cDNATet-20F20C40R-PP-DC-F9
<220> FEATURE:
<221> NAME/KEY: MISC_FEATURE
<222> LOCATION: (1)..(1)
<223> OTHER INFORMATION: X or Q represents a CAG stop

<400> SEQUENCE: 549

Xaa Val Ile Leu Cys Cys Val Pro Gly Leu Gly Leu Val Phe Met Arg
1               5                   10                  15

Asp Ala Leu Gly Val Arg Ala Gly His
            20                  25

<210> SEQ ID NO 550
<211> LENGTH: 33
<212> TYPE: PRT
<213> ORGANISM: Artificial
```

```
<220> FEATURE:
<223> OTHER INFORMATION: SAC3 (Sac domain containing inositol
      phosphatase 3); 073002-cDNATet-20F20C40R-PP-DC-G9
<220> FEATURE:
<221> NAME/KEY: MISC_FEATURE
<223> OTHER INFORMATION: # Stop Codon: TAA stop after residue 2 and
      before reside 3
<220> FEATURE:
<221> NAME/KEY: MISC_FEATURE
<222> LOCATION: (32)..(32)
<223> OTHER INFORMATION: X or Q represents a CAG stop

<400> SEQUENCE: 550

Trp Ile Ala Glu Leu Phe Gly Tyr Ala Gly Leu Asp Met Leu His Val
1               5                   10                  15

Met Ser Gly Phe Ser Glu Val Ala Cys Leu Leu Thr Val Pro Asn Xaa
            20                  25                  30

Ser

<210> SEQ ID NO 551
<211> LENGTH: 24
<212> TYPE: PRT
<213> ORGANISM: Artificial
<220> FEATURE:
<223> OTHER INFORMATION: SAC3 (Sac domain containing inositol
      phosphatase 3)

<400> SEQUENCE: 551

Ser Phe Leu Arg Ala Ser Ser Val Ser Leu Arg Ser Ser Leu Val Thr
1               5                   10                  15

Leu Pro Arg Val Ser Gly Val Leu
            20

<210> SEQ ID NO 552
<211> LENGTH: 20
<212> TYPE: PRT
<213> ORGANISM: Artificial
<220> FEATURE:
<223> OTHER INFORMATION: Cytochrome c oxidase subunit VIB;
      073002-cDNATet-20F20C40R-PP-DC-C2

<400> SEQUENCE: 552

Ser Gly Trp Pro Val Gly Gly Pro Val Cys Ile Ala Leu Arg Leu
1               5                   10                  15

Ala Gly Arg Arg
            20

<210> SEQ ID NO 553
<211> LENGTH: 25
<212> TYPE: PRT
<213> ORGANISM: Artificial
<220> FEATURE:
<223> OTHER INFORMATION: Human homolog of yeast ribosomal protein S28;
      073002-cDNATet-20F20C40R-PP-DC-C7
<220> FEATURE:
<221> NAME/KEY: MISC_FEATURE
<222> LOCATION: (11)..(11)
<223> OTHER INFORMATION: X or Q represents a CAG stop

<400> SEQUENCE: 553

Arg Thr Gly Phe Cys Cys Ser Ala Gly Cys Xaa Val Arg Val Leu Thr
1               5                   10                  15

Arg Pro Glu Gly Thr Ile Gly Met Val
            20                  25
```

```
<210> SEQ ID NO 554
<211> LENGTH: 20
<212> TYPE: PRT
<213> ORGANISM: Artificial
<220> FEATURE:
<223> OTHER INFORMATION: RCC1; 011002-OVcDNATet-20F-PP-DC-D1

<400> SEQUENCE: 554

Tyr Ala Val Gly Val Gln Pro Ala Ile Arg Val Gly Val Asn Leu Asp
1               5                   10                  15

Val His Met Ser
            20

<210> SEQ ID NO 555
<211> LENGTH: 25
<212> TYPE: PRT
<213> ORGANISM: Artificial
<220> FEATURE:
<223> OTHER INFORMATION: Caspase-3; Caspase3-20C-3-A3(4)

<400> SEQUENCE: 555

Leu Arg Gln Trp Cys Arg Trp Val Met Gly Ala Ser Arg Arg Met Pro
1               5                   10                  15

Phe Ile Cys Ala Gly Trp Asp Gly Pro
            20                  25

<210> SEQ ID NO 556
<211> LENGTH: 20
<212> TYPE: PRT
<213> ORGANISM: Artificial
<220> FEATURE:
<223> OTHER INFORMATION: PARP; PARP-20F-4-G11(2)

<400> SEQUENCE: 556

Leu Ser Arg Pro Val Ile Pro Trp Thr Ser Gly Glu Ile Gly Arg Ala
1               5                   10                  15

Thr Arg Gln Asp
            20
```

TARGET SPECIFIC SCREENING AND ITS USE FOR IDENTIFYING TARGET BINDERS

This application claims priority to Provisional Application Ser. No. 60/345,471 filed Oct. 24, 2001, hereby incorporated by reference.

FIELD OF THE INVENTION

This invention is in the general field of functional genomics through identification of biological molecules, including nucleic acids, protein, and the like, more particularly, the identification of targets and their specific binders.

BACKGROUND OF THE INVENTION

A concerted international effort has lead to the deciphering of the human genome. Originally, it was estimated that greater than 100,000 genes would be encoded within the genome. However, research indicated that the >3.2 billion DNA units comprising the genome "only" coded for 30,000–50,000 genes (Human Genome Sequencing Consortium and Celera Genomics). Despite rapid progress in identifying genes, progress in identifying the activity and function of the gene products lags significantly behind. There is additional evidence that the actual number of proteins may reach 100,000–200,000 when one considers splice variants and post-translational modifications. This indicates that the actual number of possible protein targets for drug discovery is much greater than would be anticipated from the sequencing of the human genome. Also, there are potential non-protein targets for drug discovery including nucleic acids (e.g., mRNA and promoter regions of disease related genes) and lipids (e.g., members of the phophoinositol family of secondary messages). Thus, while sequencing of the human genome was a great leap forward for modern science, it is only the first step in determining the relationships between the majority of these genes and disease and their subsequent use as validated targets for drug discovery.

Many gene products function by binding to one or more other peptides or proteins. Presently, there are few approaches for identifying a protein's binder, e.g., the protein with which the target gene product directly interacts. This information is critical as protein:ligand interactions are involved in important cell processes such as signaling (e.g., information transfer in signaling cascades) and molecular processing. The identification of protein binders can be used to determine, for example, the ligand for a receptor, the substrate for an enzyme, and the regulatory protein for an enzyme complex.

Binder information is critical to developing a target-binding assay for the identification of drug leads. There is a large number of binding assays that exist, including in vitro and in vivo formats. Most in vitro formats require input of both target and ligand or target binder, and only a few formats require only target input. However, formats that require only a protein target generate a high frequency of false positives, i.e., compounds that bind but do not cause a change in target activity. Such formats would require extensive screening to identify ligands for previously uncharacterized protein targets.

At present, there are several approaches to finding and validating new drug discovery targets. For example, functional genomics involves the use of differential techniques (such as microarrays) to discern differences between normal and disease-related genes. A subset of this approach uses computational techniques to "mine" the public and private databases for differentially expressed genes. For example, tyrosine kinases, such as the epidermal growth factor receptor (EGFR) have been shown to be involved in a wide variety of cancers such as breast, prostate and colorectal carcinoma. In addition, others have used "bait and prey" techniques to identify natural partners and validate targets for drug discovery.

In the classical approach to binder identification, the protein target and its natural partner or target binder are isolated in a complex. In a modern approach, the target and natural partner or target binder are constructed as two fusion proteins that generate a signal upon interaction. As examples of the latter, yeast two-hybrid systems have been developed. The original intent of the yeast two-hybrid was to define the interactions between two proteins in a simple high throughput manner. The system utilizes two fusion elements consisting of a DNA-binding domain or bait, and a transcriptional activation domain or prey. These two chimeras could then be introduced into yeast cells with a reporter. Binding of bait to prey leads to the activation of the reporter with the appropriate readout such as growth in defined medium. Other two-hybrid like approaches include the bacterial two hybrid system (U.S. Pat. No. 5,925,523 to Dove et al.). However, two-hybrid systems have several disadvantages, including high levels of false positives, incompatibility with certain targets (e.g., RNAs and membrane bound proteins cannot be used), and problems with postranslational modifications. Moreover, approaches based on two-hybrid systems are not easily applied to a large number of genes of unknown function.

Phage display is a useful approach as a selection technique in which a peptide or protein is expressed as a fusion with a coat protein of a bacteriophage (phage), resulting in display of the fused protein on the exterior surface of the phage virion. Briefly, phage display has been used to create a physical linkage between a large library of random peptide sequences to the DNA encoding each sequence, allowing for rapid identification of peptide ligands for a variety of target molecules, such as for example, antibodies, enzymes, cell-surface receptors, etc., by an in vitro selection process called biopanning (Parmley, S. F. and Smith, G. P. (1988) Gene 73, 305–318; Reviewed in Cortese, R. et al. (1995) Curr. Opin. Biotechnol. 6, 73–80; Noren, C. J. (1996) NEB Transcript 8 (1), 1–5).

Briefly, biopanning is performed by incubating a library of phage-displayed peptides with a target, removing unbound phage, and eluting the specifically bound phage. However, a purified target is necessary in the preferred use of this methodology. The purification of active target is a cumbersome step made much more difficult when the protein under investigation does not yet have a known function needed to monitor the production of active protein. As such methodology does not afford the investigator a means for identifying large populations of unknown proteins such as those found to be differentially expressed in one cell versus another, or under some disease related condition at a time. Furthermore, when using one target at a time, the present approach requires that once the eluted phage is amplified, several cycles, usually 3 to 4 rounds, of biopanning and amplification is essential for successfully enriching the phage pool of tightly binding sequences.

Identifying novel disease-related targets, disease related populations of proteins, and their use in high throughput drug discovery is highly desirable for pharmaceutical and biotechnology companies in the post-genomic era. The traditional process of drug discovery relies on only a limited number of targets that could be screened using small chemical or natural product libraries. With the advent of biotechnology however, recombinant proteins and monoclonal antibodies became available as drugs to treat various diseases. In general, the use of these reagents had a solid experimental base prior to their use. For example, erythropoietin (EPO) is a growth factor involved in the regeneration of red blood cells by activating its cognate receptor. Knowledge of the EPO/EPO receptor nexus allowed the search for the ligand to proceed and eventually succeed. Similarly, monoclonal antibodies such as Herceptin (anti-erb B2) and C225 (anti-EGFR) are based on a body of experimental data dating to the identification of these receptors and their relationship to cancer.

Thus, there is a need for a screening system that ameliorates or overcomes one or more of the above or other encountered problems. An ideal system would allow the sampling of very large numbers of specificities of entire populations. These populations, i.e., proteomes, could, for example, contain protein members that are differentially expressed on one cell versus another. An ideal system would allow for the sampling of populations of targets having >10$^6$ members and populations of potential target binders having >10$^{11}$ members. An ideal system would also allow for rapid sorting during a cloning round and rapid transfer of the genetic material coding for the binding molecule from one stage of the production process, to the next stage. Therefore, a rapid and unencumbered selection method for identifying and isolating novel disease-related targets and their use in high throughput drug discovery is highly desirable.

SUMMARY OF THE INVENTION

This invention provides a method for identifying molecules, including nucleic acids, polypeptides, fragments thereof, and the like, that bind to a target of interest.

The invention provides a method for identifying a biological molecule of interest or target, including nucleic acids, polypeptides, fragmnets thereof, and the like, and their corresponding target binders using a modified phage display method. The method involves mixing in a reaction vessel two separate phage, one comprising a target or target library and the other comprising a target-binder library each having different selection markers, forming mated or complexed pairs, transforming the mated or paired complexes into host cells, followed by selection to eliminate the non-paired targets and binders. After selection, the target and/or the target binders can be identified by sequencing the DNA inserts in the target and target-binder phage DNA associated with the selected pairing of target and target binder. This embodiment of the invention also allows for simultaneous screening for a single biological molecule or target, or a multiplicity of biological molecules and their target binders.

This invention can be used to identify target binders that are capable of binding a specific target having known or unknown function. The target binders may be identified from phage libraries or cDNA libraries that express, for example, a fully randomized peptide library or a partially randomized peptide library on the surface or exterior of the phage. Further, the invention can be used to identify natural binding partners from a cDNA library for a particular peptide or protein. Moreover, the invention may also be used to identify target binders found within the same or between different cDNA libraries.

This invention also relates to obtaining target binders that can be used in assays for screening the binding of a target and other target binders. The identified target binders may be used in competition assays with other molecules to screen target binding. The other molecules can be any type of molecule, for example, peptides, proteins, carbohydrates, lipids or small organic compounds.

This invention also relates to targets and target binders isolated by the methods of the invention that may be used as tools for further analysis leading to the treatment of diseases. One example of the present invention relates to the target DGI-2 and DGI-2 binders isolated by the methods of the present invention, which may be used as tools for further analysis leading to the treatment of diseases.

In another embodiment of the invention, the library from which target binders are identified according to their ability to bind to the target, is a random peptide phage display library, where peptides range in length from about 9 to about 100 amino acids, and preferably 20 to 40 amino acids. The library from which the target binders are identified is a peptide phage display library, where only certain amino acids within the peptide are selectively randomized. Also the phage display library may express a cDNA library. In this embodiment, it is possible to identify a natural binding partner of the target. In a further embodiment of the invention, both the target library and the target-binder library are cDNA libraries, which expresses the amino acid sequences encoded by the cDNA library on the surface or exterior of the phage.

It is a further object of the invention to provide target binders having biological activity (e.g., agonists, antagonists, inhibitors, or other modulators) that bind to target polypeptides, variants, or fragments thereof using a target-binder phage library and a target phage construct.

It is another object of the invention to provide a method for identifying an amino acid sequence motif that confers binding properties to a target by screening a library of expressed amino acid sequences for binding to the target, determining the amino acid sequence of the members of the library which bind to the target, and identifying as motifs common amino acid sequences.

It is yet another object of the invention to provide compositions (e.g., pharmaceutical compositions) comprising one or more targets and/or target binders polynucleotides, polypeptides, peptides, or antibodies.

It is a further object of this invention to provide target peptide binders to the protein encoded by the target gene, wherein the target peptide binders are those having SEQ ID NOs: 1–189 and SEQ ID NOs: 227–532.

Additional objects and advantages afforded by the present invention will be apparent from the detailed description and exemplification herein below.

DESCRIPTION OF THE FIGURES

The appended drawings of the figures are presented to further describe the invention and to assist in its understanding through clarification of its various aspects. In the figures of the present invention, the nucleotide and amino acid sequences are represented by their one-letter abbreviations.

FIG. 1 shows potential binding motifs of DGI-2 binders. "PP" identifies the peptides as having been isolated by the proteome panning technique described below. The other peptides were isolated using standard panning approaches as described in Pillutla et al. (BMC Biotechnology 1:6, 2001). The number shown in subscript following each peptide name represents the number of times the peptide was isolated from the DGI-2 clones. For example, DGI2-20R-4-H814 was isolated 14 times after 4 rounds of conventional panning using a random 20-mer peptide phage display library. Etag—peptide binding to E tag antibody (AAA- GAPVPYPDPLEPRP; SEQ ID NO: 190) fused to peptide; DGI-2—binding to DGI-2 polypeptide (specific binding); LDH—peptide binding to LDH polypeptide (non-specific binding); DGI-2/LDH—ratio of specific binding to non-specific binding. Values shown represent ELISA units read at 405 nm. Higher values indicated higher binding specificity for target. Q represents a CAG stop; * represents a TGA stop; # represents a TAA stop; + represents any polar amino acid (D, E, K, R, H, N, and Q); and φ represents any hydrophobic amino acid (A, F, G, I, L, M, T, V, and W).

FIGS. 2A–2B show a schematic diagram of the preparation of the cDNA libraries in the modified tetracycline-resistant phage and the use of cDNA libraries in one or both of the phage libaries.

FIG. 3 shows the DNA sequence of the DGI-2 (SEQ ID NO: 533), which was cloned into the tetracycline resistant vector, pCANTAB(tet). DGI-2 was identified as an uncharacterized gene in a public database designated KIAA0101 (GenBank Acc. No. XM 042258).

FIG. 4 shows sequences from 070902-DGI2-20M-PP-BC Proteome Pan. Amino acid sequences are represented by their one-letter abbreviations. Binding is indicated as the ratio over background, Specific/Irrelevant (Sp/Irr). LDH=Lactate dehydrogenase (control irrelevant protein).

FIGS. 5A–5B show sequences from 070902-Hras-20M-PP-BC Proteome Pan. Amino acid sequences are represented by their one-letter abbreviations. Binding is indicated as the ratio over background (Sp/Irr). LDH=Lactate dehydrogenase (control irrelevant protein).

FIG. 6 shows sequences from 070902-Leptin-20M-PP-BC Proteome Pan. Amino acid sequences are represented by their one-letter abbreviations. Binding is indicated as the ratio over background (Sp/Irr). LDH=Lactate dehydrogenase (control irrelevant protein).

FIGS. 7A–7K show results of a database query showing only Homo sapiens (human) hits transferred into Excel. The Access database can be easily queried for specific values (or value range) in all fields. Results can be easily transferred or exported. Separate tables containing results from different panning experiments can also be queried together for cross reference.

FIGS. 8A–8G show a database of human genes and the sequences of binding peptides that were identified by panning protocols using libraries, described herein (DGI Biotechnologies). The database also provides identification numbers to related information such as the gene, protein, and locus.

FIGS. 9A–9B show the sequences of DGI-5 Binders. Amino acid sequences are represented by their one-letter abbreviations. Binding is indicated as the ratio over background. Insulin growth factor receptor (IGFR) was used as the control irrelevant protein. Numbers in subscript at the end of a clone name indicate the number of times the sequence was found in that panning.

FIG. 10 shows sequences of DGI-7 Binders. Amino acid sequences are represented by their one-letter abbreviations. Binding is indicated as the ratio over background. LDH=Lactate dehydrogenase (control irrelevant protein). Numbers in subscript at the end of a clone name indicate the number of times the sequence was found in that panning.

FIG. 11 shows sequences of Vascular Endothelial Growth Factor (VEGF) Binders. Amino acid sequences are represented by their one-letter abbreviations. Binding is indicated as the ratio over background. BSA was used as the irrelevant protein because target protein was resuspended in PBS+ BSA. Numbers in subscript at the end of a clone name indicate the number of times the sequence was found in that panning.

FIGS. 12A–12B show sequences of Vascular Endothelial Growth Factor-Receptor 1/FMS-related Tyrosine Kinase 1 (VEGF-R1/FLT1) Binders. Amino acid sequences are represented by their one-letter abbreviations. Binding is indicated as the ratio over background. BSA was used as the irrelevant protein because target protein was resuspended in PBS+BSA. Numbers in subscript at the end of a clone name indicate the number of times the sequence was found in that panning.

FIG. 13 shows sequences of Vascular Endothelial Growth Factor-Receptor 2/FLK1/Kinase insert Domain protein Receptor (VEGF-R2/FLK1/KDR) Binders. Amino acid sequences are represented by their one-letter abbreviations. Binding is indicated as the ratio over background. BSA was used as the irrelevant protein because target protein was resuspended in PBS+BSA. Numbers in subscript at the end of a clone name indicate the number of times the sequence was found in that panning.

FIG. 14 shows sequences of Vascular Endothelial Growth Factor Receptor 3 (VEGF-R3) Binders. Amino acid sequences are represented by their one-letter abbreviations. Binding is indicated as the ratio over background. BSA was used as the irrelevant protein because target protein was resuspended in PBS+BSA. Numbers in subscript at the end of a clone name indicate the number of times the sequence was found in that panning.

FIG. 15 shows sequences of Epithelial Growth Factor Receptor (EGFR) Binders. Amino acid sequences are represented by their one-letter abbreviations. Binding is indicated as the ratio over background. LDH=Lactate dehydrogenase (control irrelevant protein). Numbers in subscript at the end of a clone name indicate the number of times the sequence was found in that panning. Two separate panning experiments are indicated by the subscript alpha or beta.

FIGS. 16A–16B show sequences of Fibroblast Growth Factor Receptor 1 (FGFR1) alpha and FGFR1 beta Binders. Amino acid sequences are represented by their one-letter abbreviations. Binding is indicated as the ratio over background. BSA was used as the irrelevant protein because target protein was resuspended in PBS+BSA. Numbers in subscript at the end of a clone name indicate the number of times the sequence was found in that panning.

FIGS. 17A–17B show sequences of Tie-1 Binders. Amino acid sequences are represented by their one-letter abbreviations. Binding is indicated as the ratio over background. BSA was used as the irrelevant protein because target protein was resuspended in PBS+BSA. Numbers in subscript at the end of a clone name indicate the number of times the sequence was found in that panning.

DETAILED DESCRIPTION OF THE INVENTION

Figure 2A:
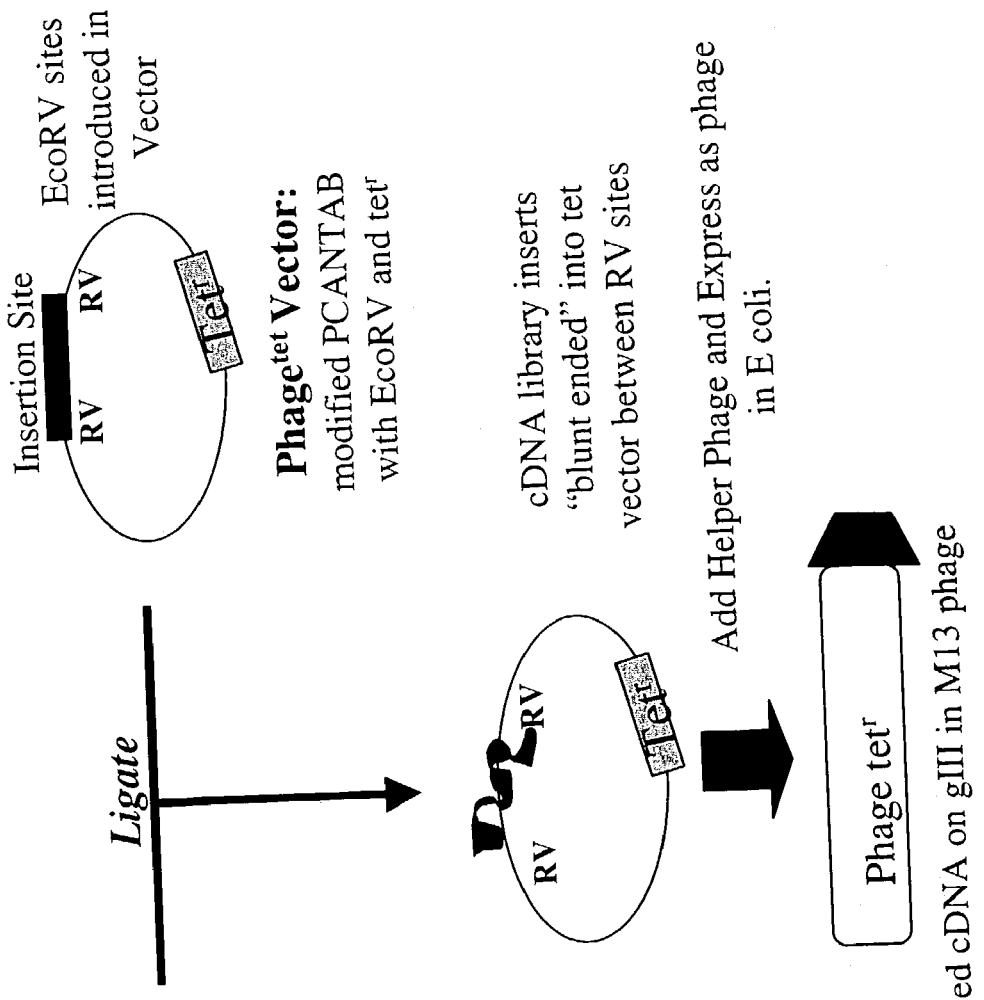

The present invention relates to methods for detecting and identifying known and unknown targets, and their target binders. The present invention involves using phage display libraries to identify target binders for known or unknown targets. The phage display libraries may be peptide libraries or cDNA libraries that express the peptides or encoded amino acid sequence on the surface or exterior of the phage. The method involves combining two separate phage to allow binding of the expressed target and target binders and then transforming host cells with the combination. The members of specific binding pairs are then selected by using multiple selection markers. The present invention also relates to the binding molecules produced by these methods.

Definitions

The term "target" as used herein refers to a biological molecule of interest, including nucleic acids, proteins (intracellular, transmembrane, extracellular), amino acids, polypeptides, fragments thereof, and the like. Targets may be, for example, receptors, enzymes, binding proteins, antibodies or polypeptides of known or unknown function. For example, the polypeptide DGI-2, amino acids, cDNAs, or peptides are targets of the invention.

The term "target binder" as used herein refers to a molecule that binds to a target and can include nucleic acids, amino acids, polypeptides, fragments thereof, and the like. Target binders also include but are not limited to ligands, small molecules, and drugs.

The term "vector" as used herein refers to a nucleic acid molecule capable of replicating another nucleic acid to which it has been linked. A vector, for example, can be a plasmid.

"Host cells" includes prokaryotes and eukaryotes. The term includes an organism or cell that is the recipient of a phage or phage library.

"Isolated", as used herein, refers to nucleic or amino acid sequences that are at least 60% free, preferably 75% free, and most preferably 90% free from other components with which they are naturally associated.

As used herein, the terms "protein" and "polypeptide" are synonymous. "Peptides" are defined as fragments or portions of polypeptides, preferably fragments or portions having at least one functional activity (e.g., binding, signaling, or antigenic activity) as the complete polypeptide sequence.

The term "antigenic" refers to the ability of a molecule (e.g., a polypeptide or peptide) to bind to its specific antibody, or an antibody fragment, with sufficiently high affinity to form a detectable antigen-antibody complex.

The term "ligand" as used herein describes any molecule, protein, peptide, or compound with the capability of directly or indirectly altering the physiological function, stability, or levels of a polypeptide or polynucleotide. In specific aspects, ligands may directly bind to a polypeptide or polynucleotide. Ligands may include nucleic acids, carbohydrates, or small organic compounds.

A "sample" as used herein refers to a biological sample, such as, for example, tissue or fluid isolated from an individual (including, without limitation, plasma, serum, cerebrospinal fluid, lymph, tears, saliva, milk, pus, and tissue exudates and secretions) or from in vitro cell culture constituents, as well as samples obtained from, for example, a laboratory procedure.

General descriptions of the foregoing terms and others are known in the art. See, e.g., Roitt et al., 1989, *Immunology*, 2$^{nd}$ Edition, C. V. Mosby Company, New York; Male et al., 1991, *Advanced Immunology*, 2$^{nd}$ Edition, Grower Medical Publishing, New York.

Proteome Panning Method

This invention provides a method of selecting and identifying target and target binders, by transforming host cells with two separate phages, one comprising a target-binder library and the other comprising a target or target library, followed by selection for the pairing of the target and target binder, where the general method is termed herein "proteome panning".

In general, the present invention involves the following steps:

1. Preparing a phage comprising a target and a selection marker, where the target may be an individual target or a mixture of known or unknown targets from, for example, cDNA or subtracted cDNA libraries. The target may be a full-length protein, parts of proteins or domains involved in biological interactions. The target may be of known or unknown function;

2. Obtaining a phage target-binder library and a second selection marker, where the phage may express peptides, full-length proteins, parts of proteins, or domains involved in biological interactions. The peptides or proteins may be fully or partially randomized or may be from cDNA library;

3. Panning, where the target phage and the target-binder phage are mixed in solution and targets and target-binders are allowed to mate or form complexed pairs. The process may be performed for 2–24 hours, preferably 2–3 hours, at a temperature range of 28° C.–37° C., preferably at a temperature range of 28° C.–30° C.

4. Transforming host cells with the mixture of target phage and target-binder phage library, wherein the mated or complexed pairs infect the host cells;

5. Selecting for host cells infected by phage that formed complexes of target and target binders by using various selection agents including, but not limited to, antibiotics such as ampicillin and tetracycline, auxotrophic markers, and fluorescent markers.

6. Analyzing target and target binders by sequencing and using computational approaches.

In a preferred embodiment of the invention, the target may be an expressed peptide or protein or a single expressed cDNA. In another preferred embodiment of the invention, the target could be a target library comprising a cDNA phage library. The cDNAs would preferably range in size from about 200 base pairs to 2500 base pairs, more preferably 350–1500 base pairs. The target-binder library is preferably a fully randomized peptide phage display library comprising peptides ranging in length from about 9 amino acids to 100 amino acids, more preferably 20–40 amino acids. In another embodiment of the invention, the target-binder library may have only particular amino acids selectively randomized or other constraints built into the its sequence. Non-limiting examples of targets for target binders include: DGI-2, DGI-5, DGI-7, DGI-9, VEGF, VEGFR1, VEGFR2, VEGFR3, EGFR, FGFR1-alpha/beta, and Tie-1. The target protein, in one embodiment, is DGI-2. DGI-2 was identified as an uncharacterized gene in a public database designated KIAA0101 (GenBank Acc. No. XM_042258). The nucleotide sequence enclosing DGI-2 (SEQ ID NO: 533) is shown in FIG. 3. The target proteins for DGI-5, DGI-7 (metallothionein-11), and DGI-9 (HEC) were identified in public databases having the GenBank Acc. No. Accession numbers AA707319, X76717, and NM_006101, respectively.

In another embodiment of the invention, techniques may be used for enriching only the high affinity binders to the targets. These may include, but are not limited to, preincubation time, changes in temperature, pH, ionic strength, incubation in the presence of competing target binders and washing steps with different buffers. Other techniques may also include a second or multiple rounds of proteomic panning which includes amplification steps, where the population of selected colonies are amplified, rescued and repanned.

In a further embodiment of the invention, the method involves proteome panning of known or unknown gene protein products or other targets expressed on phage with phage displayed libraries of random peptides or cDNA, and obtaining a set of peptides or cDNAs which bind to such targets in such a manner as to allow the identification of individual pairs of targets and target binders. Bacteria are isolated, either as a population or as single colonies containing a single pairing of one target and one target binder. The target and target binder are then sequenced, thereby providing additional functional information. When initially using a single target phage, displaying a target on the surface of the phage, multiple target binders are obtained, for example, in the order of tens to thousands. The targets and target binders are sequenced and the target binders used individually or as consensus motifs to search for genes, for example, with expressed proteins of matching amino acid sequence. These identified consensus motifs may also be used to design selectively randomized library of target binders for second proteome pannings. FIG. 1 shows four potential binding motifs of DGI-2 binders: Motif 1: GCXXFXGFCV (SEQ ID NO: 505); Motif 2: FRXWVEGφ (SEQ ID NO:512); Motif 3: SXGWXFPGWR (SEQ ID NO: 517); and Motif 4: φWR±WV±GSLxG (SEQ ID NO: 522). Sequences having at least one of these consensus motifs are also shown in FIG. 1 (SEQ ID NOs: 505–532).

Phage Display Libraries

Phage display libraries can be screened for target binders that bind to targets using proteome panning as described above. Details of the construction and analyses of these libraries are described in detail herein and have been published (see, e.g., WO 96/04557; Mandecki et al., 1997, *Display Technologies—Novel Targets and Strategies*, P. Guttry (ed), International Business Communications, Inc. Southborogh, Mass., pp. 231–254; Ravera et al., 1998, *Oncogene* 16:1993–1999; Scott and Smith, 1990, *Science* 249:386–390); Grihalde et al., 1995, *Gene* 166:187–195; Chen et al., 1996, *Proc. Natl. Acad. Sci. USA* 93:1997–2001; Kay et al., 1993, *Gene* 128:59–65; Carcamo et al., 1998, *Proc. Natl. Acad. Sci. USA* 95:11146–11151; Hoogenboom, 1997, *Trends Biotechnol.* 15:62–70; Rader and Barbas, 1997, *Curr. Opin. Biotechnol.* 8:503–508; all of which are incorporated herein by reference).

In one aspect of the invention, target cDNA phage libraries may be used. Of the numerous methods for constructing cDNA libraries, the approach based on methods described in *Gene*, 25:263 (1983) is the most widely used. Approaches to achieve enrichment of specific sequences include subtractive cDNA libraries (*Trends Genet.*, 9:70 (1993)) and normalized cDNA libraries (*Genome Res.*, 6:791 (1996)). While subtractive and normalized libraries are generally not full-length cDNAs, the frequency of full-length cDNAs has been increased by RecA-mediated triple-strand formation in a subtractive cDNA library (*Nucleic Acid Res.*, 24:3478 (1996). An advantage of the invention is that only very small amounts of the protein targets are needed, i.e., amounts sufficient for their presentation on phage coat proteins, where gene III is preferably present in 3–5 copies per phage. By using a natural process of protein generation, e.g. bacterial, to make a protein of unknown function and characteristics, large percentages of protein populations from cDNA libraries can be produced at one time for investigation.

The present invention may also use peptide libraries to identify new binders for the target of interest. Peptide libraries can be designed according to methods described in detail herein, and methods generally available to those in the art (see, e.g., U.S. Pat. No. 5,723,286 issued Mar. 3, 1998 to Dower et al.). In one aspect, commercially available phage display libraries can be used (e.g., RAPIDLIB® or GRA-BLIB®, DGI BioTechnologies, Inc., Edison, N.J.; Ph.D. C7C Disulfide Constrained Peptide Library, New England Biolabs).

In another aspect, an oligonucleotide or cDNA library can be prepared according to methods known in the art, and inserted into an appropriate vector for peptide expression. In order to construct cDNA phage display libraries, commonly known techniques in the art are employed. More particularly, three methods for producing cDNA that are used in the invention include: 1) random priming and directional cloning; 2) PCR-based oligo dT priming and directional cloning; and 3) excising cDNA from existing libraries. For example, ligation-ready subtracted or unsubtracted cDNA is produced by classical cDNA methods using random priming and poly A+RNA from various normal and cancerous tissues (see Example 14). The PCR-based oligo dT priming and directional cloning method may use a modified Smart cDNA Synthesis kit (Clontech) as described in Example 14. The third method essentially involves excising cDNA from pre-existing cDNA libraries comprising normal and cancerous tissues at the appropriate restriction enzyme sites (see Example 14). Both cDNA and subtracted cDNA phage display libraries may be commercially obtained or constructed. Briefly, poly A+RNA from various tissues may be purchased or purified from cells lines. This RNA produces double stranded cDNA of a desirable size that may be cloned into the phage display vector to make the cell library. In particular, the preferred cDNA size for insertion into the phage display vector is 100 base pairs to 3000 base pairs, and more preferably 200 base pairs to 2000 base pairs. Alternatively, cDNA may be excised from pre-existing libraries. Poly A+RNA or cDNA from cancerous tissue subtracted in multiple rounds from excess normal poly A+RNA or cDNA generates subtracted libraries.

For the phage display system, N-terminal display on gene III may be preferably chosen for its favorable high affinity interactions due to the low valency of gene III on the phage particle. However, cDNA containing stop codons eliminates gene III expression and hence there is no phage display of the recombinant protein. In order to eliminate clones with stop codons, the cDNA is first ligated to either of two expression screen vectors, one containing the green fluorescent protein (GFP) gene and the other containing the kanamycin (kan) gene. In the kanamycin screen, three reading frames are employed to increase the probability of in frame clones. Fluorescent or kanamycin resistant (kanR) clones are picked, pooled, and amplified by cell growth. A large-scale DNA preparation is carried out, digested with appropriate enzymes, and cloned into the phage display vector to construct the cell library containing all open reading frames.

For example, vectors encoding a bacteriophage structural protein, preferably an accessible phage protein, such as a bacteriophage coat protein, can be used. Although one skilled in the art will appreciate that a variety of bacteriophage may be employed in the present invention, in preferred embodiments the vector is, or is derived from, a filamentous bacteriophage, such as, for example, f1, fd, Pf1, M13, etc. In particular, the fd-tet vector has been extensively described in the literature (see, e.g., Zacher et al., 1980, *Gene* 9:127–140; Smith et al., 1985, *Science* 228:1315–1317; Parmley and Smith, 1988, *Gene* 73:305–318).

The phage vector is chosen to contain or is constructed to contain a cloning site located in the 5' region of the gene encoding the bacteriophage structural protein, so that the peptide is accessible to receptors in an affinity enrichment procedure as described herein below. The structural phage protein is preferably a coat protein. An example of an appropriate coat protein is pIII. A suitable vector may allow oriented cloning of the cDNA or the oligonucleotide sequences so that the protein or peptide is expressed at or within a distance of about 100 amino acid residues of the N-terminus of the mature coat protein. The coat protein is typically expressed as a preprotein, having a leader sequence.

Another feature of the design of these libraries enables "Rapid Partner Identification" by high throughput sequencing. The rapidity of partner identification is dependent on the ability to sequence, individually, each of the two clones within a single colony which have identical vector sequences except for the respective antibiotic resistance gene (e.g. ampicillin or tetracycline). To accomplish this, a single PCR product must be obtained when sequence is desired for the clone originating from either the ampicillin (amp) resistant (ampR) or tetracycline (tet) resistant (tetR) phage libraries. To achieve this end, minor changes were incorporated in vector sequences with corresponding specific primers which differentiate between the tet and amp library clones. Given the analysis that the human genome contains 30,000 to 66,000 genes, multiple libraries are expression screened and cloned into the phage display vector until the combined diversity is $1 \times 10^5$ expression positive clones, i.e. open reading frames (ORFs), for the unsubtracted libraries. The cell libraries are rescued and the resultant phage libraries, either amp or tet resistant are combined and used in all phases of proteome panning.

For generating subtractive cDNA phage display libraries, subtractive hybridization is utilized. Subtractive hybridization is a powerful technique that enables one to compare two populations of mRNA and obtain clones of genes that are expressed in one population, but not in the other. Briefly, both mRNA populations are converted into cDNA. The target and target binder cDNAs are hybridized and the hybrids sequences are removed. Consequently, the remaining unhybridized cDNAs represent genes that are expressed in the target comparede to the target binder. (see Example 15).

Thus, the oligonucleotide or cDNA library is desirably inserted so that the N-terminus of the processed bacteriophage outer protein is the first residue of the peptide or protein, i.e., between the 3'-terminus of the sequence encoding the leader protein and the 5'-terminus of the sequence encoding the mature protein or a portion of the 5' terminus. A cDNA library or oligonucleotide library is constructed by cloning the cDNA or an oligonucleotide which contains the variable region of library members (and any spacers, if necessary) into the selected cloning site. Using known recombinant DNA techniques (see generally, Sambrook et al., 1989, *Molecular Cloning, A Laboratory Manual*, 2d ed., Cold Spring Harbor Laboratory Press, Cold Spring Harbor, N.Y., 1989), an oligonucleotide may be constructed which, inter alia, 1) removes unwanted restriction sites and adds desired ones; 2) reconstructs the correct portions of any sequences which have been removed (such as a correct signal peptidase site, for example); 3) inserts spacer residues, if any; and/or 4) corrects the translation frame (if necessary) to produce active, infective phage.

The central portion of the oligonucleotide will generally contain one or more target binding sequences, such as for example, DGI-2-binding sequences and, optionally, spacer sequences. The sequences are ultimately expressed as peptides (with or without spacers) fused to or in the N-terminus of the mature coat protein on the outer, accessible surface of the assembled bacteriophage particles. The size of the library will vary according to the number of variable codons, and hence the size of the peptides, which are desired. Generally, the library will be at least about $10^6$ members, usually at least $10^7$, and typically $10^8$ or more members. To generate the collection of oligonucleotides which forms a series of codons encoding a random collection of amino acids and which is ultimately cloned into the vector, a codon motif is used, such as $(NNK)_x$, where N may be A, C, G, or T (nominally equimolar), K is G or T (nominally equimolar), and x is typically up to about 5, 6, 7, 8, or more, thereby producing libraries of penta-, hexa-, hepta-, and octa-peptides or larger. The third position may also be G or C, designated "S". Thus, NNK or NNS 1) code for all the amino acids; 2) code for only one stop codon; and 3) reduce the range of codon bias from 6:1 to 3:1.

It should be understood that, with longer peptides, the size of the library that is generated may become a constraint in the cloning process. The expression of peptides from randomly generated mixtures of oligonucleotides in appropriate recombinant vectors is known in the art (see, e.g., Oliphant et al., *Gene* 44:177–183). For example, the codon motif $(NNK)_6$ produces 32 codons, one for each of 12 amino acids, two for each of five amino acids, three for each of three amino acids and one (amber) stop codon. Although this motif produces a codon distribution as equitable as available with standard methods of oligonucleotide synthesis, it results in a bias against peptides containing one-codon residues. In particular, a complete collection of hexacodons contains one sequence encoding each peptide made up of only one-codon amino acids, but contains 729 ($3^6$) sequences encoding each peptide with only three-codon amino acids.

An alternative approach to minimize the bias against one-codon residues involves the synthesis of 20 activated trinucleotides, each representing the codon for one of the 20 genetically encoded amino acids. These are synthesized by conventional means, removed from the support while maintaining the base and 5-OH-protecting groups, and activated by the addition of 3'O-phosphoramidite (and phosphate protection with b-cyanoethyl groups) by the method used for the activation of mononucleosides (see, generally, McBride and Caruthers, 1983, *Tetrahedron Letters* 22:245). Degenerate oligocodons are prepared using these trimers as building blocks. The trimers are mixed at the desired molar ratios and installed in the synthesizer. The ratios will usually be approximately equimolar, but may be a controlled unequal ratio to obtain the over- to under-representation of certain amino acids coded for by the degenerate oligonucleotide collection. The condensation of the trimers to form the oligocodons is done essentially as described for conventional synthesis employing activated mononucleosides as building blocks (see, e.g., Atkinson and Smith, 1984, *Oligonucleotide Synthesis*, M. J. Gait, Ed., p. 35–82). This procedure generates a population of oligonucleotides for cloning that is capable of encoding an equal distribution (or a controlled unequal distribution) of the possible peptide sequences. Advantageously, this approach may be employed in generating longer peptide sequences, since the range of bias produced by the $(NNK)_6$ motif increases by three-fold with each additional amino acid residue.

When the codon motif is $(NNK)_x$, as defined above, and when x equals 8, there are $2.6 \times 10^{10}$ possible octa-peptides. A library containing most of the octa-peptides may be difficult to produce. Thus, a sampling of the octa-peptides may be accomplished by constructing a subset library using up to about 10% of the possible sequences, which subset of recombinant bacteriophage particles is then screened. If desired, to extend the diversity of a subset library, the recovered phage subset may be subjected to mutagenesis and then subjected to subsequent rounds of screening. This mutagenesis step may be accomplished in two general ways: the variable region of the recovered phage may be mutagenized, or additional variable amino acids may be added to the regions adjoining the initial variable sequences.

To diversify around active peptides (i.e., binders) found in proteome panning or early rounds of conventional biopanning, the selected phage can be sequenced to determine the identity of the active peptides. Oligonucleotides can then be synthesized based on these peptide sequences. The syntheses are performed with a low level of all bases incorporated at each step to produce slight variations of the primary oligonucleotide sequences. This mixture of degenerate or slightly degenerate oligonucleotides may then be cloned into the affinity phage by methods known to those in the art. This method produces systematic, controlled variations of the starting peptide sequences as part of a secondary library. It requires, however, that individual positive phage be sequenced before mutagenesis, and thus is useful for expanding the diversity of small numbers of recovered phage.

An alternate approach to diversify the selected phage allows the mutagenesis of a pool, or subset, of recovered phage. In accordance with this approach, phage recovered from panning are pooled and single stranded DNA is isolated. The DNA is mutagenized by treatment with, e.g., nitrous acid, formic acid, or hydrazine. These treatments produce a variety of damages to the DNA. The damaged DNA is then copied with reverse transcriptase, which misincorporates bases when it encounters a site of damage. The segment containing the sequence encoding the receptor-binding peptide is then isolated by cutting with restriction nuclease(s) specific for sites flanking the peptide coding sequence. This mutagenized segment is then recloned into undamaged vector DNA, the DNA is transformed into cells, and a secondary library according to known methods. General mutagenesis methods are known in the art (see Myers et al., 1985, *Nucl. Acids Res.* 13:3131–3145; Myers et al., 1985, *Science* 229:242–246; Myers, 1989, *Current Protocols in Molecular Biology Vol. I,* 8.3.1–8.3.6, F. Ausubel et al., eds, J. Wiley and Sons, New York).

In another general approach, the addition of amino acids to a peptide or peptides found to be active, can be carried out using various methods. In one, the sequences of peptides selected in proteome panning or early conventional panning are determined individually and new oligonucleotides, incorporating the determined sequence and an adjoining degenerate sequence, are synthesized. These are then cloned to produce a secondary library. Alternatively, methods can be used to add a second target-binding sequence to a pool of peptide-bearing phage. In accordance with one method, a restriction site is installed next to the first target-binding sequence. Preferably, the enzyme should cut outside of its recognition sequence. The recognition site may be placed several bases from the first binding sequence. To insert a second target-binding sequence, the pool of phage DNA is digested and blunt-ended by filling in the overhang with Klenow fragment. Double-stranded, blunt-ended, degenerately synthesized oligonucleotides are then ligated into this site to produce a second binding sequence juxtaposed to the first binding sequence. This secondary library is then amplified and screened as before.

While in some instances it may be appropriate to synthesize longer peptides to bind certain receptors, in other cases it may be desirable to provide peptides having two or more target-binding sequences separated by spacer (e.g., linker) residues. For example, the binding sequences may be separated by spacers that allow the regions of the peptides to be presented to the receptor in different ways. The distance between binding regions may be as little as 1 residue, or at least 2–20 residues, or up to at least 100 residues. Preferred spacers are 3, 6, 9, 12, 15, or 18 residues in length. For probing large binding sites or tandem binding sites, the binding regions may be separated by a spacer of residues of up to 20 to 30 amino acids. The number of spacer residues when present will typically be at least 2 residues, and often will be less than 20 residues.

The oligonucleotide library may have binding sequences which are separated by spacers (e.g., linkers), and thus may be represented by the formula: $(NNK)y-(abc)_n-(NNK)_z$ where N and K are as defined previously (note that S as defined previously may be substituted for K), and y+z is equal to about 5, 6, 7, 8, or more, a, b and c represent the same or different nucleotides comprising a codon encoding spacer amino acids, n is up to about 3, 6, 9, or 12 amino acids, or more. The spacer residues may be somewhat flexible, comprising oligo-glycine, or oligo-glycine-glycine-serine, for example, to provide the diversity domains of the library with the ability to interact with sites in a large binding site relatively unconstrained by attachment to the phage protein. Rigid spacers, such as, e.g., oligo-proline, may also be inserted separately or in combination with other spacers, including glycine spacers. It may be desired to have the target-binding sequences close to one another and use a spacer to orient the binding sequences with respect to each other, such as by employing a turn between the two sequences, as might be provided by a spacer of the sequence glycine-proline-glycine, for example. To add stability to such a turn, it may be desirable or necessary to add cysteine residues at either or both ends of each variable region. The cysteine residues would then form disulfide bridges to hold the variable regions together in a loop, and in this fashion may also serve to mimic a cyclic peptide. Of course, those skilled in the art will appreciate that various other types of covalent linkages for cyclization may also be used.

Spacer residues as described above may also be situated on either or both ends of the target-binding sequences. For instance, a cyclic peptide may be designed without an intervening spacer, by having a cysteine residue on both ends of the peptide. As described above, flexible spacers, e.g., oligo-glycine, may facilitate interaction of the peptide with the selected receptors. Alternatively, rigid spacers may allow the peptide to be presented as if on the end of a rigid arm, where the number of residues, e.g., proline residues, determines not only the length of the arm but also the direction for the arm in which the peptide is oriented. Hydrophilic spacers, made up of charged and/or uncharged hydrophilic amino acids, (e.g., Thr, His, Asn, Gln, Arg, Glu, Asp, Met, Lys, etc.), or hydrophobic spacers of hydrophobic amino acids (e.g., Phe, Leu, Ile, Gly, Val, Ala, etc.) may be used to present the peptides to receptor binding sites with a variety of local environments.

Notably, some peptides, because of their size and/or sequence, may cause severe defects in the infectivity of their carrier phage. To minimize problems associated with defective infectivity, DNA prepared from the eluted phage can be transformed into appropriate host cells, such as, e.g., *E. coli,* preferably by electroporation (see, e.g., Dower et al., *Nucl. Acids Res.* 16:6127–6145), or well known chemical means. The cells are cultivated for a period of time sufficient for marker expression, and selection is applied as typically done for DNA transformation. The colonies are amplified, and phage harvested for affinity enrichment in accordance with established methods. Phage identified in the affinity enrichment may be re-amplified by infection into the host cells. The successful transformants are selected by growth in an appropriate antibiotic(s), e.g., tetracycline or ampicillin. This may be done on solid or in liquid growth medium.

For growth on solid medium, the cells are grown at a high density (about 108 to 109 transformants per m2) on a large surface of, for example, L-agar containing the selective antibiotic to form essentially a confluent lawn. The cells and extruded phage are scraped from the surface and phage are prepared for proteome panning. For growth in liquid culture, cells may be grown in media and antibiotic through multiple doublings as necessary. The phage are harvested by standard procedures (see Sambrook et al., 1989, Molecular Cloning, 2nd ed.). Growth in liquid culture may be more convenient because of the size of the libraries, while growth on solid media likely provides less chance of bias during the amplification process.

Affinity Enrichment with Proteome Panning

For affinity enrichment of desired clones of target binders, the preincubation conditions, i.e. the binding conditions prior to transformation of the host cells, are varied to optimize the recovery of target binders with a higher affinity. Phage that associate with a target via non-specific interactions are removed by affinity enrichment.

In one example of affinity enrichment, the ratio of target phage to target-binder phage is optimized. Generally, about $10^1$ to $10^9$ library equivalents are incubated with phage expressing a target, or portion thereof, to which the desired target binder is sought. A library equivalent is equal to one member of each recombinant, e.g., $10^4$ equivalents of a library of $10^9$ members is $10^9 \times 10^4 = 10^{13}$ phage. Preferably, affinity enrichment is accomplished by incubating the target with about $10^2$ library equivalents up to about $10^6$ library equivalents and more preferably about $10^3$ to $10^4$ library equivalents. By varying the ratio between target phage and target-binder phage, particularly with the number of target binders exceeding the target, the recovery of target binders with higher affinity can be enhanced. When the number of target binders exceed the target, the better binders are able to outcompete and eliminate the poorer binders in the selection. For example, by adjusting the ratio between number of target binders to number of target the number of target binders selected, i.e. the population of surviving pairs, can be reduced to less than 300 members of target binders with better binding affinity.

In another example, affinity enrichment is accomplished by adjusting the preincubation time prior to transformation of the host cells. The preincubation time may range from 2 hours to 24 hours, preferably between 2 hrs and 3 hrs. The population of selected target binders is enriched with target binders having higher affinities by increasing the preincubation time. The preincubation time should be increased so that the two phage are allowed to reach equilibrium or steady state. In other examples, affinity enrichment is improved by varying the stringency of the preincubation conditions. For example temperature, ionic strength, volume and pH are adjusted to enrich the selected population with better target binders and eliminate or reduce the number of weaker target binders. The temperature may range from room temperature or 28° C. to 42° C., preferably 30° C.–37° C., and most preferably 30° C. The preferred pH value would be neutral. Varying the temperature, pH, ionic strength, divalent cation concentration, and the volume and duration of the preincubation time will select for target binders within particular ranges of affinity for the receptor.

Additional examples of affinity enrichment are based on slow dissociation rates of target binders. A slow dissociation rate is usually predictive of high affinity. In these examples of affinity enrichment, the continued incubation of the target phage and the target-binder phage is performed in the presence of a saturating amount of a known target binder or by increasing the volume of the incubation solution. In each case, the rebinding of dissociated target-binder phage is prevented, and with increasing time, target-binder phages of higher affinity are recovered.

The preincubation time and the preincubation conditions are optimized for each target/target-binder of interest. To monitor the effect of the varying conditions on affinity enrichment pilot experiments of proteome panning are performed. After incubation of the target phage and the target-binder phage and transformation of the host cells, the host cells are plated out onto selective media and quantified. Determining the change in the number of colonies that survive provides an easy assessment tool to determine the degree of affinity enrichment. As the number of surviving colonies declines, the number of surviving weak binders is significantly diminished, leaving fewer target binders with higher affinity. For example, the loss of the number of surviving colonies, until only 1%, 0.1%, or 0.001% survive, indicates optimal conditions for enriching target binders that bind the target having higher affinity. In some circumstance, the number of surviving colonies could be limited to about 100 colonies for analysis by sequencing. Depending on the diversity of the type of target binder library used, the number of target binders with a higher affinity may by less than 10.

The use of the above affinity-enrichment techniques allows for enrichment without necessarily performing additional rounds of panning. The affinity-enrichment techniques can be used alone or in combination. It is to be understood that the present invention could also use multiple rounds of proteome panning to provide for affinity enrichment if desired.

Peptides And Polypeptides

A further aspect of the present invention pertains to isolated peptides such as binders of DGI-2, DGI-5, DGI-7, DGI-9, VEGF, VEGFR1, VEGFR2, VEGFR3, EGFR, FGFR1-alpha, FGFR1-beta, and Tie1 (e.g., SEQ ID NOs: 1–189; SEQ ID NOs: 227–532). DGI-9 target binder sequences are shown in Table 3. The amino acid sequences are represented by their one-letter abbreviations. Binding is indicated as the ratio over background. LDH is the control irrelevant protein. Numbers in subscript at the end of a clone name indicate the number of times the sequence was found in that panning. The peptides of this invention can be isolated, synthetic, or recombinant. The target binders may be obtained as individual peptides or part of a polypeptide complex. In various aspects, a polypeptide-complex may comprise one or more molecules of target in an association with one or more target binders (e.g., multiple copies of the same peptide binder or single copies of different peptide binders).

A further embodiment of the invention is a method of identifying an amino acid sequence motif which confers binding properties to a target by screening a library of expressed amino acid sequences for binding to the target, determining the amino acid sequence of the members of the library which bind to the target, and identifying as motifs common amino acid sequences.

Yet another embodiment of the invention relates to amino acid sequence motifs which bind to the specific target. In addition to binding to the target, the amino acid sequences may also possess biological activity, not limited to agonist, partial agonist or antagonist activity at the target.

The present invention encompasses the target, target binders, and fragments and functional equivalents thereof. The term "functional equivalent" is intended to include proteins which differ in amino acid sequence from the target or target binder peptides but where such differences result in a modified protein which performs at least one characteristic function of the polypeptide (e.g., binding, signaling, or antigenic activity). For example, a functional equivalent of a polypeptide may have a modification such as a substitution, addition, or deletion of an amino acid residue that is not directly involved in the function of this polypeptide.

It is also possible to vary the structure of a target or target binder peptide for such purposes as increasing solubility, enhancing activity, antigenicity, or stability (e.g., shelf life ex vivo and resistance to proteolytic degradation in vivo). Such variants are considered functional equivalents of the polypeptides and peptides as defined herein. Preferably, polypeptides and peptides are modified so that they retain activity. Those residues shown to be essential for activity can be modified by replacing the essential amino acid with another, preferably similar amino acid residue (a conservative substitution) whose presence is shown to enhance, diminish, but not eliminate, or not effect receptor interaction. In addition, those amino acid residues that are not essential for binding or other activity can be modified by being replaced by another amino acid whose incorporation may enhance, diminish, or not effect reactivity.

Polypeptide and peptide variants include mutants differing by the addition, deletion, or substitution of one or more amino acid residues. Also included are modified polypeptides and peptides in which one or more residues are modified, and mutants comprising one or more modified residues. Useful modifications may include phosphorylation, sulfation, reduction/alkylation (Tarr, 1986, *Methods of Protein Microcharacterization,* J. E. Silver, Ed., Humana Press, Clifton, N.J., pp. 155–194); acylation (Tarr, supra); chemical coupling (Mishell and Shiigi (Eds),1980, *Selected Methods in Cellular Immunology,* W H Freeman, San Francisco, Calif.; U.S. Pat. No. 4,939,239); and mild formalin treatment (Marsh, 1971, *Int. Arch. of Allergy and Appl. Immunol.* 41:199–215). Additionally, D-amino acids, nonnatural amino acids, or non-amino acid analogs can be substituted or added to produce a modified polypeptide. Furthermore, the polypeptides disclosed herein can be modified using polyethylene glycol (PEG) according to known methods (S. I. Wie et al., 1981, *Int. Arch. Allergy Appl. Immunol.* 64(1):84–99) to produce a protein conjugated with PEG. In addition, PEG can be added during chemical synthesis of the protein. Modifications or sequence variations may occur at the amino- or carboxy-terminal positions of the reference polypeptide sequence or anywhere between those terminal positions, interspersed either individually among the amino acids in the reference sequence or in one or more contiguous groups within the reference sequence.

Polypeptides or peptides may also be modified with a label capable of providing a detectable signal, either directly or indirectly, including, but not limited to, radioisotope, fluorescent, and enzyme labels. Fluorescent labels include, for example, Cy™3, Cy™5, Alexa, BODIPY, fluorescein (e.g., FluorX, DTAF, and FITC), rhodamine (e.g., TRITC), auramine, Texas Red, AMCA blue, and Lucifer Yellow. Preferred isotope labels include $^{3}H$, $^{14}C$, 32 P, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Preferred enzyme labels include peroxidase, β-glucuronidase, β-D-glucosidase, β-D-galactosidase, urease, glucose oxidase plus peroxidase, and alkaline phosphatase (see, e.g., U.S. Pat. Nos. 3,654,090; 3,850,752 and 4,016,043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, Tyramide Signal Amplification (TSA™), are known in the art, and are commercially available (see, e.g., ABC kit, Vector Laboratories, Inc., Burlingame, Calif.; NEN® Life Science Products, Inc., Boston, Mass.).

Polypeptide and peptide variants may have "conservative" changes, wherein a substituted amino acid has similar structural or chemical properties, e.g., replacement of leucine with isoleucine. More infrequently, a variant may have "nonconservative" changes, e.g., replacement of a glycine with a tryptophan. Guidance in determining which amino acid residues can be substituted, inserted, or deleted without abolishing biological or immunological activity can be determined using computer programs well known in the art, for example, DNASTAR software (DNASTAR, Inc., Madison, Wis.).

Substantial changes in function or immunogenicity can be made by selecting substitutions that are less conservative. For example, non-conservative substitutions can be made which more significantly affect the structure of the polypeptide in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

Sequence tags (e.g., FLAG® tags) or amino acids, such as one or more lysines, can be added to the peptide sequences of the invention (e.g., at the N-terminal or C-terminal ends) as described in detail herein. Sequence tags can be used for peptide purification or localization. Lysines can be used to increase peptide solubility or to allow for biotinylation. Alternatively, amino acid residues located at the carboxy and amino terminal regions of the consensus motifs described below, which comprise sequence tags (e.g., FLAG® tags), or which contain amino acid residues that are not associated with a strong preference for a particular amino acid, may optionally be deleted providing for truncated sequences. Certain amino acids (e.g., C-terminal or N-terminal residues) such as lysine which promote the stability or biotinylation of the amino acids sequences may be deleted depending on the use of the sequence, as for example, expression of the sequence as part of a larger sequence which is soluble, or linked to a solid support.

Polypeptide or protein fragments (i.e., peptides) can range in size sufficient to contain the minimal number of amino acids to define a binding motif, typically from about 5 amino acid residues to all but one residue of the entire amino acid sequence. Thus, a peptide can be at least 5, 15, 20, 25, 30, 50, 100, or more consecutive amino acid residues of a target or target-binding protein or polypeptide. In one embodiment, the percent amino acid sequence identity between a target-binder or target-partner polypeptide or peptide, and a functional equivalent thereof is at least 50%. In a preferred embodiment, the percent amino acid sequence identity is at least 65%. More preferably, the percent amino acid sequence identity is at least 75%, still more preferably, at least 80%, and even more preferably, at least 90%. In one embodiment, the percent nucleic acid sequence identity between a target-binder or target-partner nucleotide, and a functional equivalent thereof is at least 50%. In a preferred embodiment, the percent nucleotide sequence identity is at least 65%. More preferably, the percent nucleotide sequence identity is at least 75%, still more preferably, at least 80%, and even more preferably, at least 90%.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch, 1970, J Mol. Biol. 48:443–453; 2) BLOSSUM62 comparison matrix from Hentikoff and Hentikoff, 1992, Proc. Natl. Acad. Sci. USA 89:10915–10919; 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps). Alternatively, polypeptide sequence identity can be calculated using the following equation: % identity=((the number of identical residues)/(alignment length in amino acid residues))×100. For this calculation, alignment length includes internal gaps but does not include terminal gaps.

In accordance with the present invention, polypeptide or peptide sequences may be identical to DGI-2 or DGI-2-binder polypeptides or peptides, or may include up to a certain integer number of amino acid alterations. Polypeptide alterations are selected from the group consisting of at least one amino acid deletion, substitution, including conservative and non-conservative substitution, or insertion.

The invention also relates to isolated, synthesized and/or recombinant portions or fragments of a target or target binder polypeptide as described herein. Polypeptide fragments (i.e., peptides) can be made which have full or partial function on their own, or which when mixed together (though fully, partially, or nonfunctional alone), spontaneously assemble with one or more other polypeptides to reconstitute a functional protein having at least one functional characteristic of a target protein of this invention. In addition, peptides may comprise, for example, one or more motifs of a target binder, disclosed herein.

Nucleic acids comprising protein-coding sequences can be used to direct the expression polypeptides or peptides in intact cells or in cell-free translation systems. The coding sequence can be tailored, if desired, for more efficient expression in a given host organism, and can be used to synthesize oligonucleotides encoding the desired amino acid sequences. The resulting oligonucleotides can be inserted into an appropriate vector and expressed in a compatible host organism or translation system.

The polypeptides and peptides of the present invention, including functional equivalents, may be isolated from wild-type or mutant cells (e.g., human cells or cell lines), from heterologous organisms or cells (e.g., bacteria, yeast, insect, plant, and mammalian cells), or from cell-free translation systems (e.g., wheat germ, microsomal membrane, or bacterial extracts) in which a protein-coding sequence has been introduced and expressed. Furthermore, the polypeptides and peptides may be part of recombinant fusion proteins. The polypeptides and peptides can also, advantageously, be made by synthetic chemistry. Polypeptides and peptides may be chemically synthesized by commercially available automated procedures, including, without limitation, exclusive solid phase synthesis, partial solid phase methods, fragment condensation or classical solution synthesis, described in detail below.

Methods for polypeptide and peptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide or peptide in a recombinant system in which the protein contains an additional sequence (e.g., epitope or protein) tag that facilitates purification. Non-limiting examples of epitope tags include c-myc, haemagglutinin (HA), polyhistidine, GLU-GLU, and FLAG® epitope tags. Non-limiting examples of protein tags include glutathione-S-transferase (GST), green fluorescent protein (GFP), and maltose binding protein (MBP).

In one approach, the coding sequence of a polypeptide or peptide can be cloned into a vector that creates a fusion with a sequence tag of interest. Suitable vectors include, without limitation, pRSET (Invitrogen Corp., San Diego, Calif.), pGEX (Amersham-Pharmacia Biotech, Inc., Piscataway, N.J.), pEGFP (CLONTECH Laboratories, Inc., Palo Alto, Calif.), and PMAL™ (New England BioLabs (NEB), Inc., Beverly, Mass.) plasmids. Following expression, the epitope, or protein tagged polypeptide or peptide can be purified from a crude lysate of the translation system or host cell by chromatography on an appropriate solid-phase matrix. In some cases, it may be preferable to remove the epitope or protein tag (i.e., via protease cleavage) following purification. As an alternative approach, antibodies produced against a protein or peptide can be used as purification reagents. Other purification methods are also possible.

Both the naturally occurring and recombinant forms of the polypeptides of the invention can advantageously be used to screen compounds for binding activity. Many methods of screening for binding activity are known by those skilled in the art and may be used to practice the invention. Several methods of automated assays have been developed in recent years so as to permit screening of tens of thousands of compounds in a short period of time. Such high-throughput screening methods are particularly preferred. The use of high-throughput screening assays to test for inhibitors is greatly facilitated by the availability of large amounts of purified polypeptides and peptides, as provided by the invention. The polypeptides and peptides of the invention also find use as therapeutic agents as well as antigenic components to prepare antibodies.

Many conventional techniques in molecular biology, protein biochemistry, and immunology may be used to produce the amino acid sequences for use with this invention. To obtain recombinant polypeptides and peptides, coding sequences may be cloned into any suitable vectors for expression in intact cells or in cell-free translation systems by methods well known in the art (see Sambrook et al., 1989) and described herein. The particular choice of the vector, cell, or translation system is not critical to the practice of the invention.

According to methods known in the art, polypeptides and peptides can be chemically synthesized by commercially available automated procedures, including, without limitation, exclusive solid phase synthesis, partial solid phase methods, fragment condensation, classical solution synthesis. In addition, recombinant and synthetic methods of peptide production can be combined to produce semi-synthetic polypeptides and peptides. The polypeptides and peptides of the invention are preferably prepared by solid phase peptide synthesis methods and techniques as described by Merrifield, 1963, J. Am. Chem. Soc. 85:2149; J. M. Stewart and J. D. Young, 1984, Solid Phase Peptide Synthesis, 2nd edition, Pierce Chemical Co., Rockford, Ill.; W. C. Chan and P. D. White (Eds.), 2000, Fmoc Solid Phase Peptide Synthesis: A Practical Approach, Oxford University Press; Kaiser et al., 1970, Anal. Biochem. 34:595.

This invention provides specific amino acid sequences that bind DGI-2. However, additional sequences may be obtained in accordance with the procedures described herein below.

Antibodies

Another aspect of the invention pertains to antibodies directed to the target of interest, such as target, target-binders (e.g., SEQ ID NOs: 1–189; SEQ ID NOs: 227–532), or fragments or variants thereof. Specifically included are antibodies directed to polypeptide-complexes of target and target binders, or fragments of these complexes. For example, antibodies directed to polypeptide-complexes of DGI-2/DGI-2-binders are complex-specific, i.e., the antibodies do not bind to the components separately. The invention provides polyclonal and monoclonal antibodies that bind to target, target-binders, or target-partners, fragments, or complexes thereof. The antibodies may be elicited in an animal host (e.g., rabbit, goat, mouse, or other non-human mammal) by immunization with disorder-associated immunogenic components. Antibodies may also be elicited by in vitro immunization (sensitization) of immune cells. The immunogenic components used to elicit the production of antibodies may be isolated from cells or chemically synthesized. The antibodies may also be produced in recombinant systems programmed with appropriate antibody-encoding DNA. Alternatively, the antibodies may be constructed by biochemical reconstitution of purified heavy and light chains. The antibodies include hybrid antibodies, chimeric antibodies, and univalent antibodies. Also included are Fab fragments, including Fab1 and Fab(ab)2 fragments of antibodies.

In a further example, an isolated DGI-2, DGI-2-binder peptide, or complex thereof, can be used as an immunogen to generate antibodies using standard techniques for polyclonal and monoclonal antibody preparation. Full-length polypeptides can be used or, alternatively, the invention provides antigenic peptide portions of these polypeptides for use as immunogens. The antigenic peptide of DGI-2, DGI-2-binder or a DGI-2-partner comprises a sufficient number of contiguous amino acid residues of the amino acid sequence, or a variant thereof, to encompass an epitope of a DGI-2, DGI-2-binder, or DGI-2-partner polypeptide such that an antibody raised against the peptide forms a specific immune complex with a DGI-2 or DGI-2-binder amino acid sequence. Typically, about 5 contiguous amino acids are sufficient to define an epitope.

An appropriate immunogenic preparation can contain, for example, 1) recombinantly produced DGI-2 or DGI-2-binder polypeptides or peptides; 2) chemically synthesized DGI-2 or DGI-2-binder polypeptides or peptides, 3) fragments of these polypeptides (i.e., peptides); or 4) complexes comprising these polypeptides. The preparation can further include an adjuvant, such as Freund's complete or incomplete adjuvant, or similar immunostimulatory agent. A number of adjuvants are known and used by those skilled in the art. Non-limiting examples of suitable adjuvants include incomplete Freund's adjuvant, mineral gels such as alum, aluminum phosphate, aluminum hydroxide, aluminum silica, and surface-active substances such as lysolecithin, pluronic polyols, polyanions, peptides, oil emulsions, keyhole limpet hemocyanin, and dinitrophenol. Further examples of adjuvants include stearyl tyrosine (A. Nixon-George et al., 1990, J. Immunol. 144:4798–4802; Paoletti, et al., 1997, J. Infect. Diseases 175:1237–9; U.S. Pat. No. 4,258,029 to Moloney et al.; U.S. Pat. No. 5,683,699 to Jennings, et al.), N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE), and RIBI adjuvant (e.g., Detox®, Corixa Corp., Seattle Wash.) which contains three components extracted from bacteria, monophosphoryl lipid A, trehalose dimycolate and cell wall skeleton (TDM+CWS+MPL®; Corixa Corp.) in a 2% squalene/Tween 80 emulsion. A particularly useful adjuvant comprises 5% (wt/vol) squalene, 2.5% Pluronic L121 polymer and 0.2% polysorbate in phosphate buffered saline (Kwak et al., 1992, *New Eng. J Med.* 327:1209–1215). Preferred adjuvants include complete BCG, Detox, (RIBI, Immunochem Research Inc.), ISCOMS, and aluminum hydroxide adjuvant (Superphos, Biosector). The effectiveness of an adjuvant may be determined by measuring the amount of antibodies directed against the immunogenic peptide.

Polyclonal antibodies to targets and target binders, such as, DGI-2 or DGI-2-binder polypeptides, peptides, or polypeptide-complexes thereof, can be prepared as described above by immunizing a suitable subject with a DGI-2, DGI-2-binder, or DGI-2-partner immunogen. The antibody titer in the immunized subject can be monitored over time by standard techniques, such as with an enzyme linked immunosorbent assay (ELISA) using immobilized DGI-2 DGI-2-binder polypeptide, peptide, or polypeptide-complex. If desired, the antibody molecules can be isolated from the mammal (e.g., from the blood) and further purified by well-known techniques, such as protein A chromatography to obtain the IgG fraction.

At an appropriate time after immunization, e.g., when the antibody titers are highest, antibody-producing cells can be obtained from the subject and used to prepare monoclonal antibodies by standard techniques, such as the hybridoma technique (see Kohler and Milstein, 1975, Nature 256: 495–497; Brown et al., 1981, J. Immunol. 127:539–46; Brown et al., 1980, J. Biol. Chem. 255:4980–83; Yeh et al., 1976, PNAS 76:2927–31; and Yeh et al., 1982, Int. J. Cancer 29:269–75), the human B cell hybridoma technique (Kozbor et al., 1983, Immunol. Today 4:72), the EBV-hybridoma technique (Cole et al., 1985, Monoclonal Antibodies and Cancer Therapy, Alan R. Liss, Inc., pp. 77–96) or trioma techniques.

The technology for producing hybridomas is well-known (see generally R. H. Kenneth, 1980, Monoclonal Antibodies:

A New Dimension In Biological Analyses, Plenum Publishing Corp., New York, N.Y.; E. A. Lerner, 1981, Yale J. Biol. Med., 54:387–402; M. L. Gefter et al., 1977, Somatic Cell Genet. 3:231 –36). In general, an immortal cell line (typically a myeloma) is fused to lymphocytes (typically splenocytes) from a mammal immunized with a target, target-binder, or target-partner immunogen as described above, and the culture supernatants of the resulting hybridoma cells are screened to identify a hybridoma producing a monoclonal antibody that binds target, target-binder, or target-partner polypeptides, peptides, or polypeptide-complexes.

Any of the many well known protocols used for fusing lymphocytes and immortalized cell lines can be applied for the purpose of generating an monoclonal antibody to a target, target-binder, or target-partner, peptide, or polypeptide-complex (see, e.g., G. Galfre et al., 1977, Nature 266:55052; Gefter et al., 1977; Lerner, 1981; Kenneth, 1980). Moreover, the ordinarily skilled worker will appreciate that there are many variations of such methods. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin, and thymidine (HAT medium). Any of a number of myeloma cell lines can be used as a fusion partner according to standard techniques, e.g., the P3-NS1/1-Ag4-1, P3-x63-Ag8.653, or Sp2/O-Ag14 myeloma lines. These myeloma lines are available from ATCC (American Type Culture Collection, Manassas, Va.). Typically, HAT-sensitive mouse myeloma cells are fused to mouse splenocytes using polyethylene glycol (PEG). Hybridoma cells resulting from the fusion arc then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind target, target-binder, or target-partners, peptides, or polypeptide-complexes, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the corresponding target or target-binder, peptide, or polypeptide-complex to thereby isolate immunoglobulin library members that bind these molecules. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612).

Additionally, examples of methods and reagents particularly amenable for use in generating and screening antibody display library can be found in, for example, A. Blume U.S. Pat. No. 6,010,861, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al., 1991, BioTechnology 9:1370–1372; Hay et al., 1992, Hum. Antibod. Hybridomas 3:81–85; Huse et al., 1989, Science 246:1275–1281; Griffiths et al., 1993, EMBO J 12:725–734; Hawkins et al., 1992, J. Mol. Biol. 226:889–896; Clarkson et al., 1991, Nature 352:624–628; Gram et al., 1992, PNAS 89:3576–3580; Garrad et al., 1991, BioTechnology 9:1373–1377; Hoogenboom et al., 1991, Nuc. Acid Res. 19:4133–4137; Barbas et al., 1991, PNAS 88:7978–7982; and McCafferty et al., 1990, Nature 348: 552–55.

Additionally, recombinant antibodies to a target or target-binder, peptide, or polypeptide-complex, such as chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., 1988, Science 240:1041–1043; Liu et al., 1987, PNAS 84:3439–3443; Liu et al., 1987, J. Immunol. 139:3521–3526; Sun et al., 1987, PNAS 84:214–218; Nishimura et al., 1987, Canc. Res. 47:999–1005; Wood et al., 1985, Nature 314:446–449; and Shaw et al., 1988, J. Natl. Cancer Inst. 80:1553–1559; S. L. Morrison, 1985, Science 229:1202–1207; Oi et al., 1986, BioTechniques 4:214; Winter U.S. Pat. No. 5,225,539; Jones et al., 1986, Nature 321:552–525; Verhoeyan et al., 1988, Science 239:1534; and Bcidler et al., 1988, J. Immunol. 141:4053–4060.

An antibody against a target or target-binder, peptide, or polypeptide-complex (e.g., monoclonal antibody) can be used to isolate the corresponding molecules by standard techniques, such as affinity chromatography or immunoprecipitation. For example, antibodies can facilitate the purification of a natural polypeptides or polypeptide-complexes from cells and of a recombinantly produced polypeptides or complexes produced in host cells. In addition, an antibody that binds to a target, target-binder, or target-partner, peptide, or complex can be used to detect the corresponding molecule (e.g., in a cellular lysate or cell supernatant) in order to evaluate patterns or levels of protein expression or complexation. Such antibodies can also be used diagnostically to monitor polypeptide or polypeptide-complex levels in tissue as part of a clinical testing procedure, e.g., to, for example, determine the efficacy of a given treatment regimen as described in detail herein. In addition, antibodies to a target, target-binder, or target-partner, peptide, or polypeptide-complex can be used as therapeutics for the treatment of diseases related to abnormal gene expression or function, e.g., as relating to the development of neoplasms and cancers.

Alternatively, libraries of natural compounds in the form of bacterial, fungal, plant and animal extracts can be readily produced. Methods for the synthesis of molecular libraries are readily available (see, e.g., DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carell et al., 1994, Angew. Chem. Int. Ed. Engl. 33:2059; Carell et al., 1994, Angew. Chem. Int. Ed. Engl. 33:2061; and in Gallop et al., 1994, J. Med. Chem. 37:1233). In addition, natural or synthetic compound libraries and compounds can be readily modified through conventional chemical, physical and biochemical means (see, e.g., Blondelle et al., 1996, Trends in Biotech. 14:60), and may be used to produce combinatorial libraries. In another approach, previously identified pharmacological agents can be subjected to directed or random chemical modifications, such as acylation, alkylation, esterification, amidification, and the analogs can be screened for targets and/or target-partner-modulating activity.

Numerous methods for producing combinatorial libraries are known in the art, including those involving biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer, or small molecule libraries of compounds (K. S. Lam, 1997, Anticancer Drug Des. 12:145).

Non-limiting examples of small molecules, small molecule libraries, combinatorial libraries, and screening methods are described in B. Seligmann, 1995, "Synthesis, Screening, Identification of Positive Compounds and Optimization of Leads from Combinatorial Libraries: Validation of Success" p. 69–70. Symposium: Exploiting Molecular Diversity: Small Molecule Libraries for Drug Discovery, La Jolla, Calif., Jan. 23–25, 1995 (conference summary available from Wendy Warr & Associates, 6 Berwick Court, Cheshire, UK CW4 7HZ); E. Martin et al., 1995, J. Med. Chem. 38:1431–1436; E. Martin et al., 1995, "Measuring diversity: Experimental design of combinatorial libraries for drug discovery" Abstract, ACS Meeting, Anaheim, Calif., COMP 32; and E. Martin, 1995, "Measuring Chemical Diversity: Random Screening or Rationale Library Design" p. 27–30, Symposium: Exploiting Molecular Diversity: Small Molecule Libraries for Drug Discovery, La Jolla, Calif. Jan. 23–25, 1995 (conference summary available from Wendy Warr & Associates, 6 Berwick Court, Cheshire, UK CW4 7HZ).

Libraries may be screened in solution (e.g., Houghten, 1992, Biotechniques 13:412–421), or on beads (Lam, 1991, Nature 354:82–84), chips (Fodor, 1993, Nature 364:555–556), bacteria or spores (Ladner U.S. Pat. No. 5,223,409), plasmids (Cull et al., 1992, Proc. Natl. Acad. Sci. USA 89:1865–1869), or on phage (Scott and Smith, 1990, Science 249:386–390; Devlin, 1990, Science 249: 404–406; Cwirla et al., 1990, Proc. Natl. Acad. Sci. USA 97:6378–6382; Felici, 1991, J. Mol. Biol. 222:301–310; Ladner, supra).

Where the screening assay is a binding assay, a target or target-binder polypeptide, polynucleotide, variant, polypeptide-complex, or fragment thereof, may be joined to a label, where the label can directly or indirectly provide a detectable signal. Various labels include radioisotopes, fluorophores, chemiluminescent compounds, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g., albumin, detergents, etc., which are used to facilitate optimal protein-protein binding and/or reduce non-specific or background interactions. Reagents that improve the efficiency of the assay, such as protease inhibitors, nuclease inhibitors, anti-microbial agents, etc., may be used. The components are added in any order that produces the requisite binding. Incubations are performed at any temperature that facilitates optimal activity, typically between 4° and 40° C. Incubation periods are selected for optimum activity, but may also be optimized to facilitate rapid high-throughput screening. Normally, between 0.1 and 1 hr will be sufficient. In general, a plurality of assay mixtures is run in parallel with different agent concentrations to obtain a differential response to these concentrations. Typically, one of these concentrations serves as a negative control, i.e., at zero concentration or below the level of detection.

To perform cell-free ligand screening assays, it may be desirable to immobilize either a target or target-binder polypeptide, polynucleotide, fragment, or polypeptide-complex, to a surface to facilitate identification of ligands that bind to these molecules, as well as to accommodate automation of the assay. For example, a fusion protein comprising a DGI-2 polypeptide and an affinity tag can be produced. In one embodiment, a glutathione-S-transferase/phosphodiesterase fusion protein comprising a DGI-2 polypeptide is adsorbed onto glutathione sepharose beads (Sigma Chemical, St. Louis, Mo.) or glutathione-derivatized microtiter plates. Cell lysates (e.g., containing 35S-labeled polypeptides) are added to the coated beads under conditions to allow complex formation (e.g., at physiological conditions for salt and pH). Following incubation, the coated beads are washed to remove any unbound polypeptides, and the amount of immobilized radiolabel is determined. Alternatively, the complex is dissociated and the radiolabel present in the supernatant is determined. In another approach, the beads are analyzed by SDS-PAGE to identify the bound polypeptides.

Target binders or ligand binding assays can be used to identify agonist or antagonists that alter the function or levels of a target polypeptide. Such assays are designed to detect the interaction of test agents (e.g., small molecules) with target or polypeptides, polynucleotides, polypeptide-complexes, or fragments or portions thereof. Interactions may be detected by direct measurement of binding. Alternatively, interactions may be detected by indirect indicators of binding, such as stabilization/destabilization of protein structure, or activation/inhibition of biological function. Non-limiting examples of useful ligand-binding assays are detailed below.

Ligands that bind to targets, for example, DGI-2 polypeptides, polynucleotides, polypeptide-complexes, or fragments or portions thereof, can be identified using real-time Bimolecular Interaction Analysis (BIA; Sjolander et al., 1991, Anal. Chem. 63:2338–2345; Szabo et al., 1995, Curr. Opin. Struct. Biol. 5:699–705). BIA-based technology (e.g., BIAcore™; LKB Pharmacia, Sweden) allows study of biospecific interactions in real time, without labeling. In BIA, changes in the optical phenomenon surface plasmon resonance (SPR) is used determine real-time interactions of biological molecules.

Ligands can also be identified by scintillation proximity assays (SPA, described in U.S. Pat. No. 4,568,649). In a modification of this assay that is currently undergoing development, chaperonins are used to distinguish folded and unfolded proteins. A tagged protein is attached to SPA beads, and test agents are added. The bead is then subjected to mild denaturing conditions (such as, e.g., heat, exposure to SDS, etc.) and a purified labeled chaperonin is added. If a test agent binds to a target, the labeled chaperonin will not bind; conversely, if no test agent binds, the protein will undergo some degree of denaturation and the chaperonin will bind.

Ligands can also be identified using a binding assay based on mitochondrial targeting signals (Hurt et al., 1985, EMBO J. 4:2061–2068; Eilers and Schatz, 1986, Nature 322:228–231). In a mitochondrial import assay, expression vectors are constructed in which nucleic acids encoding particular target proteins are inserted downstream of sequences encoding mitochondrial import signals. The chimeric proteins are synthesized and tested for their ability to be imported into isolated mitochondria in the absence and presence of test compounds. A test compound that binds to the target protein should inhibit its uptake into isolated mitochondria in vitro.

The ligand-binding assay described in Fodor et al., 1991, Science 251:767–773, which involves testing the binding affinity of test compounds for a plurality of defined polymers synthesized on a solid substrate, can also be used.

Several methods of automated assays have been developed in recent years so as to permit screening of tens of thousands of test agents in a short period of time. High-throughput screening methods are particularly preferred for use with the present invention. The assays described herein can be adapted for high-throughput screens, or alternative screens may be employed. For example, continuous format high throughput screens (CF-HTS) using at least one porous matrix allows the researcher to test large numbers of test agents for a wide range of biological or biochemical activity (see U.S. Pat. No. 5,976,813 to Beutel et al.). Moreover, CF-HTS can be used to perform multi-step assays.

Other useful screening assays are based on those disclosed in International application WO 96/04557, which is incorporated herein in its entirety. Briefly, WO 96/04557 discloses the use of reporter peptides that bind to active sites on targets and possess agonist or antagonist activity at the target. These reporters are identified from recombinant libraries and are either peptides with random amino acid sequences or variable antibody regions with at least one CDR region that has been randomized (rVab). The reporter peptides may be expressed in cell recombinant expression systems, such as for example in E. coli, or by phage display (see WO 96/04557 and Kay et al. 1996, Mol. Divers. 1(2):139–40, both of which are incorporated herein by reference). The reporters identified from the libraries may then be used in accordance with this invention either as therapeutics themselves, or in competition binding assays to screen for other molecules, preferably small, active molecules, which possess similar properties to the reporters and may be developed as drug candidates to provide agonist or antagonist activity. Preferably, these small organic molecules are orally active.

Additionally, an in vitro competitive receptor binding assay can be used as the basis of a heterogeneous screen for small organic molecular replacements for target-binders. Occupation of the active site of a target, e.g. DGI-2 can be quantified by time-resolved fluorometric detection (TRFD) with streptavidin-labeled europium (saEu) complexed to biotinylated peptides (bP). In this assay, saEu can form a ternary complex with bP and DGI-2 (i.e., DGI-2:bP:saEu complex). The TRFD assay format is well-established, sensitive, and quantitative (Tompkins et al., 1993, J. Immunol. Methods 163:209–216). The assay can use a single-chain antibody or a biotinylated peptide.

In such assays, soluble DGI-2, for example, is coated on the surface of microtiter wells, blocked by a solution of 0.5% bovine serum albumin (BSA) and 2% non-fat milk in PBS, and then incubated with biotinylated peptide or rVab. Unbound bP is then washed away and saEu is added to complex with receptor-bound bP. Upon addition of the acidic enhancement solution, the bound europium is released as free $Eu^{3+}$ which rapidly forms a highly fluorescent and stable complex with components of the enhancement solution. The DGI-2:bP bound saEu is then converted into its highly fluorescent state and detected by a detector such as Wallac Victor II (EG&G Wallac, Inc.)

Diagnostics

As discussed herein below, targets, such as DGI-2, may be associated with various cellular processes, including cell growth, proliferation, and attachment. Defects in these processes can lead to the development of neoplasms, including metastatic cancers. Non-limiting examples of cancers include bone cancer, brain cancer, breast cancer, endocrine system cancers, gastrointestinal cancers (e.g., colorectal and pancreatic cancers) male genituorinary cancers (e.g., prostate cancer), germ cell cancers, gynecologic cancers (e.g., ovarian, cervical, endometrial, and vulvar cancers), head and neck cancers, leukemia, lung cancer, lymphomas (e.g., Hodgkin's and non-Hodgkin's lymphomas), skin cancers (e.g., myelomas and sarcomas), and urinary cancers (e.g., bladder and kidney cancers). Metastatic cancers include, but are not limited to, cancers affecting bone, breast, lung, brain, spinal cord, skin, ovaries, bladder, and gastrointestinal tissues. Other possible indications may include diseases of the central nervous system and the cardiovascular system.

Hras (Harvey Rat sarcoma viral oncogene homolog) may be involved in the regulation of growth and/or differentiation of neural cells during development in autistic children, for example. Hras may also be involved in non-melanoma skin cancer and tumor formation. Leptin is involved in activating the sympathetic nervous system, in regulation of blood pressure, hematopoiesis, immune function, angiogenesis and brain, bone and pituitary development. Vascular endothelial growth factor receptor (VEGFR) may play an important role in vascular diseases, especially in cellular signaling: growth, differentiation, cytokine and vascular regulation. Tie plays a similar role to VEGFR and may be involved in the later stages of vessel growth and remodeling. Diseases involving VEGFR include, but are not limited to pre-eclampsia or intra-uterine growth retardation, leukemias, and gliomas. Epidermal growth factor receptor (EGFR) is involved in a wide variety of cancers such as breast, squamous cell carcinoma, prostate and colorectal carcinoma, and psoriasis. Fibroblast growth factor receptor (FGFR) is involved in growth and differentiation signaling, where colon and prostate cancers are just two examples. The present invention therefore provides compositions (e.g., diagnostic reagents) comprising DGI-2 or DGI-2-binder polynucleotides, polypeptides or peptides (e.g., SEQ ID NOs:1–189) as well as for Hras, Leptin, VEGFR, FGFR, EGFR, to name a few, antibodies, and fragments thereof that can be useful in diagnosing and monitoring the treatment of these conditions. One or more of these peptides are also suitable components for diagnostic kits.

Antibody-Based Diagnostics

In one embodiment of the present invention, antibodies which specifically bind to a target or target-binder polypeptide or peptide complex may be used for the diagnosis of conditions or diseases characterized by altered levels of target or target-binder polypeptides or peptide complexes. Alternatively, such antibodies may be used in assays to monitor patients being treated with a target or target-binder polypeptide, polynucleotide, antibody, or modulator.

The antibodies useful for diagnostic purposes may be prepared in the same manner as those for use in therapeutic methods, described herein. Antibodies may be raised to a full-length target polypeptide. Alternatively, the antibodies may be raised to portions or variants of these polypeptides. In one aspect of the invention, antibodies are prepared to bind to a target polypeptide fragment, or target binder, such as DGI-2 or DGI-2 binder, comprising one or more domains of the polypeptide (e.g., PH, GEF, or kinase domains), as described in detail herein.

Diagnostic assays for a target polypeptide include methods that utilize the antibody and a label to detect the protein in biological samples (e.g., human body fluids, cells, tissues, or extracts of cells or tissues). The antibodies may be used with or without modification, and may be labeled by joining them, either covalently or non-covalently, with a reporter molecule. A wide variety of reporter molecules that are known in the art may be used, several of which are described herein.

Many immunoassay formats are known in the art, and the particular format used is determined by the desired application. An immunoassay can use, for example, a monoclonal antibody directed against a single disease-associated epitope, a combination of monoclonal antibodies directed against different epitopes of a single disease-associated antigenic component, monoclonal antibodies directed towards epitopes of different disease-associated antigens, polyclonal antibodies directed towards the same disease-associated antigen, or polyclonal antibodies directed towards different disease-associated antigens. Protocols can also, for example, use solid supports, or may involve immunoprecipitation. Typically, immunoassays use either a labeled antibody or a labeled antigenic component (i.e., to compete with the antigen in the sample for binding to the antibody). Exemplary labels are described in the sections shown above.

In accordance with the present invention, "competitive" (U.S. Pat. Nos. 3,654,090 and 3,850,752), "sandwich" (U.S. Pat. No. 4,016,043), and "double antibody," or "DASP" assays may be used. Several procedures for measuring the amount of target, target-binder or a target-partner polypeptide in a sample (e.g., ELISA, RIA, and FACS) are known in the art and provide a basis for diagnosing altered or abnormal levels of polypeptides or polypeptide complexes. Normal or standard values for a polypeptide or polypeptide complex are established by incubating biological samples taken from normal subjects, preferably human, with antibody to a polypeptide or polypeptide complex under conditions suitable for association. The amount of standard antibody-antigen association may be quantified by various methods; photometric means are preferred. Levels of the polypeptide or polypeptide complex in the subject sample, negative control (normal) sample, and positive control (disease) sample are compared with the standard values. Deviation between standard and subject values establishes the parameters for diagnosing disease.

Kits suitable for antibody-based diagnostic applications typically include one or more of the following components:

(1) Antibodies: The antibodies may be pre-labeled. Alternatively, the antibody may be unlabeled and the ingredients for labeling may be included in the kit in separate containers, or a secondary, labeled antibody is provided. Antibodies may be monoclonal or polyclonal, and may be directed to target or target-binders, or peptide complexes thereof; and (2) Reaction components: The kit may also contain other suitably packaged reagents and materials needed for the particular immunoassay protocol, including solid-phase matrices or beads, if applicable, and standards.

The kits referred to above may include instructions for conducting the test. Furthermore, in preferred embodiments, the diagnostic kits are adaptable to high-throughput and/or automated operation.

A sample to be analyzed, such as, for example, a tissue sample (e.g., hair or buccal cavity) or body fluid sample (e.g., blood, saliva, or urine), may be contacted directly with the nucleic acid probes. Alternatively, the sample may be treated to extract the nucleic acids contained therein. It will be understood that the particular method used to extract DNA will depend on the nature of the biological sample. The resulting nucleic acid from the sample may be subjected to gel electrophoresis or other size separation techniques, or, the nucleic acid sample may be immobilized on an appropriate solid matrix without size separation.

Therapeutics

As indicated herein below, target and target-binders may be associated with various cell processes, including cell growth, proliferation, and adhesion. Uncontrolled activation of cell growth and proliferation can lead to oncogenesis, whereas inhibition of cell attachment can lead to neoplastic growth and metastasis. Non-limiting examples of cancers include bone cancer, brain cancer, breast cancer, endocrine system cancers, gastrointestinal cancers (e.g., colorectal and pancreatic cancers) male genituorinary cancers (e.g., prostate cancer), germ cell cancers, gynecologic cancers (e.g., ovarian, cervical, endometrial, and vulvar cancers), head and neck cancers, leukemia, lung cancer, lymphomas (e.g., Hodgkin's and non-Hodgkin's lymphomas), skin cancers (e.g., myelomas and sarcomas), and urinary cancers (e.g., bladder and kidney cancers). Metastatic cancers include, but are not limited to, cancers affecting bone, breast, lung, brain, spinal cord, skin, ovaries, bladder, and gastrointestinal tissues. Other possible indications may include, but are not limited to disease of the CNS and the cardiovascular system.

Drug Screening and Design

The present invention provides methods of screening for drugs using target or target-binder polypeptides, peptides, or polypeptide-complexes thereof, in competitive binding assays, according to methods well-known in the art. For example, competitive drug screening assays can be employed using a complex comprising target and a target-binder, and screening for a test compound that disrupts, enhances, or otherwise alters the polypeptide-complex.

The present invention further provides methods of rational drug design employing a target or target-binder polynucleotide, polypeptide, antibody, polypeptide-complex, or portion or functional equivalent thereof. The goal of rational drug design is to produce structural analogs of biologically active polypeptides of interest or of small molecules with which they interact (e.g., agonists, antagonists, or inhibitors). In turn, these analogs can be used to fashion drugs which are, for example, more active or stable forms of the polypeptide, or which, e.g., enhance or interfere with the function of the polypeptide in vivo (see, e.g., Hodgson, 1991, *BioTechnology,* 9:19–21). An example of rational drug design is the development of HIV protease inhibitors (Erickson et al., 1990, *Science,* 249:527–533).

Non-limiting examples of methods and computer tools for drug design are described in R. Cramer et al., 1974, *J. Med. Chem.* 17:533; H. Kubinyi (ed) 1993, 3D QSAR in Drug Design, Theory, Methods, and Applications, ESCOM, Leiden, Holland; P. Dean (ed) 1995, Molecular Similarity in Drug Design, K. Kim "Comparative molecular field analysis (ComFA)" p. 291–324, Chapman & Hill, London, UK; Y. et al., 1993, *J. Comp.-Aid. Mol. Des.* 7:83–102; G. Lauri and P. A. Bartlett, 1994, J. Comp.-Aid. Mol. Des. 8:51–66; P. J. Gane and P. M. Dean, 2000, Curr. Opin. Struct. Biol. 10(4):401–4; H. O. Kim and M. Kahn, 2000, Comb. Chem. High Throughput Screen. 3(3):167–83; G. K. Farber, 1999, Pharmacol Ther. 84(3):327–32; and H. van de Waterbeemd (Ed.) 1996, Structure-Property Correlations in Drug Research, Academic Press, San Diego, Calif.

In another aspect of the present invention, cells and animals that carry a human target gene or an variant thereof can be used as model systems to study and test for substances that have potential as therapeutic agents. After a test agent is administered to animals or applied to the cells, the phenotype of the animals/cells can be determined.

In accordance with these methods, one may design drugs that result in, for example, altered target or target-binder activity or stability. Such drugs may act as inhibitors, agonists, or antagonists of these polypeptides, or the complexes formed by these peptides. By virtue of the availability of target and target-binder nucleotide sequences, sufficient amounts of these polypeptides may be produced to perform such analytical studies as x-ray crystallography. In addition, the knowledge of the target and target-binder polypeptide sequences will guide those employing computer-modeling techniques in place of, or in addition to x-ray crystallography.

Pharmaceutical Compositions

The present invention contemplates compositions comprising a target or target-binder polynucleotide, polypeptide, antibody, ligand (e.g., agonist, antagonist, or inhibitor), polypeptide-complex, or fragments or variants thereof, and a physiologically acceptable carrier, excipient, or diluent. The present invention further contemplates pharmaceutical compositions useful in practicing the therapeutic methods of this invention. Preferably, a pharmaceutical composition includes, in admixture, a pharmaceutically acceptable excipient (carrier) and one or more of a target or target-binder polynucleotide, polypeptide, ligand, antibody, polypeptide-complex, or fragment, portion, or variant thereof, as described herein, as an active ingredient. The preparation of pharmaceutical compositions that contain target or target-binder molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH-buffering agents, which enhance the effectiveness of the active ingredient.

A target or target-binder polynucleotide, polypeptide, ligand, antibody, polypeptide-complex, or fragment, portion, or variant thereof can be formulated into the pharmaceutical composition as neutralized physiologically acceptable salt forms. Suitable salts include the acid addition salts (i.e., formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical compositions can be administered systemically by oral or parenteral routes. Non-limiting parenteral routes of administration include subcutaneous, intramuscular, intraperitoneal, intravenous, transdermal, inhalation, intranasal, intra-arterial, intrathecal, enteral, sublingual, or rectal. In one particular embodiment of the present invention, the disclosed pharmaceutical compositions are administered via mucoactive aerosol therapy (see, e.g., M. Fuloria and B. K. Rubin, 2000, Respir. Care 45:868–873; I. Gonda, 2000, J. Pharm. Sci. 89:940–945; R. Dhand, 2000, Curr. Opin. Pulm. Med. 6(1):59–70; B. K. Rubin, 2000, Respir. Care 45(6):684–94; S. Suarez and A. J. Hickey, 2000, Respir. Care. 45(6):652–66). Intravenous administration, for example, can be performed by injection of a unit dose. The term "unit dose" when used in reference to a pharmaceutical composition of the present invention refers to physically discrete units suitable as unitary dosage for humans, each unit containing a predetermined quantity of active material calculated to produce the desired therapeutic effect in association with the required diluent; i.e., carrier, or vehicle.

Pharmaceutical compositions are administered in a manner compatible with the dosage formulation, and in a therapeutically effective amount. The quantity to be administered depends on the subject to be treated, capacity of the subject's immune system to utilize the active ingredient, and degree of modulation of target, target-binder or target-partner activity desired. Precise amounts of active ingredient required to be administered depend on the judgment of the practitioner and are specific for each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusions sufficient to maintain concentrations of 10 nM to 10 µM in the blood are contemplated. An exemplary pharmaceutical formulation comprises: DGI-2 antagonist or inhibitor (5.0 mg/ml); sodium bisulfite USP (3.2 mg/ml); disodium edetate USP (0.1 mg/ml); and water for injection q.s.a.d. (1.0 ml). As used herein, "pg" means picogram, "ng" means nanogram, "µg" means microgram, "mg" means milligram, "µl" means microliter, "ml" means milliliter, and "l" means L.

For further guidance in preparing pharmaceutical formulations, see, e.g., Gilman et al. (eds), 1990, *Goodman and Gilman's: The Pharmacological Basis of Therapeutics*, 8th ed., Pergamon Press; and *Remington's Pharmaceutical Sciences*, 17th ed., 1990, Mack Publishing Co., Easton, Pa.; Avis et al. (eds), 1993, *Pharmaceutical Dosage Forms: Parenteral Medications*, Dekker, New York; Lieberman et al. (eds), 1990, *Pharmaceutical Dosage Forms: Disperse Systems*, Dekker, New York.

In yet another aspect of this invention, antibodies that specifically react with a target or target-binder polypeptide, peptides, or polypeptide-complexes comprised thereof can be used as therapeutics. In particular, such antibodies can be used to block the activity of a target or target-binder polypeptide or target/target-binder complex. Antibodies or fragments thereof can be formulated as pharmaceutical compositions and administered to a subject. It is noted that antibody-based therapeutics produced from non-human sources can cause an undesired immune response in human subjects. To minimize this problem, chimeric antibody derivatives can be produced. Chimeric antibodies combine a non-human animal variable region with a human constant region. Chimeric antibodies can be constructed according to methods known in the art (see Morrison et al., 1985, *Proc. Natl. Acad. Sci. USA* 81:6851; Takeda et al., 1985, *Nature* 314:452; U.S. Pat. No. 4,816,567 of Cabilly et al.; U.S. Pat. No. 4,816,397 of Boss et al.; European Patent Publication EP 171496; EP 0173494; United Kingdom Patent GB 2177096B).

In addition, antibodies can be further "humanized" by any of the techniques known in the art, (e.g., Teng et al., 1983, *Proc. Natl. Acad. Sci. USA* 80:7308–7312; Kozbor et al., 1983, *Immunology Today* 4: 7279; Olsson et al., 1982, *Meth. Enzymol.* 92:3–16; International Patent Application WO92/06193; EP 0239400). Humanized antibodies can also be obtained from commercial sources (e.g., Scotgen Limited, Middlesex, England). Immunotherapy with a humanized antibody may result in increased long-term effectiveness for the treatment of chronic disease situations or situations requiring repeated antibody treatments. Suitable gene transfer vectors possess a promoter sequence, preferably a promoter that is cell-specific and placed upstream of the sequence to be expressed. The vectors may also contain, optionally, one or more expressible marker genes for expression as an indication of successful transfection and expression of the nucleic acid sequences contained in the vector. In addition, vectors can be optimized to minimize undesired immunogenicity and maximize long-term expression of the desired gene product(s) (see Nabe, 1999, *Proc. Natl. Acad. Sci. USA* 96:324–326). Moreover, vectors can be chosen based on cell-type that is targeted for treatment. Notably, gene transfer therapies have been initiated for the treatment of various pulmonary diseases (see, e.g., M. J. Welsh, 1999, *J Clin. Invest.* 104(9):1165–6; D. L. Ennist, 1999, *Trends Pharmacol. Sci.* 20:260–266; S. M. Albelda et al., 2000, *Ann. Intern. Med.* 132:649–660; E. Alton and C. Kitson C., 2000, *Expert Opin. Investig. Drugs.* 9(7):1523–35).

Illustrative examples of vehicles or vector constructs for transfection or infection of the host cells include replication-defective viral vectors, DNA virus or RNA virus (retrovirus) vectors, such as adenovirus, herpes simplex virus and adeno-associated viral vectors. Adeno-associated virus vectors are single stranded and allow the efficient delivery of multiple copies of nucleic acid to the cell's nucleus. Preferred are adenovirus vectors. The vectors will normally be substantially free of any prokaryotic DNA and may comprise a number of different functional nucleic acid sequences. An example of such functional sequences may be a DNA region comprising transcriptional and translational initiation and termination regulatory sequences, including promoters (e.g., strong promoters, inducible promoters, and the like) and enhancers which are active in the host cells. Also included as part of the functional sequences is an open reading frame (polynucleotide sequence) encoding a protein of interest. Flanking sequences may also be included for site-directed integration. In some situations, the 5'-flanking sequence will allow homologous recombination, thus changing the nature of the transcriptional initiation region, so as to provide for inducible or non-inducible transcription to increase or decrease the level of transcription, as an example.

In general, the encoded and expressed target or target-binder polypeptide may be intracellular, i.e., retained in the cytoplasm, nucleus, or in an organelle, or may be secreted by the cell. For secretion, the natural signal sequence present in the polypeptide may be retained. When the polypeptide or peptide is a fragment of a full-length protein, a signal sequence may be provided so that, upon secretion and processing at the processing site, the desired protein will have the natural sequence. Specific examples of coding sequences of interest for use in accordance with the present invention include the target or target-binder polypeptide-coding sequences shown in the GenBank and GenPept entries described herein.

As previously mentioned, a marker may be present for selection of cells containing a vector construct. The marker may be an inducible or non-inducible gene and will generally allow for positive selection under induction, or without induction, respectively. Examples of marker genes include neomycin, dihydrofolate reductase, glutamine synthetase, and the like. The vector employed will generally also include an origin of replication and other genes that are necessary for replication in the host cells, as routinely employed by those having skill in the art. As an example, the replication system comprising the origin of replication and any proteins associated with replication encoded by a particular virus may be included as part of the construct. The replication system must be selected so that the genes encoding products necessary for replication do not ultimately transform the cells. Such replication systems are represented by replication-defective adenovirus (see G. Acsadi et al., 1994, *Hum. Mol. Genet.* 3:579–584) and by Epstein-Barr virus. Examples of replication defective vectors, particularly, retroviral vectors that are replication defective, are BAG, (see Price et al., 1987, *Proc. Natl. Acad. Sci. USA,* 84:156; Sanes et al., 1986, *EMBO J.,* 5:3133). It will be understood that the final gene construct may contain one or more genes of interest, for example, a gene encoding a bioactive metabolic molecule. In addition, cDNA, synthetically produced DNA or chromosomal DNA may be employed utilizing methods and protocols known and practiced by those having skill in the art.

According to one approach for gene therapy, a vector encoding a target polypeptide is directly injected into the recipient cells (in vivo gene therapy). Alternatively, cells from the intended recipients are explanted, genetically modified to encode a target polypeptide, and reimplanted into the donor (ex vivo gene therapy). An ex vivo approach provides the advantage of efficient viral gene transfer, which is superior to in vivo gene transfer approaches. In accordance with ex vivo gene therapy, the host cells are first transfected with engineered vectors containing at least one gene encoding a target or target-binder polypeptide, suspended in a physiologically acceptable carrier or excipient such as saline or phosphate buffered saline, and the like, and then administered to the host. The desired gene product is expressed by the injected cells, which thus introduce the gene product into the host. The introduced gene products can thereby be utilized to treat or ameliorate a disorder (e.g., neoplastic growth or cancer) that is related to altered levels, activities, and/or interactions of the target, target-binder or target-partner polypeptides.

Sequence Analysis

Publicly available sequence databases, e.g., GenBank, GenPept, SWISS-PROT, Protein Data Bank (PDB), Protein Information Resource (PIR), Human UniGene (National Center for Biotechnology Information), can be used to determine sequences that share homology with target, target-binder, or target-partner nucleotide or amino acid sequences, or fragments, or sequences obtained for other targets, thereof. Alternatively, privately owned sequence databases, e.g., the Incyte Genomics sequence database (Incyte Genomics), can be used. Databases with relatively few redundant sequences, e.g., PIR or SWISS-PROT databases, may be used to improve the statistical significance of a sequence match. However, databases which are more comprehensive and up-to-date, e.g., GenBank, GenPept, and Incyte Genomics sequence databases (Incyte Genomics, Inc., St. Louis, Mo.), are preferred.

Any method known in the art can be used to align and compare a DGI-2, DGI-2-binder, or DGI-2-partner sequence with the sequences present in a sequence database. Preferably, the BLAST (Basic Local Alignment Search Tool) program is used (S. F. Altschul et al., 1990, *J. Mol. Biol.* 215:403–410; S. Karlin et al., 1990, *Proc. Natl. Acad. Sci. USA* 87:2264–68; S. Karlin et al., 1993, *Proc. Natl. Acad. Sci. USA* 90:5873–7). BLAST identifies local alignments between the sequence of the previously identified protein and the protein sequences in the database, and predicts the probability of the local alignment occurring by chance. Although the original BLAST programs utilized ungapped local alignments, more recently developed BLAST programs such as WU-BLAST2/BLAST v2.0 (S. F. Altschul et al., 1996, *Methods Enzymol.* 266:460–480) have been modified to incorporate gapped local alignments similar to SSEARCH (T. F. Smith et al., 1981, *J. Mol. Biol.* 147: 195–197) and FASTA programs (W. R. Pearson, 1990, *Methods Enzymol.* 183:63–98). In addition, position-specific-iterated BLAST (PSI-BLAST) programs have been developed to identify weak but biologically relevant sequence similarities (S. F. Altschul et al., 1997, *Nucleic Acids Res.* 25:3389–3402). Furthermore, pattern-hit-initiated BLAST (PHI-BLAST) programs have been designed to identify specific patterns or sequence motifs shared by distantly-related proteins (Z. Zhang et al., 1998, *Nucleic Acids Res.* 26:3986–3990). Specialized BLAST programs are also available for performing searches of human, microbial, and malaria genome sequences, as well as searches for vector, immunoglobulin, and predicted human consensus sequences (National Center for Biotechnology Information (NCBI), Bethesda, Md.).

Both FASTA and BLAST programs identify very short exact sequence matches between the query sequence and the databases sequences, analyze the best short sequence matches ("hits") to determine if longer stretches of sequence similarity are present, and then optimize the best hits by dynamic programming (S. F. Altschul et al., 1990, *J. Mol. Biol.* 215:403–410; W. R. Pearson, 1990, *Methods Enzymol.* 183:63–98). In contrast, the SSEARCH program compares the query sequence to all the sequences in the database via pair-wise sequence comparisons (T. F. Smith et al., 1981, *J. Mol. Biol.* 147:195–197). Thus, the SSEARCH program is considered more sensitive than the BLAST and FASTA programs, but it is also significantly slower. The BLAST and FASTA programs utilize several approximations to increase their searching speed, and utilize statistical parameters (see below) to increase sensitivity and selectivity to approximate the performance of the SSEARCH program.

It is understood in the art that BLAST comparison of amino acid sequences requires a substitution matrix program (PAM30, PAM70, PAM120, PAM250, BLOSUM45, BLOSUM62, BLOSUM80, etc.; see, e.g., S. F. Altschul, 1991, *J. Mol. Biol.,* 219:555–565; S. F. Altschul, 1993, *J. Mol. Evol.* 36:290–300; M. O. Dayhoff et al., 1978, *Atlas of Protein Sequence and Structure,* 5:345–352; R. M. Schwartz and M. O. Dayhoff, 1978, *Atlas of Protein Sequence and Structure,* 5:353–358; G. H. Gonnet et al., 1992, *Science,* 256:1443–1445; S. Henikoff and J. G. Henikoff, 1992, *Proc. Natl. Acad. Sci. USA,* 89:10915–10919; S. Henikoff and J. G. Henikoff, 1993, *Proteins,* 17:49–61). A substitution matrix program scores each possible amino acid residue substitution, reflecting the probability that the residue is related to the corresponding residue in the query. Although different substitution matrices use different scoring systems for quantifying the relationship between the compared residues, the results from different substitution matrices can be readily compared and evaluated by a person of average skill in the art. In fact, it is common practice to run several parallel BLAST searches, using a different substitution matrix for each search (S. F. Altschul, 1991, *J. Mol. Biol.,* 219:555–565; S. F. Altschul, 1993, *J. Mol. Evol.,* 36:290–300; S. Henikoff and J. G. Henikoff, 1993, *Proteins,* 17(1):49–61).

In some instances, BLAST analysis of amino acid sequences may require a filtering program (e.g., SEG or XNU). A filtering program removes repetitive regions from the query sequence (e.g., proline-rich regions). Although certain filtering programs determine regions of low compositional complexity (e.g., SEG), while other filtering programs determine regions with short, periodic, internal repeats (e.g., XNU), the results from different filtering programs are comparable and can be evaluated by a person of average skill in the relevant art. Moreover, it is common practice to combine, alternate, or omit the filtering programs as required for a specific query sequence (see, e.g., B. Birren et al. (Eds), 1997, *Genome Analysis: A Laboratory Manual, Volume 1: Analyzing DNA,* Cold Spring Harbor Laboratory Press, Cold Spring Harbor, N.Y.).

In addition, BLAST analysis may utilize different search parameters (e.g., scoring matrices and filters) depending on the specific features of the query sequence. For example, it is understood by the skilled practitioner that the BLOSUM matrices are not suitable for the shortest queries. Thus, the PAM matrices, such as PAM30 or PAM70, may be used for short query sequences (R. M. Schwartz and M. O. Dayhoff, supra; M. O. Dayhoff et al., supra). In general, as understood by the skilled person in the art, the following scoring matrices are recommended:

| Query length (amino acids) | Substitution Matrix |
|---|---|
| <35 | PAM30 |
| 35–50 | PAM70 |
| 50–85 | BLOSUM80 |
| >85 | BLOSUM62 |

(see the National Center for Biotechnology Information website at Hyper Text Transfer Protocol:///World Wide Web-.National Center for Biotechnology Information.National Library of Medicine.National Institutes of Health. GOVernment/Basic Local Alignment Search Tool/matrix_info.Hyper Text Markup Language).

Additionally, PAM120 and BLOSUM62 matrices are designed to identify moderately diverged sequences, and these matrices may miss short/strong sequence similarities, or long/weak sequence similarities (S. Altschul et al., 1994, *Nat. Genet.* 6:119–129). For this reason, it has been generally recommended that researchers employ at least 3 separate substitution matrices for BLAST analysis (S. Altschul et al., 1993, *J. Mol. Evol.* 36:290–300; S. Altschul et al., 1994, *Nat. Genet.* 6:119–129). The use of different BLAST parameters with a particular query sequence is routinely practiced in the art and is well within the capability of an average artisan (see, e.g., Altschul et al., 1994, *Nature Genet.*, 6; 119–129; Altschul et al., 1996, *Methods Enzymol.*, 266: 460–480; S. Henikoff and J. G. Henikoff, 1993, *Proteins*, 17(1):49–61).

BLAST analysis of nucleic acid sequences generally require a unitary matrix program, which scores each position as "+" if the nucleotides match, or "−" if the nucleotides do not match. In addition, BLAST comparisons of nucleic acid sequences may involve a nucleic acid-specific filtering program, such as DUST (J. M. Hancock and J. S. Armstrong, 1994, *Comput. Appl. Biosci.* 10:67–70). Notably, a particular sequence alignment program (e.g., BLAST, FASTA, or SSEARCH) and appropriate parameters (e.g., scoring matrices and filters) can be chosen based on the requirements of a sequence search, or individual preferences. In some cases, it may be preferable to use more than one program or set of parameters in order to confirm or evaluate search alignment results.

The criteria for identifying a natural partner to a target using the computational approaches described above is defined as follows: a group of >5–7 amino acids identical to a sequence found by the database searches. Alternatively, the finding that 50% or more of the hits in the top cohort are identical. In addition, the following information can be used to validate the target and natural partner for use in drug discovery paradigms:

1. Information about expression, disease indication, structural elements, etc. that relate the target to the putative natural partner.
2. The ability to modulate the expected phenotype in the appropriate biological system.

Proteome panning is particularly useful in drug discovery assays where target and target binder pairs are utilized in high-throughput screening. In particular, two ELISA methods may be used. The ELISA method I utilizes target phage and target binder phage, where each is labeled with a separate and distinct tag. The target phage is incubated onto a solid support, such as a plate previously coated with the target tag specific antibody. Addition of target binder phage and test compounds from small molecule combinatorial libraries to the solid support follows. Any disruption of the target: target binder complex pairing thereby identifies test compounds or biologically active compounds that may bind to the target of interest. In order to ensure that there is no contamination, the ELISA method II utilizes pure target and target binders. This method requires subcloning, expression and purification of recombinant target protein, followed by the method of ELISA method I. These methods may be preferred in that they can produce cleaner and more reproducible assays.

Similarly, these methods may be adapted for microarrays, where target and target binder phages are incubated. Different fluorescent dyes are preferably used to distinguish between the target and the target binder. For example, Cy3 identifies the target and Cy5 identifies the target binder. If a test compound binds to a target, then only the Cy3 signal will be emitted. Target and target binder pairs will be washed off the microarray except in conditions where the test compound binds to the target: target binder complexed pair, thereby emitting a combined Cy3/Cy5 signal. This method may also be used to identify compounds binding to the target binder as well.

A high-throughput screen developed by Perking Elmer (High-Throughput ALPHAScreen™) may be used with the proteome panning method of the invention. Briefly, target phage and target binder phage, each having a separate and distinct label or tag, are incubated with test compounds prior to the addition of acceptor and donor beads. In one example, the acceptor bead may specifically bind to the target as determined by the specific tag and the donor bead binds to the target binder, thereby forming two bead complexes: target: acceptor complex and target binder: donor complex. Another example may denote the target binding the donor bead and the target binder binding the acceptor bead. The two bead complexes may form a larger complex through binding the target and target binder, i.e. target: target binder complex. A signal is emitted once a target: target binder complex is formed. If a disruption of this target: target binder complex is observed, the specific test compound used identifies the biologically active compound. The microarray and ALPHAScreen methods offer the advantage that they are simple, especially for analyzing a plurality of different test compounds at the same time. They also do not require additional steps such as phage separation, subcloning or purification. All four methods of using proteome panning for identifying biologically active compounds may be useful.

All books, articles, and patents referenced herein are incorporated by reference in toto. The following examples illustrate various aspects of the invention and in no way intended to limit the scope thereof.

EXAMPLES

The examples as set forth herein are meant to exemplify the various aspects of the present invention and are not intended to limit the invention in any way.

Example 1

Construction of DGI-2-GeneIII Fusion Proteins in pCANTAB5E

Creation of pCANTAB 5E Tetracycline Resistant Plasmid pCANTAB 5E with 2 kb LacZ stuffer (DGI vector for RAPIDLIB) and pBR322 (Promega; Madison, Wis.), carrying the genes for tetracycline (Tet) and ampicillin (Amp) resistance were used to construct the pCANTAB5E Tet resistant plasmid. pCANTAB (5 µg) was cut with Aat II (Base 65) and filled in with Pfu polymerase, followed by ScaT cleavage at base 505. This removed the first 300 bases of the Amp resistance gene and its entire promoter. The vector was purified on Low Melt agarose.

pBR322 (5 µg) was cut with Ava I (base 1425) and filled in with Pfu polymerase. and then cut with Aat II at base 4284. This removed 1500 bases containing the entire Tet resistance gene. The fragment was purified on Low Melt agarose.

The fragment and vector were ligated and plated on Tet (10 µg/ml) plates. Colonies were picked and replica plated on both Amp and Tet plates.

Five colonies that were Tet resistant and Amp sensitive were grown in Tet media. The colony that grew the best was used, Maxi-prepped and labeled pCANTAB Tet.

Example 2

Construction of a Blunt-Ended cDNA Library in Tetracycline Phage

Liver tumor HepG2 (hepatome) Lambda Uni_Zap XR (Stratagene, Cat. No. 937261) was used for constructing a cDNA library in a modified pCANTAB 5E Tet resistant vector. The library mass (350–1500 bp) was excised and cut with EcoRV and SmaI, creating two sets of blunt end fragments. The Tet vector was modified by inserting a PCR fragment with SfiI and NotI ends. The PCR fragment created EcoRV sites inside of the SfiI and NotI sites. The modified vector was cut with EcoRV and gel purified using low melt agarose. The mass of the excised blunt end fragments was less than 1 KB cut out of the gel and purified. The insert was ligated to the blunt ended Tet phage vector. Additional guidance is commonly known in the art (Savinov and Austin. *Comb. Chem. High Throughput Screen*, 4:593–7, 2001; Zucconi, et al. *J. Mol. Biol.* 307:1329–39, 2001; Crameri and Kodzius. *Comb. Chem. High Throughput Screen.* 4:145–55, 2001; Mazzarelli and Ricciardi. *Biotechniques.* 30:380–6, 2001; Sihoud, et al. *Int. J. Mol. Med.* 6:123–8, 2000; Cochrane et al. *J. Mol. Biol.* 297:89–97, 2000; and Santi, et al. *J. Mol. Biol.* 296:497–508, 2000).

In addition to the HepG2 library, subtracted cDNA libraries are used as the starting point for this process. In this case, the subtracted libraries are ligated into the Tet vector as above. The protocol that is used for subtraction is described by Clontech (Clontech PCR-Select Subtraction). This protocol is applicable to any library, such as but not limited to ovarian, breast, and colorectal cancer. This approach is used for developing subtracted libraries for other disease indications including CNS, cardiovascular, angiogenesis, etc.

Example 3

Production of Target Phage

Phage rescue was carried out to produce phage with displayed target protein. Overnight cultures of TGI cells (F' traD36 lacI$^q$ Δ(lacZ)M15 proAB)/supE Δ(hsdM-mcrB)$_5$ $r_k^-m_k^-$McrB$^-$) thi Δ(lac-proAB) harboring the target protein-gene III gene fusion plasmids (2×YT-TG) were inoculated 1:100 into 10 ml of 2×YT-TG media. The cultures were grown to an OD$_{600}$ 0.5 in 2×YT-TG at 30° C. with shaking (250 rpm). M13K07 helper phage was then added [Multiplicity of Infection (MOI)=15], and the cells were incubated for 1 hr at 37° C. with shaking (250 rpm). Following infection, cells were pelleted and the supernatant containing the helper phage was discarded. The cell pellet was resuspended in the initial culture volume of 2×YT without glucose and containing tetracycline and 50 mg/mL kanamycin (2×YT-TK) and grown overnight at 30° C. with shaking (250 rpm). The cells from the overnight culture were pelleted at 3000×g for 30 min at 4° C. and the supernatant containing the phage was recovered. The phage were titered by infecting TG1 cells and plating on tetracycline plates.

Example 4

Production of Target Binder Phage

The target binder library, 20F, was constructed by creating DNA fragments coding for peptides containing 20 random amino acids using PCR and synthetic oligonucleotides. An oligonucleotide was synthesized containing the sequence (NNK)$_{20}$ where N=A, C, T, or G and K=G or T. This oligonucleotide was used as the template in PCR reactions along with two shorter oligonucleotide primers, both of which are biotinylated at their 5' ends. The resulting PCR product was purified and concentrated (followed by digestion with SfiI and NotI). The resulting fragment was purified and the phagemid pCANTAB5E (Pharmacia) was digested with SfiI and NotI. The digested DNA was resolved using a 1% agarose gel, excised and purified by QIAEX II treatment (Qiagen). The vector and insert were ligated overnight at 15° C. The ligation product was purified and electroporations were performed at 1500 V in an electroporation cuvette (0.1 mm gap; 0.5 ml volume) containing 12.5 g DNA and 500 L of *E. coli* strain TG1 electrocompetent cells. Immediately after the pulse, 12.5 ml of pre-warmed (40° C.) 2×YT medium containing 2% glucose (YT-G) was added and the transformants grown at 37° C. for one hour. Cell transformants were pooled, the volume measured and an aliquot plated onto 2×YT-G containing 100 µg/ml ampicillin (YT-AG) to determine the number of transformants. The diversity of the random 20-mer peptide cell library was found to be >1.1×10$^{11}$ clones. Sequencing of randomly selected clones for the library revealed that about 77% of the clones were in frame. In addition, the E-tag epitope (GAPVPYP-DPLEPR; SEQ ID NO: 222) was engineered into the carboxy terminus of the peptide.

Example 5

Proteome Panning with DGI-2

For these studies, a phage library 20F, which expresses random peptides 20 amino acids long and has Ampicillin (Amp) resistance, and a phage that express the target of interest, specifically DGI-2, and has Tetracycline (Tet) resistance were used. One hundred microliters of 2.4×10$^{10}$ CFU (colony forming units) phage library 20F with a diversity of >10$^{11}$ independent clones and a total concentration of >10$^{13}$ clones/ml was mixed with 100 microliters of 1.4×107 CFU (colony forming units) phage expressing DGI-2, the target of interest, and incubated at room temperature for 2 hours. Dilutions were made ranging from 10$^{-2}$–10$^{-12}$ (including individual inputs for each library). Each dilution was plated on one of each Amp (50 µg/ml), Tet (10 µg/ml), and Amp (50 µg/ml)+Tet (10 µg/ml) plates and incubated at 37° C. overnight.

On day 2, the number of colonies that grew on all of the plates were counted and the titers were recorded. Ninety-six individual clones were picked from Amp+Tet plates and inoculated into 5001 of 2×YT media containing 40% glucose and Amp (50 µg/ml)+Tet (10 µg/ml) and incubated at 37° C. shaking 225 rpm overnight.

On day 3, 40 microliters of the Amp+Tet resistant clones were inoculated into 400 microliters of Amp only media to allow cells to selectively lose the Tet phagemid (expressing DGI-2) by removing the Tet selection pressure and retain the Amp phagemid (expressing DGI-2 binder peptide). Cells were incubated at 37° C. shaking at 250 rpm overnight.

On day 4, Amp phage (DGI-binder phage) were rescued by inoculating 40 microliters of cells from day 3 in 400 microliters 2×YT media containing 40% glucose, 50 µg/ml Amp, and M13KO7 helper phage containing kanamycin (kan) resistance (kanR) marker. Cells were incubated for 3 hours at 37° C. with shaking 250 rpm. Following infection, cells were pelleted for 15 minutes at 3500 rpm at 4° C., supernatant removed, and the pellets were resuspended in the initial culture volume of 2×YT media containing 50 µg/ml Amp and 50 µ/ml Kan. Cells were grown overnight at 37° C. with shaking at 225 rpm.

On day 5, cells from the overnight culture were pelleted and Amp resistant phage (DGI-2 binder phage) recovered in the supernatant.

Proteome Panning in the Presence of Non-Specific Phage

In order to validate the Proteome panning method, non-specific and unrelated phage is used. Phage clone(s) expressing peptides that bind specifically to the target of interest are rescued and amplified. These phage clone(s) are then mixed with unrelated phage clone(s) that do not bind the target. By proteome panning of the mixed phage population, only the binder phage and not the unrelated phage is isolated. This indicates that entry of the peptide-expressing phage into cells is dependent on interaction with the target-expressing phage.

Example 6

Expression of the DGI-2 Protein for ELISA Analysis

To verify that the selected target binders bound to DGI-2, Elisa assays were performed with recombinant DGI-2. DGI-2 was subcloned and expressed using conventional methods as described below.

An IMAGE clone containing the DGI-2 sequence (IMAGE: 3838690; accession number BE748524) was obtained from the American Type Culture Collection (ATCC, Manassas Va.). The clone included 770 bp and encompassed the entire DGI-2 open reading frame (ORF).

The 336 bp DGI-2 ORF was amplified using PCR, the amplified sequence was digested with the appropriate enzymes, the digested DNA was ligated into the appropriate expression vectors, and the cloned DNA was sequenced. DGI-2 was first expressed in E. coli. The DGI-2 ORF was cloned into expression vector pTrcHis A (Invitrogen, Carlsbad, Calif.) using restriction sites Kpn I and Hind III, which were added to the DGI-2 by PCR. The primers used for PCR amplification are shown as follows:

```
DGI-2 Kpn I forward primer for the TrcHis A vector:
5'- GGA TCC GGG TAC CAT GGT GCG GAC TAA AGC AGA CAG -3';    (SEQ ID NO: 223)

DGI-2 Hind III reverse primer for the TrcHis A vector:
5'- GGC CAG AAG CTT TTC TTT TTC ATC ATT TGT GTG ATC AGG -3'; (SEQ ID NO: 224)
```

Protein yields were satisfactory, but most of protein was found in inclusion bodies. Next, DGI-2 was expressed using an in vitro translation system (Rapid Translation System RTS 5000, Roche Diagnostics GmbH, Mannheim Germany). For this system, the DGI-2 ORF was cloned into the pIVEX2.3-MCS vector (Roche Diagnostics) using restriction sites Nde I and Hind III, which were added to DGI-2 by PCR. In this case, the protein was found to be soluble, and was used for panning and ELISA analysis. The primers used for the PCR amplification were as follows:

```
DGI 2 Nde I forward primer for the IVEX vector:
5'- GAT CTA CAT ATG GTG CGG ACT AAA GCA GAC AG c-3'.    (SEQ ID NO: 225)

DGI 2 Hind III reverse primer for the IVEX vector:
5'- GAT GGC CAG GTC GAC TTC TTT TTC ATC ATT TGT GTG ATC AGG-3'. (SEQ ID NO: 226)
```

Example 7

ELISA Analysis of Phage

For analysis of individual target binders, colonies were picked and phage prepared as described above using helper phage, M13KO7. Ninety-six-well microtiter plates were coated with 500 ng/well of specific target protein, 500 ng/well lactate dehydrogenase (LDH) irrelevant or non-specific target, 500 ng/well of positive control antibody raised against ETAG, and negative control of non-fat milk powder-PBS 2% at 4° C. overnight. Plates were then blocked with 350 microliters/well PBS containing 2% non-fat milk for 1 hr at room temperature. One hundred microliters per well of phage from isolated clones were added and plates were incubated at room temperature for 2 hr after centrifuging samples for 20 minutes at 3500 rpm at 4° C. The phage solution was then removed, and the wells were washed three times with PBS at room temperature. Antibody raised against M13 conjugated to horseradish peroxidase (Pharmacia) was diluted 1:3000 in PBS-Tween and added to each well (100 µl/well). Incubation was for 1 hr at room temperature, followed by washing with PBS-(0.5%) Tween 3 times as described. Color was developed by addition of ABTS solution (100 µl/well; Boehringer, Indianapolis, Ind.). Plates were analyzed at 405 nm. A clone was considered "positive" if the $A_{405}$ of the well was $\geq$2-fold over background.

Example 8

DGI-2 Panning Results

Overall, over 100 clones from the DGI-2 proteome panning and conventional panning experiments were sequenced. One hundred eighty-nine (189) unique peptides were identified (see Table 1), including 51 high-specificity binders (DGI-2-binders; SEQ ID NOs: 1–51), 11 weak binders (SEQ ID NOs: 52–62) and 2 potential binders (SEQ ID NOs: 63–64) as determined by proteome panning; and 84 high-specificity DGI-2 binders (SEQ ID NOs: 65–148), 12 weak binders (SEQ ID NOs: 149–160), and 29 potential binders (SEQ ID NOs: 161–189) as determined by conventional panning. Binders preferably have a binding ratio of specific phage to non-specific phage of $\geq$2.0, that is twice the background, weak binders are defined herein as those having a ratio ranging between 1.5 and 2.0, and potential binders have a binding ratio of <1.5. Each of the high-specificity DGI-2-binders were isolated multiple times. Table 1 shows the encoded amino acid sequences and results for each of the clones panned against DGI-2.

Further analysis of the DGI-2 binders resulted in the classification of several potential sequence motifs. Four motifs were identified as potential motifs for DGI-2 binders (see FIG. 1). Motif 4 was found in clones derived from a conventional panning and proteome panning method indicating that similar peptides that potentially bind to the same site of DGI-2 were identified by conventional panning and proteome panning methods. Identifying sequence motifs provides a better understanding of the structure and function of the target as well as the search for potential target binders and natural partners.

TABLE 1

| CLONE | SEQUENCE | SEQ ID NO: | ETAG (OD) | DGI-2 (OD) | LDH (OD) | DGI-2/LDH (OD) |
|---|---|---|---|---|---|---|
| DGI-2-20F-PP-C3 | LGRTFVWGTCLHLSVSRFGH | 1 | 39.9 | 5.3 | 1.0 | 5.1 |
| DGI-2-20F-PP-C9 | YAMSSRECGIRNSGLILSMW | 2 | 31.6 | 3.5 | 0.9 | 3.9 |
| DGI-2-20F-PP-F10 | VVHTRAWGSWAYGFVLRNRG | 3 | 42.5 | 3.5 | 1.3 | 2.8 |
| DGI-2-20F-PP-B3 | RGSLLLTLPRLSGAVGTAYG | 4 | 11.7 | 3.4 | 1.1 | 3.0 |
| DGI-2-20F-P0P-D6 | GITGLFCLCLRSSQSI | 5 | 5.7 | 3.3 | 1.0 | 3.2 |
| DGI-2-20F-PP-A2$_2$ | VCSGGKGTWLEIPDRVRSST | 6 | 44.1 | 3.3 | 1.0 | 3.1 |
| DGI-2-20F-PP-B2 | RSYPRLCKQKGGVIGRMLPG | 7 | 35.9 | 3.3 | 1.1 | 2.9 |
| DGI-2-20F-PP-A6 | VCGQRVARMQLNKTIRKLDS | 8 | 35.1 | 3.1 | 1.1 | 2.8 |
| DGI-2-20F-PP-F1 | ERVSKCVGRGSGRSVGQFGG | 9 | 11.1 | 3.0 | 0.9 | 3.4 |
| DGI-2-20F-PP-C4 | SIILAGCVWVMPCGQNLGGV | 10 | 36.1 | 3.0 | 0.9 | 3.2 |
| DGI-2-20F-PP-C7 | SSVWATWGSDLRTFGSVGFL | 11 | 11.0 | 3.0 | 1.1 | 2.6 |
| DGI-2-20F-PP-E6 | EVFVSVWVFRFRVMPVTPGGT | 12 | 4.1 | 3.0 | 1.2 | 2.6 |
| DGI-2-20F-PP-D9 | VRAVYSRDAYNEVGRWMRVGI | 13 | 9.0 | 2.9 | 1.0 | 2.9 |
| DGI-2-20F-PP-A3 | SLFERSARSRYHGSPDCNGS | 14 | 12.9 | 2.8 | 1.2 | 2.4 |
| DGI-2-20F-PP-C10 | DRSRAPLCADKSGRWQRYRR | 15 | 8.6 | 2.7 | 0.9 | 3.1 |
| DGI-2-20F-PP-E5 | SIVSSRSGWQRGWIAWEAPV | 16 | 30.4 | 2.7 | 1.0 | 2.7 |
| DGI-2-20F-PP-A4 | RVSYEMLGRRRRSMHGSSMR | 17 | 6.6 | 2.7 | 1.1 | 2.6 |
| DGI-2-20F-PP-G6 | GSTRLRVTVRFCSETGTPGC | 18 | 36.1 | 2.7 | 1.1 | 2.5 |
| DGI-2-20F-PP-C2 | GLYQRGLAPRCRGERFGVRN | 19 | 6.0 | 2.7 | 1.1 | 2.5 |
| DGI-2-20F-PP-D5 | WVVALRRIRLGLRRGVECLL | 20 | 33.6 | 2.7 | 1.2 | 2.3 |
| DGI-2-20F-PP-A9 | TFTRDVAGPAVSFVRLHSWN | 21 | 40.8 | 2.7 | 1.2 | 2.3 |
| DGI-2-20F-PP-A7 | GGDLGEQGVQLCPDVVRGGSL | 22 | 42.2 | 2.6 | 0.9 | 2.8 |
| DGI-2-20F-PP-B11 | VGHLLSRCAHHSPGMGASPYG | 23 | 40.8 | 2.6 | 1.0 | 2.7 |
| DGI-2-20F-PP-D4 | DRHRAFVAEGLDGFRHSTGV | 24 | 44.0 | 2.6 | 1.1 | 2.3 |
| DGI-2-20F-PP-F3 | EGQRVVFLFGALVAGLCWRDR | 25 | 18.7 | 2.6 | 1.1 | 2.2 |
| DGI-2-20F-PP-C12 | PVYRVAMCRISVGCSAGAWF | 26 | 36.4 | 2.5 | 0.9 | 2.9 |
| DGI-2-20F-PP-E8 | S#ARSLMTGVVAVCIVWRGP | 27 | 36.3 | 2.5 | 1.0 | 2.6 |
| DGI-2-20F-PP-B6 | LFRFSGTGMASLPCVGWHLV | 28 | 37.0 | 2.5 | 1.0 | 2.6 |
| DGI-2-20F-PP-A8$_2$ | CYLSRLFRSGQGIGQFGHVE | 29 | 16.5 | 2.5 | 1.1 | 2.3 |
| DGI-2-20F-PP-G4 | VLCLE#ALGLSGLGWRVVVGP | 30 | 25.6 | 2.5 | 1.1 | 2.2 |
| DGI-2-20F-PP-G10 | LGRIVRPCVVRLCGGV##GV | 31 | 30.1 | 2.5 | 1.2 | 2.0 |
| DGI-2-20F-PP-C11 | TPVAISIPAGVCSTSVCGRD | 32 | 3.2 | 2.4 | 0.9 | 2.6 |
| DGI-2-20F-PP-F2 | VTGTRFRGFAVACVRMGTWH | 33 | 1.9 | 2.4 | 1.0 | 2.5 |
| DGI-2-20F-PP-B4$_2$ | SLLCVVCRPVSGGRALGGVP | 34 | 21.5 | 2.4 | 1.0 | 2.5 |
| DGI-2-20F-PP-A10 | RRFVRCSVPVALRSAVPVSV | 35 | 16.3 | 2.4 | 1.0 | 2.4 |
| DGI-2-20F-PP-G2 | VSGVPDGSMRAAQLASGYWC | 36 | 5.6 | 2.4 | 1.1 | 2.1 |
| DGI-2-20F-PP-G5 | GASRVVDVGWRFWGKLWQRS | 37 | 27.7 | 2.4 | 1.2 | 2.0 |
| DGI-2-20F-PP-F5 | GGSLPVKSGQLVTCCTSKGG | 38 | 16.3 | 2.3 | 0.9 | 2.5 |

TABLE 1-continued

| CLONE | SEQUENCE | SEQ ID NO: | ETAG (OD) | DGI-2 (OD) | LDH (OD) | DGI-2/LDH (OD) |
|---|---|---|---|---|---|---|
| DGI-2-20F-PP-D8 | VVGYAQGDGLEGGLGSSRDGS | 39 | 2.6 | 2.3 | 1.1 | 2.2 |
| DGI-2-20F-PP-B12 | RQRSGGRWVVDRVTRVASTSP | 40 | 1.9 | 2.3 | 1.1 | 2.2 |
| DGI-2-20F-PP-H3 | DDIVCLFQFCTMFCWLDMGW | 41 | 3.7 | 2.3 | 1.8 | 1.3 |
| DGI-2-20F-PP-D2 | SVTISTSCRTGCPAGYLRRD | 42 | 30.8 | 2.2 | 0.7 | 3.1 |
| DGI-2-20F-PP-D3 | VQSGRDLGGLLRGGTGTEASP | 43 | 15.0 | 2.2 | 0.9 | 2.4 |
| DGI-2-20F-PP-C5 | SVSGGGVFGTGGRVRHQVSG | 44 | 33.9 | 2.2 | 0.9 | 2.4 |
| DGI-2-20F-PP-F12 | VGQSSGDARPLANLFVFPFV | 45 | 47.6 | 2.1 | 0.9 | 2.3 |
| DGI-2-20F-PP-H4 | CCAWNGVGVGGLGWRVVVGP | 46 | 32.9 | 2.1 | 1.0 | 2.2 |
| DGI-2-20F-PP-F7 | DSEA*RVWYSGFLRRLGHMC | 47 | 3.3 | 2.1 | 1.0 | 2.1 |
| DGI-2-20F-PP-E11 | SAFGCPLPRALGGGGARFYA | 48 | 15.2 | 2.0 | 0.9 | 2.2 |
| DGI-2-20F-PP-D1 | RISVGQCGTSRCGGGRRGGG | 49 | 3.0 | 2.0 | 1.1 | 1.9 |
| DGI-2-20F-PP-F8 | LLLPVRWRDAQPRSLLMEWI | 50 | 7.6 | 2.0 | 1.1 | 1.9 |
| DGI-2-20F-PP-E10 | MGADTCMGGKMPFDQMFGAV | 51 | 44.6 | 2.0 | 1.2 | 1.7 |
| DGI-2-20F-PP-B9 | LGPAHPHGRVCRVSSS#S | 52 | 5.0 | 1.9 | 0.7 | 2.7 |
| DGI-2-20F-PP-B10 | KVWGCGARRGWERLGHLNQV | 53 | 27.1 | 1.9 | 0.8 | 2.4 |
| DGI-2-20F-PP-H7 | FRVALLSVSAGPCEGSGNT | 54 | 3.7 | 1.8 | 0.8 | 2.1 |
| DGI-2-20F-PP-E1 | FGSTAYADMLSQFRKFAMNIS | 55 | 33.4 | 1.8 | 1.0 | 1.9 |
| DGI-2-20F-PP-E2 | FGRDGDGIQRRQGGFSWVGDR | 56 | 11.6 | 1.7 | 0.7 | 2.4 |
| DGI-2-20F-PP-H1 | RDHRYVGWGRATFRHDQSVW | 57 | 1.4 | 1.7 | 1.2 | 1.4 |
| DGI-2-20F-PP-H11 | VSGY#SLWWCGPGWGPRSGR | 58 | 2.1 | 1.6 | 0.8 | 2.0 |
| DGI-2-20F-PP-H8 | SRGMAEAQFSAWPVLAVFPL | 59 | 32.4 | 1.6 | 0.9 | 1.9 |
| DGI-2-20F-PP-H6 | RGVNSDMPRLYICRADGQGQ | 60 | 18.9 | 1.6 | 0.8 | 1.9 |
| DGI-2-20F-PP-E7 | GAIRLSGAAWTASRTGGRAS | 61 | 21.5 | 1.6 | 0.9 | 1.8 |
| DGI-2-20F-PP-H9 | DVGAVVRSGHCASRPGE*QVR | 62 | 13.6 | 1.6 | 1.1 | 1.5 |
| DGI-2-20F-PP-H10 | GRAGTSMTELVAWGFVQRVG | 63 | 13.0 | 1.4 | 0.7 | 1.9 |
| DGI-2-20F-PP-G1 | RTLFINGGCCGKGSGGGRPL | 64 | 21.8 | 1.4 | 1.0 | 1.4 |
| DGI-2-20R-4-F1$_{20}$ | GWSDFVATGSWSGQVSAALN | 65 | 16.5 | 13.6 | 1.1 | 12.2 |
| DGI-2-20R-4-G1$_{14}$ | DGRGWGAMWMRWAEGLGADI | 66 | 16.5 | 12.9 | 1.2 | 11.0 |
| DGI-2-20R-3-A5 | VWRDWVNGTVGLRNREKPGV | 67 | 14.9 | 10.9 | 1.1 | 9.8 |
| DGI-2-20R-4-G4 | VWAAWVEGSLLSPRQEPVRD | 68 | 13.6 | 10.2 | 1.0 | 9.8 |
| DGI-2-20R-4-H2 | GHGAGDWAAELFVCPVAFLTGFAWR | 69 | 12.9 | 9.9 | 1.1 | 9.2 |
| DGI-2-20R-3-A12$_2$ | WWREWVDGSLRGGGGTVLKD | 70 | 15.1 | 9.6 | 1.0 | 9.4 |
| DGI-2-20R-4-H6$_{26}$ | RRGVCEIFTGWCVGQTNERP | 71 | 13.5 | 9.6 | 1.1 | 8.8 |
| DGI-2-20R-4-H8$_{14}$ | LVIGQRSFLSACSLFDGFCV | 72 | 13.5 | 9.5 | 1.1 | 9.0 |
| DGI-2-20R-4-H1 | GRWDGWEVCGIWGADDCASG | 73 | 14.0 | 9.3 | 1.2 | 7.8 |
| DGI-2-20R-4-F9$_3$ | LSLEGGWMWDTKGGDGGSAQ | 74 | 19.5 | 9.0 | 1.1 | 8.4 |
| DGI-2-20R-3-B5$_2$ | LWRRWSEGQLLGDGELRGDG | 75 | 15.8 | 8.7 | 1.0 | 8.4 |
| DGI-2-20R-3-D4 | CGGWGAMWEAWVQGLNGAGC | 76 | 18.9 | 8.7 | 1.1 | 8.1 |

TABLE 1-continued

| CLONE | SEQUENCE | SEQ ID NO: | ETAG (OD) | DGI-2 (OD) | LDH (OD) | DGI-2/LDH (OD) |
|---|---|---|---|---|---|---|
| DGI-2-20R-3-C11 | SRELGKWGRLWQDWSSGNFS | 77 | 18.9 | 8.6 | 1.0 | 8.3 |
| DGI-2-20R-3-B4 | RKGWGVFCIPGLRFCDWSDP | 78 | 17.4 | 8.4 | 1.0 | 8.6 |
| DGI-2-20R-3-D3 | WEVGQVEKFSRGVGGWWPTG | 79 | 16.8 | 8.3 | 1.0 | 8.3 |
| DGI-2-20R-3-C1 | LFSATGCALMSGFCLGSDGS | 80 | 14.0 | 8.2 | 1.0 | 8.3 |
| DGI-2-20R-3-D2 | FRMWVQSCFWGQPGTGCGEG | 81 | 14.3 | 7.9 | 1.1 | 7.5 |
| DGI-2-20R-3-C3 | TIDVARRFGYGWWDLWLDGD | 82 | 20.2 | 7.9 | 1.1 | 7.0 |
| DGI-2-20R-4-G2$_2$ | VSFAHDWGRWWYQWEVG | 83 | 12.9 | 7.9 | 1.2 | 6.5 |
| DGI-2-40F-3-D10$_{44}$ | DRVARLATPTAGTMAAGSLGYERTVGCD SQDWFRCVVEGL | 84 | 17.7 | 7.9 | 1.3 | 6.2 |
| DGI-2-20R-3-B10 | QLDCLVWGLPGLRCDRPLEQ | 85 | 17.0 | 7.8 | 1.0 | 7.6 |
| DGI-2-20R-4-G12$_2$ | RDTMCGSVSWGIPGCEYSGM | 86 | 13.9 | 7.6 | 1.1 | 7.1 |
| DGI-2-20R-3-A2 | QMSRVAFSPGESWRRWVEGV | 87 | 14.2 | 7.5 | 1.0 | 7.5 |
| DGI-2-20R-4-G9$_9$ | DQRVVGSGWFERLRNWYDRA | 88 | 14.1 | 7.5 | 1.0 | 7.2 |
| DGI-2-20R-3-A1 | EGNWFCAVFRGFCVGDRGPE | 89 | 11.1 | 7.1 | 1.1 | 6.3 |
| DGI-2-20R-4-E6 | VLGADAGMIWFMDGCGIRCR | 90 | 19.1 | 7.0 | 1.0 | 7.0 |
| DGI-2-20R-3-A8 | RSIRLQLIDEACQFFDGLCT | 91 | 15.3 | 6.9 | 1.1 | 6.4 |
| DGI-2-40F-4-F9$_7$ | QVGGMTQVGATVLSVVTGRGSCDGEDA WYPPGVTVGLGLC | 92 | 14.0 | 6.7 | 1.0 | 6.4 |
| DGI-2-20R-3-D12$_7$ | SWACGLLWPGECGSQVARRG | 93 | 15.4 | 6.7 | 1.0 | 6.4 |
| DGI-2-20R-3-D9 | WGCVFRQWASGSGAGCARRH | 94 | 19.7 | 6.7 | 1.0 | 6.4 |
| DGI-2-20R-4-H11$_2$ | SLECWAMPGMVVRLVGCDGP | 95 | 12.3 | 6.6 | 1.1 | 6.0 |
| DGI-2-20R-3-B1 | WWERFVWGRPVDDGVVVMAT | 96 | 14.5 | 6.3 | 1.0 | 6.2 |
| DGJ-2-20R-3-A10 | RRILPWSFPGCGRMC | 97 | 16.4 | 6.2 | 1.1 | 5.9 |
| DGI-2-20R-3-C2 | RDTTSQWSWISRGWEFPGWR | 98 | 11.9 | 6.2 | 1.1 | 5.8 |
| DGI-2-20R-3-A11 | WAASCFWGHVALGCGRNGQG | 99 | 14.7 | 6.2 | 1.1 | 5.7 |
| DGI-2-20F-3-B5 | RERWGTAWNLWTEGVVDVRP | 100 | 16.4 | 6.1 | 0.9 | 6.6 |
| DGI-2-20R-3-C6 | GIMQVAWGWREMTRLWDLGMA | 101 | 20.3 | 6.0 | 1.1 | 5.2 |
| DGI-2-20R-3-B11 | GWGCSVPGILCVGGHRQGGG | 102 | 16.9 | 5.9 | 1.0 | 5.7 |
| DGI-2-20R-3-A6 | GGGRESWGGGWFMGWGSGAG | 103 | 17.7 | 5.8 | 1.0 | 5.9 |
| DGI-2-40F-3-C8 | YGTAGLFLRRACTMSDPGDPLGRRGYTG WGVLWDEWVTGS | 104 | 13.6 | 5.7 | 0.9 | 6.0 |
| DGI-2-20R-3-B12 | DGKHLTKWSGRGWWSAWVGG | 105 | 15.5 | 5.7 | 1.0 | 5.5 |
| DGI-2-20F-4-F9 | LPQSRWLSEAWASWVDGVVD | 106 | 19.6 | 5.6 | 1.0 | 5.9 |
| DGI-2-20R-3-C8 | VVRQGCMAFSGLCSGVTESE | 107 | 21.1 | 5.6 | 1.1 | 5.3 |
| DGI-2-40F-3-C4$_{24}$ | TVKFQGVVQERSRIAGFRYCGDHAVSWG LAGCPALRDKLQ | 108 | 14.8 | 5.5 | 1.1 | 5.2 |
| DGI-2-20R-3-D7 | VHSQGRMWAIPGLRGGTGAS | 109 | 18.7 | 5.2 | 1.0 | 5.3 |
| DGI-2-20R-3-C7 | MGVVLECEGGWSIPGQTCYF | 110 | 18.0 | 5.1 | 1.0 | 5.1 |

TABLE 1-continued

| CLONE | SEQUENCE | SEQ ID NO: | ETAG (OD) | DGI-2 (OD) | LDH (OD) | DGI-2/LDH (OD) |
|---|---|---|---|---|---|---|
| DGI-2-20R-3-B3 | MFQDVACDLWHSVRCLRRDV | 111 | 16.1 | 4.9 | 1.0 | 4.8 |
| DGI-2-20R-3-A7 | VLQRSLWKDWVDGVMHGGGSRGV | 112 | 13.9 | 4.8 | 0.9 | 5.1 |
| DGI-2-40F-4-F1$_{22}$ | RSQVRVVSRERSTPVLIHIRIECLLFSGWCVTSGSDEGVVWG | 113 | 8.1 | 4.7 | 0.8 | 5.7 |
| DGI-2-20C-3-C10$_{39}$ | RPVVCLAGLTLAQFGWVFPGWRGWS | 114 | 11.8 | 4.7 | 1.0 | 4.7 |
| DGI-2-20R-3-D10 | ISGQVWSSWRFPGWGGKLF | 115 | 19.6 | 4.7 | 1.1 | 4.5 |
| DGI-2-20R-4-G7 | YTPASILTGFQRGYEGAGNG | 116 | 11.6 | 4.7 | 1.2 | 3.9 |
| DGI-2-40F-4-E6$_2$ | TCWIHRGLNVVRYSVNFGVRDARLTTQGMAWFPPGCGQGCV | 117 | 14.8 | 4.6 | 1.0 | 4.5 |
| DGI-2-40F-3-A1 | REFFNQASRGAWGYMFREWVEG | 118 | 9.9 | 4.5 | 0.9 | 5.2 |
| DGI-2-20R-3-C4 | SRPGWCSRGTAWGFPGCSSS | 119 | 19.1 | 4.5 | 1.1 | 4.2 |
| DGI-2-20R-4-F12$_{12}$ | MSSTAWTDRILQRGIGLGPV | 120 | 9.8 | 4.0 | 1.2 | 3.3 |
| DGI-2-20R-4-E8$_2$ | DAGIGWVGSMWFPPGCIGAC | 121 | 19.6 | 3.9 | 1.1 | 3.7 |
| DGI-2-20F-4-E3 | RNWLDKDCVWMGDCGARAGE | 122 | 16.9 | 3.8 | 0.9 | 4.1 |
| DGI-2-20C-4-H3$_{16}$ | RWSICRGLQYSIPGCAVEDLSDVMA | 123 | 7.2 | 3.8 | 1.0 | 3.9 |
| DGI-2-40F-3-D11 | LHFGSVMGWRPPGSLWSRPFGQVHPRSWSGS | 124 | 10.5 | 3.8 | 1.3 | 2.9 |
| DGI-2-20R-4-H12 | MSTLQGPGHLFQMLRRASLG | 125 | 10.9 | 3.7 | 1.3 | 2.8 |
| DGI-2-20F-3-C1 | GSVLERGCLEFSGFCFSLGH | 126 | 14.0 | 3.4 | 1.0 | 3.4 |
| DGI-2-20R-3-A9 | LQIVRPAGMTKMPGQVGYYIG | 127 | 14.3 | 3.4 | 1.0 | 3.4 |
| DGI-2-40F-4-F6 | SYRNFAMQSSLQVRRGSVVEDGTCWWEGVRCYSG | 128 | 13.5 | 3.2 | 1.0 | 3.2 |
| DGI-2-20F-3-C12 | LTPYSLARSWLSGRPSTGAT | 129 | 15.1 | 3.2 | 1.0 | 3.1 |
| DGI-2-20R-3-B7 | SWRLWVSGELQGDRRKGLRG | 130 | 11.7 | 3.1 | 1.0 | 3.0 |
| DGI-2-40F-3-D7$_2$ | MGSLGPFGNTNSLASGIGSVRNRPLLPHGSP | 131 | 14.0 | 3.1 | 1.1 | 2.8 |
| DGI-2-20R-4-H7 | LSHPMSPLRAASQMALTQGV | 132 | 14.1 | 3.1 | 1.2 | 2.6 |
| DGI-2-40F-4-E11$_{30}$ | V#CR#LCRLCRFSMRCGGLSLVLGSAAAFFCEVFVGFCV | 133 | 8.3 | 2.9 | 0.9 | 3.2 |
| DGI-2-20C-4-E9$_{26}$ | RMYNCHYIERLYDWHAGRJLLQDPA | 134 | 17.4 | 2.9 | 1.0 | 3.0 |
| DGI-2-20E-3-A1 | CRNFGVIWGAGWVSPGCEDJ | 135 | 14.3 | 2.8 | 1.0 | 3.0 |
| DGL-2-20R-3-B6 | TSCQVMFLAGQHLLSRVPRL | 136 | 11.7 | 2.8 | 1.0 | 2.7 |
| DGI-2-20R-4-E2 | TANGHRYGGCGLWCKWMSGM | 137 | 18.2 | 2.7 | 1.1 | 2.5 |
| DGI-2-40F-3-D7 | ALRSLGSGGFGWQAGRASPQGMTHFPYFGWSGMPTARVRP | 138 | 10.3 | 2.6 | 1.0 | 2.6 |
| DGI-2-40F-3-D6 | GLEPVPFQTDKRIAMGWTREWLVNGYGAAHRRDARMQSGH | 139 | 11.4 | 2.5 | 1.0 | 2.6 |
| DGI-2-20F-3-B10$_2$ | GLRACDTYLGFCVGARRIDD | 140 | 18.0 | 2.4 | 1.0 | 2.5 |

TABLE 1-continued

| CLONE | SEQUENCE | SEQ ID NO: | ETAG (OD) | DGI-2 (OD) | LDH (OD) | DGI-2/LDH (OD) |
|---|---|---|---|---|---|---|
| DGI-2-40F-3-C6 | QMIFSKGNWLAHPEGGVALGLSRESQLFR SCREFGYCMGPM | 141 | 10.1 | 2.3 | 0.8 | 2.8 |
| DGI-2-40F-3-D12 | QGSAHVVRPPGVYDVPWKVGMFFHPQN WPNSWGRAYFRSG | 142 | 7.3 | 2.3 | 1.0 | 2.5 |
| DGI-2-20R-4-F6 | GNKCFPPHDLFWDPCDQLQS | 143 | 13.2 | 2.3 | 1.0 | 2.3 |
| DGI-2-40F-4-F12 | GLYRRAGDASVGFSRWGREDCQVYFSVE CLLGSSWGGYS | 144 | 8.7 | 2.2 | 0.9 | 2.5 |
| DGL-2-20R-3-D6 | ACSVGTALVFPQRWWYLGRS | 145 | 12.9 | 2.2 | 1.1 | 2.1 |
| DGI-2-20R-3-C10 | SLSLYWDAQVGCEVFWGYCV | 146 | 14.7 | 2.2 | 1.0 | 2.1 |
| DGI-2-40F-3-C9$_2$ | RFWSVSYQGGRVMCREWGYCLPI | 147 | 9.8 | 2.1 | 0.8 | 2.6 |
| DGI-2-20F-3-A7 | LSLLSVVVRSMGASAPQRQV | 148 | 7.0 | 2.1 | 0.9 | 2.4 |
| DGI-2-40F-3-B11 | LAPMFLQNQVRTWAASRRPLPAGPSNAR CETGSLSPWVPC | 149 | 7.9 | 1.8 | 0.9 | 2.0 |
| DGI-2-20C-3-C6$_5$ | TPDRCLIYSSIQCLLEYSARRGSAD | 150 | 7.4 | 1.8 | 1.0 | 1.8 |
| DGI-2-40F-3-B12$_2$ | HSGNRQSGSRRTHLLNIFCSSDTFVFPGW SAYLSRVCPGD | 151 | 11.0 | 1.7 | 0.8 | 2.2 |
| DGI-2-40F-3-B11$_6$ | GVVRAQQGLRYELQGDRYRLRRTQWLT VTYCSPSWAFAGC | 152 | 6.5 | 1.7 | 0.8 | 2.0 |
| DGI-2-20R-3-C12 | RWSLPAYLCRFVSQASCNSR | 153 | 14.6 | 1.6 | 1.0 | 1.6 |
| DGI-2-20F-3-B7 | WAGSTDLWQLWSLWVKPELR | 154 | 16.4 | 1.6 | 0.9 | 1.6 |
| DGI-2-20R-4-G6 | PAMGHCMQVLGPVLEGRSRDQVGR | 155 | 11.5 | 1.6 | 1.1 | 1.4 |
| DGI-2-20R-4-E4 | LTWGPQFGSLQVYSRHRGLP | 156 | 18.1 | 1.6 | 1.2 | 1.3 |
| DGL-2-40F-3-D10 | TLVTEGNIKGSVKAHKDIGVWQLWWDW LSVTDSETVGRVSH | 157 | 10.3 | 1.5 | 0.9 | 1.7 |
| DGI-2-20F-3-A6 | FSSTGILLRSGRATAVGHVT | 158 | 13.2 | 1.5 | 1.1 | 1.4 |
| DGI-2-20R-4-G8 | GMWIRPNGHMELQGGYTARS | 159 | 14.5 | 1.5 | 1.1 | 1.4 |
| DGI-2-20R-3-D5 | VAFGEQJRVAMAGTLWQRWR | 160 | 8.5 | 1.5 | 1.1 | 1.4 |
| DGI-2-20F-3-D11$_2$ | YDQVWNSLLAAVLGGQELVN | 161 | 19.9 | 1.4 | 1.0 | 1.4 |
| DGI-2-20R-4-G3$_2$ | LSVFRPGQFPHVGARGVSRT | 162 | 11.0 | 1.4 | 1.1 | 1.2 |
| DGI-2-40F-3-B10 | MQAASTLSTYMGAIRMGYPILHWDRGG VQRVDPGLYRGRV | 163 | 4.8 | 1.3 | 1.0 | 1.4 |
| DGI-2-40F-3-A2$_4$ | RCFQDGRMLALSPTYLIRRSVSPLVVGPL PTP | 164 | 11.7 | 1.3 | 0.9 | 1.4 |
| DGI-2-20F-3-C2 | MAVLPAARDFGGVVQGGVSG | 165 | 11.5 | 1.3 | 1.0 | 1.3 |
| DGI-2-40F-3-C7 | HPWVTNMLVFQRPPPPGFWLSDTTPRQR NGLGQVERPSVD | 166 | 8.8 | 1.2 | 0.8 | 1.5 |
| DGI-2-20F-3-B1 | LSRIWRGVIESAREVESRGI | 167 | 11.4 | 1.2 | 0.9 | 1.2 |
| DGI-2-20R-4-E5 | LHRLGQSMGGTLDHLQGWGV | 168 | 17.9 | 1.2 | 1.1 | 1.1 |

TABLE 1-continued

| CLONE | SEQUENCE | SEQ ID NO: | ETAG (OD) | DGI-2 (OD) | LDH (OD) | DGI-2/LDH (OD) |
|---|---|---|---|---|---|---|
| DGI-2-40F-3-D9 | RRTSADTDQLSRWEGAQAFSSLRSALSER LDSLRPGLPPS | 169 | 15.8 | 1.1 | 0.8 | 1.4 |
| DGI-2-40F-3-A4 | WFTHVVEKIF | 170 | 6.7 | 1.1 | 0.8 | 1.3 |
| DGI-2-40F-3-C10 | WRARSSGYLFALTPNFGVPHIPSSALRRM H.GLMARDLRPV | 171 | 7.7 | 1.1 | 0.9 | 1.3 |
| DGI-2-20F-3-C3 | FSSVLGLLDRRGVPVVVGED | 172 | 11.6 | 1.1 | 0.9 | 1.1 |
| DGI-2-20C-3-D12 | LVIQCSASVVACDLYWNYVGCLAAG | 173 | 3.6 | 1.1 | 1.0 | 1.1 |
| DGI-2-40F-3-C5₂ | GLLFTSSPYQCFWVHCTLTMSPLSVLGDL SSTIGRMRASR | 174 | 4.6 | 1.0 | 0.8 | 1.3 |
| DGI-2-40F-3-B7₂ | PKDGAAFKGSDFIQGGQTVMERAPALW WRDGGGQWEAPST | 175 | 10.4 | 1.0 | 0.7 | 1.3 |
| DGI-2-40F-3-B9₅ | DYKTCVSQHVHPLFGEYFYHKVTHMSIL SPTFRVTSLYG.K | 176 | 5.4 | 1.0 | 0.8 | 1.2 |
| DGI-2-40F-3-B5 | RSRSSSGASGSMLRVQNHMVLGSWMVR QPMGSMTPFHGHG | 177 | 9.2 | 1.0 | 0.9 | 1.2 |
| DGI-2-40F-3-B4 | LWLPCGLLVRPAQFYFYFSPLRHFLSSSV GSLSFPLSLLV | 178 | 1.5 | 1.0 | 0.8 | 1.1 |
| DGI-2-20F-3-C5 | LGNASSLWFLRSVQESGVR | 179 | 17.7 | 1.0 | 0.9 | 1.0 |
| DGI-2-40F-3-B6 | QSNVWVLVGVIMQGVWYQRQHYCVYV MLLSDQVSVLLAVA | 180 | 1.8 | 0.9 | 0.8 | 1.2 |
| DGI-2-40F-3-A7 | CAYRWGLFRGPGRVDYDLQVVGIMMWP GPIPDRSSRGSVA | 181 | 8.7 | 0.9 | 0.8 | 1.1 |
| DGI-2-40F-3-A12 | RRTQPAYRSGADDRTSGFYCYVTSALSA GAWMPFLPRRLA | 182 | 4.6 | 0.9 | 0.8 | 1.1 |
| DGI-2-40F-3-D3 | VQFAMTLSSRLWQHARHPLTDDAPPTVS FGTRRETLAGKA | 183 | 0.9 | 0.9 | 0.9 | 1.1 |
| DGI-2-20C-3-A12 | GEVDCVYALTHRFLSPQVQYHIHRPV | 184 | 8.1 | 0.9 | 0.9 | 1.0 |
| DGI-2-40F-3-B1 | HGTRLRGVDYVMTWAGWQGYSSRKHV QQAVAGSSPGSDEL | 185 | 6.3 | 0.8 | 0.7 | 1.2 |
| DGI-2-40F-3-A8 | GQISLAGVAVCSSERMLLAFSSRVFLPGL KVPVTTSQRGS | 186 | 1.5 | 0.8 | 0.8 | 1.1 |
| DGI-2-40F-3-A1 | QYFARGSFQFGLSHVLSAAAAFHLYVFC KRLSRGFGIKDD | 187 | 2.4 | 0.8 | 0.7 | 1.1 |
| DGI-2-40F-3-D1 | MGQGFHYNRQPYMSHQCYAFTFSTPFLD GDRIPHGVSRGL | 188 | 4.1 | 0.8 | 0.8 | 1.0 |

TABLE 1-continued

| CLONE | SEQUENCE | SEQ ID NO: | ETAG (OD) | DGI-2 (OD) | LDH (OD) | DGI-2/LDH (OD) |
|---|---|---|---|---|---|---|
| DGI-2-20C-3-B3 | DYKGRTMTSPIMSALPVYDRLHGIGSRG QNMD | 189 | 7.7 | 0.8 | 0.9 | 0.9 |

Table 1:
PP indicates that these sequences were obtained using Proteome Panning. The number shown in subscript following each peptide name represents the number of times the peptide was isolated from the DGI-2 clones; For example, DGI-2-20R-4-H8$_{14}$ was isolated 14 times after 4 rounds of conventional panning using a random 20-mer peptide phage display library;
E-Tag = peptide binding to E-tag antibody (AAAGAPVPYPDPLEPR-P; SEQ ID NO: 190) fused to peptide;
DGI-2 = binding to DGI-2 polypeptide (specific binding);
LDH = peptide binding to LDH polypeptide (non-specific binding);
DGI-2/LDH = ratio of specific binding to non-specific binding;
Values shown represent ELISA units read at 405 nm; Higher values indicated higher binding specificity for target;
Binders = peptides that showed specific binding to DGI-2;
Q represents a CAG stop;
* represents a TGA stop; and
represents a TAA stop.

Example 9

Database Analysis of DGI-2 Binders

DGI-2 binders that were identified and shown to bind specifically to DGI-2 are used to identify DGI-2-partners. A "Phenogenix" approach is used as described in co-owned patent applications, pending U.S. patent application Ser. No. 09/852,455 and published International Patent Application No. PCT/US01/15092, which are incorporated herein by reference. These methods employ several different database search programs. Initially, the entire peptide sequence and consensus motifs of the DGI-2-binders are entered into an Advanced BLAST search (Hyper Text Transfer Protocol://World Wide Web.National Center for Biotechnology Information.National Library of Medicine.National Institutes of Health.Government/Basic Local Alignment Search Tool/Basic Local Alignment Search Tool.Common Gateway Interference?Jform=1) using the following parameters:

1. Programs: BLASTP, TBLASTN;
2. Databases: protein and nucleotide databases including dbest (ESTs), dsts (STSs), and htgs (unfinished high throughput genomic sequences);
3. Expect value: 1000 to 20000;
4. Matrix: PAM30 or PAM70; and
5. Query: consensus motif alone and varying combinations of sequence at the N- and C-terminal ends.

In subsequent steps, motifs identified by sequence alignment programs like MEME (Multiple EM for Motif Elicitation), (Hyper Text Transfer Protocol://Multiple EM for Motif Elicitation.San Diego Supercomputer Center.Education/Multiple EM for Motif Elicitation/website/intro.Hyper Text Markup Language) were also used to search the available databases using MAST (Motif Alignment and Search Tool, Hyper Text Transfer Protocol://Multiple EM for Motif Elicitation.San Diego Supercomputer Center.Education/mem/website/mast-intro.Hyper Text Markup Language). Motifs and consensus domains were further used as query patterns to search the protein databases using Patternfind (Hyper Text Transfer Protocol://World Wide Web.isrec.isb-sib.ch/software/PATFND_form.Hyper Text Markup Language).

For Patternfind, the following parameters are used:
1. Databases: non-redundant, Swissprot, TREATS, and TROGON;
2. Limit: between 10 and 5000; and
3. Query: consensus motif alone and varying combinations of sequence at N- and C-terminal ends.

Data obtained from the various searches are analyzed using the following approach:
1. Results of different searches are analyzed independently and then combined to search for similar classes of proteins (e.g., nucleic acid binding proteins, kinases) that emerged;
2. The best matches identified in more than one kind of search (e.g. same protein/ORF picked up by BLAST searches using different parameters, or by both BLAST and Patternfind) are picked. The amino acid sequence of the protein in the identified region is compared with other peptide surrogates containing this amino acid sequence; and
3. The protein interaction is evaluated in view of the cellular function of the target, DGI-2.

The criteria for identification of a DGI-2-partner (i.e., partner hit) include the following:
1. Search produces an exact match of ≧5–7 amino acids;
2. Same partner appears in at least 50% of the top hits of any one search, and/or the same or related hits occur in multiple searches;
3. Search produces expected class of protein partners based on function, cellular location, or tissue/disease distribution; and
4. Partner candidate produce a phenotype change when added into the appropriate model system.

Unless there is an exact sequence match (criterion 1), the candidate partner is required to satisfy at least two other criteria to be considered a partner hit.

Example 10

Panning for High Affinity Binders and Motifs

It may be expected that, in the case of using a cDNA library as the target, only one target binder will be found per target. Also, a consensus or motif may not be obvious in the absence of multiple binders to a target. The methods described here allow one to identify multiple target binders per target as well as motifs and consensus domains on the binders. Following proteome panning and identification of the target and target binders using the computational methods described above, each clone is grown in tetracycline for two cycles (48 hours) to eliminate the ampicillin resistant phage expressing the target binders. Each target phage (tet resistant) is then rescued with helper phage and subjected to an additional round of proteome panning versus the library of target binders. As an example, if 100 colonies are picked from the first round of proteome panning and grown in tetracycline, then 100 of the Tet resistant phage are mixed with the original random library (including but not limited to RAPIDLIB20 or RAPIDLIB40, etc). This process may be performed in a 96 or 384 well format by mixing target and target-binder libraries at a ratio of 1:1. Conditions for the proteome panning step are based on conditions affecting the ability to generate high affinity pairs such as temperature, pH, ionic strength and additional washing steps with different buffers. After 2 hours, the target/target-binder phage are used to infect the host cells as described above. After plating, 100–500 colonies are picked, sequenced and subjected to computational analysis as described. It is expected that there will be at a minimum of one motif per target which may be used as the basis for generating secondary libraries to obtain the appropriate affinity, selectivity and potency.

Example 11

Panning with DGI 2, HRAS and Leptin Ligand

One hundred microliters of $3.6 \times 10^{13}$ CFU (colony forming units) per ml random peptide phage libraries (two peptide libraries were mixed—a constrained 25 amino acid peptide library, 20C, and a random 20 amino acid library, 20R) was mixed with 100 microliters of either $3.3 \times 10^8$ CFU (colony forming units) per mL phage expressing DGI-2, $4.5 \times 10^8$ CFU (colony forming units) per mL phage expressing Hras, or $2.7 \times 10^8$ CFU (colony forming units) per mL phage expressing Leptin ligand, and incubated at room temperature for 1 hour. Dilutions were made ranging from $10^{-1}$–$10^{-6}$. One hundred microliters of each dilution were used to infect competent E. coli TG1 cells and plated on Ampicillin (Amp; 50 µg/ml)+Tetracycline (Tet; 10 µg/ml) plates. Plates were incubated at 37° C. overnight.

On day 2, the number of colonies that grew on all of the plates were counted and the titers were recorded. Ninety-six individual clones were picked from Amp+Tet plates and inoculated into 500l of 2×YT media containing 40% glucose and Amp (50 µg/ml)+Tet (10 µg/ml) and incubated at 37° C. shaking 225 rpm overnight.

On day 3, 40 microliters of the Amp+Tet resistant clones were inoculated into 400 microliters of Amp only media to allow cells to select out the Tet phagemid (expressing DGI-2, Hras, or Leptin ligand) by removing the Tet selection pressure and retaining the Amp phagemid (expressing peptide binder). Cells were incubated at 37° C. shaking at 250 rpm overnight.

On day 4, Amp phage (binder phage) were rescued by inoculating 40 microliters of cells from day 3 in 400 microliters 2×YT media containing 40% glucose, 50 µg/ml Amp, and M13KO7 helper phage containing kanamycin resistance marker. Cells were incubated for 3 hours at 37° C. with shaking 250 rpm. Following infection, cells were pelleted for 15 minutes at 3500 rpm at 4° C., supernatant removed, and the pellets were resuspended in the initial culture volume of 2×YT media containing 50 µg/ml Amp and 50 µg/ml Kan. Cells were grown overnight at 37° C. with shaking at 225 rpm.

On day 5, cells from the overnight culture were pelleted and Amp resistant phage (binder phage) were re-infected into competent E. coli TG1 cells. Each clone was plated on a separate plate, individual colonies were picked from each plate and sequenced after amplification by PCR.

This method resulted in a good separation of the two interacting phage and allowed for sequencing and further analysis by ELISA where target protein was available.

Example 12

Panning of cDNA Library (cDNALIB)

One hundred microliters of $1.8 \times 10^{13}$ CFU (colony forming units) per ml of random peptide phage libraries (two peptide libraries were mixed—a constrained 25 amino acid peptide library, 20C, and a random 20 amino acid library, 20R), or $1.4 \times 10^{12}$ CFU (colony forming units) per mL cDNALIB (amp) library, or $2.3 \times 10^{11}$ CFU (colony forming units) per mL cDNALIB (amp) library, or $7.8 \times 10^{12}$ CFU (colony forming units) per mL of random peptide phage libraries (random 40 amino acid, RAPDLIB), was mixed with one hundred microliter of $7.0 \times 10^8$ CFU per mL cDNALIB (tet), and incubated at room temperature for two hours. Dilutions were made ranging from $10^{-1}$–$10^{-6}$. Fifty microliters of each dilution was used to infect competent E. coli TG1 cells and plated on Amp (50 µg/ml)+Tet (10 µg/ml) plates. Plates were incubated at 37° C. overnight.

On day 2, the number of colonies that grew on all of the plates were counted and the titers were recorded. Ninety-six individual clones were picked from Amp+Tet plates and inoculated into 400l of 2×YT media containing 40% glucose and Amp (50 µg/ml)+Tet (10 µg/ml) and incubated at 37° C. shaking 225 rpm overnight.

On day 3, 40 microliters of the Amp+Tet resistant clones were inoculated into 400 microliters of media containing either Amp (50 µg/ml) or Tet (50 µg/ml) to allow cells to select out either the Tet or the Amp phagemid respectively, by removing selection pressure for one of the two antibiotic markers. Cells were incubated at 37° C. shaking at 250 rpm overnight.

On day 4, phage were rescued by inoculating 40 microliters of cells from day 3 in 400 microliters 2×YT media containing 40% glucose, 50 µg/ml Amp or Tet, and M13KO7 helper phage containing kanamycin resistance marker. Cells were incubated for 3 hours at 37° C. with shaking 250 rpm. Following infection, cells were pelleted for 15 minutes at 3500 rpm at 4° C., supernatant removed, and the pellets were resuspended in the initial culture volume of 2×YT media containing 50 µg/ml Amp or Tet and 50 µg/ml Kan. Cells were grown overnight at 37° C. with shaking at 225 rpm.

On day 5, cells from the overnight culture were pelleted and Tet (target) or Amp (binder) resistant phage were re-infected into competent E. coli TG1 cells. Each clone was plated on a separate plate, individual colonies were picked from each plate and sequenced after amplification by PCR.

This method resulted in a good separation of the two interacting phage and allowed for sequencing and further analysis.

Example 13

Modified Panning of cDNA Library (cDNALIB)

For proteome panning, a tetracycline resistant cDNA phage displayed library (Tet$^R$ phage) was mixed with multiple ampicillin resistant RAPIDLIB™ phage displayed peptide libraries (Amp$^R$ phage) in 100 μL volume. The amount of Tet$^R$ phage particles was equal to the amount of Amp$^R$ phage and the total number of phage particles used was about $5\times10^8$.

The phage mixture was slowly rotated for 2 hours at room temperature (RT; about 25° C.) and then used to infect log phase E. coli TG1 (OD$_{600}$~0.8–1.0;~$6\times10^8$ cfu/mL) at a phage-to-cell ratio of 1:25–1000, and preferably a low phage-to-cell ratio of 1:100–500. Low cell-to-phage ratio is necessary to minimize the infection of cells by non-paired Tet$^R$ phage and Amp$^R$ phage. Cells were incubated for 30 min at 37° C. with gentle shaking to allow infection to occur and then separated from medium by centrifugation at 1000×g for 10 min. Then infected cells were resuspended in small volume of 2×YT medium and plated onto 2×YT agar medium containing 2% glucose, 10 μg/mL ampicillin and 15 μg/mL tetracycline (2×YT-GAT) to obtain individual colonies. Plates were incubated at 30° C. overnight. Grown colonies were counted and used for recovery and separation of paired Tet$^R$ phage and Amp$^R$ phage.

Separation of paired Tet$^R$ phage and Amp$^R$ phage was done by 2 consequent phage recoveries using modified phage rescue technique. Bacterial colonies bearing paired Tet$^R$ phage and Amp$^R$ phage were grown in 96 well cluster tube boxes overnight at 30° C., 250 rpm, in 2×YT/ampicillin (100 μg/mL)/tetracycline (15 μg/mL) medium containing 0.1% glucose (2×YT-0.1G/AT). Overnight cultures then were used to inoculate two sets of cluster tubes with phage rescue media (2×YT-0.01% glucose medium containing M13KO7 helper phage (~$4\times10^9$ cfu/mL) and either ampicillin or tetracycline) with dilution rate 1:10. After 2–2.5 hours of growth at 37° C., 250 rpm, kanamycin was added to final concentration 50 μg/mL and infected bacteria were incubated overnight for Tet$^R$ phage and Amp$^R$ phage amplification.

The following day phage-containing supernatants cleared of bacteria by centrifugation (1000 g, 10 min) were diluted in 2×YT medium (at the rates 1:$10^6$ for Amp$^R$ phage and 1:$10^5$ for Tet$^R$ phage) and 10 μL of dilutions were used to infect 100 μL of log phase E. coli TG1 cells. Cells were incubated at 37° C., 150 rpm, for 1 hour for efficient infection followed by addition of 2×YT-0.1% G/AT. Cells were grown overnight at 30° C., 250 rpm, and obtained cultures were used for second round of phage amplification.

After second phage rescue, recovered Amp$^R$ phage were analyzed by ELISA in order to detect the expression of phage-displayed peptides. Amp$^R$ phage with the strongest signals over background (equal or above 2×) as well as corresponding Tet$^R$ phage were diluted and used for infection of TG1 cells as described above. Cells were plated onto 2×YT-2% glucose medium containing appropriate antibiotic and incubated overnight at 30° C. Grown colonies were used for PCR and subsequent sequence analysis.

Example 14

Production of cDNA

In order to produce cDNA, three methods are utilized: 1) random priming and directional cloning; 2) PCR-based oligo dT priming and directional cloning; and 3) excision of cDNA from existing libraries.

Random Priming and Directional Cloning

Ligation-ready subtracted or unsubtracted cDNA was produced by classical cDNA methods using random priming and poly A+RNA from various normal and cancerous tissues. Priming the RNA was carried out by a random pentamer (5'-GCTCGCCCTCGGCGGCCGCNNNNNT-3'; SEQ ID NO: 191) at various concentrations which controls the length of the cDNA to obtain more positive clones in the expression screen to the preferred range of 200 bp to 2,000 bp. In order to carry out directional cloning, the random primer contained the restriction site Not I 5' to the random pentamer sequence. The poly A+RNA (2 g) for this reaction was purchased, isolated from particular cell lines or tissues, or in the case of subtracted libraries the "target specific RNA" (10 μ/d of the 20 μl), obtained from the multi-round subtractive hybridization protocol (see below).

First stand synthesis was performed by combining the RNA and the random pentamer (7 μg) primer to a final volume of 5 μl. If the final volume exceeded 5 μl (as in the case of the subtracted mRNA), the reactions that followed were scaled up. The tube containing the combined RNA and random pentamer was incubated at 72° C. for 2 minutes in order to denature the RNA and primer. The tube was then cooled by placement on ice for 2 minutes. Collection of the contents of the tube was performed by centrifuging at 14,000 rpm for 20 secs in a microcentrifuge. For the first strand reaction to occur, 2 μl (5×First Strand Buffer), 1 μl dNTP (10 mM), and 1 μl AMV Reverse Transcriptase (20 units/μl) were added to the contents of the tube. The primers were extended at 25° C. for 10 min. The contents of the tube were then mixed gently and incubated at 42° C. for 1.5 hour. To carry out the second-stand cDNA synthesis, 16 μl ($5\times2^{nd}$ strand buffer, 1.6 μl dNTP (10 mM), 4.0 μl (20×second-strand cocktail) and 48.4 μl depc-H$_2$O were added on ice to a final volume of 80 μl. Incubation of the reaction tube occurred for 2 hours at 16° C. After the incubation, 2 μl (6 units) of T4 DNA polymerase was added to the reaction tube and incubated again at 16° C. for 30 min. After the incubation 4 μl of 20×EDTA/glycogen mixture was added to the tube. Phenol extraction and precipitation of the cDNA was performed with isopropanol/sodium acetate and then phosphorylated. The kinase reaction involved adding 5 μl of T4 Kinase (10 unit/μl), 10 μl (10×T4 DNA ligase buffer), and water to the cDNA resulting in a final volume of 100 μl. The reaction tube was then incubated at 37° C. for 1 hour. After incubation, phenol extraction, precipitation, and quantitation was followed by the Picogreen method (Molecular Probes; Eugene, Oreg.). The final digestion was carried out at the common Not I site (derived from the random primer), which provided for the directional cloning of the fragments. The digestion with the Not I enzyme was performed in a total volume of 100 μl for 4 hours at 37° C. Buffer 3 (NEB). Following enzyme digestion, the cDNA was chloroform extracted, precipitated and resuspended in water. To carry out the expression screen, the cDNA derived from each tissue was ligated into the Sma I-Not I sites of the green fluorescent protein (GFP) vector or the Kan (amp or tet) vector Frames 1, 2, and 3 using a molar ratio of 1:10.

PCR-Based Oligo dT Priming And Directional Cloning

Ligation-ready subtracted or unsubtracted cDNA from various normal and cancerous tissues for directional cloning was produced by the Smart cDNA Synthesis Kit (Clontech) with some modifications. The poly A+RNA (1 μg) for the reaction was either purchased, isolated from particular cell lines or tissues, or in the case of subtracted libraries the "target specific RNA" used (10 µl of the 20 µl) was obtained from the multi-round subtractive hybridization protocol (see below). To carry out the first stand synthesis, the RNA, the 3' SMART CDS Primer IIA (10 M) and the modified 5' Smart Primer (10 µM) were combined for a final volume of 5 µl. Six versions of the modified 5' Smart Primer were used, each containing one of 3 reading frames and two sequence variations to provide for differential sequencing by PCR. If the volume exceeded 5 µl (as in the case of the subtracted mRNA), the reactions that followed were scaled up. The reaction tube was incubated at 72° C. for 2 minutes to denature the RNA and primer. The tube was placed on ice for 2 minutes. The reaction tube was centrifuged for collection of the contents. The addition of 2 µl (5×First Strand Buffer), 1 µl DTT (20 mM), 1 µl dNTP (10 mM), and 1 µl Power Script Reverse Transcriptase to the 5 µl volume provided for the first strand reaction. The contents of the tube were mixed gently and incubated at 42° C. for 1 hr and then placed on ice to terminate the reaction. PCR amplification produced double stranded cDNA by reacting 5 µl of the subtracted mRNA first strand reaction or 0.4 µl un-subtracted mRNA first strand reaction with the PCR reaction containing 10 µl (10×Advantage 2 Buffer), 2 µl (50×dNTPs), 4 µl modified Smart Primer, 4 µl 5' PCR primer, and 2 µl Advantage 2 Enzyme in a total volume of 100 µl. For the PCR amplification rounds, one preliminary cycle (95° C., 1 min) and then 24 cycles were carried out (95° C. 5 sec, 65° C. 15 sec, 68° C. 6 min). The resulting cDNA was column purified using QIAquick™ columns (Qiagen) and quantitated by Picogreen method (Molecular Probes; Eugene, Oreg.). In order to obtain preferred size fragments (100 bp to 2000 bp) for insertion into the phage display vector, the initial long cDNA fragments were digested with multiple enzymes having known infrequent cutting profiles in the mammalian genome. The digestions were conducted in the following manner. For each digestion, 5 µg of the double stranded cDNA PCR product was used, each enzyme was added in a volume of 5 µl, and 10×Buffer (15 µl) and 100×BSA were added. The total volume for each reaction was 150 µl. The digestions were as follows:

Digestion Reaction 1 containing enzymes Nar I, Nae I, and Avr II and NEB Buffer 1 was carried out for 4 hours at 37° C.

Digestion Reaction 2 containing enzymes EcoR1, Hind III, and BbvC I and NEB Buffer 2 was carried out overnight at 37° C.

Digestion Reaction 3 containing enzymes Bam HI, Xba I, and Ssp I and NEB Buffer 2 was carried out for 4 hours at 37° C.

Digestion Reaction 4 containing enzymes Bgl II, Bgl I, Xho I and NEB Buffer 3 was carried out for 4 hours at 37° C.

Digestion Reaction 5 containing enzymes Sac I, Sph I, Dra I and NEB Buffer 4 was carried out overnight at 37° C.

Digestion Reaction 6 containing enzyme Rsa I and NEB Buffer 1 was carried out for 4 hours at 37° C.

The DNA in each digestion reaction was extracted by chloroform and precipitated with isopropanol/sodium acetate. The 5' and 3' overhangs were filled in by the Pfu DNA Polymerase polishing reaction. The precipitated DNA was resuspended in 20 µl water and the polishing reaction was carried out in a total volume of 100 µl containing 10 µl (10×Buffer), 10 µl (10 mM dNTPs), and 10 µl Pfu DNA Polymerase (2.5 units/µl). The reaction was incubated at 72° C. for 30 minutes after which the cDNA was then phenol-chloroform extracted, precipitated and resuspended in 50 µl water. The final digestion was carried out at the common Sfi I site (derived from the modified Smart Primer; DGI), which provided for the directional cloning of the fragments. The digestion with the Sfi I enzyme was carried out in a total volume of 100 µl for 4 hours at 50° C. Buffer 2 (NEB). DNA quantitation was performed by the Picogreen method. The cDNA was ligated into the Sfi-Sma site of either the GFP vector or the Kan vector for the expression screen using a molar ratio of 1:10.

Excision Of cDNA From Existing Libraries

Pre-existing cDNA libraries from normal and cancerous tissues were excised at the appropriate restriction sites. This method entailed preparing and digesting the plasmid following manufacturers' instructions (Qiagen). After the digestion was complete, the DNA analysis was performed on a 1% agarose gel. The gel portion containing the resultant DNA smear was extracted by removing the DNA smear. Purification by commercial or known methods (QIAquick) was followed by optical density quantitation. In order to obtain preferred size fragments (100 bp to 3000 bp, more preferably 200 bp to 2000 bp) for insertion into the phage display vector, the initially long cDNA fragments were digested with multiple enzymes having known cutting profiles in the mammalian genome. The digestions were conducted in the manner described above for the PCR-based oligo dT Priming. To carry out the expression screen, the cDNA derived from each tissue was ligated into the Sma I—Sma I sites of the GFP vector or the Kan (amp or tet) vector Frames 1, 2, and 3 using a molar ratio of 1:10.

Example 15

Subtractive Hybridization

Subtractive hybridization was carried out at the mRNA level using the Dynabead system from Dynal Biotech as follows with some modifications. The Dynabead Oligo $(dt)_{25}$ (magnetic beads) were first conditioned in preparation for use. A volume of 1 ml of magnetic beads was transferred to the magnetic stand for 30 minutes. After the time period, the supernatant was removed and the magnetic beads were resuspended in 400 µl Binding Buffer. In the next, step poly A+RNA (normal tissue) was annealed to the magnetic beads. To do this, the 10 µg poly A+RNA (suspended in 400 µl DEPC water) and the beads (400 µl in Binding buffer) were mixed thoroughly and annealed by rotating the RNA and bead mixture on a roller for 3–5 min at room temp. The tube was then placed in the magnetic stand for 30 seconds and the supernatant was removed. The poly A+RNA/dt was washed with Wash Buffer A (800 µl) and then washed with Wash Buffer B (800 µl). The poly A+RNA/dt was then washed 2 times with Cold RT Buffer (1 ml) and the RT Buffer was removed. In the next step, solid phase synthesis of cDNA was carried out on the magnetic beads.

A combination protocol was carried out using a rTth Reverse Transcriptase, a heat stable enzyme used at elevated temperatures to reduce secondary structure. After removal of the RT Buffer by the magnetic stand above, 900 µl of the RT Reaction Buffer 1 was added to the poly A+RNA/dt containing 1 mM MnCl₂, dNTPs and rTth enzyme (225 units). The tube was transferred to the hybridization oven for 60 min at 37° C. After the incubation RT Reaction Buffer 1 was removed by the magnetic stand (30 sec) and RT Reaction Buffer 2 was then added (900 µl) containing rTth (50 units) and incubated in the hybridization oven for 10 min at 70° C. The tube was transferred to the magnetic stand and the supernatant was removed. The beads (subtractor cDNA Dynabeads) were resuspended in 900 µl 2 mM EDTA and heated at 95° C. to melt away the poly A+RNA. The supernatant was immediately removed by the magnetic stand. The subtractor cDNA Dynabeads were washed 2 times in 900 µl TE Buffer, pH 8.0 and then resuspended in 500 µl TE Buffer, pH 8.0. Subtractive hybridization proceeded in the following manner. The subtractor cDNA Dynabeads in TE Buffer and 1 µg target poly A+RNA (cancerous tissue) in hybridization buffer (200 µL) were heated simultaneously at 68° C. for 3 minutes. The supernatant for the subtractor beads was removed and the 200 µl containing the target poly A+mRNA was transferred to the tube. The tube was wrapped with parafilm and incubated at 65–68° C. for 20–24 hours under constant rolling. After the hybridization, the tube was transferred directly to ice. The subtractor Dynabeads with the mRNA/cDNA hybrids were collected by the magnetic stand on ice. The hybridization solution containing the target specific mRNA was transferred to a new tube on ice awaiting a second hybridization. The subtractor Dynabeads were regenerated by adding 20 µl water and heating for 3 minutes at 68° C. to elute mRNA. The tube containing the regenerating Dynabeads was placed in the magnetic stand and the supernatant was removed. The regenerated Dynabeads were resuspended in 100 µl TE solution, ready for a further round of hybridization. The hybridization was carried out 2 more times. After the final round, the target mRNA for the hybridization solution was isolated. To do this, 20 µl of new Dynabeads Oligo(dt)$_{25}$ were pre-washed in hybridization buffer. The 200 µl hybridization buffer containing the target specific mRNA was then added to the washed new Dynabeads. The mixture was incubated for 5–10 minutes with constant rolling at room temperature. Using the magnetic stand, the target specific mRNA/Dynabeads complex was washed once with 200 1 Buffer A and 2 times with 200 µl Buffer B. After removal of Buffer B, the target specific mRNA was eluted with 20 µl 10 mM Tris pH 7.5 by incubating at 65° C. for 2 minutes. The "target specific RNA" was then used for cDNA synthesis in the method above. Alternatively, subtraction was also accomplished by using the PCR-Select cDNA Subtraction Kit (Clontech).

Example 16

Screening for cDNAs with Open Reading Frames (ORFS)

The target diversity for the cDNA RAPID LIB library was 10⁵ "open reading frame clones." To achieve this diversity, the cDNA produced by the methods described above was cloned into expression screening vectors containing either the green fluorescent protein (GFP) or the kanamycin resistance gene. Construction of expressing cDNA-gene III fusion proteins in pCANTAB5E (phagemid) required the cDNA to be in frame with the gene III leader sequence at the 5' end and the gene III at the 3' end. To increase the number of in frame cDNAs, two screening vectors were designed. These vectors were the GFP and Kanamycin resistance screening vectors. The GFP vector was designed so that only an "in frame" ORF cDNA will produce green colonies. The out of frame and termination codon containing cDNAs generated white colonies. The high background (many colonies need to be plated) of the GFP screen led to the design of an antibiotic resistance screen using the Kanamycin resistance gene aminoglycoside phosphotransferase. Unlike the GFP screen, the Kanamycin screen only produced a resistant colony if an "in-frame" ORF was present in the clone. Preferably, the two step expression screen is performed using kanamycin screening followed by GFP screening. This is preferred since only clones with open reading frames will grow on kanamycin media, thereby eliminating much of the initial non-expressing clones. By performing the kanamycin screen first reduces the number of plates in the GFP screen by 1/10$^{th}$.

Example 17

Construction of GFP Screen for cDNAs with "In Frame ORFs"

The screen selected cDNAs with open reading frames that were "in frame" with the green fluorescent protein (GFP). The GFP used was wild type, not a mammalian codon optimized sequence. In order to construct the vector, the GFP gene was obtained by cloning the enhanced green fluorescent protein (GFP) from Clontech GFP cloning vector pEGFP-C1. The GFP ORF was trimmed to 249 amino acids, a minimum size which still retained activity. PCR primers were designed to clone the GFP ORF into the Nde I and Kpn I sites of the pUC 19 sequencing vector. Cloning the GFP ORF into pUC 19 replaced the lacZ gene. The promoter and first 19 amino acids MAPDAVFSPYASVRYFTPH (SEQ ID NO: 192) from lac Z were retained in the vector. The PCR primers were designed to incorporate 2 stop codons at the 3'end of GFP and to add a Not I site at the 5' end. For cloning, 1 µg pUC 19 plasmid (New England Biolabs) was digested with 10 units each of Nde I and Kpn I in a total volume of 20 µl and incubated at 37° C. for 1 hour. After the incubation, the DNA was treated with shrimp alkaline phosphatase for an additional hour, followed by chloroform extraction and ethanol precipitation. The GFP insert was amplified by PCR. For the reaction, 10 ng of Clontech GFP cloning vector pEGFP-C1, 1 µl of 10 uM each of:

```
GFP forward cloning primer:
5'-GCCATTCTTGGTACCGCGGCCGCCCCGGTCGCCACCATGGTGAGCAAG-3'  and   (SEQ ID NO: 193)

GFP reverse cloning primer:
5'-GGAATTCCTGCATATGCTACTATCGAGATCTGAGTCCGGACTTG,             (SEQ ID NO: 194)
```

10 µl 5×ThermalAce buffer, 1 µl of 50×dNTPs, and 1 µl Thermal Ace Polymerase (Invitrogen) were combined in a total volume of 50 µl. PCR was performed in MJ Research TETRAD cycler (one cycle of 95° C. for 5 min, 30 cycles of 60° C. for 45 sec, 72° C. for 60 sec, 94° C. for 45 sec, and a final cycle of 72° C. for 5 min). The GFP PCR product was chloroform extracted and ethanol precipitated. To prepare the insert, 500 ng of the PCR product was digested with Nde I and Kpn I as described above and then chloroform extracted and ethanol precipitated. For the ligation, 100 ng of digested PCR product was ligated to 50 ng of digested pUC19 overnight using T4 DNA ligase (New England Biolabs). The ligation was transformed into TOP10 one shot competent cells (Invitrogen) and plated on amp plates. The insert was confirmed by PCR and sequencing.

To test the vector and incorporate identical restriction sites, as in the phage display vector pCANTAB5E, a "stuffer fragment" consisting of the 705 base pair sequence of TNF R2 was cloned in at the 5' end of the GFP using PCR. The stuffer fragment only funceions to facilitate the introduction of cloning sites. There is no size limitation on the stuffer or replacement inserts. The TNF R2 sequence has been modified to have a Sfi I and a Sma I site at its 5' end. These sites are in frame with the leader sequence. It has also been modified with a Sma I and Not I site at its 3' end. The sites were in frame with GFP. The complete translation product resulted in a leader sequence, TNF R2 and GFP. For the cloning, PCR was carried out in a 50 µl reaction containing 10 ng of TNFR2 extra cellular fragment (previously cloned by RT-PCR), 1 µl of 10 M each of:

(SEQ ID NO: 192), i.e., the first 19 amino acids of the GFP fusion protein, followed by the extracellular sequence of TNF R2 and the GFP. The TNF R2 sequence served as the "stuffer fragment" for the vector and was excised when the vector fragment was prepared for ligation to the cDNAs. To produce vector fragments for insertion into cDNAs for screening, the GFP screening vector was digested with Sma I or Sfi I and Not I which excises the fragment containing the TNF R2 gene. For the screen, the cDNA fragments were inserted into either the Sma I or Sfi I/Not I sites of the pUC 19-GFP vector in the ligation reaction. Colonies were identified by the presence of GFP in the screen. The cDNA was excised and ligated into the phagemid vector (pCANTA5E) as previously described. The amino acid sequence of GFP is shown below:

```
                                        (SEQ ID NO: 197)
GRHHGEQGRGAVHRGGAHPGRAGRRRKRPQVQRVRRGRGRCHLR

QADPEVHLHHRQAARALAHPRDHPDLRRAVLQPLPRPHEAARLLQV

RHARRLRPGAHHLLQGRRQLQDPRRGEVRGRHPGEPHRAEGHRLQ

GGRQHPGAQAGVQLQQPQRLYHGRQAEERHQGELQDPPQHRGRQR

AARRPLPAEHPHRRRPRAAARQPLPEHPVRPEQRPQREARSHGPAGV

RDRRRDHSRHGRAVQVRTQISIV.
```

```
TNFR2 forward primer:
5'-GATTTCCTTGCGGTACCGGCCCAGCCGGCCATGGCCCCCGGGATGGCGTTGCCCGCCCAGGTGGC-3';   (SEQ ID NO: 195)

TNFR2 reverse primer:
5'-GATTTTCGCGGCCGCGTCGCCAGTGCTCCCTTCAGC,                                    (SEQ ID NO: 196)
```

10 µl 5×ThermalAce buffer, 1 µl of 50×dNTPs, and 1 µl ThermalAce polymerase (Invitrogen). PCR was performed in a MJ Research TETRAD cycler using the following conditions: one cycle of 95° C. for 5 min, 30 cycles of 60° C. for 45 sec, 72° C. for 60 sec, 94° C. for 45 sec, and a final cycle of 72° C. for 5 min. The PCR product was chloroform extracted and ethanol precipitated. The pUC 19-GFP construct (1 µg) was digested with Not1 and Kpn I, 10 units each, for 1 hour and then dephosphorylated. The TNF R2 PCR product (500 ng) was also digested with Not I and Kpn I. Both vector and insert was chloroform extracted and ethanol precipitated. For the ligation, 100 ng of digested PCR product was combined with 50 ng of digested pUC19-GFP overnight using T4 DNA ligase (New England Biolabs). After incubation, the DNA was transformed into TOP10 one shot competent cells (Invitrogen) and plated on AMP plates. The insert was confirmed by PCR and sequencing. The resultant clone (GFP screening vector) developed green colonies as expected. The GFP screening vector cloning sites Sma I and Sfi I/Not I have identical reading frames with the phage display vector (pCANTAB5E) at the same restriction sites so that cDNA fragments that are "in frame" with the GFP protein will also be "in frame" with gene III in the phage display vector. The complete translation product from the GFP screening vector Lac promoter was the leader sequence MAPDAVFSPYASVRYFTPH Example 18

Kanamycin Screening for cDNAs with "In Frame ORFs"

The GFP screen described above resulted in false positives and had a very high background. Replacing GFP with an antibiotic resistance gene would result in a much lower background and a reduction in the number of plates required to screen a library since only those colonies expressing the antibiotic resistance protein would grow on the plate.

Construction of Kan Screening Vector Frame 1

To construct the Kan screening vector, the kan resistance gene, obtained by PCR from the pZERO-2 vector (Invitrogen), was inserted into the GFP screening vector, replacing the GFP gene. The PCR fragment containing the kan resistance ORF contained no start codon and 2 stop codons and the sequence was modified with a Not I site at the 5' end and an Nde I site at 3' end using PCR. The GFP screening vector was cut at the Not I and Nde I sites and ligated to PCR fragment containing the kan resistance gene at the same sites. The ligation replaces the GFP gene with the kan resistance gene. For the cloning, the Kanamycin resistance gene was obtained from vector pZERO-2 using PCR. For the PCR reaction, 10 ng of pZERO-2 vector (Invitrogen), 1 µl of 10 µM each of:

```
Kan Forward primer:
5'-GCATTAATCTATAGCGGCCGCCATTGAACAAGATGGATTGCACGCAGG-3'; and (SEQ ID NO: 198)

Kan reverse primer:
5'-GCATTACTATCCCATATGTCATCAGAAGAACTCGTCAAGAAGGCG-3',           (SEQ ID NO: 199)
```

10 μl 5×ThermalAce buffer, 1 μl of 50×dNTPs, and 1 μl ThermalAce polymerase (Invitrogen) were combined in a total volume of 50 μl. PCR performed in MJ Research TETRAD cycler under the following conditions: one cycle of 95° C. for 5 min, 30 cycles of 60° C. for 45 sec ,72° C. for 60 sec, 94° C. for 45 sec, and a final cycle of 72° C. for 5 min). Both the kanamycin resistance PCR product and also the GFP pUC 19-GFP screening vector were digested with Not I and Nde I as above. Both vector and insert were chloroform extracted and ethanol precipitated. In the ligation reaction, 100 ng of digested PCR product and 50 ng of digested GFP-pUC19 were combined and incubated overnight at 15° C. using T4 DNA ligase (New England Biolabs). After incubation, the DNA was transformed into TOP10 one shot competent cells (Invitrogen) and plated on kanamycin (25 μg/ml) plates. Colonies were both amp and kan resistant. The insert was confirmed by PCR and sequencing. The complete translation product from the kan screening vector Lac promoter was the leader sequence MAPDAVFSPYAS-VRYFTPH (SEQ ID NO: 192; i.e., the first 19 amino acids of the GFP fusion protein) followed by the extracellular sequence of TNF R2 and kan resistance protein. To produce vector fragment for insertion of cDNAs for screening, the vector was digested with Sma I or Sfi I and Not I which excised the fragment containing the TNF R2 gene.

Screening involved inserting the cDNA fragments into either the Sma I or Sfi I/Not I sites of the vector in the ligation. Colonies were identified for kan resistance in the screen as described above. The amino acid sequence of the kan resistance gene is as follows:

```
Sequence of KAN ORF:                         (SEQ ID NO: 200)
IEQDGLHAGSPAAWVERLFGYDWAQQTIGCSDAAVFRLSAQGRPVL

FVKTDLSGALNELQDEAARLSWLATTGVPCAAVLDVVTEAGRDWL

LLGEVPGQDLLSSHLAPAEKVSIMADAMRRLHTLDPATCPFDHQAK

HRIERARTRMEAGLVDQDDLDEEHQGLAPAELFARLKASMPDGEDL

VVTHGDACLPNIMVENGRFSGFIDCGRLGVADRYQDIALATRDIAEE

LGGEWADRFLVLYGLAAPDSQRIAFYRLLDEFF
```

The following are the primers used to sequence cDNA fragments in the screen.

```
    Puc 19 reverse primer:
                            (SEQ ID NO: 201)
    5'-GCTTCCGGCTCGTATGTTGTGTGGAATTG-3';

kan reverse primer:
                            (SEQ ID NO: 202)
    5'-CAGTCATAGCCGAATAGCCTCTCCACC-3'.
```

Construction Of Kan Screening Vectors Frames 2 and 3

The Frame 2 and Frame 3 Kan screening vectors derived from the Frame 1 Kan vector (above) had three modifications differentiating them from the Frame 1 vector. In the first modification, Frame 2 had one base inserted before the 5' Sma I cloning site and Frame 3 had two bases before the 5' Sma I cloning site. The promoter was shifted out of frame with the kan resistance gene so in the screening vector no TNF R2—kan resistance protein fusion was produced as in Frame 1 above, and therefore there was no kanamycin resistance. Resistance was only restored when a cDNA of either reading frame 2 or 3 was inserted. The null background of relegated vectors digested with Sma I was also zero, unlike the Frame 1 vector above which was kan resistant and lead to significant background. The second and third modifications were the addition of a unique spacer and a 5' Myc tag. Any expression screening vector may be constructed to have a tag that differentiates it from target peptide binders. The tag includes, but is not limited to, 5' Myc epitope tag, FLAG, HA, and any unique sequence that facilitates sequencing. The sequence of the Myc tag is EQKLISEEDL (SEQ ID NO: 203). The Myc tag was located 3' to the Sfi site. The linker sequence, consisting of PAG-GAMAA (SEQ ID NO: 204), was inserted between the Sfi I site and the Myc tag. The 5' Myc tag was more likely to be visible to antibodies than a buried 3' E-tag. Also, the addition of the spacer and Myc tag in Frames 2 and Frame 3 enabled differential sequencing at the phagemid level (pCANTAB5E) of cDNA fragments in Frame 2 and 3 compared to "peptide" inserts in the same vector (pCANTAB5E). The two different forward sequencing primers for the differential sequencing are shown below.

```
PAMA forward "peptide" sequence forward primer:
GCC CAG CCG GCC ATG GCC           (SEQ ID NO: 205)

Myc forward 1 (Version A for Frame 2 and 3):
GGC CGC CGA ACA GAA ACT GAT TAG C (SEQ ID NO: 206)

Myc forward 2 (Version B for Frame 2 and 3):
GAT GGC CGC CGA ACA GAA ACT G     (SEQ ID NO: 207)
```

For the cloning, the PCR was carried out in a total volume of 50 μl containing 10 ng of pUC 19-GFP screening vector with stuffer, 1 μl of 10 μM each of:

```
Myc frame 2 forward primer:    (SEQ ID NO:208)
CCGAACAGAAACTGATTAGCGAAGAAGATCTGCCCGGGTTGC
CCGCCCAGGTGGC, or Myc frame 3 forward primer:    (SEQ ID NO:209)
CCGAACAGAAACTGATTAGCGAAGAAGATCTGCCCGGGTTTG
CCCGCCCAGGT, and TNFR2 reverse primer           (SEQ ID NO:210)
GATTTTCGCGGCCGCGTCGCCAGTGCTCCCTTCAGC,
```

10 μl 5×ThermalAce buffer, 1 μl of 50×dNTPs, and 1 μl ThermalAce polymerase (Invitrogen). PCR performed in a MJ Research TETRAD cycler (one cycle of 95° C. for 5 min, 30 cycles of 60° C. for 45 sec, 72° C. for 60 sec, 94° C. for 45 sec, and a final cycle of 72° C. for 5 min). Each of the PCR reactions were digested with Sfi I and Not I. Also kanamycin screening vector Frame 1 (1 μg) was digested with Sfi I and Not I. For the ligation, 100 ng of digested PCR product was combined with 50 ng of digested kanamycin screening vector and incubated overnight using T4 DNA ligase (New England Biolabs). After the incubation, the DNA was transformed into TOP10 one shot competent cells (Invitrogen) and plated on kanamycin (25 μg/ml) plates. Colonies were both AMP and Kan resistant. The Insert was confirmed by PCR and sequencing. The final vectors were Frame 2 Myc Kan pUC19 (Kan screening vector Frame2) and Frame 3 Myc Kan pUC19 (kan screening vector Frame 3).

Example 19

Cloning Expression-Screened cDNAs into Phage Display Vector pCANTAB5E

For each cDNA fragment which corresponded to one screen, $10^5$ clones were plated corresponding to the known diversity of the human genome. In the case of the green fluorescent protein (GFP) screen, the ligations were electroporated into TOP 10 cells followed by growth for 1 hour in 2×YT-G at 37° C. Colonies were plated on TC plates (2×YT-A+IPTG, 245×245×25 mm) so that single colonies were well separated and the plates were incubated at 37° C. overnight. Individual green colonies were selected and analyzed by PCR and sequencing. PCR analysis showed insert positive clones which contained ORFs (as analyzed by sequencing analysis). For the purpose of amplification, individual colonies were grown as a pool or individually in 2×YT-AG until the final amount of ampicillin resistant (amp$^r$)cells was approximately $2-5\times10^{11}$ cells.

In the case of the kanamycin screen, the ligations were electroporated into TOP 10 cells followed by growth for 1 hour in 2×YT-G at 37° C. Colonies were plated on TC plates (2×YT-K+IPTG, 245×245×25 mm) so that single colonies were well separated and the plates were incubated at 37° C. overnight. The colonies were scraped into PBS and 2×YT-KG media was inoculated for amplification until the amount of kanamycin (kan$^r$) cells was approximately $2-5\times10^{11}$. After amplification, cells were pelleted and plasmid preparations were carried out. In general, $2-5\times10^{11}$ cells yielded 200–400 μg of DNA quantitated by optical density. Multiple screens were carried out until the targeted diversity was achieved for the library. In order to excise the ORF inserts from the purified plasmid preparations, 170 μg of plasmid was digested in a reaction containing Not I 10 μl (50 units/μl), 1×NEB Buffer 3, and 1×BSA in a total volume of 800 μl. The tube was incubated for 2 hours at 37° C. After the incubation, the DNA was phenol-chloroform extracted and precipitated with isopropanol/sodium acetate. The DNA pellet was resuspended in 100 μl H$_2$O. The DNA was then digested with in a reaction containing Sfi I 30 1 (20 units/μl), 1×NEB Buffer 2, and 1×BSA in a total volume of 800 μl. The tube was incubated for 2 hours at 50° C. After incubating, the digestion was run on a 1% agarose gel to visualize the DNA "smear". The gel portion which contained the DNA smear was cut out purified. The DNA was purified using QIAquick (Qiagen) and quantitated by optical density. The purified DNA corresponding to ORFs was ligated to the pCANTAB5E (phage display vector) amp or tet using a molar ratio of 1:5. Production of cell and phage display libraries was carried out as described below.

Example 20

Construction of Cell Libraries

To prepare electrocompetent cells, an overnight culture of E. coli TG1 cells (F'traD36lacI$^q$Δ(lacZ)M15proA+B+/supEΔ(hsdM-mcrB)5r$_k$-m$_k$-McrB-thiΔ(lac-proAB) was diluted to an optical density of O.D.$_{600}$=0.05–0.1 (1:100) in 500 ml 2×YT, then grown at 37° C. in 4 liter Erlenmeyer flasks to an O.D.$_{600}$=0.5–0.6. The culture was poured into pre-chilled centrifuge bottles and incubated on ice for 30 minutes prior to centrifugation at 2000×g for 10 minutes (2°–40° C.). The supernatant was poured off, and the cell pellet was resuspended in a total of 400 ml of ice-cold sterile distilled water. The process of centrifugation and resuspension was repeated two more times. After the last centrifugation, the pellet was resuspended in a total of 25 ml of ice-cold sterile water containing 10% glycerol. The cell suspension was transferred to pre-chilled 35 ml centrifuge bottles, and was then pelleted at 2000×g for 10 minutes at 2°–40° C. The cells were then suspended in 0.3 ml of ice-cold sterile 10% glycerol solution, aliquoted, and snap-frozen. The aliquots were stored at −80° C.

The ligation product was purified using QIAquick spin columns (Qiagen) with 3 consequent washes and eluted with sterile deionized water. Electrotransformations were performed at 1500 Volts in electroporation cuvettes (0.1 mm gap; 0.1 ml volume) containing 100–300 ng of DNA and 40–80 L of TG1 electrocompetent cells. Immediately after the pulse, 1–2 ml of pre-warmed (40° C.) 2×YT medium containing 2% glucose (2×YT-G) was added and the transformants were grown at 37° C. for 1 hour at 250 rpm. Cell transformants were pooled, the volume measured, and an aliquot was plated onto 2×YT-G containing 100 μg/ml ampicillin (2×YT-GA) or 50 μg/ml tetracycline (2×YT-GT) plates to determine the total number of transformants and to perform PCR and sequence analysis of randomly selected clones.

To amplify the library, the transformants were plated onto 2×YT-GA or 2×YT-GT TC dishes (245×245×25 mm) in order to obtain individual colonies ($2-8\times10^3$ cfu/plate) and grown for 16–20 hours at 30° C. The cells were collected by scraping colonies into sterile PBS for a final concentration about $1\times10^{10}$ cfu/ml. Sterile glycerol was added to a final concentration of 10%; the library was aliquoted and stored at −80° C. Exact concentration of transformants was determined by plating an aliquot onto 2×YT-GA or 2×YT-GT plates.

Phage Rescue of cDNALIBs

Phage rescue of the library was carried out using the standard phage preparation protocol with the following changes. At least $10^8$ cfu/ml was inoculated with 2×YT-GA or 2×YT-GT media. Cells were grown to O.D.$_{600}$=0.6–0.8 at 37° C. with shaking (250 rpm). Helper phage (M13K07) was then added (MOI=15), and the cells were incubated for 30 minutes at 37° C. with shaking (250 rpm), followed by 30 minutes at 37° C. without shaking. Following infection, cells were pelleted (2000×g, 15 min) and the supernatant containing the helper phage was discarded. The cell pellet was resuspended in 3 times initial culture volume of 2×YT-A or 2×YT-T media for recombinant phage amplification (5 hours, 37° C., 250 rpm). The solution of phage in medium was then separated from cells by centrifugation (3000×g, 30 min, 4° C.), passed through a 0.45 μm filter, aliquoted and stored at −80° C. The phage was titered by infecting TG1 competent cells and plating onto 2×YT-GA or 2×YT-GT media. The phage titer was $10^{9-10^{11}}$ cfu/ml.

Construction of Breast Tumor cDNALIB Libraries

The poly A+RNA (1 μg) isolated from breast tumor tissue was used to produce cDNA. To carry out the first strand synthesis, the RNA, the 3' SMART CDS Primer IIA (10 μM)

and the modified 5' Smart Primer (10 μM) were added together for a final volume of 5 μl. The tube was incubated at 72° C. for 2 minutes to denature the RNA and primer. The tube was placed on ice for 2 minutes and then centrifuged at 14,000 rpm for 20 secs to collect the contents. To the 5 μl final volume, 2 μl (5×First Strand Buffer), 1 μl DTT (20 mM), 1 μl dNTP (10 mM), and 1 μl Power Script Reverse Transcriptase were added to carry out the first strand reaction. The contents of the tube were mixed gently and incubated at 42° C. for 1 hr and then placed on ice to terminate the reaction. To carry out the PCR amplification for producing double stranded cDNA, 5 μl of the subtracted mRNA first strand reaction or 0.4 μl un-subtracted mRNA first strand reaction was used in the PCR reaction containing 10 μl (10×Advantage 2 Buffer), 2 μl (50×dNTPs), 4 μl modified Smart Primer, 4 μl 5' PCR primer, and 2 μl Advantage 2 Enzyme in a total volume of 100 μl. For the PCR amplification rounds, one preliminary cycle (95° C., 1 min) and then 24 cycles were carried out (95° C. for 5 sec, 65° C. for 15 sec, 68° C. for 6 min). The cDNA that resulted was column purified using QIAquick™ columns (Qiagen) and quantitated by Picogreen Method (Molecular Probes; Eugene, Oreg.). In order to obtain preferred size fragments ranging from 100 bp to 3000 bp, more preferably from 200 bp to 2000 bp for insertion into the phage display vector, the initial long cDNA fragments were digested with multiple enzymes with known infrequent cutting profiles in the mammalian genome. The digestions were conducted in the following manner. For each digestion, 5 μl of each enzyme, 10×Buffer (15 μl), and 100×BSA were added to 5 μg of the double stranded cDNA PCR product. The total volume for each reaction was 150 μl. The digestions were as follows:

Digestion Reaction 1 containing enzymes Nar I, Eco R1, and Avr II and NEB Buffer 1 was carried out for 4 hours at 37° C.
Digestion Reaction 2 containing enzymes EcoR1, Hind III, and Xho I and NEB Buffer 2 was carried out overnight at 37° C.
Digestion Reaction 3 containing enzymes Bam HI, Xba I, and Avr II and NEB Buffer 2 was carried out for 4 hours at 37° C.
Digestion Reaction 4 containing enzymes Bgl II, EcoR1 Xho I and NEB Buffer 3 was carried out for 4 hours at 37° C.

The DNA in each digestion reaction was chloroform extracted and precipitated with isopropanol and the 5' and 3' overhangs were filled in by the Pfu DNA Polymerase polishing reaction. The precipitated DNA was resuspended in 20 μl water and the polishing reaction was carried out in a total volume of 100 μl containing 10 μl (10×Buffer) 10 μl (10 mM dNTPs) and 10 μl Pfu DNA Polymerase (2.5 units/μl). The reaction was incubated at 72° C. for 30 minutes after which the cDNA was chloroform extracted, precipitated and resuspended in 50 μl water. DNA quantitation was performed by the Picogreen method or by optical density. The cDNA was ligated into the Sfi-Sma site of pCANTAB5E phage display vector using a molar ratio of 1:10 and 1:20. The cell library was produced as described above and colony PCR was carried out on individual colonies.

Colony PCR involved using the PCR primers which flanked the inserted cDNA fragment producing the multi-size fragments indicating a good range of DNA lengths (300–1000 bp) as was desired. Also the ligation efficiency was close to 100% with a few PCRs indicating a vector re-ligated fragment. However, in order to produce a library of ORFs, approximately $5 \times 10^{11}$ cells from the cell library were pelleted and a plasmid preparation was produced (Qiagen). The DNA was ligated into the GFP expression vector and the expression screen was carried out as described above. Following the expression screen, the cell and phage libraries (both amp and tet) in the pCANTAB5E phagmid vector were produced as previously described above. PCR analysis of the cDNA inserts in the phage and cell library show the efficiency of ligation to be 100% among the 36 clones (cell library) and 34 clones (phage library) examined. Furthermore the inserts ranged in size from 400 bp to 1000 bp as expected.

Example 21

Construction of Individual Target(s)

Construction of DGI 2-Gene III Fusion Proteins in pCANTAB5E (tet)

DGI-2 was identified as an uncharacterized gene in a public database designated KIAA0101 (GenBank Ace. No. XM_042258). The DNA sequence that encodes DGI-2 is shown in FIG. 3.

An IMAGE clone containing the DGI-2 sequence (IMAGE: 3838690; accession number BE748524) was obtained from the American Type Culture Collection (ATCC, Manassas Va.). The clone included 770 bp and encompassed the entire DGI-2 open reading frame (ORF).

The 400 base pair DNA sequence encoding the target protein DGI-2 protein (111 amino acid residues), was cloned into the Sfi I and Not I restriction sites in the pCANTAB5E (tet) vector. The resulting fusion protein consisted of the DGI-2 protein fused to the C-terminus of the geneIII signal sequence and to the N-terminus of the gene III protein. For ligation of the sequence encoding the target protein into the vector, primers were designed to add the appropriate restriction sites and amino acids for signal peptide cleavage at the 5' and 3' end of the sequences. The primer sequences were as follows:

```
Forward ligation primer: 5'TgT TCC TTT CTA TgC ggC CCA gCC ggC    (SEQ ID NO:211)
CAT ggC gAT ggT gCg gAC
TAA AgC AgA 3'

Reverse ligation primer: 5'CgA AAT CTT TTg gAC TCA CAC TgC ggC    (SEQ ID NO:212)
CgC TTC TTT TTC ATC ATT
TgT gTg ATC 3'.
```

The primers were used in the PCR reaction with a high fidelity DNA polymerase (ThermalAce, Invitrogen) using the IMAGE clone containing the DGI-2 sequence (IMAGE: 3838690; Accession Number BE748524) as the template to generate the insert for ligation. The pCANTAB5E vector plasmid was digested with Sfi I and Not I and the vector fragment was gel purified. The vector (100 ng), insert (50–100 ng), and 0.5 µl of ligase (BM) were mixed in a 10 µl ligation reaction and incubated over night at 15° C. The ligation product was purified and electroporations were performed with *Escherichia coli* strain TG1 electrocompetent cells ((F' traD36 lacI$^q$ Δ(lacZ)M15 proAB)/supE Δ(hsdM-mcrB)$_5$r$_k^-$m$_k^-$McrB$^-$) thi Δ(lac-proAB). Cell transformants were pooled and an aliquot was plated on plates containing 10 µg/ml tetracycline. The correct constructs were determined by colony PCR followed by sequence analysis using primers for the pCANATAB5E vector.

Construction of Hras—GENE III Fusion Proteins in pCANTAB5E (tet)

Hras was identified from GenBank accession number NM_005343—*Homo sapiens* v-Ha-ras Harvey rat sarcoma viral oncogene homolog (Hras) mRNA. The Genbank sequence was used to design cloning primers. The primers extended into the 5' and 3' untranslated regions and generated the 570 base pair open reading frame. Cloned from Human Universal QUICK-Clone™ cDNA from Clontech using ThermalAce high fidelity polymerase from Invitrogen. Sequence confirmed by sequencing after sub cloning into pZERO cloning vector from Invitrogen.

```
Forward cloning primer:    (SEQ ID NO:213)
5'-CCCTGAGGAGCGATGACGGAATATAAGCTG-3'

Reverse cloning primer:    (SEQ ID NO:214)
5'-GTCCCCCTCACCTGCGTCAGGAGAGCACAC-3'.
```

The Hras sequence was not activated. Activated Hras was created by substituting the base G to T at position 29 as demonstrated in oncogene T24. The base substitution was performed using a mutagenesis primer, the above reverse cloning primer, and PCR using ThermalAce high fidelity polymerase from Invitrogen.

```
Activation forward primer   (SEQ ID NO:215)
5'-ATGACGGAATATAAGCTGGTGGTGGTGGTCGCCG-3'.
```

Construction of Leptin Ligand—GENE III Fusion Proteins in pCANTAB5E (tet)

Leptin ligand was identified from GenBank accession number NM_000230—*Homo sapiens* leptin (obesity homolog, mouse) (LEP) mRNA. The Genbank sequence was used to design cloning primers.

The primers extended into the 5' and 3' untranslated regions and generated the 501 base pair open reading frame. Cloned from Human Universal QUICK-Clone™ cDNA from Clontech using ThermalAce high fidelity polymerase from Invitrogen. The sequence was confirmed by sequencing after subcloning into the pZERO cloning vector from Invitrogen.

```
Forward cloning oligo   (SEQ ID NO:216)
5'-CCATCCTGGGAAGGAAAATGCATTG-3'

Reverse cloning oligo   (SEQ ID NO:217)
5'-AGGGAAATTGACAGAGTCCTGGATAAGGGG-3'.
```

Both Hras and Leptin genes were cloned into Sfi I and Not I sites of the pCANTAB5E (tet) vector using PCR. The following forward primers added the Sfi I site and required signal sequence to activate Hras and Leptin ligand.

```
Hras forward primer                  (SEQ ID NO:218)
5'-CTTAAAGCTTGGCCCAGCCGGCCATGGCGGAATATAAGCT
GGTGGTGG-3'

Leptin Ligand forward primer         (SEQ ID NO:219)
5'-GCGGCCCAGCCGGCCATGGCGCATTGGGGAACCCTGTGCG
GATTC-3'

The reverse primers added the required Not I clon-
ing site.
Hras reverse primer                  (SEQ ID NO:220)
5'-GCAATTCTCTGAGCTCGCGGCCGCGGAGAGCACACACTTG
CAGCTCATG-3'

Leptin Ligand reverse primer         (SEQ ID NO:221)
5'-GATTCCTTGCGGCCGCGCACCCAGGGCTGAGGTCCAGCTGC-3'
```

PCR products were cut with Sfi I and Not I (NEB) and ligated into pCANTAB5E cut with Sfi I and Not I. Fusion proteins with Hras or Leptin Ligand fused to the C-terminus of the gene III signal sequence and to the N-terminus of the gene III protein resulted.

Example 22

Drug Discovery Using Target: Partner Pairs for High-Throughput Screening

Proteome Panning may be directly used for drug discovery. Listed below are non-limiting examples of methods that can be used to develop assays for high-throughput screening. The basic idea in all of the assays is to identify compounds from combinatorial libraries that inhibit target: target binder interaction.

ELISA Method I

In this approach, the target phage and partner phage express separate distinguishing tags including, but not limited to, myc, FLAG, etag, hexahistidine, etc. Initially, the target and partner phage are separated as described previously. Briefly, target phage is captured on plates previously coated with the Tag-specific antibody overnight at 4° C. The partner phage is added followed by compounds from a small molecule combinatorial library at a final concentration of 20 µM. Following a 1 hour incubation at room temperature, the plates are washed and probed with an antibody specific for the partner phage specific-Tag and labeled with a reporter including, but not limited to horse radish peroxidase, fluorescin, luciferase, etc. After a second washing step, the chromogen is added and the plates read in the appropriate instrument.

ELISA Method II

In this approach, the target is first synthesized by in vitro translation and then screened as described above in ELISA Method I.

Cloning and in vitro Expression of Target Polypeptide:

The DNA coding sequence for the target is directly cloned into the pIVEX 2.3 d circular expression vector (Roche) from the pCantab vectors using the following primers

```
Forward primer                              (SEQ ID NO:225)
5'-CTT TAA GAA GGA GAT ATA CCA TGG CCC AGC CGG CCA
TGG C- 3'

Reverse primer:                             (SEQ ID NO:226)
5'-TGA TGA TGA GAA CCC CCC CCC GGA TAC GGC ACC GGC
GCA CC- 3'
``` for use in the Rapid Translation System RTS 500 (RTS 500 E. coli HY kit, Roche Diagnostics GmbH). In each case, the coding sequence is inserted between the 5' Nde I and 3' Xho I sites, in frame with the his-tag provided in the vector. Expression reactions are performed by pipetting 10 ml Feeding Solution and 1 ml Reaction Solution into their respective compartments in the reaction device (provided with the kit). Following this, 10 µg of plasmid DNA is added to each reaction mixture and the reaction is allowed to continue for 24 h at 30° C. in the RTS 500 Instrument prior to harvesting the expressed protein.

Solubilizing, Refolding and Purification of Insoluble Proteins:

Analysis of protein products from the in vitro system indicates that adequate expression levels may be obtained. However, high expression levels cause segregation of the protein products to the insoluble fraction of the expression reaction. The expressed proteins are thereby recovered as insoluble pellets, are denatured and subjected to a standard refolding regimen prior to use in panning experiments or other assays. After overnight expression at 4° C. in the Roche RTS in vitro expression system, the reaction mixtures are removed from their disposable reaction vessels. The insoluble fractions are pelleted by a 10 min centrifugation at maximum speed in a microfuge. The pellet from each reaction mixture is dissolved by gentle vortexing in 1.0 ml Denaturation Buffer (50 mM TRIS, 8 M urea, 20 mM β-mercaptoethanol). Another 10 min spin in the microfuge removes insoluble material. Bradley assay (Bio-Rad Protein Assay) determines the protein concentration of the soluble fraction. For refolding, aliquots of solubilized proteins are diluted to a protein concentration of 25 µg/ml in Denaturation Buffer and the diluted mixtures are loaded into 10,000 molecular weight cut off dialysis cassettes (Slide-A-Lyzer®, Pierce). Each 10 ml dilution mixture is dialyzed against three changes of 4L Dialysis/Refold Buffer (50 mM ammonium bicarbonate, 100 mM NaCl, pH 9.0) at 4° C. The first two changes are performed for a minimum of 2 h, each. The final dialysis is carried out overnight. The his-tagged proteins are purified by loading them onto a 1.6×1.2 cm Ni-Superflo column (2.4 ml, QIAGEN) equilibrated with Equilibration Buffer (50 mM $NaH_2PO_4$, 300 mM NaCl, 10 mM imidazole, pH 8.0) followed by elution with Equilibration Buffer containing 500 mM imidazole.

Target is captured on $Ni^{++}$ coated plates overnight at 4° C. The partner phage is added followed by compounds from a small molecule combinatorial library at a final concentration of 20 µM. Following a one hour incubation at room temperature, the plates are washed and probed with an antibody specific for the partner phage specific-Tag and labeled with a reporter including but not limited to horse radish peroxidase, fluorescin, luciferase, etc. After a second washing step, the chromogen is added and the plates read in the appropriate instrument.

Microarrays

In this approach, microarrays consisting of 10,000–30,000 chemical compounds from a combinatorial library are arrayed on microscope slides using an instrument such as the OmniGrid® Microarray (Gene Machines). The slides can be uncoated or coated with various chemicals such as bovine serum albumin, glycerin, etc. and the small molecules can be plated directly onto the solid phase, e.g. solid support, matrix or slides, or captured with linkers. The target and partner phage with distinguishing tags (e.g., myc, FLAG, etag, etc.) are added together in an incubation chamber. After a short incubation period, the phage are washed off and binding is probed with anti-target antibody conjugated to the fluorescent dye Cy3 and an anti-partner antibody conjugated to the fluorescent dye Cy5. Slides are read in any Microarray reader such as the GenePix 4100A or 4000B (Axon Instruments, Inc.). If the combi-chem compound binds to the domain on the target recognized by the partner (i.e., hotspot), only the Cy3 signal will be visualized. If the small molecule binds outside the hotspot, both antibodies can bind and a combined Cy3/Cy5 can be read. Conversely, compounds binding to the partner can also be detected in the same assay by the Cy5 signal.

High-throughput ALPHASCREEN™ assay

Compound Library:

A library of compounds synthesized by combinatorial chemistry techniques may be obtained from a supplier of in-house designed and synthesized novel drug-like organic molecules for high throughput screening.

Assay Development:

Bead-based technology established by the principle of luminescent oxygen channeling (Ullman et al., 1996, *Clin. Chem.* 42:1518–1526; Ullman et al:, 1994, *Proc. Natl. Acad. Sci. USA* 91:5426–5430) is commercially available (e.g., ALPHAScreen; PerkinElmer). This assay format offers the advantages of being homogeneous, fluorescence-based, and easy to miniaturize or reduce for robotics. In addition, the format does not suffer from the distance limitations of TR-FRET (time-resolved fluorescence resonance energy transfer) assays. The detection limit of ALPHAScreen™ assays is 200 nm, whereas the detection limit of TR-FRET assays is 9 nm.

A mixture of target (10 µl) (6×His-tagged) and binder (myc-tagged) phage expressing target and partner respectively are added to 384-well low volume polystyrene microplates (e.g., ProxiPlate™-384; PerkinElmer Life Sciences, Boston, Mass.). Nickel-conjugated acceptor beads and anti-myc conjugated donor beads are added at a final concentration of 20 µg/ml. The final assay volume is 20 µl. Plates are then incubated for 60 min in the dark at room temperature. At the end of the incubation period, the fluorescence signal at 520 nm is read on a plate reader (e.g., Fusion-α HT; PerkinElmer). The values are expressed as AlphaScreen™ activity in counts per second (cps) and plotted against Log (Target phage) (CFU/ml). Assay optimization may include variation of phage concentrations, and variation of detector reagents (acceptor and donor bead concentrations), order of reagent addition and time of incubation.

High-Throughput Methods:

Relative potencies of combinatorial chemistry compounds as compared to binder phage are analyzed in a competition system. Detection of the target binder interaction will be measured in an amplified luminescent proximity homogeneous assay (ALPHAScreen™; PerkinElmer). The assay may be performed in 384-well low volume polystyrene microplates (e.g., ProxiPlate™-384; PerkinElmer Life Sciences) with a final volume of 20 µl. Final incubation conditions are combi-chem compounds at $10^{-5}$ M, 0.025 M HEPES (pH 7.4 at 25° C.), 0.100 M NaCl, 0.1 % BSA (Cohn Fraction V; Sigma Chemical Co., St. Louis, Mo.), 5–20 µg/ml nickel-conjugated acceptor beads, and 5–20 µg/ml antimyc-conjugated donor beads.

First, target and binder phage, and combi-chem compound are incubated for 2 h at room temperature. Next, acceptor and donor beads are added and the incubation is continued for an additional 1 h. At the end of the incubation period, the fluorescence signal at 520 nm is read on a plate reader (e.g., Fusion-α HT; Packard BioScience Co.). Primary data are analyzed, e.g., by importing into Activity-Base™ (ID Business Solutions Ltd, Guildford, UK), background corrected, normalized to buffer controls and then expressed as percent specific binding. Data is be validated if the Z'-factor (Zhang et al., 1999, *J. Biomol. Screen.* 4:67–73) for this assay is expected to be greater than 0.7 ($Z'=1-(3\sigma_+ + 3\sigma_-)/|\mu_+ - \mu_-|$) and the signal-to-background (S/B) ratio is expected to be between 30 and 300.

$IC_{50}$ Analysis of "HITS":

HITS are evaluated in a competitive binding assay to determine their ability to disrupt target:binder interaction in a dose-dependent manner. This allows an accurate estimation of HIT potency, $IC_{50}$, relative to phage concentration. The data are fit to a four-parameter non-linear regression analysis ($y=\min+(\max-\min)/(1+10^{((\log IC_{50}-x)*Hillslope)})$), and are used to determine $IC_{50}$ values. The Z'-factor (Zhang et al., 1999, *J. Biomol. Screen.* 4:67–73) for this assay is expected to be greater than 0.7 ($Z'=1-(3\sigma_+ + 3\sigma_-)/|\mu_+ - \mu_-|$) and the signal-to-background (S/B) ratio is expected to be between 30 and 300.

Microarray and ALPHAScreen methods are advantageous in that they do not require additional processing steps such as phage separation, sub-cloning or purification. However, in certain instances the target: binder phage interaction may be disrupted too easily giving too many false positives. Conversely, target: binder phage interactions may be too difficult to disrupt and inhibitors may go undetected. Also, detection and quantitation of the interaction and the range of inhibition that can be detected may be limiting factors. In such cases, the ELISA methods may offer an advantage. ELISA method I requires separation of the target and binder phage while ELISA method II requires sub-cloning, expression and purification of recombinant target protein. These methods provide cleaner more reproducible assays.

Example 23

Informatics for Data Management and Analyses

In order to manage and analyze large volumes of data from proteome panning, guidelines for nomenclature and monitor information flow were established.

1. Easy To Use Naming System

This system utilizes excel and visual basic macro to facilitate mapping samples in plates to meaningful names. It can help researchers to track their sample based on sample name, it also reduces the amount of work necessary for naming samples.

2. Pre-Processing Of Raw DNA Sequence, End Trimming, Vector Trimming

Raw sequencing data have several errors, especially at the two ends, which includes bad sequence due to sequencing machine's capability and vector sequences. Contamination has to be removed from the sequences before processing. Two criteria can be used, first, Phred program can be used for base calling based on sequence quality, secondly, if there is vector sequence contamination, trimming based on sequence characteristics will be used.

3. Automated Blast Search With Pre-Defined Parameters Will Be Performed After Sequences Are Transferred To Linux Cluster Sequences were transferred through network, samba server running on the linux cluster support connection between Microsoft and linux machine. Sequences in one project were put under the same folder. GCG commands were called for sequence processing using pre-defined parameters. For nucleotide sequence, blastx program was used to dynamically translate query sequence in all 6 possible reading frames and compare the resulting protein sequence with SwissProt database. Results were stored in the same folder with name "file_name.blastx".

4. Blast Results Parsed And Hits Information Entered Into Access Database

Blast result parsers were developed that are capable of parsing blast results based on user defined parameters thereby generating reports automatically. For proteome panning, no parameter was needed, as all hits in the blast file were saved into database. Further query was performed in the database. By doing so, no information was lost during the first run of parsing. Sorthits, the main program used for proteome panning, generated three files automatically for each run:

1. hits.csv: contained all the parsed blast results, all properties were separated by comma, this file was imported to database for further analysis;
2. hit.summary: contained each unique hit found in database, together with how many times they were found by query sequences, followed by the name of query sequence(s) that produced this hit.
3. hits.txt: contained information on each and every hit, a short description of their identity, start/end portion of query sequence and subject sequence. In addition to this, the name of the hit(s) was used to query a database of known house-keeping genes and reported whether any hit was one of the house keeping genes.

5. Database Can Be Queried To Generate Reports

The hits.csv files generated by sorthits were imported directly into Access database and queried for specific hits. After parsing, the blast hits reported were separated into different fields that are relevant for analysis (listed in Table 2, example query shown in FIG. 7).

The parser utilized the open source blast.pm as its main parse engine. Once the result was in the database, queries for any of the different fields, such as a specific sequence, organism, or E (expectation) value were easily performed. The results were exported in multiple formats to facilitate data sharing.

6. Hits Information Generated And Verified By Querying Existing Protein-Protein Interaction Databases The automatic querying machinery was updated on a regular basis to accommodate the change in database design. To obtain protein-protein network information, the hits, especially those after verification, were used to query for all known protein-protein interaction network database for verification.

For example, hit A from *Homo sapiens* was used to search yeast protein interaction network to retrieve the homolog's interaction network in yeast. The interaction network thus provided was used to search against the database for potential hits. By iterating this process, a protein interaction network inferred from multiple species/organism was generated, stored, and queried for useful information.

For hits that have no homologs, their interaction partners' (derived from our Phenogenix technology) homologs provided information about their potential function, cellular localization, etc. This feature of the database showed the power of this technology, not only can it verify known protein-protein interaction network, it is also capable of uncovering unknown protein-protein networks.

The database was queried. All hits in the catalog were linked to their partners. Hits were also linked to various outside databases for their function description, map position in genome (if available). The search engine automatically downloaded this information to a local server for efficient data access during query.

TABLE 2

| | |
|---|---|
| 1 QUERY_NAME | Sequence identifier of the query |
| 2 QUERY_LENGTH | Full length of the query sequence |
| 3 SBJCT_NAME | Sequence identifier of the sbjct ("hit") |
| 4 SBJCT_LENGTH | Full length of the sbjct sequence |
| 5 EXPECT | Expect value for the alignment |
| 6 SCORE | Blast score for the alignment |
| 7 BITS | Bit score for the alignment |
| 8 NUM_HSPS | Number of HSPs (not the "N" value) |
| 9 HSP_FRAC_IDENTICAL | Fraction of identical substitutions |
| 10 HSP_FRAC_CONSERVED | fraction of conserved ("positive") substitutions |
| 11 HSP_QUERY_ALN_LENGTH | Length of the aligned portion of the query sequence |

TABLE 2-continued

| | |
|---|---|
| 12 HSP_SBJCT_ALN_LENGTH | Length of the aligned portion of the sbjct sequence |
| 13 HSP_QUERY_GAPS | Number of gaps in the aligned query sequence |
| 14 HSP_SBJCT_GAPS | Number of gaps in the aligned sbjct sequence |
| 15 HSP_QUERY_START | Starting coordinate of the query sequence |
| 16 HSP_QUERY_END | Ending coordinate of the query sequence |
| 17 HSP_SBJCT_START | Starting coordinate of the sbjct sequence |
| 18 HSP_SBJCT_END | Ending coordinate of the sbjct sequence |
| 19 HSP_QUERY_STRAND | Strand of the query sequence (TBLASTN/X only) |
| 20 HSP_SBJCT_STRAND | Strand of the sbjct sequence (TBLASTN/X only) |
| 21 HSP_FRAME | Frame for the sbjct translation (TBLASTN/X only) |
| 22 SBJCT_DESCRIPTION (optional) | Full description of the sbjct sequence from the alignment |
| 23 Alignments | Alignment of query sequence and sbjct sequence |

TABLE 3

| Clone # | Lib | Sequence | E-Tag | DGI-9 | LDH | DGI9/LDH |
|---|---|---|---|---|---|---|
| DGI9-20M-4-A4$_{14}$ | 20F | FLLQDFIMDAGSFVKPIGVG | 32.6 | 8.7 | 1.1 | 8.1 |
| DGI9-20M-4-E3 | 20F | MAGFRGSGLSGYSEARLPRV | 34.5 | 7.0 | 1.0 | 7.1 |
| DGI9-20M-4-A6$_{27}$ | 20R | WDWSRFGAQLRGAILGRATG | 27.2 | 6.0 | 0.9 | 6.5 |
| DGI9-20M-4-A12 | 20R | SRLALSSQHGLSLVAGRRRG | 20.7 | 1.9 | 0.9 | 2.1 |

As various changes can be made in the above compositions and methods without departing from the scope and spirit of the invention, it is intended that all subject matter contained in the above description, shown in the accompanying drawings, or defined in the appended claims be interpreted as illustrative, and not in a limiting sense.

The contents of all patents, patent applications, published articles, books, reference manuals, texts and abstracts cited herein are hereby incorporated by reference in their entirety to more fully describe the state of the art to which the present invention pertains.

What is claimed is:

1. A method of selecting target and target binder pairs comprising:
   (a) preparing a phage comprising a library of biological targets comprising polypeptides encoded by a cDNA library and a distinguishable first selection marker;
   (b) obtaining a peptide target binder library selected from the group consisting of a random peptide phage target binder library and a cDNA library encoding a polypeptide, and a second selection marker, and the first selection marker is different from the second selection market;
   (c) panning, where the target phage and the target binder phage are mixed in solution and targets and target binders are allowed to mate or form complexed pairs;
   (d) transforming host cells with a mixture of the target phage and target binder phage libraries, wherein the mated or complexed pairs infect the host cells; and
   selecting for host cells infected by phage that formed complexes of target and target binders based on the selection markers.

2. The method of claim 1, wherein the first selection and second selection markers marker are selected from a group consisting of: tetracycline, ampicillin, and kanamycin.

3. The method of claim 1, wherein the host cell is selected from the group consisting of: bacteria, mammalian, yeast, insect, and plant cells.

4. The method of claim 3, wherein the host cell is *Escherichia coli*.

5. The method of claim 1, wherein the library of biological targets in step (a) comprise a polypeptide of known function.

6. The method of claim 1, wherein the library of biological targets in step (a) comprise a polypeptide of unknown function.

7. The method of claim 1, wherein the library of target binders in step (a) comprise polypeptides encoded by a cDNA library.

8. A cell population comprising a mixture of phage according to steps (a) and (b) of claim 1.

* * * * *